(12) United States Patent
Reeves et al.

(10) Patent No.: US 7,125,661 B1
(45) Date of Patent: Oct. 24, 2006

(54) **SEQUENCES FOR THE DETECTION OF *ESCHERICHIA COLI***

(75) Inventors: Peter Richard Reeves, Glebe (AU); Lei Wang, North Ryde (AU)

(73) Assignee: The University of Sydney, New South Wales (AU)

( * ) Notice: Subject to any disclaimer, the term of this patent is extended or adjusted under 35 U.S.C. 154(b) by 0 days.

(21) Appl. No.: 09/701,132

(22) PCT Filed: May 21, 1999

(86) PCT No.: PCT/AU99/00385

§ 371 (c)(1),
(2), (4) Date: Jun. 15, 2001

(87) PCT Pub. No.: WO99/61458

PCT Pub. Date: Dec. 2, 1999

(30) Foreign Application Priority Data

May 21, 1998 (AU) .................................. PP3634

(51) Int. Cl.
C12Q 1/68 (2006.01)
C12P 19/34 (2006.01)
C07H 21/02 (2006.01)
C07H 21/04 (2006.01)

(52) U.S. Cl. ................. 435/6; 435/91.2; 536/23.1; 536/23.7; 536/24.32; 536/24.33

(58) Field of Classification Search ............ 435/6, 435/91.2; 536/23.7, 24.32, 24.33
See application file for complete search history.

(56) References Cited

U.S. PATENT DOCUMENTS 6,090,549 A * 7/2000 Mirzabekov et al. .......... 435/6

FOREIGN PATENT DOCUMENTS

JP 09-168391 6/1997

OTHER PUBLICATIONS

Journal of Bacteriology, (Jan. 1999) 181 (1), Reid S D et al. 153-160.
Molecular Microbiology (1994) 12(2) Tominaga A et al. 277-285.
Journal of Molecular Biology (1994) 238, Fahrner K. A. et al. 173-186.
Science (1997) 277(5331) Blattner FR et al. 1453-1462.
Journal of Bacteriology (Sep. 1993) 175(17) Schoenhals G. 5395-5402.
Journal of Bacteriology (Feb. 1998) 180(4) Ratiner Y A 979-984.
FEMS Microbiology Letters (1987) 48 Ratiner Y A 97-104.
FEMS Microbiology Letters (1985) 29, Ratiner YA, 317-323.
Ratiner Y A FEMS Microbiol. Lett 15 (1982) 33-36.
Ratiner Y A FEMS Microbiol. Lett. 19 (1983) 37-41.
Bastin D A et al. 1991 Mo. Microbiol. 5:9 2223-2231.
Yao Z. 1994 J. Bacteriol. 176: 4133-4143.
Stevenson et al. 1994. J. Bacteriol. 176: 4144-4156.
Bastin D A et al. 1995 Gene 164: 17-23.
Bilge et al. 1996 Inf and Immun 64: 4795-4801.
Kuwajiwa et al. 1988 J. Bacteriol. 170: 485-488.
Gannon et al., (Mar. 1997) *Journ. of Clin. Microbiology* 35 (3):656-662.
European Supplemental Search Report from EP 99923309.1 dated Jun. 6 2005.

* cited by examiner

*Primary Examiner*—Carla J. Myers
(74) *Attorney, Agent, or Firm*—Welsh & Katz, Ltd.

(57) ABSTRACT

An isolated nucleic acid molecule comprising a nucleotide sequence encoding a transcriptional enhancer of cytochrome P450 (P450) CYP3A4 production or expression is disclosed, as are uses of the nucleic acid molecule for screening compounds for xenobiotic induction of CYP3A4 expression in cells and animals.

24 Claims, 95 Drawing Sheets

```
GATCTGATGGCCGTAGGGCGCTACGTGCTTTCTGCTGATATCTGGGCTGAGTTGGAAAAA        60
ACTGCTCCAGGTGCCTGGGGACGTATTCAACTGACTGATGCTATTGCAGAGTTGGCTAAA       120
AAACAGTCTGTTGATGCCATGCTGATGACCGGCGACAGCTACGACTGCGGTAAGAAGATG       180
GGCTATATGCAGGCATTCGTTAAGTATGGGCTGCGCAACCTTAAAGAAGGGGCGAAGTTC       240
CGTAAGAGCATCAAGAAGCTACTGAGTGAGTAGAGATTTACACGTCTTTGTGACGATAAG       300
CCAGAAAAAATAGCGGCAGTTAACATCCAGGCTTCTATGCTTTAAGCAATGGAATGTTAC       360
TGCCGTTTTTTATGAAAAATGACCAATAATAACAAGTTAACCTACCAAGTTTAATCTGCT       420
TTTTGTTGGATTTTTTCTTGTTTCTGGTCGCATTTGGTAAGACAATTAGCGTGAGTTTTA       480
GAGAGTTTTGCGGGATCTCGCGGAACTGCTCACATCTTTGGCATTTAGTTAGTGCACTGG       540
TAGCTGTTAAGCCAGGGGCGGTAGCTTGCCTAATTAATTTTTAACGTATACATTTATTCT       600
TGCCGCTTATAGCAAATAAAGTCAATCGGATTAAACTTCTTTTCCATTAGGTAAAAGAGT       660
GTTTGTAGTCGCTCAGGGAAATTGGTTTTGGTAGTAGTACTTTTCAAATTATCCATTTTC       720
```

Start of orf1
```
           M  L  L  C  I  H  I  N  V  Y  Y  L  L
CGATTTAGATGGCAGTTGATGTTACTATGCTGCATACATATCAATGTATATTATTTACTT       780
 L  E  C  D  M  K  K  I  V  I  I  G  N  V  A  S  M  M  L  R
TTAGAATGTGATATGAAAAAAATAGTGATCATAGGCAATGTAGCGTCAATGATGTTAAGG       840
 F  R  K  E  L  I  M  N  L  V  R  Q  G  D  N  V  Y  C  L  A
TTCAGGAAAGAATTAATCATGAATTTAGTGAGGCAAGGTGATAATGTATATTGTCTAGCA       900
 N  D  F  S  T  E  D  L  K  V  L  S  S  W  G  V  K  G  V  K
AATGATTTTTCCACTGAAGATCTTAAAGTACTTTCGTCATGGGGCGTTAAGGGGGTTAAA       960
 F  S  L  N  S  K  G  I  N  P  F  K  D  I  I  A  V  Y  E  L
TTCTCTCTTAACTCAAAGGGTATTAATCCTTTTAAGGATATAATTGCTGTTTATGAACTA      1020
 K  K  I  L  K  D  I  S  P  D  I  V  F  S  Y  F  V  K  P  V
AAAAAAATTCTTAAGGATATTTCCCCAGATATTGTATTTTCATATTTTGTAAAGCCAGTA      1080
 I  F  G  T  I  A  S  K  L  S  K  V  P  R  I  V  G  M  I  E
ATATTTGGAACTATTGCTTCAAAGTTGTCAAAAGTGCCAAGGATTGTTGGAATGATTGAA      1140
 G  L  G  N  A  F  T  Y  Y  K  G  K  Q  T  T  K  T  K  M  I
GGTCTAGGTAATGCCTTCACTTATTATAAGGGAAAGCAGACCACAAAAACTAAAATGATA      1200
 K  W  I  Q  I  L  L  Y  K  L  A  L  P  M  L  D  D  L  I  L
AAGTGGATACAAATTCTTTTATATAAGTTAGCATTACCGATGCTTGATGATTTGATTCTA      1260
 L  N  H  D  D  K  K  D  L  I  D  Q  Y  N  I  K  A  K  V  T
TTAAATCATGATGATAAAAAGATTTAATCGATCAGTATAATATTAAAGCTAAGGTAACA      1320
 V  L  G  G  I  G  L  D  L  N  E  F  S  Y  K  E  P  P  K  E
GTGTTAGGTGGGATTGGATTGGATCTTAATGAGTTTTCATATAAAGAGCCACCGAAAGAG      1380
 K  I  T  F  I  F  I  A  R  L  L  R  E  K  G  I  F  E  F  I
AAAATTACCTTTATTTTTATAGCAAGGTTATTAAGAGAGAAAGGGATATTTGAGTTTATT      1440
 E  A  A  K  F  V  K  T  T  Y  P  S  S  E  F  V  I  L  G  G
GAAGCCGCAAAGTTCGTTAAGACAACTTATCCAAGTTCTGAATTTGTAATTTTAGGAGGT      1500
```

Fig. 5A

```
                F   E   S   N   N   P   F   S   L   Q   K   N   E   I   E   S   L   R   K   E
                TTTGAGAGTAATAATCCTTTCTCATTACAAAAAAATGAAATTGAATCGCTAAGAAAAGAA            1560

H   D   L   I   Y   P   G   H   V   E   N   V   Q   D   W   L   E   K   S   S
                CATGATCTTATTTATCCTGGTCATGTGGAAAATGTTCAAGATTGGTTAGAGAAAAGTTCT            1620

V   F   V   L   P   T   S   Y   R   E   G   V   P   R   V   I   Q   E   A   M
                GTTTTTGTTTTACCTACATCATATCGAGAAGGCGTACCAAGGGTGATCCAAGAAGCTATG            1680

A   I   G   R   P   V   I   T   T   N   V   P   G   C   R   D   I   I   N   D
                GCTATTGGTAGACCTGTAATAACAACTAATGTACCTGGGTGTAGGGATATAATAAATGAT            1740

G   V   N   G   F   L   I   P   P   F   E   I   N   L   L   A   E   K   M   K
                GGGGTCAATGGCTTTTTGATACCTCCATTTGAAATTAATTTACTGGCAGAAAAAATGAAA            1800

Y   F   I   E   N   K   D   K   V   L   E   M   G   L   A   G   R   K   F   A
                TATTTTATTGAGAATAAAGATAAAGTACTCGAAATGGGGCTTGCTGGAAGGAAGTTTGCA            1860

E   K   N   F   D   A   F   E   K   N   N   R   L   A   S - I   I   K   S   N
                GAAAAAAACTTTGATGCTTTTGAAAAAAATAATAGACTAGCATCAATAATAAAATCAAAT            1920

End of orf1
                N   D   F   *
                AATGATTTTTGACTTGAGCAGAAATTATTTATATTTCAATCTGAAAAATAAAGGCTGTTA            1980

Start of orf2
                    M   N   K   V   A   L   I   T   G   I   T   G   Q   D   G   S   Y   L   A
                TTATGAATAAAGTGGCATTAATTACTGGTATCACTGGGCAAGATGGCTCCTATTTGGCAG            2040

E   L   L   E   K   G   Y   E   V   H   G   I   K   R   R   A   S   S   F
                AATTATTGTTAGAAAAAGGTTATGAAGTTCATGGTATTAAACGCCGTGCATCTTCATTTA            2100

N   T   E   R   V   D   H   I   Y   Q   D   S   H   L   A   N   P   K   L   F
                ATACTGAGCGAGTGGATCACATCTATCAGGATTCACATTTAGCTAATCCTAAACTTTTTC            2160

L   H   Y   G   D   L   T   D   T   S   N   L   T   R   I   L   K   E   V   Q
                TACACTATGGCGATTTGACAGATACTTCCAATCTGACCCGTATTTTAAAAGAAGTTCAAC            2220

P   D   E   V   Y   N   L   G   A   M   S   H   V   A   V   S   F   E   S   P
                CAGATGAAGTTTACAATTTGGGGGCGATGAGCCATGTAGCGGTATCATTTGAGTCACCAG            2280

E   Y   T   A   D   V   D   A   I   G   T   L   R   L   L   E   A   I   R   I
                AATACACTGCTGATGTTGATGCGATAGGAACATTGCGTCTTCTTGAAGCTATCAGGATAT            2340

L   G   L   E   K   K   T   K   F   Y   Q   A   S   T   S   E   L   Y   G   L
                TGGGGCTGGAAAAAAAGACAAAATTTTATCAGGCTTCAACTTCAGAGCTTTATGGTTTGG            2400

V   Q   E   I   P   Q   K   E   T   T   P   F   Y   P   R   S   P   Y   A   V
                TTCAAGAAATTCCACAAAAAGAGACTACGCCATTTTATCCACGTTCGCCTTATGCTGTTG            2460

A   K   L   Y   A   Y   W   I   T   V   N   Y   R   E   S   Y   G   M   F   A
                CAAAATTATATGCCTATTGGATCACTGTTAATTATCGTGAGTCTTATGGTATGTTTGCCT            2520

C   N   G   I   L   F   N   H   E   S   P   R   R   G   E   T   F   V   T   R
                GCAATGGTATTCTCTTTAACCACGAATCACCTCGCCGTGGCGAGACCTTTGTTACTCGTA            2580

K   I   T   R   G   I   A   N   I   A   Q   G   L   D   K   C   L   Y   L   G
                AAATAACACGCGGGATAGCAAATATTGCTCAAGGTCTTGATAAATGCTTATACTTGGGAA            2640

N   M   D   S   L   R   D   W   G   H   A   K   D   Y   V   K   M   Q   W   M
                ATATGGATTCTCTGCGTGATTGGGGACATGCTAAGGATTATGTCAAAATGCAATGGATGA            2700
```

Fig. 5B

```
      M  L  Q  Q  E  T  P  E  D  F  V  I  A  T  G  I  Q  Y  S  V
      TGCTGCAGCAAGAAACTCCAGAAGATTTTGTAATTGCTACAGGAATTCAATATTCTGTCC      2760

R  E  F  V  T  M  A  A  E  Q  V  G  I  E  L  A  F  E  G  E
      GTGAGTTTGTCACAATGGCGGCAGAGCAAGTAGGCATAGAGTTAGCATTTGAAGGTGAGG      2820

G  V  N  E  K  G  V  V  V  S  V  N  G  T  D  A  K  A  V  N
      GAGTAAATGAAAAAGGTGTTGTTGTTTCGGTCAATGGCACTGATGCTAAAGCTGTAAACC      2880

P  G  D  V  I  I  S  V  D  P  R  Y  F  R  P  A  E  V  E  T
      CGGGCGATGTAATTATATCTGTAGATCCAAGGTATTTTAGGCCTGCAGAAGTTGAAACCT      2940

L  L  G  D  P  T  N  A  H  K  K  L  G  W  S  P  E  I  T  L
      TGCTTGGCGATCCTACTAATGCGCATAAAAAATTAGGATGGAGCCCTGAAATTACATTGC      3000

R  E  M  V  K  E  M  V  S  S  D  L  A  I  A  K  K  N  V  L
      GTGAAATGGTAAAAGAAATGGTTTCCAGCGATTTAGCAATAGCGAAAAAGAACGTCTTGC      3060

End of orf2
      L  K  A  N  N  I  A  T  N  I  P  Q  E  *
      TGAAAGCTAATAACATTGCCACTAATATTCCGCAAGAATAAAAAGATAATACATTAAAT       3120

Start of orf3
                                                         M  F
      AATTAAAAATGGTGCTAGATTTATTAGTACCATTATTTTTTTTGGGTGACTAATGTTTA       3180

I  T  S  D  K  F  R  E  I  I  K  L  V  P  L  V  S  I  D  L
      TTACATCAGATAAATTTAGAGAAATTATCAAGTTAGTTCCATTAGTATCAATTGATCTGC      3240

L  I  E  N  E  N  G  E  Y  L  F  G  L  R  N  N  R  P  A  K
      TAATTGAAAACGAGAATGGTGAATATTTATTTGGTCTTAGGAATAATCGACCGGCCAAAA      3300

N  Y  F  F  V  P  G  G  R  I  R  K  N  E  S  I  K  N  A  F
      ATTATTTTTTTGTTCCAGGTGGTAGGATTCGCAAAAATGAATCTATTAAAAATGCTTTTA      3360

K  R  I  S  S  M  E  L  G  K  E  Y  G  I  S  G  S  V  F  N
      AAAGAATATCATCTATGGAATTAGGTAAAGAGTATGGTATTTCAGGAAGTGTTTTTAATG      3420

G  V  W  E  H  F  Y  D  D  G  F  F  S  E  G  E  A  T  H  Y
      GTGTATGGGAACATTTCTATGATGATGGTTTTTTTTCTGAAGGCGAGGCAACACATTATA      3480

I  V  L  C  Y  T  L  K  V  L  K  S  E  L  N  L  P  D  D  Q
      TAGTGCTTTGTTACACACTGAAAGTTCTTAAAAGTGAATTGAATCTCCCAGATGATCAAC      3540

H  R  E  Y  L  W  L  T  K  H  Q  I  N  A  K  Q  D  V  H  N
      ATCGTGAATACCTTTGGCTAACTAAACACCAAATAAATGCTAAACAAGATGTTCATAACT      3600

End of orf3            Start of orf4
      Y  S  K  N  Y  F  L  *                                M
      ATTCAAAAAATTATTTTTTGTAATTTTTATTAAAAATTAATATGCGAGAGAATTGTATGT      3660

S  Q  C  L  Y  P  V  I  I  A  G  G  T  G  S  R  L  W  P  L
      CTCAATGTCTTTACCCTGTAATTATTGCCGGAGGAACCGGAAGCCGTCTATGGCCGTTGT      3720

S  R  V  L  Y  P  K  Q  F  L  N  L  V  G  D  S  T  M  L  Q
      CTCGAGTATTATACCCTAAACAATTTTTAAATTTAGTTGGGGATTCTACAATGTTGCAAA      3780

T  T  I  T  R  L  D  G  I  E  C  E  N  P  I  V  I  C  N  E
      CAACAATTACGCGTTTGGATGGCATCGAATGCGAAAATCCAATTGTTATCTGCAATGAAG      3840

D  H  R  F  I  V  A  E  Q  L  R  Q  I  G  K  L  T  K  N  I
      ATCACCGATTTATTGTAGCAGAGCAATTACGACAGATTGGTAAGCTAACCAAGAATATTA      3900

I  L  E  P  K  G  R  N  T  A  P  A  I  A  L  A  A  F  I  A
      TACTTGAGCCGAAAGGCCGTAATACTGCACCTGCCATAGCTTTAGCTGCTTTTATCGCTC      3960
```

Fig. 5C

```
  Q  K  N  N  P  N  D  D  P  L  L  L  V  L  A  A  D  H  S  I
AGAAGAATAATCCTAATGACGACCCTTTATTATTAGTACTTGCGGCAGACCACTCTATAA      4020

N  N  E  K  A  F  R  E  S  I  I  K  A  M  P  Y  A  T  S  G
ATAATGAAAAGCATTTCGAGAGTCAATAATAAAAGCTATGCCGTATGCAACTTCTGGGA      4080

K  L  V  T  F  G  I  I  P  D  T  A  N  T  G  Y  G  Y  I  K
AGTTAGTAACATTTGGAATTATTCCGGACACGGCAAATACTGGTTATGGATATATTAAGA     4140

R  S  S  S  A  D  P  N  K  E  F  P  A  Y  N  V  A  E  F  V
GAAGTTCTTCAGCTGATCCTAATAAAGAATTCCCAGCATATAATGTTGCGGAGTTTGTAG    4200

E  K  P  D  V  K  T  A  Q  E  Y  I  S  S  G  N  Y  Y  W  N
AAAAACCAGATGTTAAAACAGCACAGGAATATATTTCGAGTGGGAATTATTACTGGAATA     4260

S  G  M  F  L  F  R  A  S  K  Y  L  D  E  L  R  K  F  R  P
GCGGAATGTTTTTATTTCGCGCCAGTAAATATCTTGATGAACTACGGAAATTTAGACCAG    4320

D  I  Y  H  S  C  E  C  A  T  A  T  A  N  I  D  M  D  F  V
ATATTTATCATAGCTGTGAATGTGCAACCGCTACAGCAAATATAGATATGGACTTTGTCC    4380

R  I  N  E  A  E  F  I  N  C  P  E  E  S  I  D  Y  A  V  M
GAATTAACGAGGCTGAGTTTATTAATTGTCCTGAAGAGTCTATCGATTATGCTGTGATGG    4440

E  K  T  K  D  A  V  V  L  P  I  D  I  G  W  N  D  V  G  S
AAAAAACAAAAGACGCTGTAGTTCTTCCGATAGATATTGGCTGGAATGACGTGGGTTCTT    4500

W  S  S  L  W  D  I  S  Q  K  D  C  H  G  N  V  C  H  G  D
GGTCATCACTTTGGGATATAAGCCAAAAGGATTGCCATGGTAATGTGTGCCATGGGGATG    4560

V  L  N  H  D  G  E  N  S  F  I  Y  S  E  S  S  L  V  A  T
TGCTCAATCATGATGGAGAAAATAGTTTTATTTACTCTGAGTCAAGTCTGGTTGCGACAG   4620

V  G  V  S  N  L  V  I  V  Q  T  K  D  A  V  L  V  A  D  R
TCGGAGTAAGTAATTTAGTAATTGTCCAAACCAAGGATGCTGTACTGGTTGCGGACCGTG   4680

D  K  V  Q  N  V  K  N  I  V  D  D  L  K  K  R  K  R  A  E
ATAAAGTCCAAAATGTTAAAAACATAGTTGACGATCTAAAAAAGAGAAAACGTGCTGAAT    4740

Y  Y  M  H  R  A  V  F  R  P  W  G  K  F  D  A  I  D  Q  G
ACTACATGCATCGTGCAGTTTTTCGCCCTTGGGGTAAATTCGATGCAATAGACCAAGGCG   4800

D  R  Y  R  V  K  K  I  I  V  K  P  G  E  G  L  D  L  R  M
ATAGATATAGAGTAAAAAAAATAATAGTTAAACCAGGAGAAGGGTTAGATTTAAGGATGC    4860

H  H  H  R  A  E  H  W  I  V  V  S  G  T  A  K  V  S  L  G
ATCATCATAGGGCAGAGCATTGGATTGTTGTATCCGGTACTGCTAAAGTTTCACTAGGTA   4920

S  E  V  K  L  L  V  S  N  E  S  I  Y  I  P  Q  G  A  K  Y
GTGAAGTTAAACTATTAGTTTCTAATGAGTCTATATATATCCCTCAGGGAGCAAAATATA    4980

S  L  E  N  P  G  V  I  P  L  H  L  I  E  V  S  S  G  D  Y
GTCTTGAGAATCCAGGCGTAATACCTTTGCATCTAATTGAAGTAAGTTCTGGTGATTACC   5040

L  E  S  D  D  I  V  R  F  T  D  R  Y  N  S  K  Q  F  L  K
TTGAATCAGATGATATAGTGCGTTTTACTGACAGATATAACAGTAAACAATTCCTAAAGC    5100
```

End of orf4 Start of orf5
```
              M  N  K  I  T  C  F  K  A  Y  D  I  R  G  R  L
  R  D  *
GAGATTGATAAATATGAATAAAATAACTTGCTTCAAAGCATATGATATACGTGGGCGTCT——5160
```

Fig. 5D

```
          G  A  E  L  N  D  E  I  A  Y  R  I  G  R  A  Y  G  E  F  F
         TGGTGCTGAATTGAATGATGAAATAGCATATAGAATTGGTCGCGCTTATGGTGAGTTTTT         5220

K  P  Q  T  V  V  V  G  G  D  A  R  L  T  S  E  S  L  K  K
         TAAACCTCAAACTGTAGTTGTGGGAGGAGATGCTCGCTTAACAAGTGAGAGTTTAAAGAA         5280

S  L  S  N  G  L  C  D  A  G  V  N  V  L  D  L  G  M  C  G
         ATCACTCTCAAATGGGCTATGTGATGCAGGCGTAAATGTCTTAGATCTTGGAATGTGTGG         5340

T  E  E  I  Y  F  S  T  W  Y  L  G  I  D  G  G  I  E  V  T
         TACTGAAGAGATATATTTTTCCACTTGGTATTTAGGAATTGATGGTGGAATCGAGGTAAC         5400

A  S  H  N  P  I  D  Y  N  G  M  K  L  V  T  K  G  A  R  P
         TGCAAGCCATAATCCAATTGATTATAATGGAATGAAATTAGTAACCAAAGGTGCTCGACC         5460

I  S  S  D  T  G  L  K  D  I  Q  Q  L  V  E  S  N  N  F  E
         AATCAGCAGTGACACAGGTCTCAAAGATATACAACAATTAGTAGAGAGTAATAATTTTGA         5520

E  L  N  L  E  K  K  G  N  I  T  K  Y  S  T  R  D  A  Y  I
         AGAGCTCAACCTAGAAAAAAAGGGAATATTACCAAATATTCCACCCGAGATGCCTACAT         5580

N  H  L  M  G  Y  A  N  L  Q  K  I  K  K  I  K  I  V  V  N
         AAATCATTTGATGGGCTATGCTAATCTGCAAAAAATAAAAAAAATCAAAATAGTTGTGAA         5640

S  G  N  G  A  A  G  P  V  I  D  A  I  E  E  C  F  L  R  N
         TTCTGGGAATGGTGCAGCTGGTCCTGTTATTGATGCTATTGAGGAATGCTTTTTACGGAA         5700

N  I  P  I  Q  F  V  K  I  N  N  T  P  D  G  N  F  P  H  G
         CAATATTCCGATTCAGTTTGTAAAAATAAATAATACACCCGATGGTAATTTTCCACATGG         5760

I  P  N  P  L  L  P  E  C  R  E  D  T  S  S  A  V  I  R  H
         TATCCCTAATCCATTACTACCTGAGTGCAGAGAAGATACCAGCAGTGCGGTTATAAGACA         5820

S  A  D  F  G  I  A  F  D  G  D  F  D  R  C  F  F  F  D  E
         TAGTGCTGATTTTGGTATTGCATTTGATGGTGATTTTGATAGGTGTTTTTTCTTTGATGA         5880

N  G  Q  F  I  E  G  Y  Y  I  V  G  L  L  A  E  V  F  L  G
         AAATGGACAATTTATTGAAGGATACTACATTGTTGGTTTATTAGCGGAAGTTTTTTTAGG         5940

K  Y  P  N  A  K  I  I  H  D  P  R  L  I  W  N  T  I  D  I
         GAAATATCCAAACGCAAAAATCATTCATGATCCTCGCCTTATATGGAATACTATTGATAT         6000

V  E  S  H  G  G  I  P  I  M  T  K  T  G  H  A  Y  I  K  Q
         CGTAGAAAGTCATGGTGGTATACCTATAATGACTAAAACCGGTCATGCTTACATTAAGCA         6060

R  M  R  E  E  D  A  V  Y  G  G  E  M  S  A  H  H  Y  F  K
         AAGAATGCGTGAAGAGGATGCCGTATATGGCGGCGAAATGAGTGCGCATCATTATTTTAA         6120

D  F  A  Y  C  D  S  G  M  I  P  W  I  L  I  C  E  L  L  S
         AGATTTTGCATACTGCGATAGTGGAATGATTCCTTGGATTTTAATTTGTGAACTTTTGAG         6180

L  T  N  K  K  L  G  E  L  V  C  G  C  I  N  D  W  P  A  S
         TCTGACAAATAAAAAATTAGGTGAACTGGTTTGTGGTTGTATAAACGACTGGCCGGCAAG         6240

G  E  I  N  C  T  L  D  N  P  Q  N  E  I  D  K  L  F  N  R
         TGGAGAAATAAACTGTACACTAGACAATCCGCAAAATGAAATAGATAAATTATTTAATCG         6300

Y  K  D  S  A  L  A  V  D  Y  T  D  G  L  T  M  E  F  S  D
         TTACAAAGATAGTGCCTTAGCTGTTGATTACACTGATGGATTAACTATGGAGTTCTCTGA         6360

W  R  F  N  V  R  C  S  N  T  E  P  V  V  R  L  N  V  E  S
         TTGGCGTTTTAATGTTAGATGCTCAAATACAGAACCTGTAGTACGATTGAATGTAGAATC         6420

R  N  N  A  I  L  M  Q  E  K  T  E  E  I  L  N  F  I  S  K
         TAGGAATAATGCTATTCTTATGCAGGAAAAAACAGAAGAAATTCTGAATTTTATATCAAA         6480
```

Fig. 5E

End of orf5            Start of orf6

```
                                        M  K  V  L  L  T  G
ATAAATTTGCACCTGAGTTCATAATGGGAACAAGAAATATATGAAAGTACTTCTGACTGG      6540

S  T  G  M  V  G  K  N  I  L  E  H  D  S  A  S  K  Y  N  I
CTCAACTGGCATGGTTGGTAAGAATATATTAGAGCATGATAGTGCAAGTAAATATAATAT      6600

L  T  P  T  S  S  D  L  N  L  L  D  K  N  E  I  E  K  F  M
ACTTACTCCAACCAGCTCTGATTTGAATTTATTAGATAAAAATGAAATAGAAAAATTCAT      6660

L  I  N  M  P  D  C  I  I  H  A  A  G  L  V  G  G  I  H  A
GCTTATCAACATGCCAGACTGTATTATACATGCAGCGGGATTAGTTGGAGGCATTCATGC      6720

N  I  S  R  P  F  D  F  L  E  K  N  L  Q  M  G  L  N  L  V
AAATATAAGCAGGCCGTTTGATTTTCTGGAAAAAAATTTGCAGATGGGTTTAAATTTAGT      6780

S  V  A  K  K  L  G  I  K  K  V  L  N  L  G  S  S  C  M  Y
TTCCGTCGCAAAAAAACTAGGTATCAAGAAAGTGCTTAACTTGGGTAGTTCATGCATGTA      6840

P  K  N  F  E  E  A  I  P  E  K  A  L  L  T  G  E  L  E  E
CCCCAAAAACTTTGAAGAGGCTATTCCTGAGAAAGCTCTGTTAACTGGTGAGCTAGAAGA      6900

T  N  E  G  Y  A  I  A  K  I  A  V  A  K  A  C  E  Y  I  S
AACTAATGAGGGATATGCTATTGCGAAAATTGCTGTAGCAAAAGCATGCGAATATATATC      6960

R  E  N  S  N  Y  F  Y  K  T  I  I  P  C  N  L  Y  G  K  Y
AAGAGAAAACTCTAATTATTTTTATAAAACAATTATCCCATGTAATTTATATGGGAAATA      7020

D  K  F  D  D  N  S  S  H  M  I  P  A  V  I  K  K  I  H  H
TGATAAATTTGATGATAACTCGTCACATATGATTCCGGCAGTTATAAAAAAAATCCATCA      7080

A  K  I  N  N  V  P  E  I  E  I  W  G  D  G  N  S  R  R  E
TGCGAAAATTAATAATGTCCCAGAGATCGAAATTTGGGGGGATGGTAATTCGCGCCGTGA      7140

F  M  Y  A  E  D  L  A  D  L  I  F  Y  V  I  P  K  I  E  F
GTTTATGTATGCAGAAGATTTAGCTGATCTTATTTTTTATGTTATTCCTAAAATAGAATT      7200

M  P  N  M  V  N  A  G  L  G  Y  D  Y  S  I  N  D  Y  Y  K
CATGCCTAATATGGTAAATGCTGGTTTAGGTTACGATTATTCAATTAATGACTATTATAA      7260

I  I  A  E  E  I  G  Y  T  G  S  F  S  H  D  L  T  K  P  T
GATAATTGCAGAAGAAATTGGTTATACTGGGAGTTTTTCTCATGATTTAACAAAACCAAC      7320

G  M  K  R  K  L  V  D  I  S  L  L  N  K  I  G  W  S  S  H
AGGAATGAAACGGAAGCTAGTAGATATTTCATTGCTTAATAAAATTGGTTGGTCAAGTCA      7380

F  E  L  R  D  G  I  R  K  T  Y  N  Y  Y  L  E  N  Q  N  K
CTTTGAACTCAGAGATGGCATCAGAAAGACCTATAATTATTACTTGGAGAATCAAAATAA      7440
```

Start of orf7, End of orf6

```
    M  I  T  Y  P  L  A  S  N  T  W  D  E  Y  E  Y  A  A  I  Q
  * 
ATGATTACATACCCACTTGCTAGTAATACTTGGGATGAATATGAGTATGCAGCAATACAG      7500

S  V  I  D  S  K  M  F  T  M  G  K  K  V  E  L  Y  E  K  N
TCAGTAATTGACTCAAAAATGTTTACCATGGGTAAAAAGGTTGAGTTATATGAGAAAAAT      7560

F  A  D  L  F  G  S  K  Y  A  V  M  V  S  S  G  S  T  A  N
TTTGCTGATTTGTTTGGTAGCAAATATGCCGTAATGGTTAGCTCTGGTTCTACAGCTAAT      7620
```

Fig. 5F

```
         L  L  M  I  A  A  L  F  F  T  N  K  P  K  L  K  R  G  D  E
         CTGTTAATGATTGCTGCCCTTTCTTCACTAATAAACCAAAACTTAAAAGAGGTGATGAA       7680

I  I  V  P  A  V  S  W  S  T  T  Y  Y  P  L  Q  Q  Y  G  L
         ATAATAGTACCTGCAGTGTCATGGTCTACGACATATTACCCTCTGCAACAGTATGGCTTA       7740

K  V  K  F  V  D  I  N  K  E  T  L  N  I  D  I  D  S  L  K
         AAGGTGAAGTTTGTCGATATCAATAAAGAAACTTTAAATATTGATATCGATAGTTTGAAA       7800

N  A  I  S  D  K  T  K  A  I  L  T  V  N  L  L  G  N  P  N
         AATGCTATTTCAGATAAAACAAAAGCAATATTGACAGTAAATTTATTAGGTAATCCTAAT       7860

D  F  A  K  I  N  E  I  I  N  N  R  D  I  I  L  L  E  D  N
         GATTTTGCAAAAATAAATGAGATAATAAATAATAGGGATATTATCTTACTAGAAGATAAC       7920

C  E  S  M  G  A  V  F  Q  N  K  Q  A  G  T  F  G  V  M  G
         TGTGAGTCGATGGGCGCGGTCTTTCAAAATAAGCAGGCAGGCACATTCGGAGTTATGGGT       7980

T  F  S  S  F  Y  S  H  H  I  A  T  M  E  G  G  C  V  V  T
         ACCTTTAGTTCTTTTTACTCTCATCATATAGCTACAATGGAAGGGGCTGCGTAGTTACT       8040

D  D  E  E  L  Y  H  V  L  L  C  L  R  A  H  G  W  T  R  N
         GATGATGAAGAGCTGTATCATGTATTGTTGTGCCTTCGAGCTCATGGTTGGACAAGAAAT       8100

L  P  K  E  N  M  V  T  G  T  K  S  D  D  I  F  E  E  S  F
         TTACCAAAAGAGAATATGGTTACAGGCACTAAGAGTGATGATATTTTCGAAGAGTCGTTT       8160

K  F  V  L  P  G  Y  N  V  R  P  L  E  M  S  G  A  I  G  I
         AAGTTTGTTTTACCAGGATACAATGTTCGCCCACTTGAAATGAGTGGTGCTATTGGGATA       8220

E  Q  L  K  K  L  P  G  F  I  S  T  R  R  S  N  A  Q  Y  F
         GAGCAACTTAAAAAGTTACCAGGTTTTATATCCACCAGACGTTCCAATGCACAATATTTT       8280

V  D  K  F  K  D  H  P  F  L  D  I  Q  K  E  V  G  E  S  S
         GTAGATAAATTTAAAGATCATCCATTCCTTGATATACAAAAAGAAGTTGGTGAAAGTAGC       8340

W  F  G  F  S  F  V  I  K  E  G  A  A  I  E  R  K  S  L  V
         TGGTTTGGTTTTTCCTTCGTTATAAAGGAGGGAGCTGCTATTGAGAGGAAGAGTTTAGTA       8400

N  N  L  I  S  A  G  I  E  C  R  P  I  V  T  G  N  F  L  K
         AATAATCTGATCTCAGCAGGCATTGAATGCCGACCAATTGTTACTGGGAATTTTCTCAAA       8460

N  E  R  V  L  S  Y  F  D  Y  S  V  H  D  T  V  A  N  A  E
         AATGAACGTGTTTTGAGTTATTTTGATTACTCTGTACATGATACGGTAGCAAATGCCGAA       8520

Y  I  D  K  N  G  F  F  V  G  N  H  Q  I  P  L  F  N  E  I
         TATATAGATAAGAATGGTTTTTTTGTCGGAAACCACCAGATACCTTTGTTTAATGAAATA       8580

End of orf7
         D  Y  L  R  K  V  L  K  *

GATTATCTACGAAAAGTATTAAAATAACTAACGAGGCACTCTATTTCGAATAGAGTGCCT       8640

Start of orf8
              M  V  L  T  V  K  K  I  L  A  F  G  Y  S  K  V  L  P
         TTAAGATGGTATTAACAGTGAAAAAAATTTTAGCGTTTGGCTATTCTAAAGTACTACCAC       8700

P  V  I  E  Q  F  V  N  P  I  C  I  F  I  I  T  P  L  I  L
         CGGTTATTGAACAGTTTGTCAATCCAATTTGCATCTTCATTATCACACCACTAATACTCA       8760

N  H  L  G  K  Q  S  Y  G  N  W  I  L  L  I  T  I  V  S  F
         ACCACCTGGGTAAGCAAAGCTATGGTAATTGGATTTTATTAATTACTATTGTATCTTTTT       8820
```

Fig. 5G

```
S  Q  L  I  C  G  G  C  S  A  W  I  A  K  I  I  A  E  Q  R
CTCAGTTAATATGTGGAGGATGTTCCGCATGGATTGCAAAAATCATTGCAGAACAGAGAA      8880

I  L  S  D  L  S  K  K  N  A  L  R  Q  I  S  Y  N  F  S  I
TTCTTAGTGATTTATCAAAAAAAAATGCTTTACGTCAAATTTCCTATAATTTTTCAATTG      8940

V  I  I  A  F  A  V  L  I  S  F  L  I  L  S  I  C  F  F  D
TTATTATCGCATTTGCGGTATTGATTTCTTTTCTTATATTAAGTATTTGTTTCTTCGATG      9000

V  A  R  N  N  S  S  F  L  F  A  I  I  I  C  G  F  F  Q  E
TTGCGAGGAATAATTCTTCATTCTTATTCGCGATTATTATTTGTGGTTTTTTTCAGGAAG      9060

V  D  N  L  F  S  G  A  L  K  G  F  E  K  F  N  V  S  C  F
TTGATAATTTATTTAGTGGTGCGCTAAAAGGTTTTGAAAAATTTAATGTATCATGTTTTT      9120

F  E  V  I  T  R  V  L  W  A  S  I  V  I  Y  G  I  Y  G  N
TTGAAGTAATTACAAGAGTGCTCTGGGCTTCTATAGTAATATATGGCATTTACGGAAATG      9180

A  L  L  Y  F  T  C  L  A  F  T  I  K  G  M  L  K  Y  I  L
CACTCTTATATTTTACATGTTTAGCCTTTACCATTAAAGGTATGCTAAAATATATTCTTG      9240

V  C  L  N  I  T  G  C  F  I  N  P  N  F  N  R  V  G  I  V
TATGTCTGAATATTACCGGTTGTTTCATCAATCCTAATTTTAATAGAGTTGGGATTGTTA      9300

N  L  L  N  E  S  K  W  M  F  L  Q  L  T  G  G  V  S  L  S
ATTTGTTAAATGAGTCAAAATGGATGTTTCTTCAATTAACTGGTGGCGTCTCACTTAGTT      9360

L  F  D  R  L  V  I  P  L  I  L  S  V  S  K  L  A  S  Y  V
TGTTTGATAGGCTCGTAATACCATTGATTTTATCTGTCAGTAAACTGGCTTCTTATGTCC      9420

P  C  L  Q  L  A  Q  L  M  F  T  L  S  A  S  A  N  Q  I  L
CTTGCCTTCAACTAGCTCAATTGATGTTCACTCTTTCTGCGTCTGCAAATCAAATATTAC      9480

L  P  M  F  A  R  M  K  A  S  N  T  F  P  S  N  C  F  F  K
TACCAATGTTTGCTAGAATGAAAGCATCTAACACATTTCCCTCTAATTGTTTTTTTAAAA      9540

I  L  L  V  S  L  I  S  V  L  P  C  L  A  L  F  F  G  R
TTCTGCTTGTATCACTAATTTCTGTTTTGCCTTGTCTTGCGTTATTCTTTTTTGGTCGTG      9600

D  I  L  S  I  W  I  N  P  T  F  A  T  E  N  Y  K  L  M  Q
ATATATTATCAATATGGATAAACCCTACATTTGCAACTGAAAATTATAAATTAATGCAAA      9660

I  L  A  I  S  Y  I  L  L  S  M  M  T  S  F  H  F  L  L  L
TTTTAGCTATAAGTTACATTTTATTGTCAATGATGACATCTTTTCATTTCTTGTTATTAG      9720

G  I  G  K  S  K  L  V  A  N  L  N  L  V  A  G  L  A  L  A
GAATTGGTAAATCTAAGCTTGTTGCAAATTTAAATCTGGTTGCAGGGCTGCACTTGCTG      9780

A  S  T  L  I  A  A  H  Y  G  L  Y  A  I  S  M  V  K  I  I
CTTCAACGTTAATCGCAGCTCATTATGGCCTTTATGCAATATCTATGGTAAAAATAATAT      9840

Y  P  A  F  Q  F  Y  Y  L  Y  V  A  F  V  Y  F  N  R  A  K
ATCCGGCTTTTCAATTTTATTACCTTTATGTAGCTTTTGTCTATTTTAATAGAGCGAAAA      9900
```

Start of orf9, End of orf8
```
       M  S  I  D  L  L  F  S  I  T  E  I  A  I  V  F  S  C  T  I
N  V  Y  *
ATGTCTATTGATTTACTTTTTTCAATTACTGAAATCGCAATTGTTTTTCTTGCACTATT      9960

Y  I  F  T  Q  C  L  L  M  R  R  I  Y  L  D  K  S  I  L  I
TACATATTTACTCAATGTTTGTTAATGCGGAGGATCTATTTAGATAAAAGTATTTTAATT      10020

L  L  C  L  L  F  F  L  V  I  I  Q  L  P  E  L  N  V  N  G
CTTTTATGCTTGCTCTTTTTTTTAGTAATCATTCAACTTCCTGAGCTTAATGTAAACGGT      10080
```

Fig. 5H

```
    L   V   D   S   L   K   L   S   L   P   L   L   M   V   F   I   A   F   Q   K
 TTGGTCGATTCTTTAAAGTTATCACTGCCTTTATTGATGGTCTTTATCGCTTTTCAAAAA          10140

P   K   L   C   W   V   I   I   A   L   L   F   L   N   S   A   F   N   F
 CCGAAATTATGCTTGTGGGTTATTATTGCATTGTTGTTTTGAACTCTGCATTTAATTTT           10200

L   Y   L   K   T   F   D   K   F   S   S   F   P   F   T   F   F   I   L   L
 TTATATTTAAAGACATTCGATAAGTTTAGCTCATTTCCTTTTACTTTTTTTATATTGCTG          10260

F   Y   L   F   R   L   G   I   G   N   L   P   V   Y   K   N   K   K   F   Y
 TTTTACTTGTTTAGATTGGGAATTGGTAATTTACCGGTTTATAAAAATAAAAAATTTTAC          10320

A   L   I   F   L   F   I   L   I   D   I   M   Q   S   L   L   I   N   Y   R
 GCGTTGATTTTTCTCTTTATATTAATAGACATAATGCAGTCATTGTTAATAAATTATAGG          10380

G   Q   I   L   Y   S   V   I   C   I   L   I   L   V   F   K   V   N   L   R
 GGGCAGATTTTATATTCCGTAATTTGCATCCTGATACTTGTGTTTAAAGTTAATTTAAGA          10440

K   K   I   P   Y   F   F   L   M   L   P   V   L   Y   V   I   I   M   A   Y
 AAAAAGATTCCATACTTTTTTTTAATGCTGCCAGTTTTATATGTAATTATTATGGCTTAT          10500

I   G   F   N   Y   F   N   K   G   V   T   F   F   E   P   T   A   S   N   I
 ATTGGTTTTAATTATTTCAATAAAGGCGTAACTTTTTTTGAACCTACAGCAAGTAATATT          10560

E   R   T   G   M   I   Y   Y   L   V   S   Q   L   G   D   Y   I   F   H   G
 GAACGTACGGGGATGATATATTATTTGGTTTCACAGCTTGGTGATTATATATTCCATGGT          10620

M   G   T   L   N   F   L   N   N   G   G   Q   Y   K   T   L   Y   G   L   P
 ATGGGACATTAAATTTCTTAAATAACGGCGGACAATATAAGACGTTATATGGACTTCCA          10680

S   L   I   P   N   D   P   H   D   F   L   L   R   F   F   I   S   I   G   V
 TCATTAATTCCTAATGACCCTCATGATTTTTTATTACGGTTCTTTATAAGTATTGGTGTG         10740

I   G   A   L   V   Y   H   S   I   F   F   V   F   F   R   R   I   S   F   L
 ATAGGAGCATTGGTTTATCATTCTATATTTTTTGTTTTTTTAGGAGAATATCTTTCTTA          10800

L   Y   E   R   N   A   P   F   I   V   V   S   C   L   L   L   L   Q   V   V
 TTATATGAGAGAAATGCTCCTTTCATTGTTGTAAGTTGTTTGTTACTGTTACAAGTTGTG         10860

L   I   Y   T   L   N   P   F   D   A   F   N   R   L   I   C   G   L   T   V
 TTAATTTATACATTAAACCCTTTTGATGCTTTTAATCGATTGATTTGCGGGCTTACAGTT         10920

Start of orf10                              End of orf9
    G   V   V   Y   G   F   A   K   I   R   *
                M   D   L   Q   K   L   D   K   Y   T   C   N   G   N   L   D   A
 GGAGTTGTTTATGGATTTGCAAAAATTAGATAAGTATACCTGTAATGGAAATTTAGACGC          10980

P   L   V   S   I   I   I   A   T   Y   N   S   E   L   D   I   A   K   C   L
 TCCACTTGTTTCAATAATCATTGCAACTTATAATTCTGAACTTGATATAGCTAAGTGTTT         11040

Q   S   V   T   N   Q   S   Y   K   N   I   E   I   I   I   M   D   G   G   S
 GCAATCGGTAACTAATCAATCTTATAAGAATATTGAAATCATAATAATGGATGGAGGATC         11100

S   D   K   T   L   D   I   A   K   S   F   K   D   D   R   I   K   I   V   S
 TTCTGATAAAACGCTTGATATTGCAAAATCGTTTAAAGACGACCGAATAAAAATAGTTTC         11160

E   K   D   R   G   I   Y   D   A   W   N   K   A   V   D   L   S   I   G   D
 AGAGAAAGATCGTGGAATTTATGATGCCTGGAATAAAGCAGTTGATTTATCCATTGGTGA         11220

W   V   A   F   I   G   S   D   D   V   Y   Y   H   T   D   A   I   A   S   L
 TTGGGTAGCATTTATTGGTTCAGATGATGTTTACTATCATACAGATGCAATTGCTTCATT         11280

M   K   G   V   M   V   S   N   G   A   P   V   V   Y   G   R   T   A   H   E
 GATGAAGGGGGTTATGGTATCTAATGGCGCCCCTGTGGTTTATGGAGGACAGCGCACGA          11340
```

Fig. 51

```
             G  P  D  R  N  I  S  G  F  S  G  S  E  W  Y  N  L  T  G  F
         AGGTCCCGATAGGAACATATCTGGATTTTCAGGCAGTGAATGGTACAACCTAACAGGATT       11400

K  F  N  Y  Y  K  C  N  L  P  L  P  I  M  S  A  I  Y  S  R
         TAAGTTTAATTATTACAAATGTAATTTACCATTGCCCATTATGAGCCAATATATTCTCG        11460

D  F  F  R  N  E  R  F  D  I  K  L  K  I  V  A  D  A  D  W
         TGATTTCTTCAGAAACGAACGTTTTGATATTAAATTAAAAATTGTTGCTGACGCTGATTG       11520

F  L  R  C  F  I  K  W  S  E  K  S  P  Y  F  I  N  D  T
         GTTTCTGAGATGTTTCATCAAATGGAGTAAAGAGAAGTCACCTTATTTTATTAATGACAC       11580

T  P  I  V  R  M  G  Y  G  G  V  S  T  D  I  S  S  Q  V  K
         GACCCCTATTGTTAGAATGGGATATGGTGGGGTTTCGACTGATATTTCTTCTCAAGTTAA       11640

T  T  L  E  S  F  I  V  R  K  K  N  N  I  S  C  L  N  I  Q
         AACTACGCTAGAAAGTTTCATTGTACGCAAAAAGAATAATATATCCTGTTAAACATACA       11700

L  I  L  R  Y  A  K  I  L  V  M  V  A  I  K  N  I  F  G  N
         GCTGATTCTTAGATATGCTAAAATTCTGGTGATGGTAGCGATCAAAAATATTTTTGGCAA       11760

N  V  Y  K  L  M  H  N  G  Y  H  S  L  K  K  I  K  N  K  I
         TAATGTTTATAAATTAATGCATAACGGGTATCATTCCCTAAAGAAAATCAAGAATAAAAT      11820

Start of orf11, End of orf10
             M  K  I  V  Y  I  I  T  G  L  T  C  G  G  A  E  H  L  M  T
             *
         ATGAAGATTGTTTATATAATAACCGGGCTTACTTGTGGTGGAGCCGAACACCTTATGACG       11880

Q  L  A  D  Q  M  F  I  R  G  H  D  V  N  I  I  C  L  T  G
         CAGTTAGCAGACCAAATGTTTATACGCGGGCATGATGTTAATATTATTTGTCTAACTGGT       11940

I  S  E  V  K  P  T  Q  N  I  N  I  H  Y  V  N  M  D  K  N
         ATATCTGAGGTAAAGCCAACACAAAATATTAATATTCATTATGTTAATATGGATAAAAAT       12000

F  R  S  F  F  R  A  L  F  Q  V  K  K  I  I  V  A  L  K  P
         TTTAGAAGCTTTTTTAGAGCTTTATTTCAAGTAAAAAAAATAATTGTCGCCTTAAAGCCA       12060

D  I  I  H  S  H  M  F  H  A  N  I  F  S  R  F  I  R  M  L
         GATATAATACATAGTCATATGTTTCATGCTAATATTTTTAGTCGTTTTATTAGGATGCTG       12120

I  P  A  V  P  L  I  C  T  A  H  N  K  N  E  G  G  N  A  R
         ATTCCAGCGGTGCCCCTGATATGTACCGCACACAACAAAAATGAAGGTGGCAATGCAAGG       12180

M  F  C  Y  R  L  S  D  F  L  A  S  I  T  T  N  V  S  K  E
         ATGTTTTGTTATCGACTGAGTGATTTTTTAGCTTCTATTACTACAAATGTAAGTAAAGAG       12240

A  V  Q  E  F  I  A  R  K  A  T  P  K  N  K  I  V  E  I  P
         GCTGTTCAAGAGTTTATAGCAAGAAAGGCTACACCTAAAAATAAAATAGTAGAGATTCCG       12300

N  F  I  N  T  N  K  F  D  F  D  I  N  V  R  K  K  T  R  D
         AATTTTATTAATACAAATAAATTTGATTTTGATATTAATGTCAGAAAGAAAACGCGAGAT       12360

A  F  N  L  K  D  S  T  A  V  L  L  A  V  G  R  L  V  E  A
         GCTTTTAATTTGAAAGACAGTACAGCAGTACTGCTCGCAGTAGGAAGACTTGTTGAAGCA       12420

K  D  Y  P  N  L  L  N  A  I  N  H  L  I  L  S  K  T  S  N
         AAAGACTATCCGAACTTATTAAATGCAATAAATCATTTGATTCTTTCAAAAACATCAAAT       12480

C  N  D  F  I  L  L  I  A  G  D  G  A  L  R  N  K  L  L  D
         TGTAATGATTTTATTTTGCTTATTGCTGGCGATGGCGCATTAAGAAATAAATTATTGGAT       12540

L  V  C  Q  L  N  L  V  D  K  V  F  F  L  G  Q  R  S  D  I
         TTGGTTTGTCAATTGAATCTTGTGGATAAAGTTTTCTTCTTGGGGCAAAGAAGTGATATT       12600
```

Fig. 5J

```
         K  E  L  M  C  A  A  D  L  F  V  L  S  S  E  W  E  G  F  G
        AAAGAATTAATGTGTGCTGCAGATCTTTTTGTTTGAGTTCTGAGTGGGAAGGTTTTGGT        12660

L  V  V  A  E  A  M  A  C  E  R  P  V  V  A  T  D  S  G  G
        CTCGTTGTTGCAGAAGCTATGGCGTGTGAACGTCCCGTTGTTGCTACCGATTCTGGTGGA        12720

V  K  E  V  V  G  P  H  N  D  V  I  P  V  S  N  H  I  L  L
        GTTAAAGAAGTCGTTGGACCTCATAATGATGTTATCCCTGTCAGTAATCATATTCTGTTG        12780

A  E  K  I  A  E  T  L  K  I  D  D  N  A  R  K  I  I  G  M
        GCAGAGAAAATCGCTGAGACACTTAAAATAGATGATAACGCAAGAAAAATAATAGGTATG        12840

K  N  R  E  Y  I  V  S  N  F  S  I  K  T  I  V  S  E  W  E
        AAAAATAGAGAATATATTGTTTCCAATTTTTCAATTAAAACGATAGTGAGTGAGTGGGAG        12900

End of orf11
         R  L  Y  F  K  Y  S  K  R  N  N  I  I  D  *
        CGCTTATATTTTAAATATTCCAAGCGTAATAATATAATTGATTGAAAATATAAGTTTGTA        12960

CTCTGGATGCAATAGTTTCTCTATGCTGTTTTTTTACTGGCTCCGTATTTTTACTTATAG        13020

CTGGATTTTGTTATATATCAGTATTAATCTGTCTCAACTTCATCTAGACTACATTCAAGC        13080

Start of gnd
                                                       M  S  K  Q  Q  I
        CGCGCATGCGTCGCGCGGTGACTACACCTGACAGGAGTATGTAATGTCCAAGCAACAGAT        13140

G  V  V  G  M  A  V  M  G  R  N  L  A  L  N  I  E  S  R  G
        CGGCGTCGTCGGTATGGCAGTGATGGGGCGCAACCTGGCGCTCAACATCGAAAGCCGCGG        13200

Y  T  V  S  I  F  N  R  S  R  E  K  T  E  E  V  V  A  E  N
        TTATACCGTCTCCATCTTCAACCGCTCCCGCGAGAAAACTGAAGAAGTTGTTGCCGAGAA        13260

P  D  K  K  L  V  P  Y  Y  T  V  K  E  F  V  E  S  L  E  T
        CCCGGATAAGAAACTGGTTCCTTATTACACGGTGAAAGAGTTCGTCGAGTCTCTTGAAAC        13320

P  R  R  I  L  L  M  V  K  A  G  A  G  T  D  A  A  I  D  S
        CCCACGTCGTATCCTGTTAATGGTAAAAGCAGGGGCGGGAACTGATGCTGCTATCGATTC        13380

L  K  P  Y  L  D  K  G  D  I  I  I  D  G  G  N  T  F  F  Q
        CCTGAAGCCGTATCTGGATAAAGGCGACATCATTATTGATGGTGGCAACACCTTCTTCCA        13440

D  T  I  R  R  N  R  E  L  S  A  E  G  F  N  F  I  G  T  G
        GGACACTATCCGTCGTAACCGTGAACTGTCCGCGGAAGGCTTTAACTTCATCGGTACCGG        13500

V  S  G  G  E  E  G  A  L  K  G  P  S  I  M  P  G  G  Q  K
        CGTGTCCGGCGGTGAAGAGGGCGCCCTGAAAGGCCCATCTATCATGCCAGGTGGCCAGAA        13560

E  A  Y  E  L  V  A  P  I  L  T  K  I  A  A  V  A  E  D  G
        AGAAGCGTATGAGCTGGTTGCGCCTATCCTGACCAAGATTGCTGCGGTTGCTGAAGATGG        13620

E  P  C  I  T  Y  I  G  A  D  G  A  G  H  Y  V  K  M  V  H
        CGAACCATGTATAACTTACATCGGTGCTGACGGTGCGGGTCACTACGTGAAGATGGTGCA        13680

N  G  I  E  Y  G  D  M  Q  L  I  A  E  A  Y  S  L  L  K  G
        CAACGGTATCGAATATGGCGATATGCAGCTGATTGCTGAAGCCTATTCTCTGCTTAAAGG        13740

G  L  N  L  S  N  E  E  L  A  T  T  F  T  E  W  N  E  G  E
        CGGCCTTAATCTGTCTAACGAAGAGCTGGCAACCACTTTTACCGAGTGGAATGAAGGCGA        13800

L  S  S  Y  L  I  D  I  T  K  D  I  F  T  K  K  D  E  E  G
        GCTAAGTAGCTACCTGATTGACATCACCAAAGACATCTTCACCAAAAAAGATGAAGAGGG        13860
```

Fig. 5K

```
              K   Y   L   V   D   V   I   L   D   E   A   A   N   K   G   T   G   K   W   T
           TAAATACCTGGTTGATGTGATCCTGGACGAAGCTGCGAACAAAGGCACCGGTAAATGGAC         13920

S   Q   S   S   L   D   L   G   E   P   L   S   L   I   T   E   S   V   F   A
           CAGCCAGAGCTCTCTGGATCTGGGTGAACCGCTGTCGCTGATCACCGAATCCGTATTCGC         13980

R   Y   I   S   S   L   K   D   Q   R   I   A   A   S   K   V   L   S   G   P
           TCGCTACATCTCTTCTCTGAAAGACCAGCGCATTGCGGCATCTAAAGTGCTGTCTGGTCC         14040

Q   A   K   L   A   G   D   K   A   E   F   V   E   K   V   R   R   A   L   Y
           GCAGGCTAAACTGGCTGGTGATAAAGCAGAGTTCGTTGAGAAAGTCCGTCGCGCGCTGTA         14100

L   G   K   I   V   S   Y   A   Q   G   F   S   Q   L   R   A   A   S   D   E
           CCTGGGTAAAATCGTCTCTTATGCCCAAGGCTTCTCTCAACTGCGTGCCGCGTCTGACGA         14160

Y   N   W   D   L   N   Y   G   E   I   A   K   I   F   R   A   G   C   I   I
           ATACAACTGGGATCTGAACTACGGCGAAATCGCGAAGATCTTCCGCGCGGGCTGCATCAT         14220

R   A   Q   F   L   Q   K   I   T   D   A   Y   A   E   N   K   G   I   A   N
           TCGTGCGCAGTTCCTGCAGAAAATTACTGACGCGTATGCTGAAAACAAAGGCATTGCTAA         14280

L   L   L   A   P   Y   F   K   N   I   A   D   E   Y   Q   Q   A   L   R   D
           CCTGTTGCTGGCTCCGTACTTCAAAAATATCGCTGATGAATATCAGCAAGCGCTGCGTGA         14340

V   V   A   Y   A   V   Q   N   G   I   P   V   P   T   F   S   A   A   V   A
           TGTAGTGGCTTATGCTGTGCAGAACGGTATTCCGGTACCGACCTTCTCTGCAGCGGTAGC         14400

Y   Y   D   S   Y   R   S   A   V   L   P   A   N   L   I   Q   A   Q   R   D
           CTACTACGACAGCTACCGTTCTGCGGTACTGCCGGCTAATCTGATTCAGGCACAGCGTGA         14460

Y   F   G   A   H   T   Y   K   R   T   D   K   E   G   V   F   H   T   G
           TTACTTCGGTGCGCACACGTATAAACGCACTGATAAAGAAGGTGTGTTCCACACCG         14516
```

Fig. 5L

```
GTAACCAAGGGCGGTACGTGCATAAATTTTAATGCTTATCAAAACTATTAGCATTAAAAA      60

Start of orf1
             M  N  K  E  T  V  S  I  I  M  P  V  Y  N
TATATAAGAAATTCTCAAATGAAGAAAGAAACCGTTTCAATAATTATGCCCGTTTACAAT    120

G  A  K  T  I  I  S  S  V  E  S  I  I  H  Q  S  Y  Q  D  F
GGGGCCAAAACTATAATCTCATCAGTAGAATCAATTATACATCAATCTTATCAAGATTTT    180

V  L  Y  I  I  D  D  C  S  T  D  D  T  F  S  L  I  N  S  R
GTTTTGTATATCATTGACGATTGTAGCACCGATGATACATTTTCATTAATCAACAGTCGA    240

Y  K  N  N  Q  K  I  R  I  L  R  N  K  T  N  L  G  V  A  E
TACAAAAACAATCAGAAAATAAGAATATTGCGTAACAAGACAAATTTAGGTGTTGCAGAA    300

S  R  N  Y  G  I  E  M  A  T  G  K  Y  I  S  F  C  D  A  D
AGTCGAAATTATGGAATAGAAATGGCCACGGGGAAATATATTTCTTTTTGTGATGCGGAT    360

D  L  W  H  E  K  K  L  E  R  Q  I  E  V  L  N  N  E  C  V
GATTTGTGGCACGAGAAAAAATTAGAGCGTCAAATCGAAGTGTTAAATAATGAATGTGTA    420

D  V  V  C  S  N  Y  Y  V  I  D  N  N  R  N  I  V  G  E  V
GATGTGGTATGTTCTAATTATTATGTTATAGATAACAATAGAAATATTGTTGGCGAAGTT    480

N  A  P  H  V  I  N  Y  R  K  M  L  M  K  N  Y  I  G  N  L
AATGCTCCTCATGTGATAAATTATAGAAAAATGCTCATGAAAAACTACATAGGGAATTTG    540

T  G  I  Y  N  A  N  K  L  G  K  F  Y  Q  K  K  I  G  H  E
ACAGGAATCTATAATGCCAACAAATTGGGTAAGTTTTATCAAAAAAAGATTGGTCACGAG    600

D  Y  L  M  W  L  E  I  N  K  T  N  G  A  I  C  I  Q  D
GATTATTTGATGTGGCTGGAAATAATTAATAAAACAAATGGTGCTATTTGTATTCAAGAT    660

N  L  A  Y  Y  M  R  S  N  N  S  L  S  G  N  K  I  K  A  A
AATCTGGCGTATTACATGCGTTCAAATAATTCACTATCGGGTAATAAAATTAAAGCTGCA    720

K  W  T  W  S  I  Y  R  E  H  L  H  L  S  F  P  K  T  L  Y
AAATGGACATGGAGTATATATAGAGAACATTTACATTTGTCCTTTCCAAAAACATTATAT    780

Y  F  L  L  Y  A  S  N  G  V  M  K  K  I  T  H  S  L  L  R
TATTTTTTATTATATGCTTCAAATGGAGTCATGAAAAAAATAACACATTCACTATTAAGG    840

Start of orf2, End of orf1
             R  K  E  T  K  K  *
                        V  K  S  A  A  K  L  I  F  L  F  L  F  T
AGAAAGGAGACTAAAAAGTGAAGTCAGCGGCTAAGTTGATTTTTTTATTCCTATTTACAC    900

L  Y  S  L  Q  L  Y  G  V  I  I  D  D  R  I  T  N  F  D  T
TTTATAGTCTCCAGTTGTATGGGGTTATCATAGATGATCGTATAACAAATTTTGATACAA    960

K  V  L  T  S  I  I  I  I  F  Q  I  F  F  V  L  L  F  Y  L
AGGTATTAACTAGTATTATAATTATATTTCAGATTTTTTTTGTTTATTATTTTATCTAA   1020

T  I  I  N  E  R  K  Q  Q  K  K  F  I  V  N  W  E  L  K  L
CGATTATAAATGAAAGAAAACAGCAGAAAAAATTTATCGTGAACTGGGAGCTAAAGTTAA   1080

I  L  V  F  L  F  V  T  I  E  I  A  A  V  V  L  F  L  K  E
TACTCGTTTTCCTTTTTGTGACTATAGAAATTGCTGCTGTAGTTTTATTTCTTAAAGAAG   1140

G  I  P  I  F  D  D  D  P  G  G  A  K  L  R  I  A  E  G  N
GTATTCCTATATTTGATGATGATCCAGGGGGGGCTAAACTTAGAATAGCTGAAGGTAATG   1200
```

Fig. 6A

```
       G  L  Y  I  R  Y  I  K  Y  F  G  N  I  V  V  F  A  L  I  I
      GACTTTACATTAGATATATTAAGTATTTTGGTAATATAGTTGTGTTTGCATTAATTATTC        1260

L  Y  D  E  H  K  F  K  Q  R  T  I  I  F  V  Y  F  T  T  I
      TTTATGATGAGCATAAATTCAAACAGAGGACCATCATATTTGTATATTTTACAACGATTG        1320

A  L  F  G  Y  R  S  E  L  V  L  L  I  L  Q  Y  I  L  I  T
      CTTTATTTGGTTATCGTTCTGAATTGGTGTTGCTCATTCTTCAATATATATTGATTACCA        1380

N  I  L  S  K  D  N  R  N  P  K  I  K  R  I  I  G  Y  F  L
      ATATCCTGTCAAAGGATAACCGTAATCCTAAAATAAAAAGAATAATAGGGTATTTTTTAT        1440

L  V  G  V  V  C  S  L  F  Y  L  S  L  G  Q  D  G  E  Q  N
      TGGTAGGGGTTGTATGCTCGTTGTTTTATCTAAGTTTAGGACAAGACGGAGAACAAAATG        1500

D  S  Y  N  N  M  L  R  I  I  N  R  L  T  I  E  Q  V  E  G
      ACTCATATAATAATATGTTAAGGATAATTAATAGGTTAACAATAGAGCAAGTTGAAGGTG        1560

V  P  Y  V  V  S  E  S  I  K  N  D  F  F  P  T  P  E  L  E
      TTCCATATGTTGTTTCTGAATCTATTAAGAACGATTTCTTTCCGACACCAGAGTTAGAAA        1620

K  E  L  K  A  I  I  N  R  I  Q  G  I  K  H  Q  D  L  F  Y
      AGGAATTAAAAGCAATAATAAATAGAATACAGGGAATAAAGCATCAAGACTTATTTTATG        1680

G  E  R  L  H  K  Q  V  F  G  D  M  G  A  N  F  L  S  V  T
      GAGAACGGTTACATAAACAAGTATTTGGAGACATGGGAGCAAATTTTTTATCAGTTACTA        1740

T  Y  G  A  E  L  L  V  F  F  G  F  L  C  V  F  I  I  P  L
      CGTATGGAGCAGAACTGTTAGTTTTTTTTGGTTTTCTCTGTGTATTCATTATCCCTTTAG        1800

G  I  Y  I  P  F  Y  L  L  K  R  M  K  K  T  H  S  S  I  N
      GGATATATATACCTTTTTATCTTTTAAAGAGAATGAAAAAAACCCATAGCTCGATAAATT        1860

C  A  F  Y  S  Y  I  I  M  I  L  L  Q  Y  L  V  A  G  N  A
      GCGCATTCTATTCATATATCATTATGATTTTATTGCAATACTTAGTGGCTGGGAATGCAT        1920

S  A  F  F  F  G  P  F  L  S  V  L  I  M  C  T  P  L  I  L
      CGGCCTTCTTTTTTGGTCCTTTTCTCTCCGTATTGATAATGTGTACTCCTCTGATCTTAT        1980

Start of orf3
                                  M  K  I  S  V  I  T  V  T  Y
       L  H  D  T  L  K  R  L  S  R  N  E  N  I  S  Y  N  C  D  L
      TGCATGATACGTTAAAGAGATTATCACGAAATGAAAATATCAGTTATAACTGTGACTTAT        2040

End of orf2
       N  N  A  E  G  L  E  K  T  L  S  S  L  S  I  L  K  I  K  P
       *
      AATAATGCTGAAGGGTTAGAAAAAACTTTAAGTAGTTTATCAATTTTAAAAATAAAACCT        2100

F  E  I  I  V  D  G  G  S  T  D  G  T  N  R  V  I  S  R
      TTTGAGATTATTATAGTTGATGGCGGCTCTACAGATGGAACGAATCGTGTCATTAGTAGA        2160

F  T  S  M  N  I  T  H  V  Y  E  K  D  E  G  I  Y  D  A  M
      TTTACTAGTATGAATATTACACATGTTTATGAAAAAGATGAAGGGATATATGATGCGATG        2220

N  K  G  R  M  L  A  K  G  D  L  I  H  Y  L  N  A  G  D  S
      AATAAGGGCCGAATGTTGGCCAAAGGCGACTTAATACATTATTTAAACGCCGGCGATAGC        2280

V  I  G  D  I  Y  K  N  I  K  E  P  C  L  I  K  V  G  L  F
      GTAATTGGAGATATATATAAAAATATCAAAGAGCCATGTTTGATTAAAGTTGGCCTTTTC        2340

E  N  D  K  L  L  G  F  S  S  I  T  H  S  N  T  G  Y  C  H
      GAAAATGATAAACTTCTGGGATTTTCTTCTATAACCCATTCAAATACAGGGTATTGTCAT        2400
```

Fig. 6B

```
      Q  G  V  I  F  P  K  N  H  S  E  Y  D  L  R  Y  K  I  C  A
   CAAGGGGTGATTTTCCCAAAGAATCATTCAGAATATGATCTAAGGTATAAAATATGTGCT      2460

D  Y  K  L  I  Q  E  V  F  P  E  G  L  R  S  L  S  L  I  T
   GATTATAAGCTTATTCAAGAGGTGTTTCCTGAAGGGTTAAGATCTCTATCTTTGATTACT      2520

S  G  Y  V  K  Y  D  M  G  G  V  S  S  K  K  R  I  L  R  D
   TCGGGTTATGTAAAATATGATATGGGGGGAGTATCTTCAAAAAAAGAATTTTAAGAGAT       2580

K  E  L  A  K  I  M  F  E  K  N  K  K  N  L  I  K  F  I  P
   AAAGAGCTTGCCAAAATTATGTTTGAAAAAAATAAAAAAAACCTTATTAAGTTTATTCCA      2640

I  S  I  I  K  I  L  F  P  E  R  L  R  R  V  L  R  K  M  Q
   ATTTCAATAATCAAAATTTTATTCCCTGAACGTTTAAGAAGAGTATTGCGGAAAATGCAA     2700

Start of orf4   End of orf3
   Y  I  C  L  T  L  F  F  M  K  N  S  S  P  Y  D  N  E  *
                                         M  I  M  N  K  I
   TATATTTGTCTAACTTTATTCTTCATGAAGAATAGTTCACCAT ATG ATAATGAATAAAAT    2760

K  K  I  L  K  F  C  T  L  K  K  Y  D  T  S  S  A  L  G  R
   CAAAAAAATACTTAAATTTTGCACTTTAAAAAAATATGATACATCAAGTGCTTTAGGTAG    2820

E  Q  E  R  Y  R  I  I  S  L  S  V  I  S  S  L  I  S  K  I
   AGAACAGGAAAGGTACAGGATTATATCCTTGTCTGTTATTTCAAGTTTGATTAGTAAAAT   2880

L  S  L  L  S  L  I  L  T  V  S  L  T  L  P  Y  L  G  Q  E
   ACTCTCACTACTTTCTCTTATATTAACTGTAAGTTTAACTTTACCTTATTTAGGACAAGA   2940

R  F  G  V  W  M  T  I  T  S  L  G  A  A  L  T  F  L  D  L
   GAGATTTGGTGTATGGATGACTATTACCAGTCTTGGTGCTGCTCTGACATTTTTGGACTT   3000

G  I  G  N  A  L  T  N  R  I  A  H  S  F  A  C  G  K  N  L
   AGGTATAGGAAATGCATTAACAAACAGGATCGCACATTCATTTGCGTGTGGCAAAAATTT   3060

K  M  S  R  Q  I  S  G  G  L  T  L  L  A  G  L  S  F  V  I
   AAAGATGAGTCGGCAAATTAGTGGTGGGCTCACTTTGCTGGCTGGATTATCGTTTGTCAT   3120

T  A  I  C  Y  I  T  S  G  M  I  D  W  Q  L  V  I  K  G  I
   AACTGCAATATGCTATATTACTTCTGGCATGATTGATTGGCAACTAGTAATAAAAGGTAT   3180

N  E  N  V  Y  A  E  L  Q  H  S  I  K  V  F  V  I  I  F  G
   AAACGAGAATGTGTATGCAGAGTTACAACACTCAATTAAAGTCTTTGTAATCATATTTGG   3240

L  G  I  Y  S  N  G  V  Q  K  V  Y  M  G  I  Q  K  A  Y  I
   ACTTGGAATTTATTCAAATGGTGTGCAAAAAGTTTATATGGAATACAAAAAGCCTATAT    3300

S  N  I  V  N  A  I  F  I  L  L  S  I  I  T  L  V  I  S  S
   AAGTAATATTGTTAATGCCATATTTATATTGTTATCTATTATTACTCTAGTAATATCGTC   3360

K  L  H  A  G  L  P  V  L  I  V  S  T  L  G  I  Q  Y  I  S
   GAAACTACATGCGGGACTACCAGTTTTAATTGTCAGCACTCTTGGTATTCAATACATATC   3420

G  I  Y  L  T  I  N  L  I  I  K  R  L  I  K  F  T  K  V  N
   GGGAATCTATTTAACAATTAATCTTATTATAAAGCGATTAATAAAGTTTACAAAAGTTAA   3480

I  H  A  K  R  E  A  P  Y  L  I  L  N  G  F  F  F  F  I  L
   CATACATGCTAAAAGAGAAGCTCCATATTTGATATTAAACGGTTTTTTCTTTTTTATTTT   3540

Q  L  G  T  L  A  T  W  S  G  D  N  F  I  I  S  I  T  L  G
   ACAGTTAGGCACTCTGGCAACATGGAGTGGTGATAACTTTATAATATCTATAACATTGGG   3600
```

Fig. 6C

```
           V  T  Y  V  A  V  F  S  I  T  Q  R  L  F  Q  I  S  T  V  P
         TGTTACTTATGTTGCTGTTTTTAGCATTACACAGAGATTATTTCAAATATCTACGGTCCC    3660
           L  T  I  Y  N  I  P  L  W  A  A  Y  A  D  A  H  A  R  N  D
         TCTTACGATTTATAACATCCCGTTATGGGCTGCTTATGCAGATGCTCATGCACGCAATGA    3720
           T  Q  F  I  K  K  T  L  R  T  S  L  K  I  V  G  I  S  S  F
         TACTCAATTTATAAAAAAGACGCTCAGAACATCATTGAAAATAGTGGGTATTTCATCATT    3780
           L  L  A  F  I  L  V  V  F  G  S  E  V  V  N  I  W  T  E  G
         CTTATTGGCCTTCATATTAGTAGTGTTCGGTAGTGAAGTCGTTAATATTTGGACAGAAGG    3840
           K  I  Q  V  P  R  T  F  I  I  A  Y  A  L  W  S  V  I  D  A
         AAAGATTCAGGTACCTCGAACATTCATAATAGCTTATGCTTTATGGTCTGTTATTGATGC    3900
           F  S  N  T  F  A  S  F  L  N  G  L  N  I  V  K  Q  Q  M  L
         TTTTTCGAATACATTTGCAAGCTTTTTAAATGGTTTGAACATAGTTAAACAACAAATGCT    3960
           A  V  V  T  L  I  L  I  A  I  P  A  K  Y  I  I  V  S  H  F
         TGCTGTTGTAACATTGATATTGATCGCAATTCCAGCAAAATACATCATAGTTAGCCATTT    4020
           G  L  T  V  M  L  Y  C  F  I  F  I  Y  I  V  N  Y  F  I  W
         TGGGTTAACTGTTATGTTGTACTGCTTCATTTTTATATATATTGTAAATTACTTTATATG    4080

Start of orf5, End of orf4
                                                          M  K  M
           Y  K  C  S  F  K  K  H  I  D  R  Q  L  N  I  R  G  *
         GTATAAATGTAGTTTTAAAAAACATATCGATAGACAGTTAAATATAAGAGGATGAAAATG    4140
           K  Y  I  P  V  Y  Q  P  S  L  T  G  K  E  K  E  Y  V  N  E
         AAATATATACCAGTTTACCAACCGTCATTGACAGGAAAAGAAAAAGAATATGTAAATGAA    4200
           C  L  D  S  T  W  I  S  S  K  G  N  Y  I  Q  K  F  E  N  K
         TGTCTGGACTCAACGTGGATTTCATCAAAAGGAAACTATATTCAGAAGTTTGAAAATAAA    4260
           F  A  E  Q  N  H  V  Q  Y  A  T  T  V  S  N  G  T  V  A  L
         TTTGCGGAACAAAACCATGTGCAATATGCAACTACTGTAAGTAATGGAACGGTTGCTCTT    4320
           H  L  A  L  L  A  L  G  I  S  E  G  D  E  V  I  V  P  T  L
         CATTTAGCTTTGTTAGCGTTAGGTATATCGGAAGGAGATGAAGTTATTGTTCCAACACTG    4380
           T  Y  I  A  S  V  N  A  I  K  Y  T  G  A  T  P  I  F  V  D
         ACATATATAGCATCAGTTAATGCTATAAAATACACAGGAGCCACCCCCATTTTCGTTGAT    4440
           S  D  N  E  T  W  Q  M  S  V  S  D  I  E  Q  K  I  T  N  K
         TCAGATAATGAAACTTGGCAAATGTCTGTTAGTGACATAGAACAAAAAATCACTAATAAA    4500
           T  K  A  I  M  C  V  H  L  Y  G  H  P  C  D  M  E  Q  I  V
         ACTAAAGCTATTATGTGTGTCCATTTATACGGACATCCATGTGATATGGAACAAATTGTA    4560
           E  L  A  K  S  R  N  L  F  V  I  E  D  C  A  E  A  F  G  S
         GAACTGGCCAAAAGTAGAAATTTGTTTGTAATTGAAGATTGCGCTGAAGCCTTTGGTTCT    4620
           K  Y  K  G  K  Y  V  G  T  F  G  D  I  S  T  F  S  F  F  G
         AAATATAAAGGTAAATATGTGGGAACATTTGGAGATATTTCTACTTTTAGCTTTTTTGGA    4680
           N  K  T  I  T  T  G  E  G  G  M  V  V  T  N  D  K  T  L  Y
         AATAAAACTATTACTACAGGTGAAGGTGGAATGGTTGTCACGAATGACAAAACACTTTAT    4740
           D  R  C  L  H  F  K  G  Q  G  L  A  V  H  R  Q  Y  W  H  D
         GACCGTTGTTTACATTTTAAAGGCCAAGGATTAGCTGTACATAGGCAATATTGGCATGAC    4800
           V  I  G  Y  N  Y  R  M  T  N  I  C  A  A  I  G  L  A  Q  L
         GTTATAGGCTACAATTATAGGATGACAAATATCTGCGCTGCTATAGGATTAGCCCAGTTA    4860
```

Fig. 6D

```
E   Q   A   D   D   F   I   S   R   K   R   E   I   A   D   I   Y   K   K   N
GAACAAGCTGATGATTTTATATCACGAAAACGTGAAATTGCTGATATTTATAAAAAAAT                         4920

I   N   S   L   V   Q   V   H   K   E   S   K   D   V   F   H   T   Y   W   M
ATCAACAGTCTTGTACAAGTCCACAAGGAAAGTAAAGATGTTTTTCACACTTATTGGATG                        4980

V   S   I   L   T   R   T   A   E   E   R   E   E   L   R   N   H   L   A   D
GTCTCAATTCTAACTAGGACCGCAGAGGAAAGAGAGGAATTAAGGAATCACCTTGCAGAT                        5040

K   L   I   E   T   R   P   V   F   Y   P   V   H   T   M   P   M   Y   S   E
AAACTCATCGAAACAAGGCCAGTTTTTTACCCTGTCCACACGATGCCAATGTACTCGGAA                        5100

K   Y   Q   K   H   P   I   A   E   D   L   G   W   R   G   I   N   L   P   S
AAATATCAAAAGCACCCTATAGCTGAGGATCTTGGTTGGCGTGGAATTAATTTACCTAGT                        5160

F   P   S   L   S   N   E   Q   V   I   Y   I   C   E   S   I   N   E   F   Y
TTCCCCAGCCTATCGAATGAGCAAGTTATTTATATTTGTGAATCTATTAACGAATTTTAT                        5220

End of orf5                         Start of orf6
S   D   K   *                                       M   K   I   A   L   N   S   D
AGTGATAAATAGCCTAAAATATTGTAAAGGTCATTCATGAAAATTGCGTTGAATTCAGAT                        5280

G   F   Y   E   W   G   G   G   I   D   F   I   K   Y   I   L   S   I   L   E
GGATTTTACGAGTGGGGCGGTGGAATTGATTTTATTAAATATATTCTGTCAATATTAGAA                        5340

T   K   P   E   I   C   I   D   I   L   L   P   R   N   D   I   H   S   L   I
ACGAAACCAGAAATATGTATCGATATTCTTTTACCGAGAAATGATATACATTCTCTTATA                        5400

R   E   K   A   F   P   P   F   K   S   I   L   K   A   I   L   K   R   E   R   P
AGAGAAAAAGCATTTCCTTTTAAAAGTATATTAAAAGCAATTTTAAAGAGGGAAAGGCCT                        5460

R   W   I   S   L   N   R   F   N   E   Q   Y   Y   R   D   A   F   T   Q   N
CGATGGATTTCATTAAATAGATTTAATGAGCAATACTATAGAGATGCCTTTACACAAAAT                        5520

N   I   E   T   N   L   T   F   I   K   S   K   S   S   A   F   Y   S   Y   F
AATATAGAGACGAATCTTACCTTTATTAAAAGTAAGAGCTCTGCCTTTTATTCATATTTT                        5580

D   S   S   D   C   D   V   I   L   P   C   M   R   V   P   S   G   N   L   N
GATAGTAGCGATTGTGATGTTATTCTTCCTTGCATGCGTGTTCCTTCGGGAAATTTGAAT                        5640

K   K   A   W   I   G   Y   I   Y   D   F   Q   H   C   Y   Y   P   S   F   F
AAAAAAGCATGGATTGGTTATATTTATGACTTTCAACACTGTTACTATCCTTCATTTTTT                        5700

S   K   R   E   I   D   Q   R   N   V   F   F   K   L   M   L   N   C   A   N
AGTAAGCGAGAAATAGATCAAAGGAATGTGTTTTTTAAATTGATGCTCAATTGCGCTAAC                        5760

N   I   I   V   N   A   H   S   V   I   T   D   A   N   K   Y   V   G   N   Y
AATATTATTGTTAATGCACATTCAGTTATTACCGATGCAAATAAATATGTTGGGAATTAT                        5820

S   A   K   L   H   S   L   P   F   S   P   C   P   Q   L   K   W   F   A   D
TCTGCAAAACTACATTCTCTTCCATTTAGTCCATGCCCTCAATTAAAATGGTTCGCTGAT                        5880

Y   S   G   N   I   A   K   Y   N   I   D   K   D   Y   F   I   I   C   N   Q
TACTCTGGTAATATTGCCAAATATAATATTGACAAGGATTATTTTATAATTTGCAATCAA                        5940

F   W   K   H   K   D   H   A   T   A   F   R   A   F   K   I   Y   T   E   Y
TTTTGGAAACATAAAGATCATGCAACTGCTTTTAGGGCATTTAAAAATTTATACTGAATAT                       6000

N   P   D   V   Y   L   V   C   T   G   A   T   Q   D   Y   R   F   P   G   Y
AATCCTGATGTTTATTTAGTATGCACGGGAGCTACTCAAGATTATCGATTCCCTGGATAT                        6060

F   N   E   L   M   V   L   A   K   K   L   G   I   E   S   K   I   K   I   L
TTTAATGAATTGATGGTTTTGGCAAAAAAGCTCGGAATTGAATCGAAAATTAAGATATTA                        6120
```

Fig. 6E

```
          G  H  I  P  K  L  E  Q  I  E  L  I  K  N  C  I  A  V  I  Q
          GGGCATATACCTAAACTTGAACAAATTGAATTAATCAAAAATTGCATTGCTGTAATACAA      6180

P  T  L  F  E  G  G  P  G  G  G  V  T  F  D  A  I  A  L  G
          CCAACCTTATTTGAAGGCGGGCCTGGAGGGGGGGTAACATTTGACGCTATTGCATTAGGG      6240

K  K  V  I  L  S  D  I  D  V  N  K  E  V  N  C  G  D  V  Y
          AAAAAAGTTATACTATCTGACATAGATGTCAATAAAGAAGTTAATTGCGGTGATGTATAT      6300

F  F  Q  A  K  N  H  Y  S  L  N  D  A  M  V  K  A  D  E  S
          TTCTTTCAGGCAAAAAACCATTATTCATTAAATGACGCGATGGTAAAAGCTGATGAATCT      6360

K  I  F  Y  E  P  T  T  L  I  E  L  G  L  K  R  R  N  A  C
          AAAATTTTTTATGAACCTACAACTCTGATAGAATTGGGTCTCAAAAGACGCAATGCGTGT      6420

End of orf6
          A  D  F  L  L  D  V  V  K  Q  E  I  E  S  R  S   *
          GCAGATTTTCTTTTAGATGTTGTGAAACAAGAAATTGAATCCCGATCT TAATATATTCAA     6480

Start of orf7
                      M  T  K  V  A  L  I  T  G  V  T  G  Q  D  G  S  Y
          GAGGTATATAATGACTAAAGTCGCTCTTATTACAGGTGTAACTGGACAAGATGGATCTTA      6540

L  A  E  F  L  L  D  K  G  Y  E  V  H  G  I  K  R  R  A  S
          TCTAGCTGAGTTTTTGCTTGATAAAGGGTATGAAGTTCATGGTATCAAACGCCGAGCCTC      6600

S  F  N  T  E  R  I  D  H  I  Y  Q  D  P  H  G  S  N  P  N
          ATCTTTTAATACAGAACGCATAGACCATATTTATCAAGATCCACATGGTTCTAACCCAAA      6660

F  H  L  H  Y  G  D  L  T  D  S  S  N  L  T  R  I  L  K  E
          TTTTCACTTGCACTATGGAGATCTGACTGATTCATCTAACCTCACTAGAATTCTAAAGGA      6720

V  Q  P  D  E  V  Y  N  L  A  A  M  S  H  V  A  V  S  F  E
          GGTACAGCCAGATGAAGTATATAATTTAGCTGCTATGAGTCACGTAGCAGTTTCTTTTGA      6780

S  P  E  Y  T  A  D  V  D  A  I  G  T  L  R  L  L  E  A  I
          GTCTCCAGAATATACAGCCGATGTCGATGCAATTGGTACATTACGTTTACTGGAAGCAAT      6840

R  F  L  G  L  E  N  K  T  R  F  Y  Q  A  S  T  S  E  L  Y
          TCGCTTTTTAGGATTGGAAAACAAAACGCGTTTCTATCAAGCTTCAACCTCAGAATTATA      6900

G  L  V  Q  E  I  P  Q  K  E  S  T  P  F  Y  P  R  S  P  Y
          TGGACTTGTTCAGGAAATCCCTCAAAAAGAATCCACCCCTTTTTATCCTCGTTCCCCTTA      6960

A  V  A  K  L  Y  A  Y  W  I  T  V  N  Y  R  E  S  Y  G  I
          TGCAGTTGCAAAACTTTACGCATATTGGATCACGGTAAATTATCGAGAGTCATATGGTAT      7020

Y  A  C  N  G  I  L  F  N  H  E  S  P  R  R  G  E  T  F  V
          TTATGCATGTAATGGTATATTGTTCAATCATGAATCTCCACGCCGTGGAGAAACGTTTGT      7080

T  R  K  I  T  R  G  L  A  N  I  A  Q  G  L  E  S  C  L  Y
          AACAAGGAAAATTACTCGAGGACTTGCAAATATTGCACAAGGCTTGGAATCATGTTTGTA      7140

L  G  N  M  D  S  L  R  D  W  G  H  A  K  D  Y  V  R  M  Q
          TTTAGGGAATATGGATTCGTTACGAGATTGGGGACATGCAAAAGATTATGTTAGAATGCA      7200

W  L  M  L  Q  Q  E  Q  P  E  D  F  V  I  A  T  G  V  Q  Y
          ATGGTTGATGTTACAACAGGAGCAACCCGAAGATTTTGTGATTGCAACAGGAGTCCAATA      7260

S  V  R  Q  F  V  E  M  A  A  A  Q  L  G  I  K  M  S  F  V
          CTCAGTCCGTCAGTTTGTCGAAATGGCAGCAGCACAACTTGGTATTAAGATGAGCTTTGT      7320
```

Fig. 6F

```
              G  K  G  I  E  E  K  G  I  V  D  S  V  E  G  Q  D  A  P  G
           TGGTAAAGGAATCGAAGAAAAAGGCATTGTAGATTCGGTTGAAGGACAGGATGCTCCAGG      7380

V  K  P  G  D  V  I  V  A  V  D  P  R  Y  F  R  P  A  E  V
           TGTGAAACCAGGTGATGTCATTGTTGCTGTTGATCCTCGTTATTTCCGACCAGCTGAAGT      7440

D  T  L  L  G  D  P  S  K  A  N  L  K  L  G  W  R  P  E  I
           TGATACTTTGCTTGGAGATCCGAGCAAAGCTAATCTCAAACTTGGTTGGAGACCAGAAAT      7500

T  L  A  E  M  I  S  E  M  V  A  K  D  L  E  A  A  K  K  H
           TACTCTTGCTGAAATGATTTCTGAAATGGTTGCCAAAGATCTTGAAGCCGCTAAAAAACA      7560

Start of orf8, End of orf7
                                                                M  M  M  N  K
              S  L  L  K  S  H  G  F  S  V  S  L  A  L  E  *
           TTCTCTTTTAAAATCGCATGGTTTTTCTGTAAGCTTAGCTCTGGAATGATGATGAATAAG      7620

Q  R  I  F  I  A  G  H  Q  G  M  V  G  S  A  I  T  R  R  L
           CAACGTATTTTTATTGCTGGTCACCAAGGAATGGTTGGATCAGCTATTACCCGACGCCTC      7680

K  Q  R  D  D  V  E  L  V  L  R  T  R  D  E  L  N  L  L  D
           AAACAACGTGATGATGTTGAGTTGGTTTTACGTACTCGGGATGAATTGAACTTGTTGGAT      7740

S  S  A  V  L  D  F  F  S  S  Q  K  I  D  Q  V  Y  L  A  A
           AGTAGCGCTGTTTTGGATTTTTTTTCTTCACAGAAAATCGACCAGGTTTATTTGGCAGCA      7800

A  K  V  G  G  I  L  A  N  S  S  Y  P  A  D  F  I  Y  E  N
           GCAAAAGTCGGAGGTATTTTAGCTAACAGTTCTTATCCTGCCGATTTTATATATGAGAAT      7860

I  M  I  E  A  N  V  I  H  A  A  H  K  N  N  V  N  K  L  L
           ATAATGATAGAGGCGAATGTCATTCATGCTGCCCACAAAAATAATGTAAATAAACTGCTT      7920

F  L  G  S  S  C  I  Y  P  K  L  A  H  Q  P  I  M  E  D  E
           TTCCTCGGTTCGTCGTGTATTTATCCTAAGTTAGCACACCAACCGATTATGGAAGACGAA      7980

L  L  Q  G  K  L  E  P  T  N  E  P  Y  A  I  A  K  I  A  G
           TTATTACAAGGGAAACTTGAGCCAACAAATGAACCTTATGCTATCGCAAAAATTGCAGGT      8040

I  K  L  C  E  S  Y  N  R  Q  F  G  R  D  Y  R  S  V  M  P
           ATTAAATTATGTGAATCTTATAACCGTCAGTTTGGGCGTGATTACCGTTCAGTAATGCCA      8100

T  N  L  Y  G  P  N  D  N  F  H  P  S  N  S  H  V  I  P  A
           ACCAATCTTTATGGTCCAAATGACAATTTTCATCCAAGTAATTCTCATGTGATTCCGGCG      8160

L  L  R  R  F  H  D  A  V  E  N  N  S  P  N  V  V  V  W  G
           CTTTTGCGCCGCTTTCATGATGCTGTGGAAAACAATTCTCCGAATGTTGTTGTTTGGGGA      8220

S  G  T  P  K  R  E  F  L  H  V  D  D  M  A  S  A  S  I  Y
           AGTGGTACTCCAAAGCGTGAATTCTTACATGTAGATGATATGGCTTCTGCAAGCATTTAT      8280

V  M  E  M  P  Y  D  I  W  Q  K  N  T  K  V  M  L  S  H  I
           GTCATGGAGATGCCATACGATATATGGCAAAAAAATACTAAAGTAATGTTGTCTCATATC      8340

N  I  G  T  G  I  D  C  T  I  C  E  L  A  E  T  I  A  K  V
           AATATTGGAACAGGTATTGACTGCACGATTTGTGAGCTTGCGGAAACAATAGCAAAAGTT      8400

V  G  Y  K  G  H  I  T  F  D  T  T  K  P  D  G  A  P  R  K
           GTAGGTTATAAAGGGCATATTACGTTCGATACAACAAAGCCCGATGGAGCCCCTCGAAAA      8460

L  L  D  V  T  L  L  H  Q  L  G  W  N  H  K  I  T  L  H  K
           CTACTTGATGTAACGCTTCTTCATCAACTAGGTTGGAATCATAAAATTACCCTTCACAAG      8520
```

Fig. 6G

```
                                                      End of orf8
       G  L  E  N  T  Y  N  W  F  L  E  N  Q  L  Q  Y  R  G  *
       GGTCTTGAAAATACATACAACTGGTTTCTTGAAAACCAACTTCAATATCGGGGG TAATAA      8580

Start of orf9
M  -F  L  H  S  Q  D  F  A  T  I  V  R  S  T  P  L  I  S  I
TGTTTTTACATTCCCAAGACTTTGCCACAATTGTAAGGTCTACTCCTCTTATTTCTATAG             8640

D  L  I  V  E  N  E  F  G  E  I  L  L  G  K  R  I  N  R  P
    ATTTGATTGTGGAAAACGAGTTTGGCGAAATTTTGCTAGGAAAACGAATCAACCGCCCGG          8700

A  Q  G  Y  W  F  V  P  G  G  R  V  L  K  D  E  K  L  Q  T
    CACAGGGCTATTGGTTCGTTCCTGGTGGTAGGGTGTTGAAAGATGAAAAATTGCAGACAG          8760

A  F  E  R  L  T  E  I  E  L  G  I  R  L  P  L  S  V  G  K
    CCTTTGAACGATTGACAGAAATTGAACTAGGAATTCGTTTGCCTCTCTCTGTGGGTAAGT          8820

F  Y  G  I  W  Q  H  F  Y  E  D  N  S  M  G  G  D  F  S  T
    TTTATGGTATCTGGCAGCACTTCTACGAAGACAATAGTATGGGGGAGACTTTTCAACGC           8880

H  Y  I  V  I  A  F  L  L  K  L  Q  P  N  I  L  K  L  P  K
    ATTATATAGTTATAGCATTCCTTCTTAAATTACAACCAAACATTTTGAAATTACCGAAGT          8940

S  Q  H  N  A  Y  C  W  L  S  R  A  K  L  I  N  D  D  D  V
    CACAACATAATGCTTATTGCTGGCTATCGCGAGCAAAGCTGATAAATGATGACGATGTGC          9000

H  Y  N  C  R  A  Y  F  N  N  K  T  N  D  A  I  G  L  D  N
    ATTATAATTGTCGCGCATATTTTAACAATAAAACAAATGATGCGATTGGCTTAGATAATA         9060

Start of orf10    End of orf9
              M  S  D  A  P  I  I  A  V  V  M  A  G  G  T  G  S
    K  D  I  I  C  L  M  R  Q  *
    AGGATATAATATGTCTGATGCGCCAATAATTGCTGTAGTTATGGCCGGTGGTACAGGCAG         9120

R  L  W  P  L  S  R  E  L  Y  P  K  Q  F  L  Q  L  S  G  D
       TCGTCTTTGGCCACTTTCTCGTGAACTATATCCAAAGCAGTTTTTACAACTCTCTGGTGA       9180

N  T  L  L  Q  T  T  L  L  R  L  S  G  L  S  C  Q  K  P  L
       TAACACCTTGTTACAAACGACTTTGCTACGACTTTCAGGCCTATCATGTCAAAAACCATT       9240

V  I  T  N  E  Q  H  R  F  V  V  A  E  Q  L  R  E  I  N  K
       AGTGATAACAAATGAACAGCATCGCTTTGTTGTGGCTGAACAGTTAAGGGAAATAAATAA       9300

L  N  G  N  I  I  L  E  P  C  G  R  N  T  A  P  A  I  A  I
       ATTAAATGGTAATATTATTCTAGAACCATGCGGGCGAAATACTGCACCAGCAATAGCGAT       9360

S  A  F  H  A  L  K  R  N  P  Q  E  D  P  L  L  L  V  L  A
       ATCTGCGTTTCATGCGTTAAAACGTAATCCTCAGGAAGATCCATTGCTTCTAGTTCTTGC       9420

A  D  H  V  I  A  K  E  S  V  F  C  D  A  I  K  N  A  T  P
       GGCAGACCACGTTATAGCTAAAGAAAGTGTTTTCTGTGATGCTATTAAAAATGCAACTCC       9480

I  A  N  Q  G  K  I  V  T  F  G  I  I  P  E  Y  A  E  T  G
       CATCGCTAATCAAGGTAAAATTGTAACGTTTGGAATTATACCAGAATATGCTGAAACTGG       9540

Y  G  Y  I  E  R  G  E  L  S  V  P  L  Q  G  H  E  N  T  G
       TTATGGGTATATTGAGAGAGGTGAACTATCTGTACCGCTTCAAGGGCATGAAAATACTGG       9600

F  Y  Y  V  N  K  F  V  E  K  P  N  R  E  T  A  E  L  Y  M
       TTTTTATTATGTAAATAAGTTTGTCGAAAAGCCTAATCGTGAAACCGCAGAATTGTATAT       9660

T  S  G  N  H  Y  W  N  S  G  I  F  M  F  K  A  S  V  Y  L
       GACTTCTGGTAATCACTATTGGAATAGTGGAATATTCATGTTTAAGGCATCTGTTTATCT      9720
```

Fig. 6H

```
         E  E  L  R  K  F  R  P  D  I  Y  N  V  C  E  Q  V  A  S  S
TGAGGAATTGAGAAAATTTAGACCTGACATTTACAATGTTTGTAACAGGTTGCCTCATC           9780

S  Y  I  D  L  D  F  I  R  L  S  K  E  Q  F  Q  D  C  P  A
CTCATACATTGATCTAGATTTTATTCGATTATCAAAAGAACAATTTCAAGATTGTCCTGC          9840

E  S  I  D  F  A  V  M  E  K  T  E  K  C  V  V  C  P  V  D
TGAATCTATTGATTTTGCTGTAATGGAAAAAACAGAAAAATGTGTTGTATGCCCTGTTGA          9900

I  G  W  S  D  V  G  S  W  Q  S  L  W  D  I  S  L  K  S  K
TATTGGTTGGAGTGACGTTGGATCTTGGCAATCGTTATGGGACATTAGTCTAAAATCGAA         9960

T  G  D  V  C  K  G  D  I  L  T  Y  D  T  K  N  N  Y  I  Y
AACAGGAGATGTATGTAAAGGTGATATATTAACCTATGATACTAAGAATAATTATATCTA         10020

S  E  S  A  L  V  A  A  I  G  I  E  D  M  V  I  V  Q  T  K
CTCTGAGTCAGCGTTGGTAGCCGCCATTGGAATTGAAGATATGGTTATCGTGCAAACTAA         10080

D  A  V  L  V  S  K  K  S  D  V  Q  H  V  K  K  I  V  E  M
AGATGCCGTTCTTGTGTCTAAAAAGAGTGATGTACAGCATGTAAAAAAAATAGTCGAAAT         10140

L  K  L  Q  Q  R  T  E  Y  I  S  H  R  E  V  F  R  P  W  G
GCTTAAATTGCAGCAACGTACAGAGTATATTAGTCATCGTGAAGTTTTCCGACCATGGGG         10200

K  F  D  S  I  D  Q  G  E  R  Y  K  V  K  K  I  I  V  K  P
AAAATTTGATTCGATTGACCAAGGTGAGCGATACAAAGTCAAGAAAATTATTGTGAAACC         10260

G  E  G  L  S  L  R  M  H  H  H  R  S  E  H  W  I  V  L  S
TGGTGAGGGGCTTTCTTTAAGGATGCATCACCATCGTTCTGAACATTGGATCGTGCTTTC         10320

G  T  A  K  V  T  L  G  D  K  T  K  L  V  T  A  N  E  S  I
TGGTACAGCAAAAGTAACCCTTGGCGATAAAACTAAACTAGTCACCGCAAATGAATCGAT         10380

Y  I  P  L  G  A  A  Y  S  L  E  N  P  G  I  I  P  L  N  L
ATACATTCCCCTTGGCGCAGCGTATAGTCTTGAGAATCCGGGCATAATCCCTCTTAATCT         10440

I  E  V  S  S  G  D  Y  L  G  E  D  D  I  I  R  Q  K  E  R
TATTGAAGTCAGTTCAGGGGATTATTTGGGAGAGGATGATATTATAAGACAGAAAGAACG         10500

End of orf10    Start of orf11
         Y  K  H  E  D  *        M  K  S  L  T  C  F  K  A  Y  D  I  R
TTACAAACATGAAGATTAACAT ATG AAATCTTTAACCTGCTTTAAAGCCTATGATATTCG       10560

G  K  L  G  E  E  L  N  E  D  I  A  W  R  I  G  R  A  Y  G
CGGGAAATTAGGCGAAGAACTGAATGAAGATATTGCCTGGCGCATTGGGCGTGCCTATGG        10620

E  F  L  K  P  K  T  I  V  L  G  G  D  V  R  L  T  S  E  A
CGAATTTCTCAAACCGAAAACCATTGTTTTAGGCGGTGATGTCCGCCTCACCAGCGAAGC        10680

L  K  L  A  L  A  K  G  L  Q  D  A  G  V  D  V  L  D  I  G
GTTAAAACTGGCGCTTGCGAAAGGTTTACAGGATGCGGGCGTCGATGTGCTGGATATCGG       10740

M  S  G  T  E  E  I  Y  F  A  T  F  H  L  G  V  D  G  G  I
TATGTCCGGCACCGAAGAGATCTATTTCGCCACGTTCCATCTCGGAGTGGATGGCGGCAT       10800

E  V  T  A  S  H  N  P  M  D  Y  N  G  M  K  L  V  R  E  G
CGAAGTTACCGCCAGCCATAACCCGATGGATTACAACGGCATGAAGCTGGTGCGCGAAGG      10860

A  R  P  I  S  G  D  T  G  L  R  D  V  Q  R  L  A  E  A  N
GGCTCGCCCGATCAGCGGTGATACCGGACTGCGCGATGTCCAGCGTCTGGCAGAAGCCAA     10920

D  F  P  P  V  D  E  T  K  R  G  R  Y  Q  Q  I  N  L  R  D
TGACTTCCCTCCTGTCGATGAAACCAAACGTGGTCGCTATCAGCAAATCAATCTGCGTGA    10980
```

Fig. 61

```
         A   Y   V   D   H   L   F   G   Y   I   N   V   K   N   L   T   P   L   K   L
       CGCTTACGTTGATCACCTGTTCGGTTATATCAACGTCAAAAACCTCACGCCGCTCAAGCT    11040
         V   I   N   S   G   N   G   A   A   G   P   V   V   D   A   I   E   A   R   F
       GGTGATCAACTCCGGGAACGGCGCAGCGGGTCCGGTGGTGGACGCCATTGAAGCCCGATT    11100
         K   A   L   G   A   P   V   E   L   I   K   V   H   N   T   P   D   G   N   F
       TAAAGCCCTCGGCGCACCGGTGGAATTAATCAAAGTACACAACACGCCGGACGGCAATTT    11160
         P   N   G   I   P   N   P   L   L   P   E   C   R   D   D   T   R   N   A   V
       CCCCAACGGTATTCCTAACCCGCTGCTGCCGGAATGCCGCGACGACACCCGTAATGCGGT    11220
         I   K   H   G   A   D   M   G   I   A   F   D   G   D   F   D   R   C   F   L
       CATCAAACACGGCGCGGATATGGGCATTGCCTTTGATGGCGATTTTGACCGCTGTTTCCT    11280
         F   D   E   K   G   Q   F   I   E   G   Y   Y   I   V   G   L   L   A   E   A
       GTTTGACGAAAAAGGGCAGTTTATCGAGGGCTACTACATTGTCGGCCTGCTGGCAGAAGC    11340
         F   L   E   K   N   P   G   A   K   I   I   H   D   P   R   L   S   W   N   T
       GTTCCTCGAAAAAAATCCCGGCGCGAAGATCATCCACGATCCACGTCTCTCCTGGAACAC    11400
         V   D   V   V   T   A   A   G   G   T   P   V   M   S   K   T   G   H   A   F
       CGTTGATGTGGTGACTGCCGCAGGCGGCACCCCGGTAATGTCGAAAACCGGACACGCCTT    11460
         I   K   E   R   M   R   K   E   D   A   I   Y   G   G   E   M   S   A   H   H
       TATTAAAGAACGTATGCGCAAGGAAGACGCCATCTACGGTGGCGAAATGAGCGCTCACCA    11520
         Y   F   R   D   F   A   Y   C   D   S   G   M   I   P   W   L   L   V   A   E
       TTACTTCCGTGATTTCGCTTACTGCGACAGCGGCATGATCCCGTGGCTGCTGGTCGCCGA    11580
         L   V   C   L   K   G   K   T   L   G   E   M   V   R   D   R   M   A   A   F
       ACTGGTGTGCCTGAAAGGAAAAACGCTGGGCGAAATGGTGCGCGACCGGATGGCGGCGTT    11640
         P   A   S   G   E   I   N   S   K   L   A   Q   P   V   E   A   I   N   R   V
       TCCGGCAAGCGGTGAGATCAACAGCAAACTGGCGCAACCCGTTGAGGCAATTAATCGCGT    11700
         E   Q   H   F   S   R   E   A   L   A   V   D   R   T   D   G   I   S   M   T
       GGAACAGCATTTTAGCCGCGAGGCGCTGGCGGTGGATCGCACCGATGGCATCAGCATGAC    11760
         F   A   D   W   R   F   N   L   R   S   S   N   T   E   P   V   V   R   L   N
       CTTTGCCGACTGGCGCTTTAACCTGCGCTCCTCCAACACCGAACCGGTGGTGCGGTTGAA    11820
         V   E   S   R   G   D   V   K   L   M   E   K   K   T   K   A   L   L   K   L
       TGTGGAATCACGCGGTGATGTAAAGCTAATGGAAAAGAAAACTAAAGCTCTTCTTAAATT    11880
              End of orf11
         L   S   E   *
       GCTAAGTGAG TGATTATTTACATTAATCATTAAGCGTATTTAAGATTATATTAAAGTAAT    11940

GTTATTGCGGTATATGATGAATATGTGGGCTTTTTTATGTATAACGACTATACCGCAACT    12000

Start of H-repeat
       TTATCTAGGAAAAGATTAATAGAAATAAAGTTTTGTACTGACCAATTTGCATTTCACGTC    12060

ACGATTGAGACGTTCCTTTGCTTAAGACATTTTTTCATCGCTTATGTAATAACAAATGTG    12120

CCTTATATAAAAAGGAGAACAAAATGGAACTTAAAATAATTGAGACAATAGATTTTTATT    12180

ATCCCTGTTTACGATATTATAGCCAAAGTTGTATCCTGCATCAGTCCTGCAATATTTCAC    12240

GAGTGCTTTGTTAACTGAATACATGTCTGCCATTTTCCAGATGATAACGACGTCATCGCA    12300

ATTGATGGTAAAACACTTCGGCACACTTATGACAAGAGTCGTCGCAGAGGAGTGGTTCAT    12360
```

Fig. 6J

```
GTCATTAGTGCGTTTCAGCAATGCACAGTCTGGTCCTCGGATAGATCAAGACGGATGAGA    12420

AACCTAATGCGTTCACAGTTATTCATGAACTTTCTAAAATGATGGGTATTAAAGGAAAAA    12480

TAATCATAACTGATGCGATGGCTTGCCAGAAAGATATTGCAGAGAAGATATAAAAACAGA    12540

GATGTGATTATTTATTCGCTGTAAAAGGAAATAAGAGTCGGCTTAATAGAGTCTTTGAGG    12600

AGATATTTACGCTGAAAGAATTAAATAATCCAAAACATGACAGTTACGCAATTAGTGAAA    12660

AGAGGCACGGCAGAGACGATGTCCGTCTTCATATTGTTTGAGATGCTCCTGATGAGCTTA    12720

TTGATTTCACGTTTGAATGGAAAGGGCTGCAGAATTTATGAATGGCAGTCCACTTTCTCT    12780

CAATAATAGCAGAGCAAAAGAAAGAATCCGAAATGACGATCAAATATTATATTAGATCTG    12840

CTGCTTTAACCGCAGAGAAGTTCGCCACAGTAAATCGAAATCACTGGCGCATGGAGAATA    12900

AGTTGCACAGTAGCCTGATGTGGTAATGAATGAAATCGACTATAATATAAGAAGGCGAGT    12960

TGCATTCGAATGATTTTCTAGAATGCGGCACATCGCTATTAATATCTGACAATGATAATG    13020

TATTCAAGGCAGGATTATCATGTAAGATGCGAAAAGCAGTCATGGACAGAAACTTCCTAG    13080
```
                                                       End of the H-repeat
```
CGTCAGGCATTGCAGCGTGCGGGCTTTCATAATCTTGCAT TGGTTTTGATAAGATATTTC    13140
```
                                    Start of orf12
```
                    M  N  L  Y  G  I  F  G  A  G  S  Y  G  R  E
TTTGGAGATGGGAAA ATGAATTTGTATGGTATTTTTGGTGCTGGAAGTTATGGTAGAGAA     13200

T  I  P  I  L  N  Q  Q  I  K  Q  E  C  G  S  D  Y  A  L  V
ACAATACCCATTCTAAATCAACAAATAAAGCAAGAATGTGGTTCTGACTATGCTCTGGTT     13260

F  V  D  D  V  L  A  G  K  K  V  N  G  F  E  V  L  S  T  N
TTTGTGGATGATGTTTTGGCAGGAAAGAAAGTTAATGGTTTTGAAGTGCTTTCAACCAAC     13320

C  F  L  K  A  P  Y  L  K  K  Y  F  N  V  A  I  A  N  D  K
TGCTTTCTAAAAGCCCCTTATTTAAAAAAGTATTTTAATGTTGCTATTGCTAATGATAAG     13380

I  R  Q  R  V  S  E  S  I  L  L  H  G  V  E  P  I  T  I  K
ATACGACAGAGAGTGTCTGAGTCAATATTATTACACGGGGTTGAACCAATAACTATAAAA     13440

H  P  N  S  V  V  Y  D  H  T  M  I  G  S  G  A  I  I  S  P
CATCCAAATAGCGTTGTTTATGATCATACTATGATAGGTAGTGGCGCTATTATTTCTCCC     13500

F  V  T  I  S  T  N  T  H  I  G  R  F  F  H  A  N  I  Y  S
TTTGTTACAATATCTACTAATACTCATATAGGGAGGTTTTTTCATGCAAACATATACTCA     13560

Y  V  A  H  D  C  Q  I  G  D  Y  V  T  F  A  P  G  A  K  C
TACGTTGCACATGATTGTCAAATAGGAGACTATGTTACATTTGCTCCTGGGGCTAAATGT     13620

N  G  Y  V  V  I  E  D  N  A  Y  I  G  S  G  A  V  I  K  Q
AATGGATATGTTGTTATTGAAGACAATGCATATATAGGCTCGGGTGCAGTAATTAAGCAG     13680

G  V  P  N  R  P  L  I  I  G  A  G  A  I  I  G  M  G  A  V
GGTGTTCCTAATCGCCCACTTATTATTGGCGCGGGAGCCATTATAGGTATGGGGGCTGTT     13740

V  T  K  S  V  P  A  G  I  T  V  C  G  N  P  A  R  E  M  K
GTCACTAAAAGTGTTCCTGCCGGTATAACTGTGTGCGGAAATCCAGCAAGAGAAATGAAA     13800
```
                              End of orf12
```
 R  S  P  T  S  I  *
AGATCGCCAACATCTATT TAATGGGAATGCGAAAACACGTTCCAAATGGGACTAATGTTT     13860
```

Fig. 6K

```
AAAATATATATAATTTCGCTAATTTACTAAATTATGGCTTCTTTTTAAGCTATCCTTTAC    13920

TTAGTTATTACTGATACAGCATGAAATTTATAATACTCTGATACATTTTTATACGTTATT    13980

CAAGCCGCATATCTAGCGGTAACCCCTGACAGGAGTAAACAATG    14024
```

Fig. 6L

```
ATGGCACAAGTCATTAATACCAACAGCCTCTCGCTGATCACTCAAAATAATATCAACAAG
AACCAGTCTGCGCTGTCGAGTTCTATCGAGCGTCTGTCTTCTGGCTTGCGTATTAACAGC
GCGAAGGATGACGCCGCGGGTCAGGCGATTGCTAACCGTTTTACTTCTAACATTAAAGGC
CTGACTCAGGCTGCACGTAACGCCAACGACGGTATTTCTGTTGCACAGACCACTGAAGGC
GCGCTGTCCGAAATCAACAACAACTTACAGCGTATCCGTGAGCTGACGGTTCAGGCTTCT
ACCGGGACTAACTCTGATTCGGATCTGGACTCCATTCAGGACGAAATCAAATCCCGTCTC
GACGAAATTGACCGCGTATCCGGTCAGACCCAGTTCAACGGCGTGAACGTACTGGCAAAA
GACGGTTCGATGAAAATTCAGGTAGGTGCGAACGACGGCCAGACTATCACTATTGATCTG
AAGAAAATTGACTCTGATACGCTGGGGCTGAATGGTTTTAACGTGAATGGTTCCGGTACG
ATAGCCAATAAAGCGGCGACCATTAGCGACCTGACAGCAGCGAAAATGGATGCTGCAACT
AATACTATAACTACAACAAATAATGCGCTGACTGCATCAAAGGCCCTTGATCAACTGAAA
GATGGTGACACTGTTACTATCAAAGCAGATGCAGCTCAAACTGCCACGGTCTATACATAC
AATGCATCTGCTGGTAACTTCTCATTCAGTAATGTATCGAATAATACTTCAGCAAAAGCA
GGTGATGTAGCAGCTAGCCTTCTCCCGCCGGCTGGGCAAACTGCTAGTGGTGTTTACAAA
GCAGCAAGCGGTGAAGTGAACTTTGATGTTGATGCGAATGGTAAAATTACAATCGGAGGA
CAGGAAGCCTATTTAACTAGTGATGGTAACTTAACTACAAACGATGCTGGTGGTGCGACT
GCGGCTACGCTTGATGGTTTATTCAAGAAAGCTGGTGATGGTCAATCAATCGGGTTTAAT
AAGACTGCATCAGTCACGATGGGGGGAACAACTTATAACTTTAAAACGGGTGCTGATGCT
GGTGCTGCAACTGCTAACGCAGGGGTATCGTTCACTGATACAGCTAGCAAAGAAACCGTT
TTAAATAAAGTGGCTACAGCTAAACAAGGCACAGCAGTTGCAGCTAACGGTGATACATCC
GCAACAATTACCTATAAATCTGGCGTTCAGACGTATCAGGCGGTATTTGCCGCAGGTGAC
GGTACTGCTAGCGCAAAATATGCCGATAATACTGACGTTTCTAATGCAACAGCAACATAC
ACAGATGCTGATGGTGAAATGACTACAATTGGTTCATACACCACGAAGTATTCAATCGAT
GCTAACAACGGCAAGGTAACTGTTGATTCTGGAACTGGTTCGGGTAAATATGCGCCGAAA
GTCGGGGCTGAAGTATATGTTAGTGCTAATGGTACTTTAACAACAGATGCAACTAGCGAA
GGCACAGTAACAAAAGATCCACTGAAAGCTCTGGATGAAGCTATCAGCTCCATCGACAAA
TTCCGTTCATCCCTGGGGGCTATCCAAAACCGTTTGGATTCCGCCGTCACCAACCTGAAC
AACACCACTACCAACCTGTCTGAAGCGCAGTCCCGTATTCAGGACGCCGACTATGCGACC
GAAGTGTCCAACATGTCGAAAGCGCAGATTATCCAGCAGGCCGGTAACTCCGTGCTGGCA
AAAGCCAACCAGGTACCGCAGCAGGTTCTGTCTCTACTGCAGGGTTAA
```

Figure 7

```
AACAAATCTCAGTCTTCTCTTAGCTCTGCTATT
GAGCGTCTGTCTTCTGGTCTGCGTATTAACAGCGCAAAAGACGATGCAGCAGGTCAGGCG
ATTGCTAACCGTTTTACGGCAAATATTAAAGGTCTGACCCAGGCTTCCCGTAACGCAAAT
GATGGTATTTCTGTTGCGCAGACCACTGAAGGTGCGCTGAATGAAATTAACAACAACCTG
CAGCGTATTCGTGAACTTTCTGTTCAGGCAACTAACGGTACTAACTCTGACAGTGACCTG
ACCTCCATCCAGTCCGAAATCCAGCAGCGTCTGAGTGAAATTGACCGTGTTTCTGGTCAG
ACTCAGTTTAACGGCGTTAAAGTGCTGGCTTCTGATCAGGATATGACTATTCAGGTTGGT
GCAAACGACGGCGAAACAATTACTATTAAACTGCAGGAAATTAATTCCGACACACTGGGA
TTATCTGGTTTTGGTATTAAAGATCCTACTAAATTAAAAGCCGCAACGGCTGAAACAACC
TATTTTGGATCGACAGTTAAGCTTGCTGACGCTAATACACTTGATGCAGATATTACAGCT
ACAGTTAAAGGCACTACGACTCCGGGCCAACGTGACGGTAATATTATGTCTGATGCTAAC
GGTAAGTTGTACGTTAAAGTTGCCGGTTCAGATAAACCCGCTGAAAATGGTTATTATGAA
GTTACTGTGGAGGATGATCCGACATCTCCTGATGCAGGTAAGCTGAAGCTGGGGGCTCTA
GCGGGTACCCAGCCTCAAGCTGGTAATTTAAAGGAAGTCACAACGGTGAAAGGGAAGGGG
GCTATTGATGTTCAGTTGGGTACTGATACCGCAACCGCTTCTATCACAGGTGCAAAACTC
TTTAAGTTAGAAGACGCCAATGGCAAAGATACTGGTTCATTTGCGTTGATTGGTGATGAC
GGTAAACAGTATGCAGCGAATGTTGATCAGAAAACAGGAGCAGTTTCCGTTAAAACAATG
TCTTACACTGATGCTGACGGTGTCAAACACGACAATGTTAAAGTTGAACTGGGTGGAAGC
GATGGCAAAACCGAAGTTGTAACTGCAACCGATGGCAAAACTTACAGTGTTAGTGATTTA
CAAGGTAAGAGCCTGAAAACTGATTCTATTGCAGCAATTTCTACGCAGAAAACAGAAGAT
CCTTTGGCTGCTATCGATAAAGCACTGTCTCAGGTTGACTCGTTGCGTTCTAACCTAGGT
GCAATTCAAAATCGTTTCGACTCTGCCATCACCAACCTTGGCAACACCGTAAACAACCTG
TCTTCTGCCCGTAGCCGTATCGAAGATGCTGACTACGCGACCGAAGTGTCTAACATGTCT
CGTGCGCAGATCCTGCAACAAGCGGGTACCTCTGTTCTGGCGCAG
```

Figure 8

```
AACAAATCTCAGTCTTCTCTGAGCTCCGCCATTGAACGTCTCTCTTC
TGGCCTGCGTATTAACAGTGCTAAAGATGACGCAGCAGGTCAGGCGATTGCTAACCGTTT
TACAGCAAATATTAAAGGTCTGACTCAGGCTTCCCGTAACGCGAATGATGGTATTTCTGT
TGCGCAGACCACTGAAGGTGCGCTTTCTGAAATCAACAATAACTTACAGCGTATTCGTGA
ATTGTCAGTACAGGCCACTAATGGTACAAACTCTGACTCCGACCTGAATTCAATTCAGGA
TGAAATTACACAACGCCTTAGTGAAATTGATCGTGTTTCTAACCAGACACAATTTAATGG
TGTAAAAGTTCTGGCTTCTGATCAGACTATGAAAATTCAAGTAGGTGCGAACGATGGTGA
AACCATTGAGATTGCCCTTGATAAAATTGATGCTAAAACCTTGGGGCTTGATAACTTTAG
CGTAGCACCAGGAAAAGTTCCAATGTCCTCTGCGGTTGCACTTAAGAGCGAAGCCGCTCC
TGACTTAACTAAGGTAAATGCAACTGATGGTAGTGTGGGAGGTGCTAAAGCATTCGGTAG
CAATTATAAAAATGCTGATGTTGAAACTTATTTTGGTACCGGTAATGTACAAGATACAAA
GGATACAACTGATGCGACCGGTACTGCAGGAACAAAAGTTTATCAAGTACAGGTGGAAGG
GCAGACTTATTTTGTTGGTCAAGATAATAATACCAACACGAACGGTTTTACATTATTGAA
ACAAAACTCTACAGGTTATGAAAAAGTTCAGGTGGGTGGTAAGGATGTTCAGTTAGCAAA
CTTTGGTGGTCGTGTAACTGCATTTGTTGAAGATAATGGTTCTGCCACATCAGTTGATTT
AGCTGCGGGTAAAATGGGTAAAGCATTAGCTTATAATGATGCACCAATGTCTGTTTATTT
TGGGGGAAAAAACCTAGATGTCCACCAAGTACAAGATACCCAAGGGAATCCTGTACCTAA
TTCATTTGCTGCTAAAACATCAGACGGCACCTACATTGCAGTAAATGTAGATGCCGCTAC
AGGTAACACGTCTGTTATTACTGATCCTAATGGTAAGGCAGTTGAATGGGCAGTAAAAAA
TGATGGTTCTGCACAGGCAATTATGCGTGAAGATGATAAGGTTTATACAGCCAATATCAC
GAATAAGACGGCAACCAAAGGTGCTGAACTCAGTGCCTCAGATTTGAAAGCCTTAGCAAC
CACAAATCCATTATCCACATTAGACGAAGCTTTGGCAAAAGTTGATAAGTTGCGCAGTTC
TTTGGGTGCAGTACAAAACCGTTTCGACTCTGCCATCACCAACCTTGGCAACACCGTAAA
CAACCTGTCTTCTGCCCGTAGCCGTATAGAAGATGCTGACTACGCAACCGAAGTGTCTAA
CATGTCTCGTGCGCAGATCCTGCAACAAGCGGGTACCTCTGTTCTGGCACAG
```

Figure 9

```
AACAAAAACCAGTCTGCGCTGTCGACTTCTATCGAG
CGCCTCTCTTCTGGTCTGCGTATTAACAGCGCTAAAGATGACGCCGCGGGCCAGGCGATT
GCTAACCGCTTTACTTCTAACATCAAAGGTCTGACTCAGGCCGCACGTAACGCCAACGAC
GGTATTTCTCTGGCGCAGACGGCTGAAGGCGCGCTGTCAGAGATTAACAACAACTTGCAG
CGTATTCGTGAACTGACCGTTCAGGCCTCTACCGGCACGAACTCTGATTCCGACCTGTCT
TCTATTCAGGACGAAATCAAATCCCGTCTTGATGAAATTGACCGTGTATCTGGTCAGACC
CAGTTCAACGGTGTGAACGTGCTGTCGAAAAACGATTCGATGAAGATTCAGATTGGTGCC
AATGATAACCAGACGATCAGCATTGGCTTGCAACAAATCGACAGTACCACTTTGAATCTG
AAAGGATTTACCGTGTCCGGCATGGCGGATTTCAGCGCGGCGAAACTGACGGCTGCTGAT
GGTACAGCAATTGCTGCTGCGGATGTCAAGGATGCTGGGGGTAAACAAGTCAATTTACTG
TCTTACACTGACACCGCGTCTAACAGTACTAAATATGCGGTCGTTGATTCTGCAACCGGT
AAATACATGGAAGCCACTGTAGTCATTACCGGTACGGCGGCGGCGGTAACTGTTGGTGCA
GCGGAAGTGGCGGGAGCCGCTACAGCCGATCCGTTAAAAGCACTGGATGCCGCAATCGCT
AAAGTCGACAAATTCCGCTCCTCCCTCGGTGCCGTTCAAAACCGTCTGGATTCTGCGGTC
ACCAACCTGAACAACACCACCACCAACCTGTCTGAAGCGCAGTCCCGTATTCAGGACGCC
GACTATGCGACCGAAGTGTCCAACATGTCGAAAGCGCAGATTATCCAGCAGGCGGGCAAC TCCGTGCTGTCTAA
```

Figure 10

```
AACAAAAACCAGTCTGCGCTGTCGACTTCTAT
CGAGCGCCTCTCTTCTGGTCTGCGTATTAACAGCGCTAAAGATGACGCCGCGGGCCAGGC
GATTGCTAACCGCTTCACTTCTAACATCAAAGGTCTGACTCAGGCCGCACGTAACGCCAA
CGACGGTATCTCTCTGGCGCAGACCACTGAAGGCGCGCTGTCTGAAATCAACAACAACTT
GCAGCGTGTGCGTGAGTTGACCGTTCAGGCGACGACCGGGACTAACTCTGATTCTGACCT
GTCTTCTATTCAGGACGAAATCAAATCCCGTCTGGATGAAATTGATCGCGTTTCCGGTCA
GACCCAGTTCAACGGCGTGAATGTGCTGGCGAAAGATGGTTCGATGAAGATTCAGGTTGG
CGCGAATGATGGGCAGACTATTAGCATTGATTTGCAGAAGATTGACTCTTCTACATTAGG
ACTGAACGGTTTCTCCGTTTCGGGTCAGTCACTTAACGTTAGTGATTCCATTACTCAAAT
TACCGGTGCCGCCGGGACAAAACCTGTTGGTGTTGATTTCACTGCTGTTGCGAAAGATCT
GACTACTGCGACAGGTAAAACAGTCGATGTTTCTAGCCTGACGTTACACAACACTCTGGA
TGCGAAAGGGGCTGCTACATCACAGTTCGTCGTTCAATCCGGCAATGATTTCTACTCCGC
GTCGATTAATCATACAGACGGCAAAGTCACGTTGAATAAAGCCGATGTCGAATACACAGA
CACCGATAATGGACTAACGACTGCGGCTACTCAGAAAGATCAACTGATTAAAGTTGCCGC
TGACTCTGACGGCTCGGCTGCGGGATATGTAACATTCCAAGGTAAAAACTACGCTACAAC
GGTTTCAACGGCACTTGATGATAATACTGCGGCAAAAGCAACAGATAATAAAGTTGTTGT
TGAATTATCAACAGCAAAACCGACTGCACAGTTCTCAGGGGCTTCTTCTGCTGATCCACT
GGCACTTTTAGACAAAGCTATTGCACAGGTTGATACTTTCCGCTCCTCCCTCGGTGCGGT
GCAAACCGTCTGGATTCCGCAGTAACCAACCTGAACAACACCACCACCAACCTGTCTGA
AGCGCAGTCCCGTATTCAGGACGCCGACTATGCTACAGAAGTGTCCAACATGTCGAAAGC
GCAGATCATCCAGCAGGCAGGTAACTCGGTGCTGTCCAAA
```

Figure 11

```
ATGGCACAAGTCATTAATACCAACAGCCTCTCGC
TGATCACTCAAAATAATATCAACAAGAACCAGTCTGCGCTGTCGAGTTCTATCGAGCGTC
TGTCTTCTGGCTTGCGTATTAACAGCGCGAAGGATGACGCCGCGGGTCAGGCGATTGCTA
ACCGTTTTACTTCTAACATTAAAGGCCTGACTCAGGCTGCACGTAACGCCAACGACGGTA
TTTCTGTTGCGCAGACCACCGAAGGCGCGCTGTCCGAAATTAACAACAACTTACAGCGTA
TTCGTGAACTGACGGTTCAGGCTTCTACCGGGACTAACTCTGATTCGGATCTGGACTCCA
TTCAGGACGAAATCAAATCCCGTCTCGACGAAATTGACCGCGTATCCGGTCAGACCCAGT
TCAACGGCGTGAACGTACTGGCAAAAGACGGTTCGATGAAAATTCAGGTTGGTGCGAATG
ACGGCCAGACTATCACTATTGATCTGAAGAAAATTGACTCTGATACGCTGGGGCTGAATG
GGTTTAATGTGAACGGCAAAGGGGAAACGGCTAATACGGCAGCAACCCTGAAAGATATGT
CTGGATTCACAGCTGCGGCGGCACCAGGGGGAACTGTTGGTGTAACTCAATATACTGACA
AATCGGCTGTAGCAAGTAGCGTAGATATTCTAAATGCTGTTGCTGGCGCAGATGGAAATA
AAGTTACAACTAGCGCCGATGTTGGTTTTGGTACACCAGCCGCTGCTGTAACCTATACCT
ACAATAAAGACACTAATTCATATTCCGCCGCTTCTGATGATATTTCCAGCGCTAACCTGG
CTGCTTTCCTCAATCCTCAGGCCGGAGATACGACTAAAGCTACAGTTACAATTGGTGGCA
AAGATCAAGATGTAAACATCGATAAATCCGGTAATTTAACTGCTGCTGATGATGGCGCAG
TACTTTATATGGATGCTACCGGTAACTTAACTAAAAATAATGCTGGTGGTGATACACAAG
CTACTTTGGCTAAACTTGCTACTGCTACTGGTGCTAAAGCCGCGACCATCCAAACTGATA
AAGGAACATTCACCAGTGACGGTACAGCGTTTGATGGTGCATCAATGTCCATTGATACCA
ATACATTTGCAAATGCAGTAAAAAATGACACTTATACTGCCACTGTAGGTGCTAAGACTT
ATAGCGTAACAACAGGTTCTGCTGCTGCAGACACCGCTTATATGAGCAATGGGGTTCTCA
GTGATACTCCGCCAACTTACTATGCACAAGCTGATGGAAGTATCACAACTACTGAGGATG
CGGCTGCCGGTAAACTGGTCTACAAAGGTTCCGATGGTAAGTTAACAACGGATACGACTA
GCAAAGCAGAATCAACATCAGATCCGCTGGCAGCTCTTGACGACGCTATCAGCCAGATCG
ACAAATTCCGCTCCTCCCTGGGTGCGGTGCAAAACCGTCTGGATTCCGCAGTGACCAACC
TGAACAACACCACTACCAACCTGTCTGAAGCGCAGTCCCGTATTCAGGACGCCGACTATG
CGACCGAAGTGTCCAACATGTCGAAAGCGCAGATTATCCAGCAGGCCGGTAACTCCGTGC
TGGCAAAAGCTAACCAGGTTCCGCAGCAGGTTCTGTCTCTGCTGCAGGGTTAA
```

Figure 12

```
ATGGCACAAG TCATTAATAC CAACAGCCTC TCGCTGATCA CTCAAAATAA TATCAACAAG
AACCAGTCTG CGCTGTCGAG TTCTATCGAG CGTCTGTCTT CTGGCTTGCG TATTAACAGC
GCGAAGGATG ACGCCGCGGG TCAGGCGATT GCTAACCGTT TTACTTCTAA CATTAAAGGC
CTGACTCAGG CTGCACGTAA CGCCAACGAC GGTATTTCTG TTGCACAGAC CACCGAAGGC
GCGCTGTCTG AAATCAACAA CAACTTACAG CGTATCCGTG AGCTGACGGT TCAGGCTTCT
ACCGGAACTA ACTCTGATTC GGATCTGGAC TCCATTCAGG ACGAAATCAA ATCCCGTCTT
GATGAAATTG ACCGCGTATC CGGCCAGACC CAGTTCAACG GCGTGAACGT ACTGGCAAAA
GACGGTTCGA TGAAAATTCA GGTTGGTGCG AATGACGGTG AAACTATCAC TATCGACCTG
AAGAAAATCG ATTCTGATAC TCTGGGTCTG AATGGTTTTA ACGTAAATGG TAAAGGTACT
ATTACCAACA AAGCTGCAAC GGTAAGTGAT TTAACTTCTG CTGGCGCGAA GTTAAACAC
CACGACAGGT CTTTATGATC TGAAAACCGA AAATACCTTG TTAACTACCG ATGCTGCATT
CGATAAATTA GGGAATGGCG ATAAAGTCAC CGTTGGCGGC GTAGATTATA CTTACAACGC
TAAATCTGGT GATTTTACTA CCACCAAATC TACTGCTGGT ACGGGTGTAG ACGCCGCGGC
GCAGGCTACT GATTCAGCTA AAAAACGTGA TGCGTTAGCT GCCACCCTTC ATGCTGATGT
GGGTAAATCT GTTAATGGTT CTTACACCAC AAAAGATGGT ACTGTTTCTT TCGAAACGGA
TTCAGCAGGT AATATCACCA TCGGTGGAAG CCAGGCATAC GTAGACGATG CAGGCAACTT
GACGACTAAC AACGCTGGTA GCGCAGCTAA AGCTGATATG AAAGCGCTGC TTAAAGCCGC
GAGCGAAGGT AGTGACGGTG CTTCTCTGAC ATTCAATGGC ACTGAATATA CTATCGCAAA
AGCAACTCCT GCGACAACCT CTCCAGTAGC TCCGTTAATC CCTGGTGGGA TTACTTATCA
GGCTACAGTG AGTAAAGATG TAGTATTGAG CGAAACCAAA GCGGCTGCCG CGACATCTTC
AATTACCTTT AATTCCGGTG TACTGAGCAA AACTATTGGG TTTACCGCGG GTGAATCCAG
TGATGCTGCG AAGTCTTATG TGGATGATAA AGGTGGTATT ACTAACGTTG CCGACTATAC
AGTCTCTTAC AGCGTTAACA AGGATAACGG CTCTGTGACT GTTGCCGGGT ATGCTTCAGC
GACTGATACC AATAAAGATT ATGCTCCAGC AATTGGTACT GCTGTAAATG TGAACTCCGC
GGGTAAAATC ACTACTGAGA CTACCAGTGC TGGTTCTGCA ACGACCAACC CGCTTGCTGC
CCTGGACGAC GCTATCAGCT CCATCGACAA ATTCCGTTCT TCCCTGGGT CTATCCAGAA
CCGTCTGGAT TCCGCAGTCA CCAACCTGAA CAACACCACT ACCAACCTGT CTGAAGCGCA
GTCCCGTATT CAGGACGCCG ACTATGCGAC CGAAGTGTCC AACATGTCGA AAGCGCAGAT
TATCCAGCAG GCCGGTAACT CCGTGCTGGC AAAAGCCAAC CAGGTACCGC AGCAGGTTCT
GTCTCTGCTG CAGGGTTAA
```

Figure 13

```
AACAAATCTCAGTCTTCTCTTAGCTCTGCTA
TTGAGCGTCTGTCTTCTGGTCTGCGTATTAACAGCGCAAAAGACGATGCAGCAGGTCAGG
CGATTGCTAACCGTTTTACGGCAAATATTAAAGGTCTGACCCAGGCTTCCCGTAACGCAA
ATGATGGTATTTCTGTTGCGCAGACCACTGAAGGTGCGCTGAATGAAATTAACAACAACC
TGCAGCGTATTCGTGAACTTTCTGTTCAGGCAACTAACGGTACTAACTCTGACAGCGATC
TTTCTTCTATCCAGGCTGAAATTACTCAACGTCTGGAAGAAATTGACCGTGTATCTGAGC
AAACTCAGTTTAACGGCGTGAAAGTCCTTGCTGAAAATAATGAAATGAAAATTCAGGTTG
GTGCTAATGATGGTGAAACCATCACTATCAATCTGGCAAAAATTGATGCGAAAACTCTCG
GCCTGGACGGTTTTAATATCGATGGCGCGCAGAAAGCAACAGGCAGTGACCTGATTTCTA
AATTTAAAGCGACAGGTACTGATAATTATGATGTTGGCGGTAAAACTTATACCGTGAATG
TGGAGAGCGGCGCGGTTAAGAATGATGCTAATAAAGATGTTTTTGTAAGCGCAGCTGATG
GATCGCTGACGACCAGTAGTGATACTAAAGTATCCGGTGAAAGTATTGATGCAACAGAAC
TAGCGAAACTTGCAATAAAATTAGCTGACAAAGGCTCCATTGAATACAAGGGCATTACAT
TTACTAACAACACTGGCGCAGAGCTTGATGCTAATGGTAAAGGTGTTTTGACCGCAAATA
TTGATGGTCAAGATGTTCAATTTACTATTGACAGTAATGCACCCACGGGTGCCGGCGCAA
CAATAACTACAGACACAGCTGTTTACAAAACAGTGCGGGCCAGTTCACCACTACAAAAG
TGGAAAATAAAGCCGCAACACTCTCTGATCTGGATCTTAATGCAGCCAAGAAAACAGGTA
GCACTTTAGTTGTAAATGGCGCCACCTACAATGTCAGCGCAGATGGTAAAACGGTAACTG
ATACTACTCCTGGTGCCCCTAAAGTGATGTATCTGAGCAAATCAGAAGGTGGTAGCCCGA
TTCTGGTAAACGAAGATGCAGCAAAATCGTTGCAATCTACCACCAACCCGCTCGAAACTA
TCGACAAGGCATTGGCTAAAGTTGACAATCTGCGTTCTGACCTCGGTGCAGTACAAAACC
GTTTCGACTCTGCCATCACCAACCTTGGCAACACCGTAAACAACCTGTCTTCTGCCCGTA
GCCGTATCGAAGATGCTGACTACGCGACCGAAGTGTCTAACATGTCTCGTGCGCAGATCC
TGCAACAAGCGGGTACCTCTGTTCTGGCGCAG
```

Figure 14

```
ATGGCACAAGTCATTAATACCAACAGCCTCTCG
CTGATCACTCAAAATAATATCAACAAGAACCAGTCTGCGCTGTCGAGTTCTATCGAGCGT
CTGTCTTCTGGCTTGCGTATTAACAGCGCGAAGGATGACGCCGCGGGTCAGGCGATTGCT
AACCGTTTTACTTCTAACATTAAAGGCCTGACTCAGGCTGCACGTAACGCCAACGACGGT
ATTTCCGTTGCACAGACCACTGAAGGCGCGCTGTCCGAAATTAACAACAACTTACAGCGT
ATTCGTGAACTGACGGTTCAGGCTTCTACCGGGACTAACTCCGATTCGGATCTGGACTCC
ATTCAGGACGAAATCAAATCCCGTCTGGACGAAATTGACCGCGTATCCGGCCAGACCCAG
TTCAACGGCGTGAACGTGCTGTCCAAAGATGGCTCGATGAAAATTCAGGTCGGCGCGAAC
GATGGCGAAACGATTACTATTGATCTGAAGAAAATTGACTCTGATACGCTGAATCTGGCT
GGTTTTAACGTTAACGGTAAAGGTTCTGTAGCGAATACAGCTGCGACAAGCGACGATTTA
AAACTGGCTGGTTTCACTAAGGGCACCACAGATACCAATGGCGTGACCGCGTATACAAAC
ACAATTAGTAATGACAAAGCCAAAGCTTCCGATCTGTTAGCTAATATCACCGATGGATCA
GTGATCACTGGGGGAGGGCAAACGCTTTTGGCGTGGCTGCAAAGAATGGTTACACCTAT
GATGCAGCAAGTAAATCTTATAGTTTTGCTGCAGATGGTGCCGATTCAGCGAAGACGTTA
AGCATCATTAATCCAAACACCGGTGATTCGTCGCAGGCGACAGTGACTATTGGTGGTAAA
GAGCAGAAAGTTAATATTTCCCAGGATGGAAAAATTACTGCGGCAGATGATAATGCGACG
CTGTATTTAGATAAACAGGGAAACTTGACAAAAACGAATGCAGGTAACGATACCGCAGCG
ACTTGGGATGGTTTAATTTCCAACAGCGATTCTACCGGTGCGGTTCCAGTTGGGGTTGCA
ACTACAATTACAATTACTTCTGGTACAGCTTCCGGAATGTCTGTTCAGTCCGCAGGAGCA
GGAATTCAGACCTCAACAAATTCTCAGATTCTTGCAGGTGGTGCATTTGCGGCTAAGGTA
AGTATTGAGGGAGGCGCTGCTACAGACATTTTGGTAGCAAGTAATGGAAACATAACAGCG
GCTGATGGTAGTGCACTTTATCTTGATGCGACTACTGGTGGATTCACTACAACGGCTGGA
GGAAATACAGCTGCTTCGTTAGATAATTTAATTGCTAACAGTAAGGATGCTACCTTAACC
GTAACTTCAGGTACCGGCCAGAACACTGTTTATAGCACAACAGGAAGTGGCGCTCAGTTC
ACCAGTTTAGCAAAAGTAGACACAGTCAATGTCACCAACGCACATGTCAGTGCCGAAGGT
ATGGCAAATCTGACAAAAAGCAATTTTACCATTGATATGGGCGGTACAGGTACAGTAACT
TACACAGTTTCCAATGGGGATGTGAAAGCTGCTGCAAATGCTGATGTTTATGTCGAAGAT
GGTGCACTTTCAGCCAATGCTACAAAAGATGTAACCTACTTTGAACAAAAAAATGGGGCT
ATTACCAACAGCACCGGTGGTACCATCTATGAAACAGCTGATGGTAAGTTAACAACAGAA
GCTACTACTGCATCCAGTTCCACCGCCGATCCCCTGAAAGCTCTGGACGAAGCCATCAGC
TCCATCGACAAATTCCGCTCCTCCCTCGGTGCGGTGCAAAACCGTCTGGATTCCGCGGTC
ACCAACCTGAACAACACCACTACCAACCTGTCCGAAGCGCAGTCCCGTATTCAGGACGCC
GACTATGCGACCGAAGTGTCCAACATGTCGAAAGCGCAGATCATCCAGCAGGCCGGTAAC
TCCGTGCTGGCAAAAGCTAACCAGGTACCGCAGCAGGTTCTGTCTCTGCTGCAGGGTTAA
```

Figure 15

```
ATGGCACAAGTCATTAATACCAACAGC
CTCTCGCTGATCACTCAAAATAATATCAACAAGAACCAGTCTGCGCTGTCGAGTTCTATC
GAGCGTCTGTCTTCTGGCTTGCGTATTAACAGCGCGAAGGATGACGCCGCGGGTCAGGCG
ATTGCTAACCGTTTTACTTCTAACATTAAAGGCCTGACTCAGGCTGCACGTAACGCCAAC
GACGGTATTTCTGTTGCGCAGACCACCGAAGGCGCGCTGTCCGAAATTAACAACAACTTA
CAGCGTGTGCGTGAGCTGACTGTTCAGGCGACCACCGGTACTAACTCTGAGTCTGACCTG
TCTTCTATCCAGGACGAAATCAAATCTCGCCTGGAAGAGATTGATCGTGTTTCAAGTCAG
ACTCAATTTAACGGCGTGAATGTTTTGGCTAAAGATGGGAAAATGAACATTCAGGTTGGG
GCAAATGATGGACAGACTATCACTATTGATCTGAAAAAGATCGATTCATCTACACTAAAC
CTCTCCAGTTTTGATGCTACAAACTTGGGCACCAGTGTTAAAGATGGGGCCACCATCAAT
AAGCAAGTGGCAGTAGGTGCTGGCGACTTTAAAGATAAAGCTTCAGGATCGTTAGGTACC
CTAAAATTAGTTGAGAAAGACGGTAAGTACTATGTAAATGACACTAAAAGTAGTAAGTAC
TACGATGCCGAAGTAGATACTAGTAAGGGTAAAATTAACTTCAACTCTACAAATGAAAGT
GGAACTACTCCTACTGCAGCGACGGAAGTAACTACTGTTGGCCGCGATGTAAAATTGGAT
GCTTCTGCACTTAAAGCCAACCAATCGCTTGTCGTGTATAAAGATAAAAGCGGCAATGAT
GCTTATATCATTCAGACCAAAGATGTAACAACTAATCAATCAACTTTCAATGCCGCTAAT
ATCAGTGATGCTGGTGTTTTATCTATTGGTGCATCTACAACCGCGCCAAGCAATTTAACA
GCTAACCCGCTTAAGGCTCTTGATGATGCAATTGCATCTGTTGATAAATTCCGCTCTTCT
CTCGGTGCCGTTCAGAACCGTCTGGATTCTGCCATTGCCAACCTGAACAACACCACTACC
AACCTGTCTGAAGCGCAGTCCCGTATTCAGGACGCTGACTATGCGACCGAAGTGTCCAAC
ATGTCGAAAGCGCAGATTATCCAGCAGGCCGGTAACTCCGTGCTGGCAAAAGCCAACCAG
GTACCGCAGCAGGTTCTGTCTCTGCTGCAGGGTTAA
```

Figure 16

```
AACAAATCTCAGTCTTCTCTGAGCTCCGCCAT
TGAACGTCTCTCTTCTGGCCTGCGTATTAACAGTGCTAAAGATGACGCAGCAGGTCAGGC
GATTGCTAACCGTTTTACAGCAAATATTAAAGGTCTGACTCAGGCTTCCCGTAACGCGAA
TGATGGTATTTCTGTTGCGCAGACCACTGAAGGTGCGCTGAATGAAATTAACAACAACCT
GCAGCGTGTACGTGAACTGACTGTTCAGGCAACTAACGGTACTAACTCTGACAGCGATCT
TTCTTCTATCCAGGCTGAAATTACTCAACGTCTGGAAGAAATTGACCGTGTATCTGAGCA
AACTCAGTTTAACGGCGTGAAAGTCCTTGCTGAAAATAATGAAATGAAAATTCAGGTTGG
TGCTAATGATGGTGAAACCATCACTATCAATCTGGCAAAAATTGATGCGAAAACTCTCGG
CCTGGACGGTTTTAATATCGATGGCGCGCAGAAAGCAACTGGCAGTGACCTGATTTCTAA
ATTTAAAGCGACAGGTACTGATAACTATGATGTTGGCGGTGATGCTTATACTGTTAACGT
AGATAGCGGAGCTGTTAAAGATACTACAGGGAATGATATTTTTGTTAGTGCAGCAGATGG
TTCACTGACAACTAAATCTGACACAAACATAGCTGGTACAGGGATTGATGCTACAGCACT
CGCAGCAGCGGCTAAGAATAAAGCACAGAATGATAAATTCACGTTTAATGGAGTTGAATT
CACAACAACAACTGCAGCGGATGGCAATGGGAATGGTGTATATTCTGCAGAAATTGATGG
TAAGTCAGTGACATTTACTGTGACAGATGCTGACAAAAAGCTTCTTTGATTACGAGTGA
GACAGTTTACAAAAATAGCGCTGGCCTTTATACGACAACCAAAGTTGATAACAAGGCTGC
CACACTTTCCGATCTTGATCTCAATGCAGCTAAGAAAACAGGAAGCACGTTAGTTGTTAA
CGGTGCAACTTACGATGTTAGTGCAGATGGTAAAACGATAACGGAGACTGCTTCTGGTAA
CAATAAAGTCATGTATCTGAGCAAATCAGAAGGTGGTAGCCCGATTCTGGTAAACGAAGA
TGCAGCAAAATCGTTGCAATCTACCACCAACCCGCTCGAAACTATCGACAAAGCATTGGC
TAAAGTTGACAATCTGCGTTCTGACCTCGGTGCAGTACAAAACCGTTTCGACTCTGCTAT
CACCAACCTTGGCAACACCGTAAACAACCTGTCTTCTGCCCGTAGCCGTATCGAAGATGC
TGACTACGCGACCGAAGTGTCTAACATGTCTCGTGCGCAGATCCTGCAACAAGCGGGTAC
CTCTGTTCTGGCGCAG
```

Figure 17

ATGGCACAAGTCATTAATACCAACAGCCTCTCGCTGATCA
CTCAAAATAATATCAACAAGAACCAGTCTGCGCTGTCGAGTTCTATCGAGCGTCTGTCTT
CTGGCTTGCGTATTAACAGCGCGAAGGATGACGCAGCGGGTCAGGCGATTGCTAACCGTT
TCACCTCTAACATTAAAGGCCTGACTCAGGCGGCCCGTAACGCCAACGACGGTATCTCCG
TTGCGCAGACCACCGAAGGCGCGCTGTCCGAAATCAACAACAACTTACAGCGTATCCGTG
AACTGACGGTTCAGGCTTCTACCGGGACTAACTCCGATTCGGATCTGGACTCCATTCAGG
ACGAAATCAAATCCCGTCTGGACGAAATTGACCGCGTATCTGGCCAGACCCAGTTCAACG
GCGTGAACGTACTGGCGAAAGACGGTTCAATGAAAATTCAGGTTGGTGCGAATGACGGCC
AGACTATCACGATTGATCTGAAGAAAATTGACTCAGATACGCTGGGGCTGAATGGTTTTA
ACGTGAATGGTTCCGGTACGATAGCCAATAAAGCGGCGACCATTAGCGACCTGACAGCAG
CGAAAATGGATGCTGCAACTAATACTATAACTACAACAAATAATGCGCTGACTGCATCAA
AGGCGCTTGATCAACTGAAAGATGGTGACACTGTTACTATCAAAGCAGATGCTGCTCAAA
CTGCCACGGTTTATACATACAATGCATCAGCTGGTAACTTCTCATTCAGTAATGTATCGA
ATAATACTTCAGCAAAAGCAGGTGATGTAGCAGCTAGCCTTCTCCCGCCGGCTGGGCAAA
CTGCTAGTGGTGTTTATAAAGCAGCAAGCGGTGAAGTGAACTTTGATGTTGATGCGAATG
GTAAAATCACAATCGGAGGACAGAAAGCATATTTAACTAGTGATGGTAACTTAACTACAA
ACGATGCTGGTGGTGCGACTGCGGCTACGCTTGATGGTTTATTCAAGAAAGCTGGTGATG
GTCAATCAATCGGGTTTAAGAAGACTGCATCAGTCACGATGGGGGGAACAACTTATAACT
TTAAAACGGGTGCTGATGCTGATGCTGCAACTGCTAACGCAGGGGTATCGTTCACTGATA
CAGCTAGCAAAGAAACCGTTTTAAATAAAGTGGCTACAGCTAAACAAGGCAAAGCAGTTG
CAGCTGACGGTGATACATCCGCAACAATTACCTATAAATCTGGCGTTCAGACGTATCAGG
CTGTATTTGCCGCAGGTGACGGTACTGCTAGCGCAAAATATGCCGATAAAGCTGACGTTT
CTAATGCAACAGCAACATACACTGATGCTGATGGTGAAATGACTACAATTGGTTCATACA
CCACGAAGTATTCAATCGATGCTAACAACGGCAAGGTAACTGTTGATTCTGGAACTGGTA
CGGGTAAATATGCGCCGAAAGTAGGGGCTGAAGTATATGTTAGTGCTAATGGTACTTTAA
CAACAGATGCAACTAGCGAAGGCACAGTAACAAAAGATCCACTGAAAGCTCTGGATGAAG
CTATCAGCTCCATCGACAAATTCCGTTCTTCCCTGGGTGCTATCCAGAACCGTCTGGATT
CCGCAGTCACCAACCTGAACAACACCACTACCAACCTGTCCGAAGCGCAGTCCCGTATTC
AGGACGCCGACTATGCGACCGAAGTGTCCAACATGTCGAAAGCGCAGATCATTCAGCAGG
CCGGTAACTCCGTGCTGGCAAAAGCCAACCAGGTACCGCAGCAGGTTCTGTCTCTGCTGC AGGGTTAA

Figure 18

```
ATGGCACAAGTCATTAATACCAACAGCCTCTCGCTGATCACTCAAAATA
ATATCAACAAGAACCAGTCTGCGCTGTCGAGTTCTATCGAGCGTCTGTCTTCTGGCTTGC
GTATTAACAGCGCGAAGGATGACGCCGCAGGTCAGGCGATTGCTAACCGTTTTACTTCTA
ACATTAAAGGCCTGACTCAGGCTGCACGTAACGCCAACGACGGTATTTCCGTTGCGCAGA
CCACTGAAGGTGCGCTGTCCGAAATCAACAACAACTTACAGCGTATTCGTGAGCTGACGG
TTCAGGCTTCTACCGGGACTAACTCCGATTCTGACCTGGACTCCATCCAGGACGAAATCA
AGTCTCGTCTGGACGAAATTGACCGCGTATCCGGTCAGACCCAGTTCAACGGCGTGAACG
TGCTGGCGAAAGACGGTTCGATGAAAATTCAGGTTGGTGCGAATGACGGCCAGACTATCA
CGATTGATCTGAAGAAAATTGACTCAGATACGCTGGGGCTGAGTGGGTTTAATGTGAATG
GTGGCGGGGCTGTTGCTAACACTGCTGCATCTAAAGCTGACTTGGTAGCTGCTAATGCAA
CTGTGGTAGGCAACAAATATACTGTGAGTGCGGGTTACGATGCTGCTAAAGCGTCTGATT
TGCTGGCTGGAGTTAGTGATGGTGATACTGTTCAGGCAACCATTAATAACGGCTTCGGAA
CGGCGGCTAGTGCAACGAATTACAAGTATGACAGTGCAAGTAAGTCTTACTCTTTTGATA
CCACAACGGCTTCAGCTGCCGATGTTCAGAAATATTTGACCCCGGGCGTTGGTGATACCG
CTAAGGGCACTATTACTATCGATGGTTCTGCACAGGATGTTCAGATCAGCAGTGATGGTA
AAATTACGTCAAGCAATGGAGATAAACTTTACATTGATACAACTGGGCGCTTAACGAAAA
ACGGCTTTAGTGCTTCTTTGACTGAGGCTAGTCTGTCCACACTTGCAGCCAATAATACCA
AAGCGACAACCATTGACATTGGCGGTACCTCTATCTCCTTTACCGGTAATAGTACTACGC
CGAACACTATTACTTATTCAGTAACAGGTGCAAAAGTTGATCAGGCAGCTTTCGATAAAG
CTGTATCAACCTCTGGAAACGATGTTGATTTCACTACCGCAGGTTATAGCGTCGACGGCG
CAACTGGCGCTGTAACAAAAGGTGTTGCTCCGGTTTATATTGATAACAACGGGGCGTTGA
CCACATCTGATACTGTAGATTTTTATCTACAGGATGATGGTTCAGTGACTAACGGCAGCG
GTAAGGCAGTTTATAAAGATGCTGACGGTAAATTGACGACAGATGCTGAAACTAAAGCTG
CAACCACCGCCGATCCCCTGAAAGCTCTGGACGAAGCCATCAGCTCCATCGACAAATTCC
GCTCCTCCCTCGGTGCGGTGCAGAACCGTCTGGATTCCGCGGTCACCAACCTGAACAACA
CCACTACCAACCTGTCTGAAGCGCAGTCCCGTATTCAGGACGCTGACTATGCGACCGAAG
TATCCAACATGTCGAAAGCGCAGATCATCCAGCAGGCCGGTAACTCCGTGCTGGCAAAAG
CTAACCAGGTACCACAGCAGGTTCTGTCTCTGCTGCAGGGTTAA
```

Figure 19

```
ATGGCACAAGTCATTAATACCAACAGC
CTCTCGCTGATCACTCAAAATAATATCAACAAGAACCAGTCTGCGCTGTCGAGTTCTATC
GAGCGTCTGTCTTCTGGCTTGCGTATTAACAGCGCGAAGGATGACGCCGCAGGTCAGGCG
ATTGCTAACCGTTTTACTTCTAACATTAAAGGCCTGACTCAGGCTGCACGTAACGCCAAC
GACGGTATTTCTGTTGCACAGACCACTGAAGGCGCGCTGTCCGAAATCAACAACAACTTA
CAGCGTGTGCGTGAACTGACCGTTCAGGCAACCACCGGTACCAACTCCCAGTCTGACCTG
GACTCTATCCAGGACGAAATTAAATCCCGTCTGGACGAAATTGATCGCGTATCCGGTCAG
ACCCAGTTCAACGGCGTGAACGTGCTGGCAAAAGACGGTTCCATGAAAATTCAGGTTGGC
GCGAACGATGGCCAGACCATCACTATCGACCTGAAGAAGATTGACTCTTCTACCTTGAAC
CTGACAGGTTTTAACGTTAACGGTTCTGGTTCTGTGGCGAATACTGCAGCAACTAAAGCT
GATTTAACCGCTGCTCAACTCTCTGCACCGGGTGCAGCAGACGCAAATGGTACAGTTACT
TATACTGTCAGTGCTGGTTATAAAGAATCCACTGCTGCAGATGTTATTGCTAGCATCAAA
GACGGCAGTGCTCCGACTTCTGCAATTACTGCAACCATTAATAATGGCTTCGGTGATTCC
AGTGCGCTGACTTCCAATGACTATACTTATGACCCAGCAAAAGGCGACTTCACTTACGAC
GTAGCTTCAAGCGCCAATAATACTGCTGCCCAGGTTCAGTCCTTCCTGACGCCGAAAGCA
GGTGATACCGCAAATCTGAAAGTAACCGTTGGTACGACATCGGTTGATGTCGTTCTGGCC
AGTGATGGTAAGATTACAGCAAAAGATGGTTCTGCATTATATATCGACAGTACAGGTAAC
CTGACTCAGAACAGTGCTGGCTTGACCTCTGCTAAACTGGCTACTCTGACTGGCCTTCAG
GGCTCTGGTGTTGCTTCAACCATCACTACTGAAGATGGCACTAATATTGATATTGCTGCT
AACGGTAATATTGGTCTGACCGGTGTTCGTATCAGTGCTGATTCTCTGCAGTCAGCGACT
AAATCTACGGGCTTTACTGTTGGTACTGGCGCTACAGGTCTGACCGTAGGTACTGATGGT
AAAGTGACTATCGGCGGGACTACTGCTCAGTCCTACACCAGCAAAGATGGTTCCCTGACT
ACTGATAACACCACTAAACTGTATCTGCAGAAAGATGGCTCTGTAACCAACGGTTCAGGT
AAAGCGGTCTATGTAGAAGCGGATGGTGATTTCACTACCGACGCTGCAACCAAAGCCGCA
ACCACCACCGATCCGCTGAAAGCCCTGGATGAGGCAATCAGCCAGATCGATAAGTTCCGT
TCATCCCTGGGTGCTATCCAGAACCGTCTGGATTCCGCGGTCACCAACCTGAACAACACC
ACTACCAACCTGTCTGAAGCGCAGTCCCGTATTCAGGACGCCGACTATGCGACCGAAGTG
TCCAACATGTCGAAAGCGCAGATCATTCAGCAGGCCGGTAACTCCGTGCTGGCAAAAGCC
AACCAGGTACCGCAACAGGTTCTGTCTCTGCTGCAGGGCTAA
```

Figure 20

ATGGCACAAGTCATTAATACCAACAGCCTCTCGCTGATCAC
TCAAAATAATATCAACAAGAACCAGTCTGCGCTGTCGAGTTCTATCGAGCGTCTGTCTTC
TGGCTTGCGTATTAACAGCGCGAAGGATGACGCCGCAGGTCAGGCGATTGCTAACCGTTT
TACTTCTAACATTAAAGGCCTGACTCAGGCTGCACGTAACGCCAACGACGGTATTTCTGT
TGCACAGACCACTGAAGGCGCGCTGTCCGAAATCAACAACAACTTACAGCGTGTGCGTGA
ACTGACCGTTCAGGCAACCACCGGTACCAACTCCCAGTCTGACCTGGACTCTATCCAGGA
CGAAATTAAATCCCGTCTGGACGAAATTGATCGCGTATCCGGTCAGACCCAGTTCAACGG
CGTGAACGTGCTGGCAAAAGACGGTTCCATGAAAATTCAGGTTGGCGCGAACGATGGCCA
GACCATCACTATCGACCTGAAGAAGATTGACTCTTCTACCTTGAACCTGACAGGTTTTAA
CGTTAACGGTTCTGGTTCTGTGGCGAATACTGCAGCAACTAAAGCTGATTTAACCGCTGC
TCAACTCTCTGCACCGGGTGCAGCAGACGCAAATGGTACAGTTACTTATACTGTCAGTGC
TGGTTATAAAGAATCCACTGCTGCAGATGTTATTGCTAGCATCAAAGACGGCAGTGCTCC
GACTTCTGCAATTACTGCAACCATTAATAATGGCTTCGGTGATTCCAGTGCGCTGACTTC
CAATGACTATACTTATGACCCAGCAAAGGCGACTTCACTTACGACGTAGCTTCAAGCGC
CAATAATACTGCTGCCCAGGTTCAGTCCTTCCTGACGCCGAAAGCAGGTGATACCGCAAA
TCTGAAAGTAACCGTTGGTACGACATCGGTTGATGTCGTTCTGGCCAGTGATGGTAAGAT
TACAGCAAAAGATGGTTCTGCATTATATATCGACAGTACAGGTAACCTGACTCAGAACAG
TGCTGGCTTGACCTCTGCTAAACTGGCTACTCTGACTGGCCTTCAGGGCTCTGGTGTTGC
TTCAACCATCACTACTGAAGATGGCACTAATATTGATATTGCTGCTAACGGTAATATTGG
TCTGACCGGTGTTCGTATCAGTGCTGATTCTCTGCAGTCAGCGACTAAATCTACGGGCTT
TACTGTTGGTACTGGCGCTACAGGTCTGACCGTAGGTACTGATGGTAAAGTGACTATCGG
CGGGACTACTGCTCAGTCCTACACCAGCAAAGATGGTTCCCTGACTACTGATAACACCAC
TAAACTGTATCTGCAGAAAGATGGCTCTGTAACCAACGGTTCAGGTAAAGCGGTCTATGT
AGAAGCGGATGGTGATTTCACTACCGACGCTGCAACCAAAGCCGCAACCACCACCGATCC
GCTGAAAGCCCTGGATGAGGCAATCAGCCAGATCGATAAGTTCCGTTCATCCCTGGGTGC
TATCCAGAACCGTCTGGATTCCGCGGTCACCAACCTGAACAACACCACTACCAACCTGTC
TGAAGCGCAGTCCCGTATTCAGGACGCCGACTATGCGACCGAAGTGTCCAACATGTCGAA
AGCGCAGATCATTCAGCAGGCCGGTAACTCCGTGCTGGCAAAAGCCAACCAGGTACCGCA
ACAGGTTCTGTCTCTGCTGCAGGGCTAA

Figure 21

```
GCGCTGTCGACTTCTATCGAGCGCCTCTCTTCTGGTCTGCGTATTAACAGCGCTAAA
GATGACGCTGCGGGCCAGGCGATTGCTAACCGCTTCACTTCTAACATCAAAGGTCTGACT
CAGGCCGCACGTAACGCCAACGACGGTATTTCTCTGGCGCAGACGGCTGAAGGCGCGCTG
TCAGAGATTAACAACAACTTGCAGCGTATTCGTGAACTGACCGTTCAGGCCTCTACCGGC
ACGAACTCTGATTCCGACCTGTCTTCTATTCAGGACGAAATCAAATCCCGTCTTGATGAA
ATTGACCGTGTATCTGGTCAGACCCAGTTCAACGGTGTGAACGTGCTGTCGAAAAACGAT
TCGATGAAGATTCAGATTGGTGCCAATGATAACCAGACGATCAGCATTGGCTTGCAACAA
ATCGACAGTACCACTTTGAATCTGAAAGGATTTACCGTGTCCGGCATGGCGGATTTCAGC
GCGGCGAAACTGACGGCTGCTGATGGTACAGCAATTGCTGCTGCGGATGTCAAGGATGCT
GGGGGTAAACAAGTCAATTTACTGTCTTACACTGACACCGCGTCTAACAGTACTAAATAT
GCGGTCGTTGATTCTGCAACCGGTAAATACATGGCAGCCACTGTAGTCATTACCAGTACG
GCGGCGGCGGTAACTGTTGGTGCAACGGAAGTGGCGGGAGCCGCTACAGCCGAACCGTTA
AAAGCACTGGATGCCGCAATCGCTAAAGTCGACAAATTCCGCTCCTCCCTCGGTGCCGTT
CAAAACCGTCTGGATTCTGCGGTCACCAACCTGAACAACACCACCACCAACCTGTCTGAA
GCGCAGTCCCGTATTCAGGACGCCGACTATGCGACCGAAGTGTCCAACATGTCGAAAGCG
CAGATTATCCAGCAGGCG
```

Figure 22

```
ATGGCACAAGTCATTAATACCAACAGCCTCTCGCTGATCACTCAAAATA
ATATCAACAAGAACCAGTCTGCGCTGTCGAGTTCTATCGAGCGTCTGTCTTCTGGCTTGC
GTATTAACAGCGCGAAGGATGACGCCGCAGGTCAGGCGATTGCTAACCGTTTTACTTCTA
ATATTAAAGGCCTGACTCAGGCTGCACGTAACGCCAATGACGGTATTTCTGTTGCACAGA
CCACTGAAGGCGCGCTGTCCGAAATCAACAACAACTTACAGCGTATTCGTGAACTGACGG
TTCAGGCCACTACAGGGACTAACTCCGATTCTGACCTGGACTCCATCCAGGACGAAATCA
AATCTCGTCTGGACGAAATTGACCGCGTATCCGGTCAGACCCAGTTCAACGGCGTGAACG
TGCTGTCCAAAGATGGTTCAATGAAAATTCAGGTCGGCGCAAATGATGGTGAAACCATCA
CGATTGATCTGAAGAAAATTGACTCTGATACGCTGAATCTGGCTGGTTTTAACGTGAATG
GCGAAGGTGAAACAGCCAATACTGCTGCAACACTTAAAGATATGGTTGGTTTAAAACTCG
ATAATACGGGGGTCACTACAGCTGGAGTTAATAGATATATTGCTGACAAAGCCGTCGCAA
GTAGCACGGATATTTGAATGCGGTAGCTGGTGTTGATGGCAGTAAAGTTTCCACGGAGG
CAGATGTTGGTTTTGGTGCAGCTGCCCCTGGTACGCCAGTGGAATATACTTATCATAAAG
ATACTAACACATATACGGCTTCTGCTTCAGTTGATGCGACTCAACTGGCGGCATTCCTGA
ATCCTGAAGCGGGTGGTACCACTGCTGCAACAGTAAGTATTGGCAACGGTACAACAGCTC
AAGAGCAAAAAGTCATTATTGCTAAAGATGGTTCTTTAACTGCTGCTGATGACGGTGCCG
CTCTCTATCTTGATGATACTGGTAACTTAAGTAAAACTAACGCAGGCACTGATACTCAAG
CTAAACTGTCTGACTTAATGGCAAACAATGCTAATGCCAAAACAGTCATTACAACAGATA
AAGGTACATTTACTGCTAATACGACAAAGTTTGATGGGGTAGATATTTCTGTTGATGCTT
CAACGTTTGCTAACGCCGTTAAAAATGAGACTTACACTGCAACTGTTGGTGTAACTTTAC
CTGCGACATATACAGTCAATAATGGCACTGCTGCATCAGCGTATTTAGTCGATGGAAAAG
TGAGCAAAACTCCTGCCGAGTATTTTGCTCAAGCTGATGGCACTATTACTAGTGGTGAAA
ATGCGGCTACCAGTAAAGCTATCTATGTAAGTGCCAATGGTAACTTAACGACTAATACAA
CTAGTGAATCTGAAGCTACTACCAACCCGCTGGCAGCATTGGATGACGCTATCGCGTCTA
TCGACAAATTCCGTTCTTCCCTGGGTGCTATCCAGAACCGTCTGGATTCCGCAGTCACCA
ACCTGAACAACACCACTACCAACCTGTCTGAAGCGCAGTCCCGTATTCAGGACGCCGACT
ATGCGACCGAAGTGTCCAACATGTCGAAAGCGCAGATCATTCAGCAGGCCGGTAACTCCG
TGCTGGCAAAAGCCAACCAGGTACCGCAGCAGGTTCTGTCTCTGCTGCAGGGTTAA
```

Figure 23

```
ATGGCACAAGTCATTAATACCAACAGCCTCTCGCTGATCACTCAAAATAATAT
CAACAAGAACCAGTCTGCGCTGTCGAGTTCTATCGAGCGTCTGTCTTCTGGCTTGCGTAT
TAACAGCGCGAAGGATGACGCCGCAGGTCAGGCGATTGCTAACCGTTTTACTTCTAACAT
TAAAGGCCTGACTCAGGCTGCACGTAACGCCAACGACGGTATTTCTGTTGCGCAGACCAC
TGAAGGCGCGCTGTCCGAAATTAACAACAACTTACAGCGTATTCGTGAACTGACGGTTCA
GGCGACGACCGGAACTAACTCCACCTCTGACCTGGACTCCATCCAGGACGAAATCAAATC
CCGTCTTGACGAAATTGACCGCGTATCTGGTCAGACCCAGTTCAACGGCGTGAACGTGCT
GTCTAAAGATGGCTCGATGAAAATTCAGGTCGGCGCGAACGATGGCGAAACGATTACTAT
TGATCTGAAGAAAATTGACTCTGATACGCTGAATCTGGCTGGTTTTAACGTTAACGGTAA
AGGTTCTGTAGCGAATACCGCTGCGACTACAGATAATCTGACATTGGCTGGTTTTACAGC
GGGTACTAAAGCTGCTGATGGCACCGTAACTTATAGCAAAAATGTCCAGTTTGCCGCCGC
GACTGCAAGCAATGTACTGGCTGCTGCTAAAGATGGCGACGAAATTACGTTCGCTGGTAA
TAACGGCACAGGTATAGCTGCAACTGGGGGGACTTATACTTATCATAAGGACTCTAACTC
ATACAGCTTTAGCGCAACGGCTGCATCTAAAGATTCTCTGTTGAGCACACTGGCACCAAA
CGCTGGCGATACATTTACCGCTAAAGTGACTATTGGTTCTAAATCGCAAGAAGTTAACGT
TAGCAAAGATGGTACGATTACATCCAGCGATGGTAAGGCGCTGTATTTAGATGAGAAGGG
CAACCTGACCCAAACAGGTAGTGGCACAACCAAAGCTGCAACCTGGGATAACCTGATGGC
CAATACAGATACTACAGGCAAAGATGCCTATGGTAACTCTGCGGCAGCAGCTGTTGGGAC
AGTAATCGAAGCAAAAGGAATGACCATCACTTCTGCTGGTGGTAATGCTCAGGTGTTAAA
AGACGCGGCTTATAATGCCGCATATGCGACCTCAATTACTACTGGTACTCCGGGTGATGC
GGGAGCCGCGGGAGCCGCTGCAACTGCGGGTAATGCCGCGGTGGGAGCGCTGGGCGCAAC
GGCAGTTGATAATACCACGGCAGATGTTGCCGATATCTCTATCTCAGCTTCGCAAATGGC
GAGCATCCTTCAGGATAAAGATTTCACCTTAAGTGATGGTAGTGATACTTACAACGTGAC
CAGCAATGCTGTCACTATCAATGGCAAAGCAGCAAACATTGATGACAGCGGCGCAATCAC
AGACCAAACCAGTAAAGTTGTCAATTATTTCGCTCATACTAACGGTAGCGTGACTAACGA
TACAGGCTCCACTATTTATGCGACAGAAGATGGTAGCCTGACCACCGATGCAGCAACCAA
AGCCGAAACCACCGCCGATCCCCTGAAAGCTCTGGACGAAGCCATCAGCTCCATCGACAA
ATTCCGCTCCTCCCTCGGTGCGGTGCAAAACCGTCTGGATTCCGCGGTCACCAACCTGAA
CAACACCACCACCAACCTGTCTGAAGCGCAGTCCCGTATTCAGGACGCCGACTATGCGAC
CGAAGTGTCCAACATGTCGAAAGCGCAGATTATCCAGCAGGCCGGTAACTCCGTGCTGGC
AAAAGCTAACCAGGTACCACAGCAGGTTCTGTCTCTGCTGCAGGGTTAA
```

Figure 24

```
ATGGCACAAGTCATTAATACCAACAGCCTCTCGCTG
ATCACTCAAAATAATATCAACAAGAACCAGTCTGCGCTGTCGAGTTCTATCGAGCGTCTG
TCTTCTGGCTTGCGTATTAACAGCGCGAAGGATGACGCCGCAGGTCAGGCGATTGCTAAC
CGTTTTACTTCTAACATTAAAGGCCTGACTCAGGCGGCCCGTAACGCCAACGACGGTATT
TCTGTTGCGCAGACCACCGAAGGCGCGCTGTCCGAAATTAACAACAACTTACAGCGTGTG
CGTGAGCTGACTGTTCAGGCGACCACCGGTACCAACTCCCAGTCTGATCTGGACTCTATC
CAGGACGAAATCAAATCCCGTCTGGACGAAATTGACCGCGTATCCGGTCAGACCCAGTTC
AACGGCGTGAACGTGCTGGCAAAAGACGGTTCCATGAAAATTCAGGTTGGCGCGAATGAT
GGCCAGACCATCACTATCGACCTGAAGAAGATTGACTCTTCTACGTTGAAACTGACTGGT
TTTAACGTGAATGGTTCTGGTTCTGTGGCGAATACTGCGGCGACTAAAGCGGATTTGGCT
GCTGCTGCAATTGGTACCCCTGGGGCAGCAGATTCTACAGGTGCCATTGCTTACACAGTA
AGTGCTGGGCTGACTAAAACTACAGCCGCAGATGTACTGTCTAGCCTCGCTGATGGTACG
ACTATTACAGCCACAGGCGTGAAAAATGGCTTTGCTGCAGGAGCCACTTCCAATGCCTAT
AAACTTAACAAAGATAATAATACATTTACTTATGACACGACTGCTACGACAGCTGAGCTG
CAGTCTTACCTGACTCCGAAAGCGGGCGACACTGCAACATTCAGTGTTGAAATTGGTGGT
ACTACACAAGACGTCGTGCTGTCCAGTGATGGCAAACTCACTGCTAAGGATGGCTCTAAG
CTTTACATTGATACAACTGGTAATTTAACTCAGAATGGTGGTAATAACGGTGTTGGAACA
CTCGCGGAAGCGACTCTGAGTGGTTTAGCTCTGAACAAAAATGGTTTAACGGCTGTTAAA
TCCACAATTACTACAGCTGATAACACTTCGATTGTACTGAATGGTTCAAGCGATGGTACT
GGTAATGCTGGTACTGAAGGTACGATTGCTGTTACAGGCGCTGTAATTAGTTCAGCTGCT
CTGCAATCTGCAAGCAAAACGACTGGTTTCACTGTTGGTACAGTAGACACAGCTGGTTAT
ATCTCTGTAGGTACTGATGGGAGTGTTCAGGCATATGATGCTGCGACTTCTGGCAACAAA
GCTTCTTACACCAACACTGACGGTACACTGACTACTGATAACACCACTAAACTGTATCTG
CAGAAAGATGGCTCTGTAACCAACGGTTCAGGTAAAGCGGTCTATGTAGAAGCGGATGGT
GATTTCACTACCGACGCTGCAACCAAAGCCGCAACCACCACCGATCCGCTGGCCGCTCTG
GATGACGCAATCAGCCAGATCGACAAGTTCCGTTCATCCTTGGGTGCTATCCAGAACCGT
CTGGATTCTGCAGTCACCAACCTGAACAACACCACCACCAACCTGTCTGAAGCGCAGTCC
CGTATTCAGGACGCCGACTATGCGACCGAAGTGTCCAATATGTCGAAAGCGCAGATCATC
CAGCAGGCCGGTAACTCCGTGCTGGCAAAAGCCAACCAGGTACCGCAGCAGGTTCTGTCT
CTGCTGCAGGGTTAA
```

Figure 25

```
AACAAATCTCAGTCTTCTCTGAGCTCCGCCATTGAA
CGTCTCTCTTCTGGCCTGCGTATTAACAGTGCTAAAGATGACGCAGCAGGTCAGGCGATT
GCTAACCGTTTTACAGCAAATATTAAAGGTCTGACTCAGGCTTCCCGTAACGCGAATGAT
GGTATTTCTGTTGCGCAGACCACTGAAGGTGCGCTGAATGAAATTAACAACAACCTGCAG
CGTATTCGTGAACTTTCTGTTCAGGCAACTAACGGTACTAACTCTGACAGCGATCTTTCT
TCTATCCAGGCTGAAATTACTCAACGTCTGGAAGAAATTGACCGTGTATCTGAGCAAACT
CAGTTTAACGGCGTGAAAGTCCTTGCTGAAAATAATGAAATGAAAATTCAGGTTGGTGCT
AATGATGGTGAAACCATCACTATCAATCTGGCAAAAATTGATGCGAAAACTCTCGGCCTG
GACGGTTTTAATATCGATGGCGCGCAGAAAGCAACCGGCAGTGACCTGATTTCTAAATTT
AAAGCGACAGGTACTGATAATTATCAAATTAACGGTACTGATAACTATACTGTTAATGTA
GATAGTGGCGTAGTACAGGATAAAGATGGCAAACAAGTTTATGTGAGTACTGCGGATGGT
TCACTTACGACCAGCAGTGATACTCAATTCAAGATTGATGCAACTAAGCTTGCAGTGGCT
GCTAAAGATTTAGCTCAAGGGAATAAGATTGTCTACGAAGGTATCGAATTTACAAATACC
GGCACTGTCGCTATAGATGCCAAAGGTAATGGTAAATTAACCGCCAATGTTGATGGTAAG
GCTGTTGAATTCACTATTTCGGGGAGTACTGATACATCAGGTACTAGTGCAACCGTTGCC
CCTACGACAGCCCTATACAAAAATAGTGCAGGGCAATTGACTGCAACAAAAGTTGAAAAT
AAAGCAGCGACACTATCTGATCTTGATCTGAACGCTGCCAAGAAAACAGGAAGCACGTTA
GTTGTTAACGGTGCAACTTACGATGTTAGTGCAGATGGTAAAACGATAACGGAGACTGCT
TCTGGTAACAATAAAGTCATGTATCTGAGCAAATCAGAAGGTGGTAGCCCGATTCTGGTA
AACGAAGATGCAGCAAAATCGTTGCAATCTACCACCAACCCGCTCGAAACTATCGACAAA
GCATTGGCTAAAGTTGACAATCTGCGTTCTGACCTCGGTGCAGTACAAAACCGTTTCGAC
TCTGCCATCACCAACCTTGGCAACACCGTAAACAACCTGTCTTCTGCCCGTAGCCGTATC
GAAGATGCTGACTACGCGACCGAAGTGTCTAACATGTCTCGTGCGCAGATCCTGCAACAA
GCGGGTACCTCTGTTCTGGCACAG
```

Figure 26

```
ATGGCACAAGTCATTAATACCAACAGCCTCTCGCTGATCACTCAAAATA
ATATCAACAAGAACCAGTCTGCGCTGTCGAGTTCTATCGAGCGTCTGTCTTCTGGCTTGC
GTATTAACAGCGCGAAGGATGACGCAGCGGGTCAGGCGATTGCTAACCGTTTTACTTCTA
ACATTAAAGGCCTGACTCAGGCGGCACGTAACGCCAACGACGGTATCTCTCTGGCGCAGA
CCACCGAAGGTGCGCTGTCTGAAATCAACAACAACTTACAGCGTGTACGTGAACTGACCG
TTCAGGCAACCACCGGTACTAACTCCGACTCCGACCTGGCTTCTATTCAGGACGAAATCA
AATCCCGTCTGGATGAAATTGACCGCGTATCTGGTCAGACTCAGTTCAACGGCGTGAACG
TGCTGGCAAAAGACGGTTCCATGAAAATTCAGGTAGGTGCTAACGACGGCCAGACTATCA
CTATTGACCTGAAAAAAATCGACTCTGATACTCTGGGCCTGAATGGTTTTAACGTGAATG
GTTCTGGGACGATTACCAACAAAGCAGCAACTGTCAGTGATGTTACTCGCGCAGGCGGTA
CATTGGTGAATGGTGCCTATGATATAAAAACCACTAACACAGCGCTGACTACAACTGATG
CCTTCGCGAAATTGAATGATGGTGATGTTGTTACTATCAATAATGGTAAGGATACTGCCT
ATAAATATAATGCTGCTACAGGTGGGTTTACGACGGATGTCTCCATCTCCGGGGATCCTA
CCGCTGCTGACGCTACTGCTAATAAAACTGCCCGTGATGCACTTGCGGCGTCTTTACATG
CTGAGCCGGGTAAAACTGTTAATGGTTCTTGGACTACGAATGATGGTACGGTAAAATTTG
ATACCGATGCCGATGGTAAGATTTCTATTGGTGGTGTTGCTGCTTATGTAGATGCAGCAG
GCAACCTGACCACTAACGCAGCAGGTATGACGACTCAAGCAACAACTACCGATTTGGTTA
CTGCTGCTGCATCTGCTACTGGTAAGGGTGGATCCCTGACCTTTGGTGACACGACGTATA
AAATTGGTCAGGGTACGGCTGGGGTTGATCCTGATGACGCTTCAGATGATGTACTGGGCA
CCATTTCTTACTCTAAATCAGTAAGCAAGGATGTTGTTCTTGCTGATACTAAAGCAACTG
GTAACACGACAACAGTTGATTTCAACTCCGGTATCATGACTTCAAAGGTTAGTTTCGATG
CAGGTACATCAACTGATACATTCAAAGATGCAGATGGTGCTATCACCAAAACTAAAGAAT
ACACCACTTCTTATGCTGTAAATAAAGATACTGGTGAAGTTACCGTTGCTGATTATGCTG
CGGTAGATAGCGCCGATAAGGCTGTTGATGATACTAAATATAAACCGACTATCGGCGCGA
CAGTTAACCTGAATTCTGCAGGTAAATTGACCACTGATACCACCAGTGCAGGCACAGCAA
CCAAAGATCCTCTGGCTGCCCTGGACGCTGCTATCAGCTCCATCGACAAATTCCGTTCAT
CCCTGGGTGCTATCCAGAACCGTCTGGATTCCGCAGTCACCAACCTGAACAACACCACTA
CCAACCTGTCCGAAGCGCAGTCCCGTATTCAGGACGCCGACTATGCGACCGAAGTGTCCA
ACATGTCGAAAGCGCAGATTATCCAGCAGGCCGGTAACTCCGTGCTGGCAAAAGCCAACC
AGGTACCGCAGCAGGTTCTGTCTCTGCTACAGGGTTAA
```

Figure 27

```
AACAAAAACCAGTCTGCGCTGTCGACTTCTATC
GAGCGCCTTTCTTCTGGTCTGCGTATTAACAGCGCTAAAGATGACGCTGCGGGCCAGGCG
ATTGCTAACCGCTTCACTTCTAACATCAAAGGTCTGACTCAGGCCGCACGTAACGCCAAC
GACGGTATTTCTCTGGCGCAGACCACTGAAGGCGCGCTGTCTGAGATTAACAACAACTTG
CAGCGTGTGCGTGAGTTGACTGTACAGGCGACGACCGGGACTAACTCTGATTCTGACCTG
TCTTCTATCCAGGATGAAATCAAATCCCGTTTAAGCGAAATTGACCGTGTATCTGGTCAG
ACTCAGTTTAACGGCGTGAACGTACTGGCTAAGAATGACACCCTGTCTATTCAGGTAGGT
GCAAATGACGGTCAGACTATCAATATTGACCTGCAGCAAATCGATTCTCATACACTGGGT
CTGGATGGTTTCAGCGTTAAAAATAATGATGCAGTGAAAACCAGTGCTGCCGTGAATACT
CTTGGGGGGGGGCAGGTTCTGTTGCTGTCGACTTCGCAACAACCAGTTTGACTGCTATC
ACTGGTCTCGGTAGCGGTGCTATCAGCGAAATTGCTAAAGACGATAATGGTGATTACTAC
GCGCATGTCACAGGGACTACGGGTAATACTGCTGATGGTTACTATGCTGTCGATATCGAC
AAGGCTACCGGTGAGGTCGCTCTGAAAGATGGTAACGTAGATACACCGACAGGTACGCCA
ACGACGACAAGCACATATGACTTCACAGACGCTGGTCAAACCGTTTCCTTTGGCACTGAT
GCTGCAACAGCCGGTATCAGCACTGGTGCTTCTCTCGTTAAACTTCAGGATGAGAAAGGC
AATGATACTGCTACTTATGCAATCAAAGCACAAGATGGCAGCCTGTATGCCGCCAACGTT
GATGAGGCTACCGGTAAAGTCACTGTCAAAACCGCCAGCTATACTGATGCTGACGGCAAA
GCAGTGACCGATGCCGCTGTAAAACTGGGTGGTGACAATGGCACAACCGAAATTGTTGTC
GATGCTGCGTCAGGTAAAACTTACGATGCTGGTGCACTGCAAAACGTTGATCTCTCCAGT
GCAACCAACACGGTAACCGCAATCCCGAACGGTAAAACCACGTCTCCGCTGGCTGCCCTT
GACGACGCAATCAGCCAGATCGACAAATTCCGCTCCTCCCTCGGTGCGGTGCAGAACCGT
CTGGATTCCGCGGTCACCAACCTGAACAACACCACTACCAACCTGTCTGAAGCGCAGTCC
CGTATTCAGGACGCTGACTATGCGACCGAAGTATCCAACATGTCGAAAGCGCAGATCATC
CAGCAGGCAGGTAACTCCGTGCTGTCCAAA
```

Figure 28

```
GCGCTGTCGACTTCTATCGAGCGCCTCTCTTCTGGTCTGCGCATTAACAGCGCTAAAG
ATGACGCTGCGGGCCAAGCGATTGCTAACCGCTTCACTTCTAACATCAAAGGTCTGACTC
AGGCCGCACGTAACGCCAACGACGGTATTTCTCTGGCGCAGACCACTGAAGGCGCACTGT
CTGAAATCAACAACAACTTGCAGCGTGTTCGTGAACTGACCGTTCAGGCCACTACCGGTA
CTAACTCTGATTCTGACCTGTCTTCAATACAGGACGAAATCAAATCCCGTCTCGATGAAA
TTGACCGCGTATCCGGTCAGACTCAGTTCAACGGCGTTAATGTTCTTTCCAAAGATGGTT
CAATGAAAATTCAGGTTGGTGCGAATGATGGTCAAACTATCTCCATCGATCTGAAGAAAA
TTGATTCTTCAACTTTGGGGCTGAATGGCTTCTCAGTTTCTAAAAACTCTCTTAATGTCA
GCAATGCTATCACATCTATCCCGCAAGCCGCTAGCAATGAACCTGTTGATGTTAACTTCG
GTGATACTGATGAGTCTGCAGCAATCGCAGCCAAATTGGGGGTTTCCGATACGTCAAGCC
TGTCGCTGCACAACATCCTTGATAAAGATGGTAAGGCAACAGCTGATTATGTTGTTCAGT
CAGGTAAAGACTTCTATGCTGCTTCTGTTAATGCCGCTTCAGGTAAAGTAACCTTAAACA
CCATTGATGTTACTTATGATGATTATGCGAACGGTGTTGACGATGCCAAGCAAACAGGTC
AGCTGATCAAAGTTTCAGCAGATAAAGACGGCGCAGCTCAAGGTTTTGTCACACTTCAAG
GCAAAAACTATTCTGCTGGTGATGCGGCAGACATTCTTAAGAATGGAGCAACAGCTCTTA
AGTTAACTGATCTGAATTTAAGTGATGTTACTGATACTAATGGTAAGGTAACCACAACTG
CGACTGAGCAATTTGAAGGTGCTTCAACTGAGGATCCGCTGGCGCTTCTGGATAAAGCTA
TTGCATCAGTCGACAAATTCCGGTCTTCTCTAGGTGCCGTGCAGAACCGTCTCGATTCCG
CTATCACCAACCTGAACAACACCACCACCAACCTGTCTGAAGCGCAGTCCCGTATTCAGG
ACGCCGACTATGCGACCGAAGTGTCCAACATGTCGAAAGCGCAGATCATCCAGCAGGCA
```

Figure 29

```
ATGGCACAAGTCATTAATACCAACAGCCTCTCG
CTGATCACTCAAAATAATATCAACAAGAACCAGTCTGCGCTGTCGAGTTCTATCGAGCGT
CTGTCTTCTGGCTTGCGTATTAACAGCGCGAAGGATGACGCCGCAGGTCAGGCGATTGCT
AACCGTTTTACTTCTAACATTAAAGGCCTGACTCAGGCTGCACGTAACGCCAACGACGGT
ATTTCTGTTGCACAGACCACTGAAGGCGCGCTGTCCGAAATCAACAACAACTTACAGCGT
ATTCGTGAACTGACGGTTCAGGCCACTACAGGGACTAACTCCGATTCTGACCTGGACTCC
ATCCAGGACGAAATCAAATCTCGTCTGGACGAAATTGACCGCGTATCTGGTCAGACCCAG
TTCAACGGCGTGAACGTGCTGTCTAAAGATGGCTCGATGAAAATTCAGGTCGGCGCGAAC
GATGGCGAAACGATTACTATTGATCTGAAGAAAATTGACTCTGATACGCTAAATCTGGCT
GGTTTTAACGTGAATGGTGCTGGCTCTGTTGATAATGCCAAGGCGACTGGCAAAGATCTT
ACTGATGCTGGTTTTACGGCAAGCGCAGCTGATGCTAATGGCAAAATCACTTATACCAAA
GACACCGTTACTAAATTCGACAAAGCGACAGCGGCTGATGTATTGGGCAAAGCGGCTGCT
GGCGATAGCATTACCTATGCGGGCACTGATACTGGCTTAGGAGTCGCTGCTGATGCCTCG
ACTTACACCTACAATGCAGCCAATAAGTCTTACACTTTTGATGCTACTGGTGTTGCCAAG
GCGGATGCTGGAACGGCACTGAAAGGGTACTTAGGCGCATCTAACACCGGTAAAATTAAT
ATCGGTGGTACCGAGCAAGAAGTTAACATTGCCAAAGATGGCTCCATCACCGATACCAAT
GGCGATGCGCTGTATCTCGATAGTACCGGCAACTTAACCAAAAATACCGCGAATTTGGGG
GCTGCTGATAAAGCAACTGTAGATAAACTGTTTGCTGGTGCTCAGGATGCAACGATCACC
TTCGATAGCGGCATGACAGCTAAATTCGATCAAACTGCTGGTACCGTTGATTTCAAAGGC
GCGTCTATTTCTGCTGATGCAATGGCATCAACCTTAAATAATGGTTCCTATACAGCCAAC
GTAGGTGGTAAGGCTTATGCCGTAACCGCTGGCGCAGTTCAGACAGGTGGCGCAGATGTG
TATAAAGATACCACTGGCGCACTGACGACTGAAGATGACGAAACCGTTACCGCGACCTAC
TACGGTTTTGCTGATGGTAAAGTTTCTGACGGTGAAGGTTCTACTGTCTATAAAGCTGCT
GATGGTTCCATCACTAAAGATGCGACTACCAAGTCTGAAGCAACCACTGACCCTCTGAAA
GCCCTTGACGACGCAATCAGCCAGATCGACAAATTCCGCTCCTCCCTCGGTGCCGTTCAA
AACCGTCTGGATTCCGCCGTCACCAACCTGAACAACACCACTACCAACCTGTCTGAAGCG
CAGTCCCGTATTCAGGACGCCGACTATGCGACCGAAGTGTCCAACATGTCGAAAGCGCAG
ATCATTCAGCAGGCCGGTAACTCCGTGCTGGCAAAAGCCAACCAGGTACCGCAGCAGGTT
CTGTCTCTGCTGCAGGGTTAA
```

Figure 30

```
AACAAATCTCAGTCTTCTCTTAGCTCTGCTATTGA
GCGTCTCTCTTCTGGCCTGCGTATTAACAGTGCTAAAGATGACGCAGCAGGTCAGGCGAT
TGCTAACCGTTTTACGGCAAATATTAAAGGTCTGACTCAGGCTTCCCGTAACGCGAATGA
TGGTATTTCTGTTGCGCAGACTACTGAAGGTGCGCTGAATGAAATTAACAACAACCTGCA
GCGTGTACGTGAACTGACTGTTCAGGCAACTAACGGTACTAACTCTGACAGCGATCTTTC
TTCTATTCAGGCAGAAATTACTCAACGTCTGGAAGAAATTGACCGTGTATCTGAGCAAAC
TCAGTTTAACGGCGTGAAAGTCCTTGCCGAAAATAATGAAATGAAAATTCAGGTTGGTGC
TAATGATGGGGAAACCATCACTATCAATCTGGCAAAAATTGATGCGAAAACTCTCGGCCT
GGACGGCTTTAATATCGATGGCGCGCAGAAAGCAACTGGCAGTGACCTGATTTCTAAATT
TAAAGCGACAGGTACTGATAATTATCAAATTAACGGTACTGATAACTATACTGTTAATGT
AGATAGTGGAGCAGTTCAAAATGAGGATGGTGACGCAATTTTTGTTAGCGCTACCGATGG
TTCTCTGACTACTAAGAGTGATACAAAAGTCGGTGGTACAGGTATTGATGCGACTGGGCT
TGCAAAAGCCGCAGTTTCTTTAGCTAAAGATGCCTCAATTAAATACCAAGGTATTACTTT
CACCAACAAAGGCACTGATGCATTTGATGGCAGTGGTAACGGCACTCTAACCGCTAATAT
TGATGGCAAAGATGTAACCTTTACTATTGATGCGACAGGGAAGGACGCAACATTAAAAAC
GTCTGATCCTGTTTACAAAAATAGTGCAGGTCAGTTCACTACAACTAAGGTTGAAAACAA
AGCCGCTACAGCATCGGATCTGGACTTAAATAACGCTAAAAAAGTGGGTAGTTCTTTAGT
TGTAAATGGCGCTGATTATGAAGTTAGCGCTGATGGTAAGACAGTAACTGGGCTTGGCAA
AACTATGTATCTGAGCAAATCAGAAGGTGGTAGCCCGATTCTGGTAAAAGAAGATGCAGC
AAAATCGTTGCAATCTACTACCAACCCGCTCGAAACCATCGACAAGGCATTGGCTAAAGT
TGACAATCTGCGTTCTGACCTCGGTGCAGTACAAAACCGTTTCGACTCTGCTATCACCAA
CCTTGGCAACACCGTAAACAACCTGTCTTCTGCCCGTAGCCGTATCGAAGATGCTGACTA
CGCGACCGAAGTGTCTAACATGTCTCGTGCGCAGATCCTGCAACAAGCGGGTACCTCTGT TCTGGCGCAG
```

Figure 31

```
ATGGCACAAGTCATTAATACCAACAGCCTCTCGCTGATCACTCAAAATA
ATATCAACAAGAACCAGTCTGCGCTGTCGAGTTCTATCGAGCGTCTGTCTTCTGGCTTGC
GTATTAACAGCGCGAAGGATGACGCCGCAGGTCAGGCGATTGCTAACCGTTTTACTTCTA
ACATTAAAGGCCTGACTCAGGCTGCACGTAACGCCAACGATGGTATTTCTGTTGCACAGA
CCACTGAAGGCGCGCTGTCCGAAATCAACAACAACTTACAGCGTATCCGTGAACTGACGG
TTCAGGCTTCTACCGGGACTAACTCCGATTCGGATCTGGACTCCATTCAGGACGAAATCA
AATCCCGTCTGGACGAAATTGACCGCGTATCTGGCCAGACCCAGTTCAACGGCGTGAACG
TACTGGCGAAAGACGGTTCAATGAAAATTCAGGTTGGTGCGAATGACGGCCAGACTATCA
CGATTGATCTGAAGAAAATTGACTCTGATACGCTGGGGCTGAGTGGGTTTAATGTGAATG
GTAGCGGGGCTGTGGCTAATACTGCAGCGACTAAATCTGATTTGGCAGCAGCTCAACTCT
TGGCTCCAGGTACTGCTGATGCTAATGGTACAGTTACCTATACTGTTGGCGCAGGCCTGA
AAACATCTACAGCTGCAGATGTAATTGCGAGTTTGGCTAATAACGCAAAAGTTAATGCCA
CAATTGCAAATGGTTTTGGATCGCCAACAGCTACAGATTATACATACAACAGCGCTACAG
GCGATTTTACATATAGTGCAACTATTGCAGCTGGTACAAATTCTGGTGATAGTAACAGTG
CTCAGTTACAATCCTTCCTGACACCAAAAGCGGGCGATACTGCTAACTTAAACGTTAAAA
TTGGTTCTACGTCAATTGACGTTGTATTGGCTAGCGACGGTAAAATTACCGCGAAAGATG
GTTCAGAACTATTTATTGACGTAGATGGTAACCTCACTCAAAACAATGCTGGGACTGTCA
AAGCAGCCACTCTTGATGCACTGACTAAAAACTGGCATACAACAGGCACACCGAGTGCCG
TATCTACGGTAATTACAACTGAAGATGAAACAACCTTCACTCTGGCTGGCGGTACTGATG
CTACTACTTCTGGTGCAATCACTGTAGCAAATGCAAGAATGAGTGCTGAGTCTCTTCAAT
CGGCAACTAAGTCCACAGGATTCACAGTTGATGTTGGAGCTACTGGTACCAGCGCAGGCG
ATATTAAAGTTGATAGTAAAGGTATAGTACAACAACACACAGGTACAGGTTTTGAAGACG
CTTACACCAAAGCTGATGGTTCACTGACTACCGATAATACAACCAATCTGTTTTTGCAAA
AAGACGGAACTGTGACCAATGGTTCAGGTAAAGCAGTCTATGTTTCAGCGGATGGTAATT
TTACTACTGACGCTGAAACTAAAGCTGCAACCACCGCCGATCCACTGAAAGCTCTGGACG
AAGCGATCAGCTCCATCGACAAATTCCGTTCTTCCCTCGGTGCGGTGCAAAACCGTCTGG
ATTCCGCAGTCACCAACCTGAACAACACCACTACTAACCTGTCTGAAGCGCAGTCCCGTA
TTCAGGACGCTGACTATGCGACCGAAGTGTCCAATATGTCGAAAGCGCAGATCATCCAGC
AGGCCGGTAACTCCGTGCTGGCAAAAGCTAACCAGGTACCGCAGCAGGTTCTGTCTCTGC TGCAGGGTTAA
```

Figure 32

```
AACAAAAACCAGTCTGCGCTGTCGACTTCTATCGAGCGCCTCTCTT
CTGGTCTGCGCATTAACAGCGCTAAAGATGACGCTGCGGGCCAGGCGATTGCTAACCGCT
TCACTTCTAACATCAAAGGTCTGACTCAGGCCGCACGTAACGCCAACGACGGTATCTCTC
TGGCGCAGACCACTGAAGGCGCACTGTCTGAAATCAACAACAACTTGCAGCGTGTTCGTG
AGCTGACCGTTCAGGCCACTACCGGTACTAACTCTGATTCTGACCTGTCTTCAATCCAGG
ACGAAATCAAATCCCGTCTCGATGAAATTGACCGCGTATCCGGTCAGACTCAGTTCAACG
GCGTGAACGTACTGGCAAAAGATAACACCATGAAGATTCAGGTTGGTGCGAACGATGGTC
AGACTATATCCATCGACCTGCAAAAAATCGACTCTTCTACTCTTGGTTTGAACGGTTTCT
CCGTTTCTAAAAATGCTCTCGAAACTAGCGAAGCGATCACTCAGTTGCCGAACGGTGCGA
ATGCACCAATCGCTGTGAAGATGGATGCGTCTGTTCTGACCGATCTTAACATTACTGATG
CTTCCGCTGTTTCGCTGCACAACGTAACTAAAGGTGGTGTCGCAACGTCTACTTATGTTG
TTCAGTATGGCGATAAGAGCTATGCAGCATCTGTTGATGCGGGAGGTACAGTAAAACTGA
ATAAAGCCGACGTAACATATAACGACGCAGCAAATGGTGTTACGAATGCCACCCAGATTG
GTAGTCTGGTTCAGGTTGGTGCTGATGCAAACAATGATGCAGTTGGTTTTGTTACCGTGC
AGGGGAAAAACTATGTTGCTAATGACTCATTAGTCAATGCTAATGGCGCTGCTGGCGCTG
CAGCAACTAGAGTTACAATTGATGGTGATGGTAGCCTTGGAGCTAACCAGGCTAAAATTG
AACTTAGCCAAAATGGTGCTACTGCTGCAACATCAGAGTTCGCTGGTGCTTCAACCAACG
ATCCACTGACTCTGCTGGACAAAGCTATCGCATCTGTTGATAAATTCCGTTCTTCTTTGG
GGGCGGTACAGAACCGTCTGAGCTCCGCTGTAACCAACCTGAACAACACCACTACCAACC
TGTCTGAAGCGCAGTCCCGTATTCAGGACGCCGACTATGCGACCGAAGTGTCCAACATGT
CGAAAGCGCAGATCATCCAGCAGGCAGGTAACTCCGTGCTGTCCAAA
```

Figure 33

```
ATGGCACAAGTCATTAATACCAACAGCCTCTCGCTGATCACTCAAAATAATATCAACAAGA
ACCAGTCTGCGCTGTCGAGTTCTATCGAGCGTCTGTCTTCTGGCTTGCGTATTAACAGCG
CGAAGGATGACGCCGCAGGTCAGGCGATTGCTAACCGTTTTACTTCTAACATTAAAGGCC
TGACTCAGGCTGCACGTAACGCCAACGACGGTATTTCTGTTGCACAGACCACTGAAGGCG
CGCTGTCCGAAATCAACAACAACTTACAGCGTATTCGTGAACTGACGGTTCAGGCGACGA
CCGGAACTAACTCCACCTCTGACCTGGACTCCATTCAGGACGAAATCAAATCCCGTCTTG
ATGAAATTGACCGCGTATCCGGCCAAACCCAGTTCAACGGCGTGAACGTACTGTCAAAAG
ATGGCTCGATGAAAATTCAGGTCGGCGCAAATGATGGTGAAACCATCACGATTGATCTGA
AAAAGATCGACTCTTCTACATTGAAGCTGACCAGCTTCAATGTTAACGGTAAAGGCGCTG
TTGATAATGCTAAAGCCACTGAAGCAGATCTGACCGCTGCGGGCTTCTCCCAAGGTGCAG
TCGTCAGTGGCAACAGCACCTGGACTAAATCTACTGTTACTACCTTTAATGCAGCAACAG
CTACCGACGTGCTGGCAAGCGTTAGCGGCGGCAGCACTATTAGCGGTTATACCGGTACAA
ACAATGGATTAGGCGTAGCGGCTTCTACTGCATATACCTACAACGCAACCAGCAAGTCTT
ATTCATTTGACGCAACCGCACTTACCAATGGCGATGGTACTGGGGCCACCACTAAAGTTG
CTGATGTGCTGAAAGCCTATGCAGCAAACGGTGATAATACGGCTCAGATCTCCATCGGCG
GAAGCGCTCAGGACGTTAAAATTGCCAGCGATGGCACCCTGACTGACGTCAATGGTGATG
CTTTATATATTGGTTCTGACGGCAACCTGACTAAAAACCAGGCCGGCGGTCCAGATGCGG
CAACGTTGGACGGTATTTTCAACGGTGCGAATGGTAATGCAGCAGTTGATGCGAAGATTA
CATTCGGCAGCGGCATGACCGTTGATTTCACCCAGGCTAGCAAAAAAGTGGATATTAAGG
GCGCAACGGTATCCGCCGAAGATATGGACACTGCGTTAACTGGGCAGGCTTATACCGTAG
CTAACGGCGCACAGTCTTTTGACGTTGCCGCTGGTGGGGCAGTAACCGCTACTACAGGTG
GCGCTACCGTAAATATTGGTGCTGATGGTGAACTGACGACTGCGACCAACAAGACTGTCA
CAGAAACTTATCACGAATTTGCTAACGGCAATATTCTGGATGATGACGGCGCGGCTCTGT
ACAAAGCGGCTGACGGTTCTCTGACCACTGAAGCTACTGGTAAATCCGAAGTGACCACGG
ATCCGCTGAAAGCGCTGGACGATGCTATCGCATCCGTAGACAAATTCCGCTCCTCCCTCG
GTGCGGTGCAGAACCGTCTGGATTCCGCAGTCACCAACCTGAACAACACCACTACCAACC
TGTCTGAAGCGCAGTCCCGCATTCAGGACGCCGACTATGCGACCGAAGTGTCCAATATGT
CGAAAGCGCAGATCATCCAGCAGGCCGGTAACTCCGTGCTGGCAAAAGCCAACCAGGTAC
CGCAGCAGGTTCTGTCTCTGCTGCAGGGTTAA
```

Figure 34

```
ATGGCACAAGTCATTAATACCAACAGCCTCTCGCTGATCAC
TCAAAATAATATCAACAAGAACCAGTCTGCGCTGTCGAGTTCTATCGAGCGTCTGTCTTC
TGGCTTGCGTATTAACAGCGCTAAGGATGACGCCGCGGGTCAGGCGATTGCTAACCGTTT
TACTTCTAACATTAAAGGCCTGACTCAGGCTGCACGTAACGCCAACGACGGTATTTCTGT
TGCGCAGACCACTGAAGGCGCGCTGTCCGAAATCAACAACAACTTACAGCGTATCCGTGA
ACTGACGGTTCAGGCTTCTACCGGGACTAACTCCGATTCGGATCTGGACTCCATTCAGGA
CGAAATCAAATCCCGTCTGGACGAAATTGACCGCGTATCTGGCCAGACCCAGTTCAACGG
CGTGAACGTACTGGCGAAAGACGGTTCAATGAAAATTCAGGTTGGTGCGAATGACGGCCA
GACTATCACTATTGATCTGAAGAAAATTGACTCAGATACGCTGGGGCTGAGTGGGTTTAA
TGTGAATGGTGGCGGGGCTGTTGCTAATACTGCAGCGACTAAAGATGATTTGGTCGCTGC
ATCAGTTTCAGCTGCGGTAGGTAATGAATACACTGTCTCTGCTGGCCTGTCGAAATCAAC
TGCTGCTGATGTTATTGCTAGTCTCACAGATGGTGCGACAGTAACTGCGGCTGGTGTAAG
CAATGGTTTTGCTGCAGGGGCAACTGGAGATGCTTATAAATTCAATCAAGCAAACAACAC
TTTTACTTACAATACCACCTCAACAGCGGCAGAACTCCAATCTTACCTCACGCCTAAGGC
GGGGGATACCGCAACTTTCTCCGTTGAAATTGGTGGCACCAAGCAGGATGTTGTTCTGGC
TAGTGATGGCAAAATCACAGCAAAAGACGGGTCTAAACTTTATATTGACACCACAGGGAA
TTTAACCCAAAACGGTGGAGGTACTTTAGAAGAAGCTACCCTCAATGGCTTAGCTTTCAA
CCACTCTGGTCCAGCCGCTGCTGTACAATCTACTATTACTACTGCGGATGGAACTTCAAT
AGTTCTAGCAGGTTCTGGCGACTTTGGAACAACAAAAACTGCTGGGGCTATTAATGTCAC
AGGAGCAGTGATCAGTGCTGATGCACTTCTTTCCGCCAGTAAAGCGACTGGGTTTACTTC
TGGCACTTATACCGTAGGTACAGATGGAGTTGTTAAATCTGGTGGCAATGACGTTTATAA
CAAAGCTGACGGGACGGGATTAACTACTGACAATACCACAAAATATTATTTACAAGATGA
CGGGTCTGTAACTAATGGTTCTGGTAAAGCTGTGTATGCTGATGCAACAGGAAAACTAAC
TACTGACGCTGAAACTAAAGCCGAAACCACCGCCGATCCCCTGAAAGCTCTGGACGAAGC
GATCAGCTCCATCGACAAATTCCGTTCTTCCCTCGGTGCGGTGCAAAACCGTCTGGATTC
CGCGGTCACCAACCTGAACAACACCACTACCAACCTGTCCGAAGCGCAGTCCCGTATTCA
GGACGCCGACTATGCGACCGAAGTGTCCAACATGTCGAAAGCGCAGATCATCCAGCAGGC
CGGTAACTCCGTGCTGGCAAAAGCTAACCAGGTACCGCAGCAGGTTCTGTCTCTGCTGCA GGGTTAA
```

Figure 35

```
ATGGCACAAGTCATTAATACCAACAGCCTCTCGCTGATCAC
TCAAAATAATATCAACAAGAACCAGTCTGCGCTGTCGAGTTCTATCGAGCGTCTGTCTTC
TGGCTTGCGTATTAACAGCGCGAAGGATGACGCCGCGGGTCAGGCGATTGCTAACCGTTT
TACTTCTAACATTAAAGGCCTGACTCAGGCTGCACGTAACGCCAACGACGGTATTTCCGT
TGCGCAGACCACCGAAGGCGCGCTGTCCGAAATCAACAACAACTTACAGCGTATCCGTGA
ACTGACGGTTCAGGCCACTACCGGTACTAACTCCGATTCTGACCTGGACTCCATCCAGGA
CGAAATCAAATCTCGTCTTGATGAAATTGACCGCGTATCTGGTCAGACCCAGTTCAATGG
CGTGAATGTGTTGTCCAAAGACGGTTCAATGAAAATTCAGGTGGGCGCAAATGATGGTGA
AACCATCACGATTGACCTGAAAAAAATCGACTCTTCTACACTGAAGCTGACCAGCTTCAA
CGTCAACGGTAAAGGCGCTGTTGATAATGCAAAAGCCACTGAAGCAGATCTGACCGCTGC
GGGCTTCTCCCAAAGTGCAGTTGTCAGTGGCAATAGCACCTGGACTAAATCTACTGTTAC
TACCTTTAATGCAGCAACAGCTACCGATGTGCTGGCTAGCGTTAGTGGCGGCAGCACTAT
TAGCGGTTATGCTGGCACAAACAATGGGTTAGGCGTAGCGGCTTCTACTGCATATACCTA
CAACGCAACCAGCAAGTCTTATTCATTTGACGCAACCGCACTTACTAATGGTGATGGTAC
TGCGGGCTCAACTAAAGTTGCTGATGTTCTGAAAGCCTATGCAGCAAACGGCGATAACAC
GGCTCAGATCTCCATCGGTGGTAGCGCTCAGGAAGTTAAAATTGCCAGCGATGGTACCCT
GACGGATACTAATGGCGATGCTTTATACATTGGTGCTGACGGTAACCTGACGAAAAACCA
GGCCGGCGGCCCAGCCGCGGCAACGTTGGACGGTATTTTCAACGGTGCGAATGGTCATGA
TGCAGTTGATGCGAAGATTACCTTCGGCAGCGGCATGACCGTTGACTTCACCCAGGTTAG
CAACAATGTGGATATTAAGGGCGCGACGGTATCCGCCGAAGATATGAACACTGCGTTAAC
CGGTCAGGCTTATACCGTAGCTAACGGCGCACAGTCTTATGACGTTGCCGCTGATGGTGC
AGTAACTGCTACTACAGGTGGAGCGACCGTAAATATTGGTGCTGAGGGTGAACTGACGAC
TGCGGCCAACAAGACTGTCACAGAAACTTATCACGAATTTGCTAACGGCAATATTCTGGA
TGATGACGGCGCGGCTCTGTATAAAGCGGCTGACGGCTCTGACCACTGAAGCTACAGG
TAAATCTGAAGCGACCACGGATCCGCTGAAAGCGCTGGACGATGCTATCGCATCCGTAGA
CAAATTCCGTTCTTCCCTGGGTGCCGTGCAGAACCGTCTGGATTCCGCAGTCACCAACCT
GAACAACACCACTACCAACCTGTCCGAAGCGCAGTCCCGTATTCAGGACGCCGACTATGC
GACCGAAGTGTCCAACATGTCGAAAGCGCAGATTATTCAGCAGGCAGGTAACTCCGTGCT
GGCAAAAGCTAACCAGGTACCGCAGCAGGTTCTGTCTCTGCTGCAGGGTTAA
```

Figure 36

```
AACAAAAACCAGTCTGCGCTGTCGACTTCTAT
CGAGCGCCTCTCTTCTGGTCTGCGCATTAACAGCGCTAAAGATGACGCTGCGGGCCAGGC
GATTGCTAACCGCTTCACTTCTAACATCAAAGGTCTGACTCAGGCCGCACGTAACGCCAA
CGACGGTATCTCTCTGGCGCAGACCACTGAAGGCGCACTGTCTGAAATCAACAACAACTT
GCAGCGTGTGCGTGAGTTGACTGTTCAGGCGACGACCGGGACTAACTCTGATTCTGACCT
GTCTTCTATTCAGGACGAAATCAAATCCCGTCTGGATGAAATTGACCGTGTTTCCGGTCA
GACCCAGTTCAACGGCGTGAACGTGCTGGCTAAAAACGGTTCTATGGCGATTCAGGTTGG
CGCGAATGATGGGCAGACCATCAACATCGACCTGCAGAAAATCGACTCTTCTACTCTGGG
CCTGGGCGGCTTCTCCGTATCTAACAATGCACTGAAACTGAGCGATTCTATCACTCAGGT
TGGTGCGAGTGGTTCACTGGCAGATGTGAAACTGAGCTCTGTTGCCTCGGCTCTGGGTGT
AGACGCAAGCACTCTGACTCTGCACAACGTACAGACCCCAGCTGGCGCAGCAACAGCTAA
CTATGTTGTCTCTTCTGGTTCTGACAACTACTCAGTATCTGTTGAAGATAGCTCCGGTAC
AGTTACGCTGAACACCACTGATATAGGTTATACCGATACCGCTAATGGCGTTACTACCGG
TTCCATGACTGGTAAGTACGTTAAAGTTGGAGCTGATGCATTGGGTGCTGCTGTAGGTTA
TGTCACCGTACAGGGACAAAACTTCAAAGCTGATGCTGGCGCGCTGGTTAACTCCAAGAA
TGCTGCTGGTAGTCAGAATGTTACTTCTGCAATTGGCGATATTGCTAATAAAGCGAATGC
TAACATTTACACTGGAACCTCTTCTGCAGATCCACTGGCTCTGCTGGACAAAGCTATCGC
ATCTGTTGATAAATTCCGTTCTTCTCTAGGGGCGGTGCAGAACCGTCTGAGCTCTGCTGT
AACCAACCTGAACAACACCACTACCAACCTGTCCGAAGCGCAGTCCCGTATTCAGGACGC
CGACTATGCGACCGAAGTGTCCAACATGTCGAAAGCGCAGATCATCCAGCAGGCGGGTAA
CTCCGTGCTGTCTAAA
```

Figure 37

```
ATGGCACAAGTCATTAATACCAACAGCCTCTCGCTGATCA
CTCAAAATAATATCAACAAGAACCAGTCTGCGCTGTCGAGTTCTATCGAGCGTCTGTCTT
CTGGCTTGCGTATTAACAGCGCGAAGGATGACGCCGCCGGTCAGGCGATTGCTAACCGTT
TTACTTCTAACATTAAAGGCCTGACTCAGGCTGCACGTAACGCCAATGACGGTATTTCTG
TTGCACAGACCACTGAAGGCGCGCTGTCCGAAATCAACAACAACTTACAGCGTATTCGTG
AACTGACGGTCAGGCTTCTACCGGGACTAACTCTGATTCGGATCTGGACTCCATTCAGG
ACGAAATCAAATCCCGTCTCGACGAAATTGACCGCGTATCCGGTCAGACCCAGTTCAACG
GCGTGAACGTACTGGCAAAAGACGGTTCGATGAAAATTCAGGTTGGTGCGAACGACGGCC
AGACTATCACTATTGATCTGAAGAAAATTGACTCTGATACGCTGGGGCTGAGTGGGTTTA
ACGTAAATGGTAGCGCAGATAAGGCAAGTGTCGCGGCGACAGCTGACGGAATGGTTAAAG
ACGGATATATCAAAGGGTTAACTTCATCTGACGGCAGCACTGCATATACTAAAACTACAG
CAAATACTGCAGCAAAAGGATCTGATATTCTTGCGGCGCTTAAGACTGGCGATAAAATTA
CCGCAACAGGTGCAAATAGCCTTGCTGATAATGCGACATCGACAACTTATACTTATAATG
CAACCAGCAATACCTTCTCCTATACGGCTGACGGTGTAAACCAAACGAATGCTGCAGCAA
ATCTCATACCTGCAGCAGGGAAAACGACAGCTGCATCAGTTACTATTGGTGGGACAGCAC
AGAATGTAAATATTGATGATTCGGGCAATATTACTTCAAGTGATGGCGATCAACTTTATC
TGGATTCAACAGGTAACCTGACTAAAAACCAGGCCGGCAACCCGAAAAAAGCAACCGTTT
CTGGGCTTCTCGGAAATACGGATGCGAAAGGTACTGCTGTTAAAACAACCATCAAGACAG
AGGCTGGTGTAACAGTTACAGCTGAAGGTAATACAGGTACTGTAAAAATTGAAGGTGCTA
CTGTTTCAGCATCTGCATTTACGGGCATTGCATATTCCGCCAACACCGGTGGGAATACTT
ATGCTGTTGCCGCAAATAATACTACAAATGGTTTCCTGGCGGGGATGACTTAACCCAGG
ATGCTCAAACTGTTTCAACCTACTACTCGCAAGCCGATGGCACGGTCACGAATAGCGCAG
GCAAAGAAATCTATAAGACGCTGATGGTGTCTACAGCACAGAGAATAAAACATCGAAGA
CGTCCGATCCATTGGCTGCGCTTGACGACGCAATCAGCTCCATCGACAAATTCCGTTCAT
CCTTGGGTGCTATCCAGAACCGTCTGGATTCCGCGGTCACCAACCTGAACAACACCACTA
CCAACCTGTCCGAAGCGCAGTCCCGTATTCAGGACGCCGACTATGCGACCGAAGTGTCCA
ACATGTCGAAAGCGCAGATCATCCAGCAGGCCGGTAACTCCGTGCTGGCAAAAGCTAACC
AGGTACCGCAGCAGGTTCTGTCTCTGCTGCAGGGCTAA
```

Figure 38

```
AACAAATCTCAGTCTTCTCTGAGCTCCGCCATTGAACGTCTCTCTTCTGGCCTGCGTA
TTAACAGTGCTAAAGATGACGCAGCAGGTCAGGCGATTGCTAACCGTTTTACAGCAAATA
TTAAAGGTCTGACTCAGGCTTCCCGTAACGCGAATGATGGTATTTCTGTTGCGCAGACCA
CTGAAGGTGCGCTGAATGAAATTAACAACAACCTGCAGCGTGTACGTGAACTGACTGTTC
AGGCAACTAACGGTACTAACTCTGACAGCGATCTTTCTTCTATCCAGGCTGAAATTACTC
AACGTCTGGAAGAAATTGACCGTGTATCTGAGCAAACTCAGTTTAACGGCGTGAAAGTCC
TTGCTGAAAATAATGAAATGAAAATTCAGGTTGGTGCTAATGATGGTGAAACCATCACTA
TCAATCTGGCAAAAATTGATGCGAAAACTCTCGGCCTGGACGGTTTTAATATCGATGGCG
CGCAGAAAGCAACTGGCAGTGACCTGATTTCTAAATTTAAAGCGACAGGTACTGATAACT
ATGATGTTGGCGGTGATGCTTATACTGTTAACGTAGATAGCGGAGCTGGGTAATGACTCC
AACTTATTGATAGTGTTTTATGTTCAGATAATGCCCGATGACTTTGTCATGCAGCTCCAC
CGATTTTGAGAACGACAGCGACTTCCGTCCCAGCCGTGCCAGGTGCTGCCTCAGATTCAG
GTTATGCCGCTCAATTCGCTGCGTATATCGCTTGCTGATTACGTGCAGCTTTCCCTTCAG
GCGGGATTCATACAGCGGCCAGCCATCCGTCATCCATATCACCACGTCAAAGGGTGACAG
CAGGCTCATAAGACGCCCAGCGTCGCCATAGTGCGTTCACCGAATACGTGCGCAACAAC
CGTCTTCCGGAGCCTGTCATACGCGTAAAACAGCCAGCGCTGGCGCGATTTAGCCCCGAC
ATAGTCCCACTGTTCGTCCATTTCCGCGCAGACGATGACGTCACTGCCCGGCTGTATGCG
CGAGGTTACCGACTGCGGCCTGAGTTTTTTAAGTGACGTAAAATCGTGTTGAGGCCAACG
CCCATAATGCGGGCAGTTGCCCGGCATCCAACGCCATTCATGGCCATATCAATGATTTTC
TGGTGCGTACCGGGTTGAGAAGCGGTGTAAGTGAACTGCAGTTGCCATGTTTTACGGCAG
TGAGAGCAGAGATAGCGCTGATGTCCGGCGGTGCTTTTGCCGTTACGCACCACCCCGTCA
GTAGCTGAACAGGAGGGACAGCTGATAGAAACAGAAGCCACTGGAGCACCTCAAAACAC
CATCATACACTAAATCAGTAAGTTGGCAGCATTACCGCGGAGCTGTTAAAGATACTACAG
GGAATGATATTTTTGTTAGTGCAGCAGATGGTTCACTGACAACTAAATCTGACACAAACA
TAGCTGGTACAGGGATTGATGCTACAGCACTCGCAGCAGCGGCTAAGAATAAAGCACAGA
ATGATAAATTCACGTTTAATGGAGTTGAATTCACAACAACAACTGCAGCGGATGGCAATG
GGAATGGTGTATATTCTGCAGAAATTGATGGTAAGTCAGTGACATTTACTGTGACAGATG
CTGACAAAAAAGCTTCTTTGATTACGAGTGAGACAGTTTACAAAAATAGCGCTGGCCTTT
ATACGACAACCAAAGTTGATAACAAGGCTGCCACACTTTCCGATCTTGATCTCAATGCAG
CTAAGAAAACAGGAAGCACGTTAGTTGTTAACGGTGCAACTTACGATGTTAGTGCAGATG
GTAAAACGATAACGGAGACTGCTTCTGGTAACAATAAAGTCATGTATCTGAGCAAATCAG
AAGGTGGTAGCCCGATTCTGGTAAACGAAGATGCAGCAAAATCGTTGCAATCTACCACCA
ACCCGCTCGAAACTATCGACAAAGCATTGGCTAAAGTTGACAATCTGCGTTCTGACCTCG
GTGCAGTACAAAACCGTTTCGACTCTGCTATCACCAACCTTGGCAACACCGTAAACAACC
TGTCTTCTGCCCGTAGCCGTATCGAAGATGCTGACTACGCGACCGAAGTGTCTAACATGT
CTCGTGCGCAGATCCTGCAACAAGCGGGTACCTCTGTTCTGGCGCAG
```

Figure 39

```
AACAAGAACCAGTCTGCGCTGTCGAGTTCTATCGAGCGTCTGT
CTTCTGGCTTGCGTATTAACAGCGCGAAGGATGACGCCGCAGGTCAGGCGATTGCTAACC
GTTTTACTTCTAACATTAAAGGCCTGACTCAGGCTGCACGTAACGCCAACGACGGTATTT
CTGTTGCGCAGACCACCGAAGGCGCGCTGTCCGAAATCAACAACAACTTACAGCGTGTGC
GTGAACTGACCGTTCAGGCAACCACCGGTACCAACTCCCAGTCTGACCTGGACTCTATCC
AGGACGAAATTAAATCCCGTCTGGACGAAATTGACCGCGTATCCGGTCAGACCCAGTTCA
ACGGCGTGAACGTACTGGCAAAAGACGGTTCCATGAAAATTCAGGTTGGCGCGAACGATG
GCCAGACCATCACTATCGACCTGAAGAAGATTGACTCTTCTACGCTGAAACTGACTGGTT
TTAACGTGAATGGCAAAGCAGCGGTTGATAATGCTAAAGCGACGGATGCAAATCTGACTA
CCGCCGGTTTTACACAAGGCGTTGTGGATTCAAATGGTAATAGTACTTGGACTAAATCAA
CTACGACTAATTTCGATGCGGCAACTGCAGTAAACGTACTAGCAGCAGTTAAAGATGGCA
GCACAATCAATTACACCGGTACTGGTAATGGTTTAGGGATTGCTGCAACAAGTGCTTATA
CATATCACGATAGCACTAAATCCTATACCTTTGATTCTACGGGGGCTGCAGTAGCTGGTG
CCGCGTCCAGCCTGCAAGGTACTTTTGGTACAGATACGAATACTGCAAAAATCACCATCG
ATGGTTCTGCTCAAGAAGTAAACATCGCTAAAGATGGGAAAATTACTGATACTGATGGTA
AAGCTTTATATATCGATTCCACTGGTAATTTGACTAAGAACGGCTCTGATACTTTAACTC
AGGCAACATTGAATGATGTCCTTACTGGTGCTAATTCAGTTGATGATACAAGGATTGACT
TCGATAGCGGCATGTCTGTCACCCTTGATAAAGTGAACAGCACTGTAGATATCACTGGCG
CATCTATTTCAGCCGCTGCAATGACTAATGAGTTGACAGGTAAGGCCTATACCGTAGTAA
ATGGTGCAGAATCTTACGCTGTAGCTACTAATAACACAGTAAAAACGACTGCTGATGCTA
AAAATGTTTATGTTGATGCTAGTGGTAAATTAACTACTGATGACAAAGCCACTGTTACAG
AAACTTATCATGAATTTGCGAATGGCAATATCTATGATGATAAAGGCGCTGCTGTTTATG
CGGCGGCGGATGGTTCTCTGACTACAGAAACTACAAGTAAATCAGAAGCTACAGCTAACC
CGCTGGCCGCTCTGGACGACGCAATCAGCCAGATCGACAAATTCCGTTCATCCCTGGGTG
CTATCCAGAACCGTCTGGATTCCGCAGTCACCAACCTGAACAACACCACTACCAATCTGT
CTGAAGCGCAGTCCCGTATTCAGGACGCCGACTATGCGACCGAAGTGTCCAATATGTCGA
AAGCGCAGATCATCCAGCAGGCAGGCAACTCCGTGCTGGCAAAA
```

Figure 40

```
AACAAAAACCAGTCTGCGCTGTCGACTTCTATCGAGCGCCTCTC
TTCTGGTCTGCGCATTAACAGCGCTAAAGATGACGCTGCGGGCCAGGCGATTGCTAACCG
CTTCACTTCTAACATCAAAGGTCTGACTCAGGCCGCACGTAACGCCAACGACGGTATCTC
TCTGGCGCAGACCACTGAAGGCGCACTGTCTGAAATCAACAACAACTTGCAGCGTGTTCG
TGAACTGACCGTTCAGGCCACTACCGGTACTAACTCTGATTCTGACCTGTCTTCAATCCA
GGACGAAATCAAATCCCGTCTCGATGAAATTGACCGCGTATCCGGTCAGACTCAGTTCAA
CGGCGTGAACGTACTGGCAAAAGATGGCTCGATGAAAATTCAGGTCGGTGCAAATGATGG
TCAGACAATCAGCATTGATTTGCAGAAGATTGATTCTTCTACTTTAGGGTTAAATGGTTT
TTCTGTTTCCAAAAATGCAGTATCTGTTGGTGATGCTATTACTCAATTGCCTGGCGAGAC
GGCAGCCGATGCACCAGTAACCATCAAGTTTGATGATTCAGTAAAAACTGATTTAAAACT
GACCGATGCTTCAGGGTTAAGTCTGCATAACCTCAAAGATGAAAATGGTAATTTAACTAA
CCAGTATGTTGTACAGAATGGCGGAAAATCTTACGCTGCTACAGTCGCTGCCAATGGTAA
TGTTACGCTGAACAAAGCAAATGTAACCTACAGCGATGTCGCAAACGGTATTGATACCGC
AACGCAGTCAGGCCAGTTAGTTCAGGTTGGTGCAGATTCTACCGGTACGCCAAAAGCATT
CGTGTCTGTCCAAGGTAAAAGCTTTGGCATTGATGACGCCGCCTTGAAGAATAACACTGG
TGATGCTACCGCTACTCAACCGGGAACATCTGGGACAACAGTTGTCGCAGCGTCAATTCA
TCTGAGTACGGGCAAAAACTCTGTAGACGCTGATGTAACGGCTTCCACTGAATTCACAGG
TGCTTCAACCAACGATCCACTGACTCTGCTGGACAAAGCTATCGCATCTGTTGATAAATT
CCGTTCTTCTTTGGGGGCGGTACAGAACCGTCTGAGCTCCGCTGTAACCAACCTGAACAA
CACCACCACCAACCTGTCTGAAGCGCAGTCCCGTATTCAGGACGCCGACTATGCGACCGA
AGTGTCCAACATGTCGAAAGCGCAGATTATCCAGCAGGCAGGTAACTCCGTGCTGTCCAA A
```

Figure 41

```
AACAAAAACCAGTCTGCGCTGTCGACTTCTATCGAGCGCCTCTCTTCTGGTC
TGCGCATTAACAGCGCTAAAGATGACGCTGCGGGCCAGGCGATTGCTAACCGCTTCACTT
CTAACATCAAAGGTCTGACTCAGGCTGCACGTAACGCCAATGACGGTATTTCTCTAGCAC
AGACAGCGGAAGGCGCGCTGTCAGAGATTAACAACAACTTGCAGCGTGTGCGTGAGTTGA
CCGTGCAGGCAACCACTGGTACCAACTCTGATTCCGATCTCTCTTCTATTCAGGATGAAA
TTAAATCTCGTCTGGATGAAATTGACCGCGTCTCTGGTCAGACCCAGTTTAACGGCGTGA
ACGTACTGGCTAAAAACGGTTCTATGGCAATTCAGGTTGGCGCGAACGATGGCCAGACTA
TCTCTATCGACCTGCAGAAAATAGACTCTTCTACTCTGGGTCTGAGCGGCTTCTCTGTTT
CTCAGAACTCCCTGAAACTGAGCGATTCTATCACTACGATCGGCAATACTACTGCTGCAT
CGAAGAACGTGGACCTGAGCGCAGTAGCAACTAAACTGGGCGTGAATGCAAGCACCCTGA
GCCTGCACGAAGTTCAGGACTCTGCTGGTGACGGTACTGGTACCTTCGTTGTTTCTTCTG
GCAGCGACAACTATGCTGTGTCTGTAGACGCGGCCTCTGGTGCAGTTAACCTGAACACCA
CTGACGTCACCTATGATGACGCTACTAATGGTGTTACTGGCGCGACTCAGAACGGTCAGC
TGATCAAAGTAACTTCTGACGCCAACGGTGCAGCTGTTGGTTACGTAACCATTCAGGGTA
AAAACTATCAGGCTGGTGCGACCGGTGTTGACGTTCTGGCGAACAGCGGTGTTGCAGCTC
CAACTACAGCTGTTGATACCGGTACTCTGCAACTGAGCGGTACTGGTGCAACTACTGAGC
TGAAAGGTACTGCAACTCAGAACCCACTGGCACTATTGGACAAAGCTATCGCTTCTGTTG
ATAAATTCCGTTCTTCTCTGGGTGCGGTACAGAATCGTCTGAGCTCTGCTGTAACCAACC
TGAATAACACCACCACTAACCTGTCTGAAGCGCAGTCCCGTATTCAGGATGCCGACTATG
CGACCGAAGTGTCAAATATGTCTAAAGCGCAGATCGTTCAGCAGGCCGGTAAC
```

Figure 42

```
AACAAATCTCAGTCTTCTCTTAGCTCTGCTATTGAGCGTCTGTCTTCT
GGTCTGCGTATTAACAGCGCAAAAGACGATGCAGCAGGTCAGGCGATTGCTAACCGTTTT
ACGGCAAATATTAAAGGTCTGACCCAGGCTTCCCGTAACGCAAATGATGGTATTTCTGTT
GCGCAGACCACTGAAGGTGCGCTGAATGAAATTAACAACAACCTGCAGCGTATTCGTGAA
CTTTCTGTTCAGGCAACTAACGGTACTAACTCTGACAGCGATCTTTCTTCTATCCAGGCT
GAAATTACTCAACGTCTGGAAGAAATTGACCGTGTATCTGAGCAAACTCAGTTTAACGGC
GTGAAAGTCCTTGCTGAAAATAATGAAATGAAAATTCAGGTTGGTGCTAATGATGGTGAA
ACCATCACTATCAATCTGGCAAAAATTGATGCGAAAACTCTCGGCCTGGACGGTTTTAAT
ATCGATGGCGCGCAGAAAGCAACAGGCAGTGACCTGATTTCTAAATTTAAAGCGACAGGT
ACTGATAATTATGATGTTGGCGGTAAAACTTATACCGTGAATGTGGAGAGCGGCGCGGTT
AAGAATGATGCTAATAAAGATGTTTTTGTAAGCGCAGCTGATGGATCGCTGACGACCAGT
AGTGATACTAAAGTATCCGGTGAAAGTATTGATGCAACAGAACTAGCGAAACTTGCAATA
AAATTAGCTGACAAAGGCTCCATTGAATACAAGGGCATTACATTTACTAACAACACTGGC
GCAGAGCTTGATGCTAATGGTAAAGGTGTTTTGACCGCAAATATTGATGGTCAAGATGTT
CAATTTACTATTGACAGTAATGCACCCACGGGTGCCGGCGCAACAATAACTACAGACACA
GCTGTTTACAAAAACAGTGCGGGCCAGTTCACCACTACAAAAGTGGAAAATAAAGCCGCA
ACACTCTCTGATCTGGATCTTAATGCAGCCAAGAAAACAGGTAGCACTTTAGTTGTAAAT
GGCGCCACCTACAATGTCAGCGCAGATGGTAAAACGGTAACTGATACTACTCCTGGTGCC
CCTAAAGTGATGTATCTGAGCAAATCAGAAGGTGGTAGCCCGATTCTGGTAAACGAAGAT
GCAGCAAAATCGTTGCAATCTACCACCAACCCGCTCGAAACTATCGACAAGGCATTGGCT
AAAGTTGACAATCTGCGTTCTGACCTCGGTGCAGTACAAAACCGTTTCGACTCTGCCATC
ACCAACCTTGGCAACACCGTAAACAACCTGTCTTCTGCCCGTAGCCGTATCGAAGATGCT
GACTACGCGACCGAAGTGTCTAACATGTCTCGTGCGCAGATCCTGCAACAAGCGGGTACC
TCTGTTCTGGCGCAG
```

Figure 43

ATGGCACAAGTCATTAATACCAACAGCCTCTCGCTGATCACT
CAAAATAATATCAACAAGAACCAGTCTGCGCTGTCGAGTTCTATCGAGCGTCTGTCTTCT
GGCTTGCGTATTAACAGCGCGAAGGATGACGCCGCAGGTCAGGCGATTGCTAACCGTTTC
ACCTCTAACATTAAAGGCCTGACTCAGGCTGCACGTAACGCCAACGACGGTATTTCTGTT
GCACAGACCACCGAAGGCGCGCTGTCCGAAATCAACAACAACTTACAGCGTATCCGTGAA
CTGACGGTTCAGGCTTCTACCGGGACTAACTCTGATTCGGATCTGGACTCCATTCAGGAC
GAAATCAAATCCCGTCTGGACGAAATTGACCGCGTATCCGGCCAGACCCAGTTCAACGGC
GTGAACGTGCTGGCGAAAGACGGTTCAATGAAAATTCAGGTTGGTGCGAATGACGGCCAG
ACTATCACTATTGATCTGAAGAAAATTGACTCTGATACTCTGGGTTTGAGTGGATTTAAT
GTGAATGGCAAAGGGGCTGTGGCTAACGCAAAAGCGACCGAAGCAGATTAACGGGGGCT
GGTTTCTCTCAAGGAGCGGTGGATACAAACGGAAATAGTACTTGGACAAAATCAACCACC
ACCAATTACTCAGCTGCAACAACTGCTGACTTGTTATCGACCATTAAGGATGGCTCTACT
GTTACATATGCAGGGACAGACACCGGATTAGGGGTCGCAGCAGCAGGAAATTATACTTAT
GATGCGAACAGTAAATCTTATTCCTTCAATGCCAATGGTCTGACGGGCGCAAATACCGCA
ACTGCACTCAAAGGTTACTTGGGGACAGGTGCTAACACCGCTAAAATTTCTATCGGTGGT
ACAGAGCAGGAAGTGAATATTGCCAAAGATGGCACTATTACAGATACGAATGGTGATGCG
CTCTATCTGGATATTACCGGCAACCTGACTAAGAACTATGCGGGTTCACCACCTGCAGCA
ACGCTGGATAACGTATTAGCTTCCGCAACTGTAAATGCCACTATCAAGTTTGATAGCGGT
ATGACGGTTGATTACACTGCAGGTACTGGCGCGAATATTACAGGTGCATCCATTTCTGCA
GATGACATGGCCGCAAAACTGAGCGGAAAGGCGTACACTGTTGCCAATGGTGCTGAGTCT
TATGACGTTGCTGCAGTTACGGGGGCTGTAACAACTACAGCAGGTAATTCACCTGTGTAT
GCCGATGCAGACGGTAAATTAACGACGAGTGCCAGTAATACGGTTACTCAGACTTATCAC
GAGTTTGCTAATGGTAACATTTATGATGACAAAGGCTCGTCACTGTATAAAGCTGCAGAT
GGCTCTCTGACTTCTGAAGCTAAAGGGAAATCTGAAGCAACCGCCGATCCCCTGAAAGCT
CTGGACGAAGCCATCAGCTCCATCGACAAATTCCGCTCCTCCCTCGGTGCCGTTCAAAAC
CGTCTGGATTCTGCGGTGACCAACCTGAACAACACCACTACCAACCTGTCTGAAGCGCAG
TCCCGTATTCAGGACGCCGACTATGCGACCGAAGTGTCCAATATGTCGAAAGCGCAGATC
ATCCAGCAGGCCGGTAACTCCGTGTTGGCAAAAGCTAACCAGGTACCGCAGCAGGTTCTG
TCTCTGCTGCAGGGTTAA

Figure 44

```
GCGCTGTCGACTTCTATCGAGCGCCTCTCTTCTGGTTTGCGCATTAACAGCGCTA
AAGATGACGCTGCGGGCCAGGCGATTGCTAACCGCTTCACTTCTAACATCAAAGGTCTGA
CTCAGGCCGCACGTAACGCCAACGACGGTATCTCTCTGGCGCAGACCACTGAAGGCGCAC
TGTCTGAAATCAACAACAACTTGCAGCGTGTTCGTGAACTGACCGTTCAGGCCACTACCG
GTACTAACTCTGATTCTGACCTGTCTTCAATCCAGGACGAAATCAAATCCCGCTTGGCTG
AAATCGATCGTGTCTCTGGTCAGACCCAGTTCAACGGCGTGAACGTGCTGGCTAAAAACG
GTTCTCTGAATATTCAGGTTGGCGCGAATGATGGGCAGACCATCTCTATCGATTTGCAGA
AAATAGACTCTTCTGCCCTTGGTTTAAGTGGTTTTAGTGTTGCCGGTGGGGCGCTAAAAT
TAAGCGATACAGTGACGCAGGTCGGCGATGGTTCAGCCGCGCCAGTTAAAGTGGATCTGG
ATGCAGCAGCAACAGATATTGGTACTGCTTTGGGGCAAAAGGTTAATGCAAGTTCTTTAA
CGTTGCACAATATCTTAGACAAAGATGGTGCGGCAACTGAGAACTATGTTGTTAGCTATG
GTAGTGATAATTACGCTGCATCTGTTGCAGATGACGGGACTGTAACTCTTAATAAAACGG
ATATTACTTATTCAGGCGGTGATATTACCGGCGCTACCAAAGATGATACGTTGATTAAAG
TTGCTGCTAATTCTGACGGAGAGGCCGTTGGTTTCGCTACCGTTCAGGGTAAGAATTATG
AAATTACAGATGGTGTAAAAAACCAGTCCACTGCTGCACCAACCGATATTGCTCAGACCA
TTGATCTGGATACGGCTGATGAATTTACTGGGGCTTCCACTGCTGATCCACTGGCACTTT
TAGACAAAGCTATTGCACAGGTTGATACTTTCCGCTCCTCCCTCGGTGCCGTTCAAAACC
GTCTGGATTCCGCAGTCACCAACCTGAACAACACTACTACCAACCTGTCTGAAGCGCAGT
CCCGTATTCAGGACGCCGACTATGCGACCGAAGTGTCCAATATGTCGAAAGCGCAGATCA TCCAGCAGGCC
```

Figure 45

```
ATGGCACAAGTCATTAATACCAACAGCCTCTCGCTGATCACT
CAAAATAATATCAACAAGAACCAGTCTGCGCTGTCGAGTTCTATCGAGCGTCTGTCTTCT
GGCTTGCGTATTAACAGCGCGAAGGATGACGCAGCGGGTCAGGCGATTGCTAACCGTTTT
ACTTCTAATATTAAAGGCCTGACTCAGGCTGCACGTAACGCCAATGACGGTATTTCTCTG
GCGCAGACCACTGAAGGCGCACTGTCTGAAATCAACAACAACTTGCAGCGTGTGCGTGAA
CTGACCGTACAGGCGACAACCGGAACGAACTCCGAATCTGACCTGTCCTCTATCCAGGAC
GAAATCAAATCCCGTCTGGAAGAGATTGACCGCGTATCCGGCCAGACTCAGTTCAACGGC
GTGAATGTGCTGGCAAAAGACGGCACCATGAAAATTCAGGTAGGCGCGAACGATGGTCAG
ACTATCTCTATCGATCTGAAAAAAATCGACTCTTCAACCCTGGGCCTGACCGGTTTTGAT
GTTTCGACGAAAGCGAATATTTCTACGACAGCAGTAACGGGGCGGCAACGACCACTTAT
GCTGATAGCGCCGTTGCAATTGATATCGGAACGGATATTAGCGGTATTGCTGCTGATGCT
GCGTTAGGAACGATCAATTTCGATAATACAACAGGCAAGTACTACGCACAGATTACCAGT
GCGGCCAATCCGGGCCTTGATGGTGCTTATGAAATCCATGTTAATGACGCGGATGGTTCC
TTCACTGTAGCAGCGAGTGATAAACAAGCGGGTGCTGCTCCGGGTACTGCTCTGACAAGC
GGTAAAGTTCAGACTGCAACCACCACGCCAGGTACGGCTGTTGATGTCACTGCGGCTAAA
ACTGCTCTGGCTGCAGCAGGTGCTGACACGAGTGGCCTGAAACTGGTTCAACTGTCCAAC
ACGGATTCCGCAGGTAAAGTGACCAACGTGGGTTACGGCCTGCAGAATGACAGCGGCACT
ATCTTTGCAACCGACTACGATGGCACCACTGTGACCACGCCGGGCGCAGAGACTGTGACT
TACAAAGATGCTTCCGGTAACAGCACCACTGCGGCTGTCACACTGGGTGGCTCTGATGGC
AAAACCAATCTGGTTACCGCCGCTGACGGCAAAACGTACGGTGCGACTGCACTGAATGGT
GCTGATCTGTCCGATCCTAATAACACCGTTAAATCTGTTGCAGACAACGCTAAACCGTTG
GCTGCCCTGGATGATGCAATTGCGATGGTCGACAAATTCCGCTCCTCCCTCGGTGCGGTG
CAAAACCGTCTGGATTCCGCAGTCACCAACCTGAACAACACCACTACCAACCTGTCTGAA
GCGCAGTCCCGTATTCAGGACGCCGACTATGCGACCGAAGTGTCCAACATGTCGAAAGCG
CAGATTATCCAGCAGGCAGGTAACTCCGTGCTGTCCAAAGCTAACCAGGTTCCGCAGCAG
GTTCTGTCTCTGCTGCAGGGTTAA
```

Figure 46

```
AACAAAAACCAGTCTGCGCTGTCGACTTCTATCGAGCGCCTCTCTTCTGGT
CTGCGTATTAACAGCGCTAAAGATGACGCCGCGGGCCAGGCGATTGCTAACCGCTTTACT
TCTAACATCAAAGGTCTGACTCAGGCCGCACGTAACGCCAACGACGGTATTTCTCTGGCG
CAGACGGCTGAAGGCGCGCTGTCAGAGATTAACAACAACTTGCAGCGTATTCGTGAACTG
ACCGTTCAGGCCTCTACCGGCACGAACTCTGATTCCGACCTGTCTTCTATTCAGGACGAA
ATCAAATCCCGTCTTGATGAAATTGACCGTGTATCTGGTCAGACCCAGTTCAACGGTGTG
AACGTGCTGTCGAAAAACGATTCGATGAAGATTCAGATTGGTGCCAATGATAACCAGACG
ATCAGCATTGGCTTGCAACAAATCGACAGTACCACTTTGAATCTGAAAGGATTTACCGTG
TCCGGCATGGCGGATTTCAGCGCGGCGAAACTGACGGCTGCTGATGGTACAGCAATTGCT
GCTGCGGATGTCAAGGATGCTGGGGGTAAACAAGTCAATTTACTGTCTTACACTGACACC
GCGTCTAACAGTACTAAATATGCGGTCGTTGATTCTGCAACCGGTAAATACATGGAAGCC
ACTGTAGCCATTACCGGTACGGCGGCGGCGGTAACTGTTGGTGCAGCGGAAGTGGCGGGA
GCCGCTACAGCCGATCCGTTAAAAGCACTGGATGCCGCAATCGCTAAAGTCGACAAATTC
CGCTCCTCCCTCGGTGCCGTTCAAAACCGTCTGGATTCTGCGGTCACCAACCTGAACAAC
ACCACCACCAACCTGTCTGAAGCGCAGTCCCGTATTCAGGACGCCGACTATGCGACCGAA
GTGTCCAACATGTCGAAAGCGCAGATTATCCAGCAGGCCGGTAACTCCGTGCTGGCAAA
```

Figure 47

```
ATGGCACAAGTCATTAATACCAACAGCCTCTCGCTGATCACTC
AAAATAATATCAACAAGAACCAGTCTGCGCTGTCGAGTTCTATCGAGCGTCTGTCTTCTG
GCTTGCGTATTAACAGCGCGAAGGATGACGCAGCGGGTCAGGCGATTGCTAACCGTTTTA
CCTCTAACATTAAAGGTCTGACTCAGGCTGCACGTAACGCCAACGACGGTATTTCTGTTG
CACAGACCACTGAAGGCGCGCTGTCCGAAATCAACAACAACTTACAGCGTATCCGTGAAC
TGACGGTTCAGGCTTCTACCGGGACTAACTCCGATTCGGATCTGGACTCCATTCAGGACG
AAATCAAATCCCGTCTGGACGAAATTGACCGCGTATCCGGTCAAACCCAGTTCAACGGTG
TGAACGTACTGGCGAAAGACGGTTCGATGAAAATTCAGGTTGGTGCGAATGACGGCCAGA
CTATCACGATTGATCTGAAGAAAATTGACTCAGATACGCTGGGGCTGAATGGTTTCAACG
TTAATGGCAAAGGCACTATTGCGAACAAAGCTGCTACAGTCAGCGATCTGACCGCTGCTG
GTGCAACGGGAACAGGTCCTTATGCTGTGACCACAAACAATACAGCACTCAGCGCTAGCG
ATGCACTGTCTCGCCTGAAAACCGGAGATACAGTTACTACTACTGGCTCGAGTGCTGCGA
TCTATACTTATGATGCGGCTAAAGGGAACTTCACCACTCAAGCAACAGTTGCAGATGGCG
ATGTTGTTAACTTTGCGAATACTCTGAAACCAGCGGCTGGCACTACTGCATCAGGTGTTT
ATACTCGTAGTACTGGTGATGTGAAGTTTGATGTAGATGCTAATGGCGATGTGACCATCG
GTGGTAAAGCCGCGTACCTGGACGCCACTGGTAACCTATCTACAAACAACCCCGGCATTG
CATCTTCAGCGAAATTGTCCGATCTGTTTGCTAGCGGTAGTACCTTAGCGACAACTGGTT
CTATCCAGCTGTCTGGCACAACTTATAACTTTGGTGCAGCGGCAACTTCTGGCGTAACCT
ACACCAAAACTGTAAGCGCTGATACTGTACTGAGCACAGTGCAGAGTGCTGCAACGGCTA
ACACAGCAGTTACTGGTGCGACAATTAAGTATAATACAGGTATTCAGTCTGCAACGGCGT
CCTTCGGTGGTGTGAATACTAATGGTGCTGGTAATTCGAATGACACCTATACTGATGCAG
ACAAAGAGCTCACCACAACCGCATCTTACACTATCAACTACAACGTCGATAAGGATACCG
GTACAGTAACTGTAGCTTCAAATGGCGCAGGTGCAACTGGTAAATTTGCAGCTACTGTTG
GGGCACAGGCTTATGTTAACTCTACAGGCAAACTGACCACTGAAACCACCAGTGCAGGCA
CTGCAACCAAAGATCCTCTGGCTGCCCTGGATGAAGCTATCAGCTCCATCGACAAATTCC
GTTCATCCCTGGGTGCTATCCAGAACCGTCTGGATTCCGCGGTTACCAACCTGAACAACA
CCACTACCAACCTGTCCGAAGCGCAGTCCCGTATTCAGGACGCCGACTATGCGACCGAAG
TGTCCAACATGTCGAAAGCGCAGATTATCCAGCAGGCCGGTAACTCCGTGCTGGCAAAAG
CCAACCAGGTACCGCAGCAGGTTCTGTCTCTGCTGCAGGGTTAA
```

Figure 48

```
ATGGCACAAGTCATTAATACCAACAGCCTCTCGCTGATCAC
TCAAAATAATATCAACAAGAACCAGTCTGCGCTGTCGAGTTCTATCGAGCGTCTGTCTTC
TGGCTTGCGTATTAACAGCGCGAAGGATGACGCCGCAGGTCAGGCGATTGCTAACCGTTT
TACTTCTAATATTAAAGGCCTGACTCAGGCTGCACGTAACGCCAATGACGGTATTTCTGT
TGCACAGACCACTGAAGGCGCGCTGTCCGAAATCAACAACAACTTACAGCGTGTGCGTGA
ACTGACCGTTCAGGCGACCACCGGTACCAACTCCCAGTCTGATCTGGACTCTATCCAGGA
CGAAATCAAATCCCGTCTGGACGAAATTGACCGCGTATCCGGTCAGACTCAGTTCAACGG
CGTGAACGTACTGGCAAAAGACGGTTCCATGAAAATTCAGGTTGGCGCGAATGATGGCCA
GACCATCACTATCGACCTGAAGAAGATTGACTCTTCTACGTTGAAACTGACTGGTTTTAA
CGTGAATGGTTCTGGTTCTGTGGCGAATACTGCGGCGACTAAAGACGAACTGGCTGCTGC
TGCTGCGGCGGCGGGTACAACTCCTGCTGTCGGTACTGACGGCGTGACCAAATATACCGT
AGACGCAGGGCTTAACAAAGCCACAGCAGCAAACGTGTTTGCAAACCTTGCAGATGGTGC
TGTTGTTGATGCTAGCATTTCCAACGGTTTTGGTGCAGCAGCAGCCACAGACTACACCTA
CAATAAAGCTACAAATGATTTCACTTTCAATGCCAGCATTGCTGCTGGTGCTGCGGCCGG
TGATAGTAACAGCGCAGCTCTGCAATCCTTCCTGACTCCAAAAGCAGGTGATACAGCTAA
CCTGAGCGTCAAAATCGGTACGACATCTGTTAATGTTGTTCTGGCGAGCGATGGCAAAAT
TACAGCGAAAGATGGCTCAGCTCTGTATATCGACTCAACGGGTAACCTGACTCAGAACAG
CGCAGGCACTGTAACAGCAGCAACCCTGGATGGACTGACCAAAAACCATGATGCGACAGG
AGCTGTTGGTGTTGATATCACGACCGCAGATGGCGCAACTATCTCTCTGGCAGGCTCTGC
TAACGCGGCAACAGGTACTCAATCAGGTGCAATTACACTGAAAAATGTTCGTATCAGTGC
TGATGCTCTGCAGTCTGCTGCGAAAGGTACTGTTATCAATGTTGATAATGGTGCTGATGA
TATTTCTGTTAGTAAAACCGGGTGTCGTTACTACCGGAGGTGCGCCTACTTATACTGATG
CTGATGGTAAATTAACGACAACCAACACCGTTGATTATTTCCTGCAAACTGATGGCAGCG
TAACCAATGGTTCTGGTAAAGGGGTTTACACCGATGCAGCTGGTAAATTCACTACCGACG
CTGCAACCAAAGCCGCAACCACCACCGATCCGCTGAAAGCCCTTGATGACGCAATCAGCC
AGATCGATAAGTTCCGTTCATCCCTGGGTGCTATCCAGAACCGTCTGGATTCCGCGGTTA
CCAACCTGAACAACACCACTACCAACCTGTCCGAAGCGCAGTCCCGTATTCAGGACGCCG
ACTATGCGACCGAAGTGTCCAATATGTCGAAAGCGCAGATCATCCAGCAGGCCGGTAACT
CCGTGTTGGCAAAAGCTAACCAGGTACCGCAGCAGGTTCTGTCTCTGCTGCAGGGTTAA
```

Figure 49

```
AACAAATCTCAGTCTTCTCTTAGCTCTGCTATTGAGCGTCTGTCTTCTGGT
CTGCGTATTAACAGCGCAAAAGACGATGCAGCAGGTCAGGCGATTGCTAACCGTTTTACG
GCAAATATTAAAGGTCTGACCCAGGCTTCCCGTAACGCGAATGATGGTATTTCTGTTGCG
CAGACCACTGAAGGTGCGCTGAATGAAATTAACAACAACCTGCAGCGTATTCGTGAACTT
TCTGTTCAGGCAACTAACGGTACTAACTCTGACAGCGATCTTTCTTCTATCCAGGCTGAA
ATTACTCAACGTCTGGAAGAAATTGACCGTGTATCTGAGCAAACTCAGTTTAACGGCGTG
AAAGTCCTTGCTGAAAATAATGAAATGAAAATTCAGGTTGGTGCTAATGATGGTGAAACC
ATCACTATCAATCTGGCAAAAATTGATGCGAAAACTCTCGGCCTGGACGGTTTTAATATC
GATGGCGCGCAGAAAGCAACCGGCAGTGACCTGATTTCTAAATTTAAAGCGACAGGTACT
GATAATTATCAAATTAACGGTACTGATAACTATACTGTTAATGTAGATAGTGGAGTAGTA
CAGGATAAAGATGGCAAACAAGTTTATGTGAGTGCTGCGGATGGTTCACTTACGACCAGC
AGTGATACTCAATTCAAGATTGATGCAACTAAGCTTGCAGTGGCTGCTAAAGATTTAGCT
CAAGGTAATAAGATTGTCTACGAAGGTATCGAATTTACAAATACCGGCACTGGCGCTATA
CCTGCCACAGGTAATGGTGAATTAACCGCCAATGTTGATGGTAAGGCTGTTGAATTCACT
ATTTCGGGGAGTGCTGATACATCAGGTACTAGTGCAACCGTTGCCCCTACGACAGCCCTA
TACAAAAATAGTGCAGGGCAATTGACTGCAACAAAAGTTGAAAATAAAGCAGCGACACTA
TCTGATCTTGATCTGAACGCTGCCAAGAAAACAGGAAGCACGTTAGTTGTTAACGGTGCA
ACTTACGATGTTAGTGCAGATGGTAAAACGATAACGGAGACTGCTTCTGGTAACAATAAA
GTCATGTATCTGAGCAAATCAGAAGGTGGTAGCCCGATTCTGGTAAACGAAGATGCAGCA
AAATCGTTGCAATCTACCACCAACCCGCTCGAAACTATCGACAAAGCATTGGCTAAAGTT
GACAATCTGCGTTCTGACCTCGGTGCAGTACAAAACCGTTTCGACTCTGCCATCACCAAC
CTTGGCAACACCGTAAACAACCTGTCTTCTGCCCGTAGCCGTATCGAAGATGCTGACTAC
GCGACCGAAGTGTCTAACATGTCTCGTGCGCAGATCCTGCAACAAGCGGGTACCTCTGTT CTGGCACAG
```

Figure 50

```
ATGGCACAAGTCATTAATACCAACAGCCTCTCGCTGATCAC
TCAAAATAATATCAACAAGAACCAGTCTGCGCTGTCGAGTTCTATCGAGCGTCTGTCTTC
TGGCTTGCGTATTAACAGCGCGAAGGATGACGCAGCGGGTCAGGCGATTGCTAACCGTTT
CACCTCTAACATTAAAGGCCTGACTCAGGCGGCCCGTAACGCCAACGACGGTATCTCCGT
TGCGCAGACCACCGAAGGCGCGCTGTCCGAAATCAACAACAACTTACAGCGTGTGCGTGA
ACTGACGGTACAGGCCACTACCGGTACTAACTCTGAGTCTGATCTGTCTTCTATCCAGGA
CGAAATTAAATCCCGTCTGGATGAAATTGACCGCGTATCTGGTCAGACCCAGTTCAACGG
CGTGAACGTGCTGGCAAAAATGGCTCCATGAAAATCCAGGTTGGCGCAAATGATAACCA
GACTATCACTATCGATCTGAAGCAGATTGATGCTAAAACTCTTGGCCTTGATGGTTTTAG
CGTTAAAAATAACGATACAGTTACCACTAGTGCTCCAGTAACTGCTTTTGGTGCTACCAC
CACAAACAATATTAAACTTACTGGAATTACCCTTTCTACGGAAGCAGCCACTGATACTGG
CGGAACTAACCCAGCTTCAATTGAGGGTGTTTATACTGATAATGGTAATGATTACTATGC
GAAAATCACCGGTGGTGATAACGATGGGAAGTATTACGCAGTAACAGTTGCTAATGATGG
TACAGTGACAATGGCGACTGGAGCAACGGCAAATGCAACTGTAACTGATGCAAATACTAC
TAAAGCTACAACTATCACTTCAGGCGGTACACCTGTTCAGATTGATAATACTGCAGGTTC
CGCAACTGCCAACCTTGGTGCTGTTAGCTTAGTAAAACTGCAGGATTCCAAGGGTAATGA
TACCGATACATATGCGCTTAAAGATACAAATGGCAATCTTTACGCTGCGGATGTGAATGA
AACTACTGGTGCTGTTTCTGTTAAAACTATTACCTATACTGACTCTTCCGGTGCCGCCAG
TTCTCCAACCGCGGTCAAACTGGGCGGAGATGATGGCAAAACAGAAGTGGTCGATATTGA
TGGTAAAACATACGATTCTGCCGATTTAAATGGCGGTAATCTGCAAACAGGTTTGACTGC
TGGTGGTGAGGCTCTGACTGCTGTTGCAAATGGTAAAACCACGGATCCGCTGAAAGCGCT
GGACGATGCTATCGCATCTGTAGACAAATTCCGTTCTTCCCTCGGTGCGGTGCAAAACCG
TCTGGATTCCGCGGTTACCAACCTGAACAACACCACTACCAACCTGTCTGAAGCGCAGTC
CCGTATTCAGGACGCCGACTATGCGACCGAAGTGTCCAATATGTCGAAAGCGCAGATCAT
CCAGCAGGCCGGTAACTCCGTGTTGGCAAAAGCTAACCAGGTACCGCAGCAGGTTCTGTC
TCTGCTGCAGGGTTAA
```

Figure 51

```
ATGGCACAAGTCATTAATACCAACAGCCTCTCGCTGATCACT
CAAAATAATATCAACAAGAACCAGTCTGCGCTGTCGAGTTCTATCGAGCGTCTGTCTTCT
GGCTTGCGTATTAACAGCGCGAAGGATGACGCCGCAGGTCAGGCGATTGCTAACCGTTTT
ACTTCTAACATTAAAGGCCTGACTCAGGCTGCACGTAACGCCAACGACGGTATTTCTGTT
GCGCAGACCACCGAAGGCGCGCTGTCTGAAATCAACAACAACTTACAGCGTATTCGTGAA
CTGACGGTTCAGGCTTCTACCGGGACTAACTCTGATTCGGATCTGGACTCCATTCAGGAC
GAAATCAAATCCCGTCTGGACGAAATTGACCGCGTATCCGGTCAAACCCAGTTCAACGGT
GTGAACGTACTGGCGAAAGACGGTTCGATGAAAATTCAGGTTGGTGCGAATGACGGCCAG
ACTATCACTATTGATCTGAAGAAAATTGACTCTGATACGCTGGGGCTGAATGGTTTTAAC
GTTAACGGCAAAGGTACTATTGCGAACAAAGCGGCAACCATTAGTGATCTGGCGGCGACG
GGGGCGAATGTTACTAACTCAAGCAATATTGTTGTCACGACAAAGTTCAATGCCTTGGAT
GCAGCGACTGCATTTAGCAAACTCAAAGATGGTGATTCTGTTGCCGTTGCTGCTCAGAAA
TATACTTATAACGCATCGACCAATGATTTTACGACAGAAAATACAGTAGCGACAGGCACT
GCAACGACAGATCTTGGCGCTACTCTGAAGGCTGCTGCTGGGCAGAGTCAATCAGGTACA
TATACCTTTGCAAATGGTAAAGTTAACTTTGATGTTGATGCAAGCGGTAATATCACTATT
GGCGGCGAAAAGGCTTTCTTGGTTGGTGGAGCGCTGACTACTAACGATCCCACCGGCTCC
ACTCCAGCAACGATGTCTTCCCTGTTTAAGGCCGCGGATGACAAAGATGCCGCTCAATCC
TCGATTGATTTTGGCGGGAAAAAATACGAATTTGCTGGTGGCAATTCTACTAATGGTGGC
GGCGTTAAATTCAAAGACACGGTGTCTTCTGACGCGCTTTTGGCTCAGGTTAAAGCGGAT
AGTACTGCTAATAATGTAAAAATCACCTTTAACAATGGTCCTCTGTCATTCACTGCATCG
TTCCAAAATGGTGTATCTGGCTCCGCGGCATCGAATGCAGCCTACATTGATAGCGAAGGC
GAACTGACAACTACTGAATCCTACAACACAAATTATTCCGTAGACAAAGACACGGGGGCT
GTAAGTGTTACAGGGGGGAGCGGTACGGGTAAATACGCCGCAAACGTGGGTGCTCAGGCT
TATGTAGGTGCAGATGGTAAATTAACCACGAATACTACTAGTACCGGCTCTGCAACCAAA
GATCCACTAAATGCGCTGGATGAGGCAATTGCATCCATCGACAAATTCCGTTCTTCCCTG
GGGGCTATCCAGAACCGTCTGGATTCCGCAGTCACCAACCTGAACAACACCACTACCAAC
CTGTCTGAAGCGCAGTCCCGTATTCAGGACGCCGACTATGCGACCGAAGTGTCCAACATG
TCGAAAGCGCAGATCATCCAGCAGGCCGGTAACTCCGTGTTGGCAAAAGCTAACCAGGTA
CCGCAGCAGGTTCTGTCTCTGCTGCAGGGTTAA
```

Figure 52

```
AACAAGAACCAGTCTGCGCTGTCGAGTTCTATCGAGCGTCTGTC
TTCTGGCTTGCGTATTAACAGCGCGAAGGATGACGCCGCGGGTCAGGCGATTGCTAACCG
TTTTACTTCTAACATTAAAGGCCTGACTCAGGCTGCACGTAACGCCAACGACGGTATTTC
TGTTGCGCAGACCACCGAAGGCGCGCTGTCCGAAATTAACAACAACTTACAGCGTGTGCG
TGAGCTGACTGTTCAGGCGACCACCGGTACTAACTCTGAGTCTGACCTGTCTTCTATCCA
GGACGAAATCAAATCTCGCCTGGAAGAGATTGATCGTGTTTCAAGTCAGACTCAATTTAA
CGGCGTGAATGTTTTGGCTAAAGATGGGAAAATGAACATTCAGGTTGGGGCAAGTGATGG
ACAGACTATCACTATTGATCTGAAAAAGATCGATTCATCTACACTAAACCTCTCCAGTTT
TGATGCTACAAACTTGGGCACCAGTGTTAAAGATGGGGCCACCATCAATAAGCAAGTGGC
AGTAGATGCTGGCGACTTTAAAGATAAAGCTTCAGGATCGTTAGGTACCCTAAAATTAGT
TGAGAAAGACGGTAAGTACTATGTAAATGACACTAAAAGTAGTAAGTACTACGATGCCGA
AGTAGATACTAGTAAGGGTGAAATTAACTTCAACTCTACAAATGAAAGTGGAACTACTCC
TACTGCAGCGACGGAAGTAACTACTGTTGGCCGCGATGTAAAATTGGATGCTTCTGCACT
TAAAGCCAACCAATCGCTTGTCGTGTATAAAGATAAAAGCGGCAATGATGCTTATATCAT
TCAGACCAAAGATGTAACAACTAATCAATCAACTTTCAATGCCGCTAATATCAGTGATGC
TGGTGTTTTATCTATTGGTGCATCTACAACCGCGCCAAGCAATTTAACAGCTGACCCGCT
TAAGGCTCTTGATGATGCAATTGCATCTGTTGATAAATTCCGCTCTTCTCTCGGTGCCGT
TCAGAACCGTCTGGATTCTGCCATTGCCAACCTGAACAACACCACTACCAACCTGTCTGA
AGCGCAGTCCCGTATTCAGGACGCTGACTATGCGACCGAAGTGTCCAACATGTCGAAAGC
GCAGATTATCCAGCAGGCCGGTAACTCCGTGCTGGCAAAA
```

Figure 53

```
ATGGCACAAGTCATTAATACCAACAGCCTCTCGCTGATCACTCAAAA
TAATATCAACAAGAACCAGTCTGCGCTGTCGAGTTCTATCGAGCGTCTGTCTTCTGGCTT
GCGTATTAACAGCGCGAAGGATGACGCAGCGGGTCAGGCGATTGCTAACCGTTTCACCTC
TAACATTAAAGGCCTGACTCAGGCTGCACGTAACGCTAACGATGGTATCTCTCTGGCGCA
GACCACTGAAGGCGCACTGTCTGAGATTAACAACAACTTACAACGTGTGCGTGAGTTGAC
TGTACAGGCGACCACCGGTACTAACTCTGATTCTGACCTGGCTTCTATTCAGGACGAAAT
CAAATCCCGTTTGTCTGAAATTGACCGCGTATCCGGGCAGACCCAGTTCAACGGCGTGAA
CGTATTGTCTAAAGATGGCTCCCTGAAAATTCAGGTTGGCGCAAATGATGGTCAGACTAT
CTCTATCGACCTGAAGAAAATTGACTCTGATACTCTGGGTTTGAATGGTTTCAACGTTAA
TGGTTCTGGTACCATTGCAAACAAAGCGGCCACAATCAGTGACTTGACTGCTCAGAAAGC
CGTTGACAACGGTAATGGTACTTATAAAGTTACAACTAGCAACGCTGCACTTACTGCATC
TCAGGCATTAAGTAAGCTGAGTGATGGCGATACTGTAGATATTGCAACCTATGCTGGTGG
TACAAGTTCAACAGTTAGTTATAAATACGACGCAGATGCAGGTAACTTCAGTTATAACAA
TACTGCAAACAAAACAAGTGCTGCGGCTGGAACTCTGGCAGATACTCTTCTCCCGGCAGC
TGGCCAGACTAAAACCGGTACTTACAAGGCTGCTACTGGTGATGTTAACTTTAATGTTGA
CGCAACTGGTAATCTGACAATTGGCGGACAGCAAGCCTACCTGACTACTGATGGTAACCT
TACAACAAACAACTCCGGTGGTGCGGCTACTGCAACTCTTAAAGAGCTGTTTACTCTTGC
TGGCGATGGTAAATCTCTGGGGAACGGCGGTACTGCTACCGTTACTCTGGATAATACTAC
GTATAATTTCAAAGCTGCTGCGAACGTTACTGATGGTGCTGGTGTCATCGCTGCTGCTGG
TGTAACTTATACAGCCACTGTTTCTAAAGATGTCATTCTGGCACAACTGCAATCTGCAAG
TCAGGCAGCAGCAACCGCTACCGACGGTGATACTGTCGCAACGATCAACTATAAATCTGG
TGTCATGATCGGTTCCGCTACCTTTACCAATGGTAAAGGTACTGCCGATGGTATGACTTC
TGGTACAACTCCAGTCGTAGCTACAGGTGCTAAAGCTGTATATGTTGATGGCAACAATGA
ACTGACTTCCACTGCATCTTACGATACGACTTACTCTGTCAACGCAGATACAGGCGCAGT
AAAAGTGGTATCAGGTACTGGTACTGGTAAATTTGAAGCTGTTGCTGGTGCGGATGCTTA
TGTAAGCAAAGATGGCAAATTAACGACAGAAACCACCAGTGCAGGCACTGCAACCAAAGA
TCCTTTGGCTGCCCTGGATGCTGCTATCAGCTCCATCGACAAATTCCGTTCCTCCCTGGG
TGCTATCCAGAACCGTCTGGATTCCGCAGTCACCAACCTGAACAACACCACTACTAACCT
GTCTGAAGCGCAGTCCCGTATTCAGGACGCCGACTATGCGACCGAAGTGTCCAATATGTC
GAAAGCGCAGATCATCCAGCAGGCCGGTAACTCTGTGTTGGCAAAAGCTAACCAGGTACC
GCAGCAGGTTCTGTCTCTGCTGCAGGGTTAA
```

Figure 54

```
ATGGCACAAGTCATTAATACCAACAGCC
TCTCGCTGATCACTCAAAATAATATCAACAAGAACCAGTCTGCGCTGTCGAGTTCTATCG
AGCGTCTGTCTTCTGGCTTGCGTATTAACAGCGCGAAGGATGACGCCGCAGGTCAGGCGA
TTGCTAACCGTTTTACTTCTAACATTAAAGGCCTGACTCAGGCTGCACGTAACGCCAACG
ACGGTATTTCTGTTGCACAGACCACTGAAGGCGCGCTGTCCGAAATCAACAACAACTTAC
AGCGTATTCGTGAACTGACGGTTCAGGCTTCTACCGGGACTAACTCTGATTCGGATCTGG
ACTCCATTCAGGACGAAATCAAATCCCGTCTCGACGAAATTGACCGCGTTTCCGGTCAGA
CCCAGTTCAACGGCGTGAACGTGCTGGCGAAAGACGGTTCGATGAAGATTCAGGTTGGCG
CGAATGACGGGCAGACCATCTCTATCGATTTGCAGAAAATTGATTCTTCAACGCTGGGAT
TGAAAGGTTTCTCGGTATCAGGGAACGCATTAAAAGTTAGCGATGCGATAACTACAGTTC
CTGGTGCTAATGCTGGCGATGCCCCGGTTACGGTTAAATTTGGTGCGAACGATACCGCTG
CTGCCGCAATGGCTAAAACATTGGGAATAAGTGATACATCAGGCTTGTCCCTACATAACG
TACAAAGCGCGGATGGTAAAGCGACAGGAACCTATGTTGTTCAATCTGGTAATGACTTCT
ATTCGGCTTCCGTTAATGCTGGTGGCGTTGTTACGCTTAATACCACCAATGTTACTTTCA
CTGATCCTGCGAACGGTGTTACCACAGCAACACAGACAGGTCAGCCTATCAAGGTCACGA
CGAATAGTGCTGGCGCGGCTGTTGGCTATGTTACTATTCAAGGCAAAGATTACCTTGCTG
GTGCAGACGGTAAGGATGCAATTGAAAACGGTGGTGACGCTGCAACAAATGAAGACACAA
AAATCCAACTTACCGATGAACTCGATGTTGATGGTTCTGTAAAAACAGCGGCAACAGCAA
CATTTCTGGTACTGCAACCAACGATCCGCTGGCACTTTTAGACAAAGCTATCTCGCAAG
TTGATACTTTCCGCTCCTCCCTCGGTGCCGTACAAAACCGTCTGGATTCTGCGGTCACCA
ACCTGAATAACACCACCACCAACCTGTCTGAAGCGCAGTCCCGTATTCAGGACGCCGACT
ATGCGACCGAAGTGTCCAACATGTCGAAAGCGCAGATCATCCAGCAGGCGGGTAACTCTG
TGCTGTCTAAAGCTAACCAGGTACCGCAGCAGGTTCTGTCTCTGCTGCAGGGTTAA
```

Figure 55

```
CTTCTCTTAGCTCTGCTATTGAGCGTCTGTCTTCTGGTCTGCGTATTAACAGCGCAAAAG
ACGATGCAGCAGGTCAGGCGATTGCTAACCGTTTTACGGCAAATATTAAAGGTCTGACCC
AGGCTTCCCGTAACGCGAATGATGGTATTTCTGTTGCGCAGACCACTGAAGGTGCGCTGA
ATGAAATTAACAACAACCTGCAGCGTATTCGTGAACTTTCTGTTCAGGCAACTAACGGTA
CTAACTCTGACAGCGATCTTTCTTCTATCCAGGCTGAAATTACTCAACGTCTGGAAGAAA
TTGACCGTGTATCTGAGCAAACTCAGTTTAACGGCGTGAAAGTCCTTGCTGAAAATAATG
AAATGAAAATTCAGGTTGGTGCTAATGATGGTGAAACCATTGACCTGCCCCACGATTAG
ATACAACACTCAGTTAGTAACGTCGGAATCTTCATTCTCAGAATGACCCTTTCTCCAGCC
CGCTGCAAATTCAGACGGTGTCTGATAATTCAGCGTGGAGTGCGGGCGGCATTCGTTATA
ATCCTGCCGCCAGTCATTAATAATTTTCCTGGCATGAACGATATCGCTGAACCAGTGCTC
ATTCAAACATTCATCGCGAAATCGTCCGTTAAAGCTCTCAATAAATCCGTTCTGCGTTGG
CTTGCCCGGCTGGATTAAGCGCAACTCAACACCATGCTCAAAGGCCCATTGATCCAGTGC
ACGGCAAGTGAACTCCGGCCCCTGGTCAGTTCTTATCGTCGCCGGATAGCCTCGAAACAG
TGCAATGCTGTCCAGAATACGCGTGACCTGAACGCCTGAAATCCCAAAGGCAACAGTGAC
CGTCAGGCATTCCTTTGTGAAATCATCGACGCAGGTAAGACACTTGATCCTGCGACCGGT
GGAAAGTGCGTCCATGACGAAATCCATCGACCAGGTCAGATTGGGCGCCGCCGGACGGAG
CAGCGGCAGACGTTCTGTTGCCAGCCCTTTACGACGTCTTCTGCGTTTTACGCCCAGGCC
ACTGAGGTGATAAAGCCGGTACACGCGCTTATGATTAACATGAAGCCCTTCACGGCGCAG
CAACTGCCAAATACGACGGTAGCCAAAACGCCTGCGCTCCAGTGCCAGCTCAGTGATGCG
CCCTGATAAATGCGCATCAGCAGCCGGACGGTGAGCCTCATAGCGGCAGGTCGACAGGGA
TAAACCTGTAAGCCTGCAGGCACGACGTTGCGACAGACCGGTCGCATCACACATCAACAT
CACGGCTTCCCGCTTCTGGTCTGTCGTCAGTACTTTCGCCCAAGAGCCACCTGAAGCGCC
TCTTTATCCAGCATGGCTTCGGCAAGCAGCTTCTTGAGTCTGGTGTTCTCTTCCTCAAGC
GACTTCAGGCGCTTAACTTCAGGCACCTCCATACCGCCATACTTCTTACGCCAGGTGTAA
AACGTGGCATCGGAAATGGCATGCTTGCGGCAGAGTTCACGGGCGGGTACCCCAGCTTCG
GCTTCGCGGAGAATACTGATGATCTGTTCGTCGGAAAAACGCTTCTTCATGGGGATGTCC
TCATGTGGCTTATGAAGACATTACTAACATCGGGGTGTACTAATCAACGGGGAGCAGGTC
ACCATCACTATCAATCTGGCAAAAATTGATGCGAAAACTCTCGGCCTGGACGGTTTTAAT
ATCGATGGCGCGCAGAAAGCAACCGGCAGTGACCTGATTTCTAAATTTAAAGCGACAGGT
ACTGATAATTATCAAATTAACGGTACTGATAACTATACTGTTAATGTAGATAGTGGAGTA
GTACAGGATAAAGATGGCAAACAAGTTTATGTGAGTGCTGCGGATGGTTCACTTACGACC
AGCAGTGATACTCAATTCAAGATTGATGCAACTAAGCTTGCAGTGGCTGCTAAAGATTTA
GCTCAAGGTAATAAGATTGTCTACGAAGGTATCGAATTTACAAATACCGGCACTGGCGCT
ATACCTGCCACAGGTAATGGTAAATTAACCGCCAATGTTGATGGTAAGGCTGTTGAATTC
ACTATTTCGGGGAGTGCTGATACATCAGGTACTAGTGCAACCGTTGCCCCTACGACAGCC
CTATACAAAAATAGTGCAGGGCAATTGACTGCAACAAAAGTTGAAAATAAAGCAGCGACA
CTATCTGATCTTGATCTGAACGCTGCCAAGAAAACAGGAAGCACGTTAGTTGTTAACGGT
GCAACTTACGATGTTAGTGCAGATGGTAAAACGATAACGGAGACTGCTTCTGGTAACAAT
AAAGTCATGTATCTGAGCAAATCAGAAGGTGGTAGCCCGATTCTGGTAAACGAAGATGCA
GCAAAATCGTTGCAATCTACCACCAACCCGCTCGAAACTATCGACAAAGCATTGGCTAAA
GTTGACAATCTGCGTTCTGACCTCGGTGCAGTACAAAACCGTTTCGACTCTGCCATCACC
AACCTTGGCAACACCGTAAACAACCTGTCTTCTGCCCGTAGCCGATCGAAGATGCTGAC
TACGCGACCGAAGTGTCTAACATGTCTCGTGCGCAGATCCTGCAACAAGCGGGTACCTCT
GTTCTGGCACAGGCTAACC
```

Figure 56

```
AACAAAAACCAGTCTGCGCTGTCGACTTCTATCGAGCGCCTCTCT
TCTGGTCTGCGCATTAACAGCGCTAAAGATGACGCTGCGGGCCAGGCGATTGCTAACCGC
TTCACTTCTAACATCAAAGGTCTGACTCAGGCCGCACGTAACGCCAACGACGGTATCTCT
CTGGCGCAGACCACTGAAGGCGCACTGTCTGAAATCAACAACAACTTGCAGCGTGTTCGT
GAACTGACCGTTCAGGCCACTACCGGTACTAACTCTGATTCTGACCTGTCTTCAATCCAG
GACGAAATCAAATCCCGTCTCGATGAAATTGACCGCGTATCCGGTCAGACTCAGTTCAAC
GGCGTGAACGTACTGGCAAAAGATGGCTCGATGAAAATTCAGGTCGGTGCAAATGATGGT
CAGACAATCAGCATTGATTTGCAGAAGATTGATTCTTCTACTTTAGGGTTAAATGGTTTT
TCTGTTTCCAAAAATGCAGTATCTGTTGGTGATGCTATTACTCAATTGCCTGGCGAGACG
GCAGCCGATGCACCAGTAACCATCAAGTTTGATGATTCAGTAAAAACTGATTTAAAACTG
ACCGATGCTTCAGGGTTAAGTCTGCATAACCTCAAAGATGAAAATGGTAATTTAACTAAC
CAGTATGTTGTACAGAATGGCGGAAAATCTTACGCTGCTACAGTCGCTGCCAATGGTAAT
GTTACGCTGAACAAAGCAAATGTAACCTACAGCGATGTCGCAAACGGTATTGATACCGCA
ACGCAGTCAGGCCAGTTAGTTCAGGTTGGTGCAGATTCTACCGGTACGCCAAAAGCATTC
GTGTCTGTCCAAGGTAAAAGCTTTGGCATTGATGACGCCGCCTTGAAGAATAACACTGGT
GATGCTACCGCTACTCCACCGGGAACATCTGGGACAACAGTTGTCGCAGCGTCAATTCAT
CTGAGTACGGGCAAAAACTCTGTAGACGCTGATGTAACGGCTTCCACTGAATTCACAGGT
GCTTCAACCAACGATCCACTGACTCTGCTGGACAAAGCTATCGCATCTGTTGATAAATTC
CGTTCTTCTTTGGGGGCGGTACAGAACCGTCTGAGCTCCGCTGTAACCAACCTGAACAAC
ACCACCACCAACCTGTCTGAAGCGCAGTCCCGTATTCAGGACGCCGACTATGCGACCGAA
GTGTCCAACATGTCGAAAGCGCAGATTATCCAGCAGGCAGGTAACTCCGTGCTGTCCAAA
```

Figure 57

```
AACAAAAACCAGTCTGCGCTGTCGACTTCTATCGAACGCCTCTCTTCTGG
CCTGCGTATTAACAGTGCGAAAGATGACGCTGCCGGTCAGGCGATAGCTAACCGTTTCAC
CTCTAACATTAAAGGCCTGACTCAGGCTGCGCGTAACGCCAACGACGGTATTTCTCTGGC
GCAGACCACAGAAGGTGCGTTGTCTGAAATCAACAACAACTTGCAACGTGTGCGTGAGTT
GACCGTTCAGGCGACGACCGGTACTAACTCTGATTCTGACCTGTCATCTATTCAGGACGA
AATCAAATCCCGTCTGGATGAGATTGACCGTGTTTCCGGTCAGACCCAGTTCAACGGCGT
GAATGTACTGGCAAAAGACGGTTCGATGAAGATTCAGGTTGGCGCGAATGATGGCCAGAC
TATTAGCATTGATTTACAGAAAATTGACTCTTCTACATTAGGGTTGAATGGTTTCTCCGT
TTCTGCTCAATCACTTAACGTTGGTGATTCAATTACTCAAATTACAGGAGCCGCTGGGAC
AAAACCTGTTGGTGTTGATTTCACTGCTGTTGCGAAAGATCTGACTACTGCGACAGGTAA
AACTGTCGATGTTTCCAGCCTGACGTTACACAACACCCTGGATGCGAAAGGGGCTGCCAC
CGCACAGTTCGTCGTTCAATCCGGTAGTGATTTCTACTCCGCGTCCATTGACCATGCAAG
TGGTGAAGTGACGTTGAATAAAGCCGATGTCGAATACAAAGACACCGATAATGGACTAAC
GACTGCAGCTACTCAGAAAGATCAGCTGATTAAAGTTGCCGCTGACTCTGACGGCGCGGC
TGCGGGATATGTAACATTCCAGGGTAAAAACTACGCTACAACGGCTCCAGCGGCGCTTAA
TGATGACACTACGGCAACAGCCACAGCGAACAAAGTTGTTGTTGAATTATCTACAGCAAC
TCCGACTGCGCAGTTCTCAGGGGCTTCTTCTGCTGATCCACTGGCACTTTTAGACAAAGC
CATTGCACAGGTTGATACTTTCCGCTCCTCCCTCGGTGCCGTTCAAAACCGTCTGGACTC
TGCGGTAACCAACCTGAACAACACCACCACCAACCTGTCTGAAGCGCAGTCCCGTATTCA
GGACGCCGACTATGCGACCGAAGTGTCTAACATGTCGAAAGCGCAGATCATCCAGCAGGC
GGGTAACTCTGTGCTGTCTAAA
```

Figure 58

```
ATGGCACAAG TCATTAATAC CAACAGCCTC TCGCTGATCA CTCAAAATAA TATCAACAAG
AACCAGTCTG CGCTGTCGAG TTCTATCGAG CGTCTGTCTT CTGGCTTGCG TATTAACAGC
GCGAAGGATG ACGCCGCGGG TCAGGCGATT GCTAACCGTT TTACTTCTAA CATTAAAGGC
CTGACTCAGG CTGCACGTAA CGCCAACGAC GGTATTTCTG TTGCACAGAC CACTGAAGGC
GCGCTGTCCG AAATCAACAA CAACTTACAG CGTATCCGTG AGCTGACGGT TCAGGCTTCT
ACCGGGACTA ACTCTGATTC GGATCTGGAC TCCATTCAGG ACGAAATCAA ATCCCGTCTC
GACGAAATTG ACCGCGTATC CGGTCAGACC CAGTTCAACG GCGTGAACGT ACTGGCAAAA
GACGGTTCGA TGAAAATTCA GGTTGGTGCG AATGACGGTG AAACTATCAC TATCGACCTG
AAGAAAATCG ATTCTGATAC TCTGGGTCTG AATGGTTTTA ACGTAAATGG TAAAGGTACT
ATTACCAACA AAGCTGCAAC GGTAAGTGAT TTAACTTCTG CTGGCGCGAA GTTAAACAC
CACGACAGGT CTTTATGATC TGAAAACCGA AAATACCTTG TTAACTACCG ATGCTGCATT
CGATAAATTA GGGAATGGCG ATAAAGTCAC CGTTGGCGGC GTAGATTATA CTTACAACGC
TAAATCTGGT GATTTTACTA CCACCAAATC TACTGCTGGT ACGGGTGTAG ACGCCGCGGC
GCAGGCTACT GATTCAGCTA AAAAACGTGA TGCGTTAGCT GCCACCCTTC ATGCTGATGT
GGGTAAATCT GTTAATGGTT CTTACACCAC AAAAGATGGT ACTGTTTCTT TCGAAACGGA
TTCAGCAGGT AATATCACCA TCGGTGGAAG CCAGGCATAC GTAGACGATG CAGGCAACTT
GACGACTAAC AACGCTGGTA GCGCAGCTAA AGCTGATATG AAAGCGCTGC TTAAAGCCGC
GAGCGAAGGT AGTGACGGTG CCTCTCTGAC ATTCAATGGC ACTGAATATA CTATCGCAAA
AGCAACTCCT GCGACAACCT CTCCAGTAGC TCCGTTAATC CCTGGTGGA TTACTTATCA
GGCTACAGTG AGTAAAGATG TAGTATTGAG CGAAACCAAA GCGGCTGCCG CGACATCTTC
AATTACCTTT AATTCCGGTG TACTGAGCAA AACTATTGGG TTTACCGCGG GTGAATCCAG
TGATGCTGCG AAGTCTTATG TGGATGATAA AGGTGGTATT ACTAACGTTG CCGACTATAC
AGTCTCTTAC AGCGTTAACA AGGATAACGG CTCTGTGACT GTTGCCGGGT ATGCTTCAGC
GACTGATACC AATAAAGATT ATGCTCCAGC AATTGGTACT GCTGTAAATG TGAACTCCGC
GGGTAAAATC ACTACTGAGA CTACCAGTGC TGGTTCTGCA ACGACCAACC CGCTTGCTGC
CCTGGACGAC GCTATCAGCT CCATCGACAA ATTCCGTTCT TCCCTGGGTG CTATCCAGAA
CCGTCTGGAT TCCGCAGTCA CCAACCTGAA CAACACCACT ACCAACCTGT CTGAAGCGCA
GTCCCGTATT CAGGACGCCG ACTATGCGAC CGAAGTGTCC AACATGTCGA AAGCGCAGAT
TATCCAGCAG GCCGGTAACT CCGTGCTGGC AAAAGCCAAC CAGGTACCGC AGCAGGTTCT
GTCTCTGCTG CAGGGTTAA
```

Figure 59

```
ATGGCACAAG TCATTAATAC CAACAGCCTC TCGCTGATCA CTCAAAATAA TATCAACAAG
AACCAGTCTG CGCTGTCGAG TTCTATCGAG CGTCTGTCTT CTGGCTTGCG TATTAACAGC
GCGAAGGATG ACGCCGCAGG TCAGGCGATT GCTAACCGTT TTACTTCTAA CATTAAAGGC
CTGACTCAGG CGGCCCGTAA CGCCAACGAC GGTATTTCTG TTGCGCAGAC CACCGAAGGC
GCGCTGTCCG AAATCAACAA CAACTTACAG CGTATTCGTG AACTGACGGT TCAGGCCACT
ACAGGGACTA ACTCCGATTC TGACCTGGAC TCCATCCAGG ACGAAATCAA ATCTCGTCTT
GATGAAATTG ACCGCGTATC CGGCCAGACC CAGTTCAACG GCGTGAACGT GCTGGCGAAA
GACGGTTCAA TGAAAATTCA GGTTGGTGCG AATGACGGCG AAACCATCAC GATCGACCTG
AAAAAAATCG ATTCTGATAC TCTGGGTCTG AATGGCTTTA ACGTAAATGG TAAAGGTACT
ATTACCAACA AAGCTGCAAC GGTAAGTGAT TTAACTTCTG CTGGCGCGAA GTTAAACAC
CACGACAGGT CTTTATGATC TGAAAACCGA AAATACCTTG TTAACTACCG ATGCTGCATT
CGATAAATTA GGGAATGGCG ATAAAGTCAC AGTTGGCGGC GTAGATTATA CTTACAACGC
TAAATCTGGT GATTTTACTA CCACTAAATC TACTGCTGGT ACGGGTGTAG ACGCCGCGGC
GCAGGCTGCT GATTCAGCTT CAAAACGTGA TGCGTTAGCT GCCACCCTTC ATGCTGATGT
GGGTAAATCT GTTAATGGTT CTTACACCAC AAAAGATGGT ACTGTTTCTT TCGAAACGGA
TTCAGCAGGT AATATCACCA TCGGTGGAAG CCAGGCATAC GTAGACGATG CAGGCAACTT
GACGACTAAC AACGCTGGTA GCGCAGCTAA AGCTGATATG AAAGCGCTGC TCAAAGCAGC
GAGCGAAGGT AGTGACGGTG CCTCTCTGAC ATTCAATGGC ACAGAATATA CCATCGCAAA
AGCAACTCCT GCGACAACCA CTCCAGTAGC TCCGTTAATC CCTGGTGGGA TTACTTATCA
GGCTACAGTG AGTAAAGATG TAGTATTGAG CGAAACCAAA GCGGCTGCCG CGACATCTTC
AATTACCTTT AATTCCGGTG TACTGAGCAA AACTATTGGG TTTACCGCGG GTGAATCCAG
TGATGCTGCG AAGTCTTATG TGGATGATAA AGGTGGTATC ACTAACGTTG CCGACTATAC
AGTCTCTTAC AGCGTTAACA AGGATAACGG CTCTGTGACT GTTGCCGGGT ATGCTTCAGC
GACTGATACC AATAAAGATT ATGCTCCAGC AATTGGTACT GCTGTAAATG TGAACTCCGC
GGGTAAAATC ACTACTGAGA CTACCAGTGC TGGTTCTGCA CGACCAACC CGCTTGCTGC
CCTGGACGAC GCAATCAGCT CCATCGACAA ATTCCGTTCT TCCCTGGGTG CTATCCAGAA
CCGTCTGGAT TCCGCAGTCA CCAACCTGAA CAACACCACT ACCAACCTGT CCGAAGCGCA
GTCCCGTATT CAGGACGCCG ACTATGCGAC CGAAGTGTCC AACATGTCGA AAGCGCAGAT
CATTCAGCAG GCCGGTAACT CCGTGCTGGC AAAAGCTAAC CAGGTACCGC AGCAGGTTCT
GTCTCTGCTG CAGGGTTAA
```

Figure 60

```
ATGGCACAAG TCATTAATAC CAACAGCCTC TCGCTGATCA CTCAAAATAA TATCAACAAG
AACCAGTCTG CGCTGTCGAG TTCTATCGAG CGTCTGTCTT CTGGCTTGCG TATTAACAGC
GCGAAGGATG ACGCAGCGGG TCAGGCGATT GCTAACCGTT TTACTTCTAA CATTAAAGGC
CTGACTCAGG CTGCACGTAA CGCCAACGAC GGTATTTCTG TTGCGCAGAC CACCGAAGGC
GCGCTGTCCG AAATCAACAA CAACTTACAG CGTATTCGTG AACTGACGGT TCAGGCCACT
ACAGGGACTA ACTCCGATTC TGACCTGGAC TCCATCCAGG ACGAAATCAA ATCTCGTCTT
GATGAAATTG ACCGCGTATC CGGCCAGACC CAGTTCAACG GCGTGAACGT GCTGGCGAAA
GACGGTTCAA TGAAAATTCA GGTTGGTGCG AATGACGGCG AAACCATCAC GATCGACCTG
AAAAAAATCG ATTCTGATAC TCTGGGTCTG AATGGCTTTA ACGTAAATGG TAAAGGTACT
ATTACCAACA AAGCTGCAAC GGTAAGTGAT TTAACTTCTG CTGGCGCGAA GTTAAACAC
CACGACAGGT CTTTATGATC TGAAAACCGA AAATACCTTG TTAACTACCG ATGCTGCATT
CGATAAATTA GGGAATGGCG ATAAAGTCAC AGTTGGCGGC GTAGATTATA CTTACAACGC
TAAATCTGGT GATTTTACTA CCACTAAATC TACTGCTGGT ACGGGTGTAA ACGCCGCGGC
GCAGGCTGCT GATTCAGCTT CAAAACGTGA TGCGTTAGCT GCCACCCTTC ATGCTGATGT
GGGTAAATCT GTTAATGGTT CTTACACCAC AAAAGATGGT ACTGTTTCTT TCGAAACGGA
TTCAGCAGGT AATATCACCA TCGGTGGAAG CCAGGCATAC GTAGACGATG CAGGCAACTT
GACGACTAAC AACGCTGGTA GCGCAGCTAA AGCTGATATG AAAGCGCTGC TCAAAGCAGC
GAGCGAAGGT AGTGACGGTG CCTCTCTGAC ATTCAATGGC ACAGAATATA CCATCGCAAA
AGCAACTCCT GCGACAACCA CTCCAGTAGC TCCGTTAATC CCTGGTGGGA TTACTTATCA
GGCTACAGTG AGTAAAGATG TAGTATTGAG CGAAACCAAA GCGGCTGCCG CGACATCTTC
AATTACCTTT AATTCCGGTG TACTGAGCAA AACTATTGGG TTACCGCGG GTGAATCCAG
TGATGCTGCG AAGTCTTATG TGGATGATAA AGGTGGTATC ACTAACGTTG CCGACTATAC
AGTCTCTTAC AGCGTTAACA AGGATAACGG CTCTGTGACT GTTGCCGGGT ATGCTTCAGC
GACTGATACC AATAAAGATT ATGCTCCAGC AATTGGCACT GCTGTAAATG TGAACTCCGC
GGGTAAAATC ACTACTGAGA CTACCAGTGC TGGTTCTGCA ACGACCAACC CGCTTGCTGC
CCTGGACGAC GCAATCAGCT CCATCGACAA ATTCCGTTCT TCCCTGGGTG CTATCCAGAA
CCGTCTGGAT TCCGCGGTCA CCAACCTGAA CAACACCACT ACCAACCTGT CCGAAGCGCA
GTCCCGTATT CAGGACGCCG ACTATGCGAC CGAAGTGTCC AACATGTCGA AAGCGCAGAT
CATCCAGCAG GCCGGTAACT CCGTGCTGGC AAAAGCTAAC CAGGTACCGC AGCAGGTTCT
GTCTCTGCTG CAGGGTTAA
```

Figure 61

```
ATGGCACAAG TCATTAATAC CAACAGCCTC TCGCTGATCA CTCAAAATAA TATCAACAAG
AACCAGTCTG CGCTGTCGAG TTCTATCGAG CGTCTGTCTT CTGGCTTGCG TATTAACAGC
GCGAAGGATG ACGCCGCGGG TCAGGCGATT GCTAACCGTT TTACTTCTAA CATTAAAGGC
CTGACTCAGG CTGCACGTAA CGCCAACGAC GGTATTTCTG TTGCACAGAC CACTGAAGGC
GCGCTGTCCG AAATCAACAA CAACTTACAG CGTATCCGTG AGCTGACGGT TCAGGCTTCT
ACCGGGACTA ACTCTGATTC GGATCTGGAC TCCATTCAGG ACGAAATCAA ATCCCGTCTC
GACGAAATTG ACCGCGTATC CGGTCAGACC CAGTTCAACG GCGTGAACGT ACTGGCAAAA
GACGGTTCGA TGAAAATTCA GGTTGGTGCG AATGACGGTG AAACTATCAC TATCGACCTG
AAGAAAATCG ATTCTGATAC TCTGGGTCTG AATGGTTTTA ACGTAAATGG TAAAGGTACT
ATTACCAACA AAGCTGCAAC GGTAAGTGAT TTAACTTCTG CTGGCGCGAA GTTAAACAC
CACGACAGGT CTTTATGATC TGAAAACCGA AAATACCTTG TTAACTACCG ATGCTGCATT
CGATAAATTA GGGAATGGCG ATAAAGTCAC CGTTGGCGGC GTAGATTATA CTTACAACGC
TAAATCTGGT GATTTTACTA CCACCAAATC TACTGCTGGT ACGGGTGTAG ACGCCGCGGC
GCAGGCTACT GATTCAGCTA AAAAACGTGA TGCGTTAGCT GCCACCCTTC ATGCTGATGT
GGGTAAATCT GTTAATGGTT CTTACACCAC AAAAGATGGT ACTGTTTCTT TCGAAACGGA
TTCAGCAGGT AATATCACCA TCGGTGGAAG CCAGGCATAC GTAGACGATG CAGGCAACTT
GACGACTAAC AACGCTGGTA GCGCAGCTAA AGCTGATATG AAAGCGCTGC TTAAAGCCGC
GAGCGAAGGT AGTGACGGTG CCTCTCTGAC ATTCAATGGC ACTGAATATA CTATCGCAAA
AGCAACTCCT GCGACAACCT CTCCAGTAGC TCCGTTAATC CCTGGTGGGA TTACTTATCA
GGCTACAGTG AGTAAAGATG TAGTATTGAG CGAAACCAAA GCGGCTGCCG CGACATCTTC
AATTACCTTT AATTCCGGTG TACTGAGCAA AACTATTGGG TTTACCGCGG GTGAATCCAG
TGATGCTGCG AAGTCTTATG TGGATGATAA AGGTGGTATT ACTAACGTTG CCGACTATAC
AGTCTCTTAC AGCGTTAACA AGGATAACGG CTCTGTGACT GTTGCCGGGT ATGCTTCAGC
GACTGATACC AATAAAGATT ATGCTCCAGC AATTGGTACT GCTGTAAATG TGAACTCCGC
GGGTAAAATC ACTACTGAGA CTACCAGTGC TGGTTCTGCA ACGACCAACC CGCTTGCTGC
CCTGGACGAC GCTATCAGCT CCATCGACAA ATTCCGTTCT TCCCTGGGTG CTATCCAGAA
CCGTCTGGAT TCCGCAGTCA CCAACCTGAA CAACACCACT ACCAACCTGT CTGAAGCGCA
GTCCCGTATT CAGGACGCCG ACTATGCGAC CGAAGTGTCC AACATGTCGA AAGCGCAGAT
TATCCAGCAG GCCGGTAACT CCGTGCTGGC AAAAGCCAAC CAGGTACCGC AGCAGGTTCT
GTCTCTGCTG CAGGGTTAA
```

Figure 62

```
ATGGCACAAGTCATTAATACCAACAGCCTCTCGCTGATCACTCAAAATAATATCAACAAG
AACCAGTCTGCGCTGTCGAGTTCTATCGAGCGTCTGTCTTCTGGCTTGCGTATTAACAGC
GCGAAGGATGACGCCGCAGGTCAGGCGATTGCTAACCGTTTTACTTCTAACATTAAAGGC
CTGACTCAGGCGGCCCGTAACGCCAACGACGGTATTTCTGTTGCGCAGACCACCGAAGGC
GCGCTGTCCGAAATCAACAACAACTTACAGCGTATTCGTGAACTGACGGTTCAGGCCACT
ACAGGGACTAACTCCGATTCTGACCTGGACTCCATCCAGGACGAAATCAAATCTCGTCTT
GATGAAATTGACCGCGTATCCGGCCAGACCCAGTTCAACGGCGTGAACGTGCTGGCGAAA
GACGGTTCAATGAAAATTCAGGTTGGTGCGAATGACGGCGAAACCATCACGATCGACCTG
AAAAAAATCGATTCTGATACTCTGGGTCTGAATGGCTTTAACGTAAATGGTAAAGGTACT
ATTACCAACAAAGCTGCAACGGTAAGTGATTTAACTTCTGCTGGCGCGAAGTTAAACACC
ACGACAGGTCTTTATGATCTGAAAACCGAAATACCTTGTTAACTACCGATGCTGCATTC
GATAAATTAGGGAATGGCGATAAAGTCACAGTTGGCGGCGTAGATTATACTTACAACGCT
AAATCTGGTGATTTTACTACCACTAAATCTACTGCTGGTACGGGTGTAGACGCCGCGGCG
CAGGCTGCTGATTCAGCTTCAAAACGTGATGCGTTAGCTGCCACCCTTCATGCTGATGTG
GGTAAATCTGTTAATGGTTCTTACACCACAAAAGATGGTACTGTTTCTTTCGAAACGGAT
TCAGCAGGTAATATCACCATCGGTGGAAGCCAGGCATACGTAGACGATGCAGGCAACTTG
ACGACTAACAACGCTGGTAGCGCAGCTAAAGCTGATATGAAAGCGCTGCTCAAAGCAGCG
AGCGAAGGTAGTGACGGTGCCTCTCTGACATTCAATGGCACAGAATATACCATCGCAAAA
GCAACTCCTGCGACAACCACTCCAGTAGCTCCGTTAATCCCTGGTGGGATTACTTATCAG
GCTACAGTGAGTAAAGATGTAGTATTGAGCGAAACCAAAGCGGCTGCCGCGACATCTTCA
ATTACCTTTAATTCCGGTGTACTGAGCAAAACTATTGGGTTTACCGCGGGTGAATCCAGT
GATGCTGCGAAGTCTTATGTGGATGATAAAGGTGGTATCACTAACGTTGCCGACTATACA
GTCTCTTACAGCGTTAACAAGGATAACGGCTCTGTGACTGTTGCCGGGTATGCTTCAGCG
ACTGATACCAATAAAGATTATGCTCCAGCAATTGGTACTGCTGTAAATGTGAACTCCGCG
GGTAAAATCACTACTGAGACTACCAGTGCTGGTTCTGCAACGACCAACCCGCTTGCTGCC
CTGGACGACGCAATCAGCTCCATCGACAAATTCCGTTCTTCCCTGGGTGCTATCCAGAAC
CGTCTGGATTCCGCAGTCACCAACCTGAACAACACCACTACCAACCTGTCCGAAGCGCAG
TCCCGTATTCAGGACGCCGACTATGCGACCGAAGTGTCCAACATGTCGAAAGCGCAGATC
ATTCAGCAGGCCGGTAACTCCGTGCTGGCAAAAGCTAACCAGGTACCGCAGCAGGTTCTG
TCTCTGCTGCAGGGTTAA
```

Figure 63

```
ATGGCACAAG TCATTAATAC CAACAGCCTC TCGCTGATCA CTCAAAATAA  TATCAACAAG
AACCAGTCTG CGCTGTCGAG TTCTATCGAG CGTCTGTCTT  CTGGCTTGCG TATTAACAGC
GCGAAGGATG ACGCCGCAGG TCAGGCGATT  GCTAACCGTT TTACTTCTAA CATTAAAGGC
CTGACTCAGG CTGCACGTAA  CGCCAACGAC GGTATTTCTG TTGCGCAGAC CACCGAAGGC
GCGCTGTCCG  AAATCAACAA CAACTTACAG CGTATTCGTG AACTGACGGT TCAGGCCACT
ACAGGGACTA ACTCCGATTC TGACCTGGAC TCCATCCAGG ACGAAATCAA  ATCTCGTCTT
GATGAAATTG ACCGCGTATC CGGCCAGACC CAGTTCAACG  GCGTGAACGT GCTGGCGAAA
GACGGTTCAA TGAAAATTCA GGTTGGTGCG  AATGACGGCG AAACCATCAC GATCGACCTG
AAAAAAATCG ATTCTGATAC  TCTGGGTCTG AATGGCTTTA ACGTAAATGG TAAAGGTACT
ATTACCAACA  AAGCTGCAAC GGTAAGTGAT TTAACTTCTG CTGGCGCGAA GTTAAACAC
CACGACAGGT CTTTATGATC TGAAAACCGA AAATACCTTG TTAACTACCG  ATGCTGCATT
CGATAAATTA GGGAATGGCG ATAAAGTCAC AGTTGGCGGC  GTAGATTATA CTTACAACGC
TAAATCTGGT GATTTACTA CCACTAAATC  TACTGCTGGT ACGGGTGTAG ACGCCGCGGC
GCAGGCTGCT GATTCAGCTT  CAAAACGTGA TGCGTTAGCT GCCACCCTTC ATGCTGATGT
GGGTAAATCT  GTTAATGGTT CTTACACCAC AAAAGATGGT ACTGTTTCTT TCGAAACGGA
TTCAGCAGGT AATATCACCA TCGGTGGAAG CCAGGCATAC GTAGACGATG  CAGGCAACTT
GACGACTAAC AACGCTGGTA GCGCAGCTAA AGCTGATATG  AAAGCGCTGC TCAAAGCAGC
GAGCGAAGGT AGTGACGGTG CCTCTCTGAC  ATTCAATGGC ACAGAATATA CCATCGCAAA
AGCAACTCCT GCGACAACCA . CTCCAGTAGC TCCGTTAATC CCTGGTGGGA TTACTTATCA
GGCTACAGTG  AGTAAAGATG TAGTATTGAG CGAAACCAAA GCGGCTGCCG CGACATCTTC
AATTACCTTT AATTCCGGTG TACTGAGCAA AACTATTGGG TTTACCGCGG  GTGAATCCAG
TGATGCTGCG AAGTCTTATG TGGATGATAA AGGTGGTATC ACTAACGTTG CCGACTATAC
AGTCTCTTAC AGCGTTAACA AGGATAACGG  CTCTGTGACT GTTGCCGGGT ATGCTTCAGC
GACTGATACC AATAAAGATT  ATGCTCCAGC AATTGGCACT GCTGTAAATG TGAACTCCGC
GGGTAAAATC  ACTACTGAGA CTACCAGTGC TGGTTCTGCA ACGACCAACC CGCTTGCTGC
CCTGGACGAC GCAATCAGCT CCATCGACAA ATTCCGTTCT TCCCTGGGTG  CTATCCAGAA
CCGTCTGGAT TCCGCGGTCA CCAACCTGAA CAACACCACT  ACCAACCTGT CCGAAGCGCA
GTCCCGTATT CAGGACGCCG ACTATGCGAC  CGAAGTGTCC AACATGTCGA AAGCGCAGAT
CATCCAGCAG GCCGGTAACT  CCGTGCTGGC AAAAGCTAAC CAGGTACCGC AGCAGGTTCT
GTCTCTGCTG  CAGGGTTAA
```

Figure 64

```
ATGGCACAAG TCATTAATAC CAACAGCCTC TCGCTGATCA CTCAAAATAA TATCAACAAG
AACCAGTCTG CGCTGTCGAG TTCTATCGAG CGTCTGTCTT CTGGCTTGCG TATTAACAGC
GCGAAGGATG ACGCCGCGGG TCAGGCGATT GCTAACCGTT TTACTTCTAA CATTAAAGGC
CTGACTCAGG CTGCACGTAA CGCCAACGAC GGTATTTCTG TTGCACAGAC CACTGAAGGC
GCGCTGTCCG AAATCAACAA CAACTTACAG CGTATCCGTG AGCTGACGGT TCAGGCTTCT
ACCGGGACTA ACTCTGATTC GGATCTGGAC TCCATTCAGG ACGAAATCAA ATCCCGTCTC
GACGAAATTG ACCGCGTATC CGGTCAGACC CAGTTCAACG GCGTGAACGT ACTGGCAAAA
GACGGTTCGA TGAAAATTCA GGTTGGTGCG AATGACGGTG AAACTATCAC TATCGACCTG
AAGAAAATCG ATTCTGATAC TCTGGGTCTG AATGGTTTTA ACGTAAATGG TAAAGGTACT
ATTACCAACA AAGCTGCAAC GGTAAGTGAT TTAACTTCTG CTGGCGCGAA GTTAAACACC
ACGACAGGT CTTTATGATC TGAAAACCGA AAATACCTTG TTAACTACCG ATGCTGCATT
CGATAAATTA GGGAATGGCG ATAAAGTCAC CGTTGGCGGC GTAGATTATA CTTACAACGC
TAAATCTGGT GATTTTACTA CCACCAAATC TACTGCTGGT ACGGGTGTAG ACGCCGCGGC
GCAGGCTACT GATTCAGCTA AAAAACGTGA TGCGTTAGCT GCCACCCTTC ATGCTGATGT
GGGTAAATCT GTTAATGGTT CTTACACCAC AAAAGATGGT ACTGTTTCTT TCGAAACGGA
TTCAGCAGGT AATATCACCA TCGGTGGAAG CCAGGCATAC GTAGACGATG CAGGCAACTT
GACGACTAAC AACGCTGGTA GCGCAGCTAA AGCTGATATG AAAGCGCTGC TTAAAGCCGC
GAGCGAAGGT AGTGACGGTG CCTCTCTGAC ATTCAATGGC ACTGAATATA CTATCGCAAA
AGCAACTCCT GCGACAACCT CTCCAGTAGC TCCGTTAATC CCTGGTGGGA TTTCTTATCA
GGCTACAGTG AGTAAAGATG TAGTATTGAG CGAAACCAAA GCGGCTGCCG CGACATCTTC
AATTACCTTT AATTCCGGTG TACTGAGCAA AACTATTGGG TTTACCGCGG GTGAATCCAG
TGATGCTGCG AAGTCTTATG TGGATGATAA AGGTGGTATT ACTAACGTTG CCGACTATAC
AGTCTCTTAC AGCGTTAACA AGGATAACGG CTCTGTGACT GTTGCCGGGT ATGCTTCAGC
GACTGATACC AATAAAGATT ATGCTCCAGC AATTGGTACT GCTGTAAATG TGAACTCCGC
GGGTAAAATC ACTACTGAGA CTACCAGTGC TGGTTCTGCA ACGACCAACC CGCTTGCTGC
CCTGGACGAC GCTATCAGCT CCATCGACAA ATTCCGTTCT TCCCTGGGTG CTATCCAGAA
CCGTCTGGAT TCCGCAGTCA CCAACCTGAA CAACACCACT ACCAACCTGT CTGAAGCGCA
GTCCCGTATT CAGGACGCCG ACTATGCGAC CGAAGTGTCC AACATGTCGA AAGCGCAGAT
TATCCAGCAG GCCGGTAACT CCGTGCTGGC AAAAGCCAAC CAGGTACCGC AGCAGGTTCT
GTCTCTGCTG CAGGGTTAA
```

Figure 65

```
ATGGCACAAG TCATTAATAC CAACAGCCTC TCGCTGATCA CTCAAAATAA TATCAACAAG
AACCAGTCTG CGCTGTCGAG TTCTATCGAG CGTCTGTCTT CTGGCTTGCG TATTAACAGC
GCGAAGGATG ACGCCGCAGG TCAGGCGATT GCTAACCGTT TTACTTCTAA CATTAAAGGC
CTGACTCAGG CGGCCCGTAA CGCCAACGAC GGTATTTCTG TTGCGCAGAC CACCGAAGGC
GCGCTGTCCG AAATCAACAA CAACTTACAG CGTATTCGTG AACTGACGGT TCAGGCCACT
ACAGGGACTA ACTCCGATTC TGACCTGGAC TCCATCCAGG ACGAAATCAA ATCTCGTCTT
GATGAAATTG ACCGCGTATC CGGCCAGACC CAGTTCAACG GCGTGAACGT GCTGGCGAAA
GACGGTTCAA TGAAAATTCA GGTTGGTGCG AATGACGGCG AAACCATCAC GATCGACCTG
AAAAAAATCG ATTCTGATAC TCTGGGTCTG AATGGCTTTA ACGTAAATGG TAAAGGTACT
ATTACCAACA AAGCTGCAAC GGTAAGTGAT TTAACTTCTG CTGGCGCGAA GTTAAACAC
CACGACAGGT CTTTATGATC TGAAAACCGA AAATACCTTG TTAACTACCG ATGCTGCATT
CGATAAATTA GGGAATGGCG ATAAAGTCAC AGTTGGCGGC GTAGATTATA CTTACAACGC
TAAATCTGGT GATTTTACTA CCACTAAATC TACTGCTGGT ACGGGTGTAG ACGCCGCGGC
GCAGGCTGCT GATTCAGCTT CAAAACGTGA TGCGTTAGCT GCCACCCTTC ATGCTGATGT
GGGTAAATCT GTTAATGGTT CTTACACCAC AAAAGATGGT ACTGTTTCTT TCGAAACGGA
TTCAGCAGGT AATATCACCA TCGGTGGAAG CCAGGCATAC GTAGACGATG CAGGCAACTT
GACGACTAAC AACGCTGGTA GCGCAGCTAA AGCTGATATG AAAGCGCTGC TCAAAGCAGC
GAGCGAAGGT AGTGACGGTG CCTCTCTGAC ATTCAATGGC ACAGAATATA CCATCGCAAA
AGCAACTCCT GCGACAACCA CTCCAGTAGC TCCGTTAATC CCTGGTGGGA TTACTTATCA
GGCTACAGTG AGTAAAGATG TAGTATTGAG CGAAACCAAA GCGGCTGCCG CGACATCTTC
AATTACCTTT AATTCCGGTG TACTGAGCAA AACTATTGGG TTTACCGCGG GTGAATCCAG
TGATGCTGCG AAGTCTTATG TGGATGATAA AGGTGGTATC ACTAACGTTG CCGACTATAC
AGTCTCTTAC AGCGTTAACA AGGATAACGG CTCTGTGACT GTTGCCGGGT ATGCTTCAGC
GACTGATACC AATAAAGATT ATGCTCCAGC AATTGGTACT GCTGTAAATG TGAACTCCGC
GGGTAAAATC ACTACTGAGA CTACCAGTGC TGGTTCTGCA ACGACCAACC CGCTTGCTGC
CCTGGACGAC GCAATCAGCT CCATCGACAA ATTCCGTTCT TCCCTGGGTG CTATCCAGAA
CCGTCTGGAT TCCGCAGTCA CCAACCTGAA CAACACCACT ACCAACCTGT CCGAAGCGCA
GTCCCGTATT CAGGACGCCG ACTATGCGAC CGAAGTGTCC AACATGTCGA AGCGCAGAT
CATTCAGCAG GCCGGTAACT CCGTGCTGGC AAAAGCTAAC CAGGTACCGC AGCAGGTTCT
GTCTCTGCTG CAGGGTTAA
```

Figure 66

```
ATGGCACAAG TCATTAATAC CAACAGCCTC TCGCTGATCA CTCAAAATAA TATCAACAAG
AACCAGTCTG CGCTGTCGAG TTCTATCGAG CGTCTGTCTT CTGGCTTGCG TATTAACAGC
GCGAAGGATG ACGCCGCGGG TCAGGCGATT GCTAACCGTT TTACTTCTAA CATTAAAGGC
CTGACTCAGG CTGCACGTAA CGCCAACGAC GGTATTTCTG TTGCACAGAC CACCGAAGGC
GCGCTGTCTG AAATCAACAA CAACTTACAG CGTATCCGTG AGCTGACGGT TCAGGCTTCT
ACCGGAACTA ACTCTGATTC GGATCTGGAC TCCATTCAGG ACGAAATCAA ATCCCGTCTT
GATGAAATTG ACCGCGTATC CGGCCAGACC CAGTTCAACG GCGTGAACGT ACTGGCAAAA
GACGGTTCGA TGAAAATTCA GGTTGGTGCG AATGACGGTG AAACTATCAC TATCGACCTG
AAGAAAATCG ATTCTGATAC TCTGGGTCTG AATGGTTTTA ACGTAAATGG TAAAGGTACT
ATTACCAACA AAGCTGCAAC GGTAAGTGAT TTAACTTCTG CTGGCGCGAA GTTAAACAC
CACGACAGGT CTTTATGATC TGAAAACCGA AAATACCTTG TTAACTACCG ATGCTGCATT
CGATAAATTA GGGAATGGCG ATAAAGTCAC CGTTGGCGGC GTAGATTATA CTTACAACGC
TAAATCTGGT GATTTTACTA CCACCAAATC TACTGCTGGT ACGGGTGTAG ACGCCGCGGC
GCAGGCTACT GATTCAGCTA AAAAACGTGA TGCGTTAGCT GCCACCCTTC ATGCTGATGT
GGGTAAATCT GTTAATGGTT CTTACACCAC AAAAGATGG ACTGTTTCTT TCGAAACGGA
TTCAGCAGGT AATATCACCA TCGGTGGAAG CCAGGCATAC GTAGACGATG CAGGCAACTT
GACGACTAAC AACGCTGGTA CGCAGCTAA AGCTGATATG AAAGCGCTGC TTAAAGCCGC
GAGCGAAGGT AGTGACGGTG CTTCTCTGAC ATTCAATGGC ACTGAATATA CTATCGCAAA
AGCAACTCCT GCGACAACCT CTCCAGTAGC TCCGTTAATC CCTGGTGGGA TTACTTATCA
GGCTACAGTG AGTAAAGATG TAGTATTGAG CGAAACCAAA GCGGCTGCCG CGACATCTTC
AATTACCTTT AATTCCGGTG TACTGAGCAA AACTATTGGG TTTACCGCGG GTGAATCCAG
TGATGCTGCG AAGTCTTATG TGGATGATAA AGGTGGTATT ACTAACGTTG CCGACTATAC
AGTCTCTTAC AGCGTTAACA AGGATAACGG CTCTGTGACT GTTGCCGGGT ATGCTTCAGC
GACTGATACC AATAAAGATT ATGCTCCAGC AATTGGTACT GCTGTAAATG TGAACTCCGC
GGGTAAAATC ACTACTGAGA CTACCAGTGC TGGTTCTGCA ACGACCAACC CGCTTGCTGC
CCTGGACGAC GCTATCAGCT CCATCGACAA ATTCCGTTCT TCCCTGGGTG CTATCCAGAA
CCGTCTGGAT TCCGCAGTCA CCAACCTGAA CAACACCACT ACCAACCTGT CTGAAGCGCA
GTCCCGTATT CAGGACGCCG ACTATGCGAC CGAAGTGTCC AACATGTCGA AAGCGCAGAT
TATCCAGCAG GCCGGTAACT CCGTGCTGGC AAAAGCCAAC CAGGTACCGC AGCAGGTTCT
GTCTCTGCTG CAGGGTTAA
```

Figure 67

```
ATGGCACAAG TCATTAATAC CAACAGCCTC TCGCTGATCA CTCAAAATAA TATCAACAAG
AACCAGTCTG CGCTGTCGAG TTCTATCGAG CGTCTGTCTT CTGGCTTGCG TATTAACAGC
GCGAAGGATG ACGCCGCGGG TCAGGCGATT GCTAACCGTT TTACTTCTAA CATTAAAGGC
CTGACTCAGG CTGCACGTAA CGCCAACGAC GGTATTTCTG TTGCACAGAC CACTGAAGGC
GCGCTGTCCG AAATCAACAA CAACTTACAG CGTATCCGTG AGCTGACGGT TCAGGCTTCT
ACCGGGACTA ACTCTGATTC GGATCTGGAC TCCATTCAGG ACGAAATCAA ATCCCGTCTC
GACGAAATTG ACCGCGTATC CGGTCAGACC CAGTTCAACG GCGTGAACGT ACTGGCAAAA
GACGGTTCGA TGAAAATTCA GGTTGGTGCG AATGACGGTG AAACTATCAC TATCGACCTG
AAGAAAATCG ATTCTGATAC TCTGGGTCTG AATGGTTTTA ACGTAAATGG TAAAGGTACT
ATTACCAACA AAGCTGCAAC GGTAAGTGAT TTAACTTCTG CTGGCGCGAA GTTAAACAC
CACGACAGGT CTTTATGATC TGAAAACCGA AAATACCTTG TTAACTACCG ATGCTGCATT
CGATAAATTA GGGAATGGCG ATAAAGTCAC CGTTGGCGGC GTAGATTATA CTTACAACGC
TAAATCTGGT GATTTTACTA CCACCAAATC TACTGCTGGT ACGGGTGTAG ACGCCGCGGC
GCAGGCTACT GATTCAGCTA AAAAACGTGA TGCGTTAGCT GCCACCCTTC ATGCTGATGT
GGGTAAATCT GTTAATGGTT CTTACACCAC AAAAGATGGT ACTGTTTCTT TCGAAACGGA
TTCAGCAGGT AATATCACCA TCGGTGGAAG CCAGGCATAC GTAGACGATG CAGGCAACTT
GACGACTAAC AACGCTGGTA GCGCAGCTAA AGCTGATATG AAAGCGCTGC TTAAAGCCGC
GAGCGAAGGT AGTGACGGTG CCTCTCTGAC ATTCAATGGC ACTGAATATA CTATCGCAAA
AGCAACTCCT GCGACAACCT CTCCAGTAGC TCCGTTAATC CCTGGTGGGA TTTCTTATCA
GGCTACAGTG AGTAAAGATG TAGTATTGAG CGAAACCAAA GCGGCTGCCG CGACATCTTC
AATTACCTTT AATTCCGGTG TACTGAGCAA AACTATTGGG TTTACCGCGG GTGAATCCAG
TGATGCTGCG AAGTCTTATG TGGATGATAA AGGTGGTATT ACTAACGTTG CCGACTATAC
AGTCTCTTAC AGCGTTAACA AGGATAACGG CTCTGTGACT GTTGCCGGGT ATGCTTCAGC
GACTGATACC AATAAAGATT ATGCTCCAGC AATTGGTACT GCTGTAAATG TGAACTCCGC
GGGTAAAATC ACTACTGAGA CTACCAGTGC TGGTTCTGCA ACGACCAACC CGCTTGCTGC
CCTGGACGAC GCTATCAGCT CCATCGACAA ATTCCGTTCT TCCCTGGGTG CTATCCAGAA
CCGTCTGGAT TCCGCAGTCA CCAACCTGAA CAACACCACT ACCAACCTGT CTGAAGCGCA
GTCCCGTATT CAGGACGCCG ACTATGCGAC CGAAGTGTCC AACATGTCGA AAGCGCAGAT
TATCCAGCAG GCCGGTAACT CCGTGCTGGC AAAAGCCAAC CAGGTACCGC AGCAGGTTCT
GTCTCTGCTG CAGGGTTAA
```

Figure 68

```
ATGCGACGTATAGAACGAATACCGGGGTTATCGGCGTAAGCGGGGCAAA
GTTTACGATTTATTTTTTGGCTTAATGACACGAACAGCAACGAGGAAGGG
GAGTATTTCGACCGCTAGAAAAAAATTCTAAAGGTTGTGAGTGACCAGAC
GATAACAGGGTTGACGGCGACGAAGCCGAAGGGTGGAAGCCCAATACTT
AAACCGTAGACTTGAAAACAGGAAAATGAATCATGGCACAAGTCATTAAT
ACCAACAGCCTCTCGCTGATCACTCAAAATAATATCAACAAGAACCAGTC
TGCGCTGTCGACTTCTATCGAGCGCCTCTCTTCTGGTCTGCGCATTAACAG
CGCTAAAGATGACGCTGCGGGCCAAGCGATTGCTAACCGCTTCACTTCTA
ACATCAAAGGTCTGACTCAGGCCGCACGTAACGCCAACGACGGTATTTCT
CTGGCGCAGACCACTGAAGGCGCACTGTCTGAAATCAACAACAACTTGCA
GCGTGTTCGTGAACTGACCGTTCAGGCCACTACCGGTACTAACTCTGATTC
TGACCTGTCTTCAATACAGGACGAAATCAAATCCCGTCTCGATGAAATTG
ACCGCGTATCCGGTCAGACTCAGTTCAACGGCGTTAATGTTCTTTCCAAAG
ATGGTTCAATGAAAATTCAGGTTGGTGCGAATGATGGTCAAACTATCTCC
ATCGATCTGAAGAAAATTGATTCTTCAACTTTGGGGCTGAATGGCTTCTCA
GTTTCTAAAAACTCTCTTAATGTCAGCAATGCTATCACATCTATCCCGCAA
GCCGCTAGCAATGAACCTGTTGATGTTAACTTCGGTGATACTGATGAGTCT
GCAGCAATCGCAGCCAAATTGGGGGTTTCCGATACGTCAAGCCTGTCGCT
GCACAACATCCTTGATAAAGATGGTAAGGCAACAGCTGATTATGTTGTTC
AGTCAGGTAAAGACTTCTATGCTGCTTCTGTTAATGCCGCTTCAGGTAAAG
TAACCTTAAACACCATTGATGTTACTTATGATGATTATGCGAACGGTGTTG
ACGATGCCAAGCAAACAGGTCAGCTGATCAAAGTTTCAGCAGATAAAGAC
GGCGCAGCTCAAGGTTTTGTCACACTTCAAGGCAAAAACTATTCTGCTGGT
GATGCGGCAGACATTCTTAAGAATGGAGCAACAGCTCTTAAGTTAACTGA
TCTGAATTTAAGTGATGTTACTGATACTAATGGTAAGGTAACCACAACTGC
GACTGAGCAATTTGAAGGTGCTTCAACTGAGGATCCGCTGGCGCTTCTGG
ATAAAGCTATTGCATCAGTCGACAAATTCCGGTCTTCTCTAGGTGCCGTGC
AGAACCGTCTCGATTCCGCTATCACCAACCTGAACAACACCACCACCAAC
CTGTCTGAAGCGCAGTCCCGTATTCAGGACGCCGACTATGCGACCGAAGT
GTCCAACATGTCGAAAGCGCAGATCATCCAGCAGGCAGGTAACTCCGTGC
TGTCTAAAGCGAACCAGGTACCGCAGCAAGTTCTGTCACTGTTACAAGGC
TAATGGCCTTAACCTGCCTGACCCCGCCACCGGCGGGGTTTTTCTGTCCG
CAATTTACCGATAACCCCCAAATAACCCCTCATTTCACCCACTAATCGTCC
GATTAAAAACCCTGCAGAAACGGATAATCATGCCGATAACTCATATAACG
CAGGGCTGTTTATCGTGAATTCACTCTATACCGCTGAAGGTGTAATGGATA
AACACTCGCTG
```

Figure 69

```
AACAGCCTCTCGCTGATCACTCAGAACAACATCAACAAAAACCAGTCTTC
AATGTCTACTGCCATTGAGCGTCTGTCTTCCGGTCTGCGTATCAACAGCGC
AAAAGATGACGCTGCTGGCCAGGCGATTGCCAACCGCTTCACCTCTAACA
TCAAAGGTCTGACTCAGGCAGCTCGTAACGCCAACGACGGTATCTCCGTT
GCACAGACCACTGAAGGCGCACTGTCTGAAATCAACAACAACCTGCAGCG
TATCCGTGAGCTGACTGTTCAGTCTTCTACGGGTACTAACTCTGAATCCGA
TCTGAACTCAATCCAGGACGAAATTAAATCCCGTCTGGACGAAATTGACC
GCGTATCCGGTCAGACCCAGTTCAACGGCGTGAACGTGCTGGCAAAAGAC
GGCTCCATGAAAATTCAGGTTGGCGCGAACGATGGTGAAACCATCACCAT
CGACCTGAAAAAAATTGACTCTTCTACTTTAAACCTGACTGGGTTTAA
```

Figure 70A

```
CTCAGTATGCTGTCACCGGCAGTACAGGTGCCGTAACTTACGATCCAGAT
ACAGATCCTGCCGCGACTGGTGATATTGTTTCTGCTTATGTTGATGATGCA
GGTACATTGACAACTGATGCAAACAAAACTGTAAAATATTATGCCCACAC
TAATGGTAGCGTCACGAACGACAGTGGTTCAGCTATTTACGCAACTGAAG
CGGGCAAATTGACTACTGAAGCGTCTACAGCTGCTGAAACTACCGCTAAC
CCACTGAAAGCCCTGGACGATGCAATCAGCCAGATCGACAAATTCCGTTC
TTCTCTGGGTGCTGTACAGAACCGTCTGGATTCTGCGGTAACCAACCTGAA
CAACACCACCACCAACCTGTCTGAAGCGCAGTCCCGTATTCAGGACGCCG
ACTATGCGACCGAAGTGTCAAATATGTCTAAAGCGCAGATCATCCAGCAG
GCCGGTAACTCCGTGTTGGCTAAAGCTAACCAGGTTCCTCAGCAGGTT
```

Figure 70B

```
AGCCTGTCGCTGTTGACCCAGAATAACCTGAACAAATCTCAGTCTTCTCTG
AGCTCCGCCATTGAGCGTCTCTCTTCTGGCCTGCGTATTAACAGTGCTAAA
GATGACGCAGCAGGTCAGGCGATTGCTAACCGTTTTACAGCAAATATTAA
AGGTCTGACTCAGGCTTCCCGTAACGCGAATGATGGTATTTCTGTTGCGCA
GACCACTGAAGGCGCGCTGAATGAAATTAACAACAACCTGCAGCGTGTAC
GTGAACTGACTGTTCAGGCAACTAACGGTACTAACTCTGACAGCGATCTTT
CTTCTATCCAGGCTGAATTACTCAACGTCTGGAAGAAATTGACCGTGTAT
CTGAG CAAACTCAGTTTAACGGCGTGAAAGTCCTTGCTGAAAAT
```

Figure 71

```
GCACGTTAGTTGTTAACGGTGCAACTTACGATGTTAGTGCAGATGGTAAA
ACGATAACGGAGACTGCTTCTGGTAACAATAAAGTCATGTATCTGAGCAA
ATCAGAAGGTGGTAGCCCGATTCTGGTAAACGAAGATGCAGCAAAATCGT
TGCAATCTACCACCAACCCGCTCGAAACTATCGACAAAGCATTGGCTAAA
GTTGACAATCTGCGTTCTGACCTCGGTGCAGTACAAAACCGTTTCGACTCT
GCTATCACCAACCTTGGCAACACCGTAAACAACCTGTCTTCTGCCCGTAGC
CGTATCGAAGATGCTGACTACGCGACCGAAGTGTCTAACATGTCTCGTGC
GCAGATCCTGCAACAAGCGGGTACCTCTGTTCTGGCGCAGGCTAACCAGA
CCACGCAGAACGTAC
```

Sequence of the polylinker region of plasmid pTrc99A:

AGGA AACAGACC ATG GAA TTC GAG CTC GGT ACC CGG GGA TCC TCT AGA GTC GAC CTG CAG GCA TGC AAG CTT
SD        NcoI  EcoRI  SacI  KpnI   SmaI BamHI  XbaI   SalI  PstI   SphI HidIII

FIGURE 73B

Sequence in the junction region between vector and the 5' end of the H antigen gene:

AGGA AACAGACC ATG GCA CAA GTC ATT AAT ACC
SD        NcoI          H antigen gene

SEQUENCE LISTING

<160> NUMBER OF SEQ ID NOS: 92

<210> SEQ ID NO 1
<211> LENGTH: 1773
<212> TYPE: DNA
<213> ORGANISM: Escherichia coli

<400> SEQUENCE: 1

```
atgcgacgta tagaacgaat accgggtta tcggcgtaag cggggcaaag tttacgattt      60
attttttggc ttaatgacac gaacagcaac gaggaagggg agtatttcga ccgctagaaa    120
aaaattctaa aggttgtgag tgaccagacg ataacagggt tgacggcgac gaagccgaag    180
ggtggaagcc caatacttaa accgtagact tgaaaacagg aaaatgaatc atggcacaag    240
tcattaatac caacagcctc tcgctgatca ctcaaaataa tatcaacaag aaccagtctg    300
cgctgtcgac ttctatcgag cgcctctctt ctggtctgcg cattaacagc gctaaagatg    360
acgctgcggg ccaagcgatt gctaaccgct tcacttctaa catcaaaggt ctgactcagg    420
ccgcacgtaa cgccaacgac ggtatttctc tggcgcagac cactgaaggc gcactgtctg    480
aaatcaacaa caacttgcag cgtgttcgtg aactgaccgt tcaggccact accggtacta    540
actctgattc tgacctgtct tcaatacagg acgaaatcaa atcccgtctc gatgaaattg    600
accgcgtatc cggtcagact cagttcaacg gcgttaatgt tctttccaaa gatggttcaa    660
tgaaaattca ggttggtgcg aatgatggtc aaactatctc catcgatctg aagaaaattg    720
attcttcaac tttggggctg aatggcttct cagtttctaa aaactctctt aatgtcagca    780
atgctatcac atctatcccg caagccgcta gcaatgaacc tgttgatgtt aacttcggtg    840
atactgatga gtctgcagca atcgcagcca aattgggggt ttccgatacg tcaagcctgt    900
cgctgcacaa catccttgat aaagatggta aggcaacagc tgattatgtt gttcagtcag    960
gtaaagactt ctatgctgct tctgttaatg ccgcttcagg taaagtaacc ttaaacacca   1020
ttgatgttac ttatgatgat tatgcgaacg gtgttgacga tgccaagcaa acaggtcagc   1080
tgatcaaagt ttcagcagat aaagacggcg cagctcaagg ttttgtcaca cttcaaggca   1140
aaaactattc tgctggtgat gcggcagaca ttcttaagaa tggagcaaca gctcttaagt   1200
taactgatct gaatttaagt gatgttactg atactaatgg taaggtaacc acaactgcga   1260
ctgagcaatt tgaaggtgct tcaactgagg atccgctggc gcttctggat aaagctattg   1320
catcagtcga caaattccgg tcttctctag gtgccgtgca gaaccgtctc gattccgcta   1380
```

-continued

```
tcaccaacct gaacaacacc accaccaacc tgtctgaagc gcagtcccgt attcaggacg      1440
ccgactatgc gaccgaagtg tccaacatgt cgaaagcgca gatcatccag caggcaggta      1500
actccgtgct gtctaaagcg aaccaggtac cgcagcaagt tctgtcactg ttacaaggct      1560
aatggcctta acctgcctga ccccgccacc ggcggggttt tttctgtccg caatttaccg      1620 ataacccca aataacccct catttcaccc actaatcgtc cgattaaaaa ccctgcagaa       1680
acggataatc atgccgataa ctcatataac gcagggctgt ttatcgtgaa ttcactctat      1740
accgctgaag gtgtaatgga taaacactcg ctg                                   1773
```

<210> SEQ ID NO 2
<211> LENGTH: 500
<212> TYPE: DNA
<213> ORGANISM: Escherichia coli

<400> SEQUENCE: 2

```
aacagcctct cgctgatcac tcagaacaac atcaacaaaa accagtcttc aatgtctact       60
gccattgagc gtctgtcttc cggtctgcgt atcaacagcg caaaagatga cgctgctggc      120
caggcgattg ccaaccgctt cacctctaac atcaaaggtc tgactcaggc agctcgtaac      180
gccaacgacg gtatctccgt tgcacagacc actgaaggcg cactgtctga atcaacaac       240 aacctgcagc gtatccgtga gctgactgtt cagtcttcta cgggtactaa ctctgaatcc      300
gatctgaact caatccagga cgaaattaaa tcccgtctgg acgaaattga ccgcgtatcc      360
ggtcagaccc agttcaacgg cgtgaacgtg ctggcaaaag acggctccat gaaaattcag      420
gttggcgcga acgatggtga aaccatcacc atcgacctga aaaaaattga ctcttctact      480
ttaaacctga ctgggtttaa                                                   500
```

<210> SEQ ID NO 3
<211> LENGTH: 500
<212> TYPE: DNA
<213> ORGANISM: Escherichia coli

<400> SEQUENCE: 3

```
ctcagtatgc tgtcaccggc agtacaggtg ccgtaactta cgatccagat acagatcctg       60
ccgcgactgg tgatattgtt tctgcttatg ttgatgatgc aggtacattg acaactgatg      120
caaacaaaac tgtaaaatat tatgcccaca ctaatggtag cgtcacgaac gacagtggtt      180
cagctattta cgcaactgaa gcgggcaaat tgactactga agcgtctaca gctgctgaaa      240
ctaccgctaa cccactgaaa gccctggacg atgcaatcag ccagatcgac aaattccgtt      300
cttctctggg tgctgtacag aaccgtctgg attctgcggt aaccaacctg aacaacacca      360
ccaccaacct gtctgaagcg cagtcccgta ttcaggacgc cgactatgcg accgaagtgt      420
caaatatgtc taaagcgcag atcatccagc aggccggtaa ctccgtgttg gctaaagcta      480
accaggttcc tcagcaggtt                                                  500
```

<210> SEQ ID NO 4
<211> LENGTH: 399
<212> TYPE: DNA
<213> ORGANISM: Escherichia coli

<400> SEQUENCE: 4

```
agcctgtcgc tgttgaccca gaataacctg aacaaatctc agtcttctct gagctccgcc       60
attgagcgtc tctcttctgg cctgcgtatt aacagtgcta aagatgacgc agcaggtcag      120
```

```
gcgattgcta accgttttac agcaaatatt aaaggtctga ctcaggcttc ccgtaacgcg     180
aatgatggta tttctgttgc gcagaccact gaaggcgcgc tgaatgaaat taacaacaac     240
ctgcagcgtg tacgtgaact gactgttcag gcaactaacg gtactaactc tgacagcgat     300 cttcttcta tccaggctga aattactcaa cgtctggaag aaattgaccg tgtatctgag      360
caaactcagt ttaacggcgt gaaagtcctt gctgaaaat                            399
```

<210> SEQ ID NO 5
<211> LENGTH: 417
<212> TYPE: DNA
<213> ORGANISM: Escherichia coli
<400> SEQUENCE: 5

```
gcacgttagt tgttaacggt gcaacttacg atgttagtgc agatggtaaa acgataacgg      60
agactgcttc tggtaacaat aaagtcatgt atctgagcaa atcagaaggt ggtagcccga     120
ttctggtaaa cgaagatgca gcaaaatcgt tgcaatctac caccaacccg ctcgaaacta    180
tcgacaaagc attggctaaa gttgacaatc tgcgttctga cctcggtgca gtacaaaacc   240
gtttcgactc tgctatcacc aaccttggca acaccgtaaa caacctgtct ctgcccgta    300 gccgtatcga agatgctgac tacgcgaccg aagtgtctaa catgtctcgt gcgcagatcc   360
tgcaacaagc gggtacctct gttctggcgc aggctaacca gaccacgcag aacgtac     417
```

<210> SEQ ID NO 6
<211> LENGTH: 950
<212> TYPE: DNA
<213> ORGANISM: Escherichia coli
<400> SEQUENCE: 6

```
aacaaaaacc agtctgcgct gtcgacttct atcgagcgcc tctcttctgg tctgcgtatt     60
aacagcgcta aagatgacgc cgcgggccag gcgattgcta accgctttac ttctaacatc   120
aaaggtctga ctcaggccgc acgtaacgcc aacgacggta tttctctggc gcagacggct   180
gaaggcgcgc tgtcagagat taacaacaac ttgcagcgta ttcgtgaact gaccgttcag   240
gcctctaccg gcacgaactc tgattccgac ctgtcttcta ttcaggacga aatcaaatcc   300
cgtcttgatg aaattgaccg tgtatctggt cagacccagt tcaacggtgt gaacgtgctg   360
tcgaaaaacg attcgatgaa gattcagatt ggtgccaatg ataaccagac gatcagcatt   420
ggcttgcaac aaatcgacag taccactttg aatctgaaag gatttaccgt gtccggcatg   480
gcggatttca gcgcggcgaa actgacggct gctgatggta cagcaattgc tgctgcggat   540
gtcaaggatg ctgggggtaa acaagtcaat ttactgtctt acactgacac cgcgtctaac   600
agtactaaat atgcggtcgt tgattctgca accggtaaat acatggaagc cactgtagtc   660
attaccggta cggcggcggc ggtaactgtt ggtgcagcgg aagtggcggg agccgctaca   720
gccgatccgt taaaagcact ggatgccgca atcgctaaag tcgacaaatt ccgctcctcc   780
ctcggtgccg ttcaaaaccg tctggattct gcggtcacca acctgaacaa caccaccacc   840
aacctgtctg aagcgcagtc ccgtattcag gacgccgact atgcgaccga agtgtccaac   900
atgtcgaaag cgcagattat ccagcaggcg ggcaactccg tgctgtctaa                950
```

<210> SEQ ID NO 7
<211> LENGTH: 1212
<212> TYPE: DNA
<213> ORGANISM: Escherichia coli
<400> SEQUENCE: 7

-continued

```
aacaaaaacc agtctgcgct gtcgacttct atcgagcgcc tctcttctgg tctgcgtatt      60
aacagcgcta agatgacgc cgcgggccag gcgattgcta accgcttcac ttctaacatc     120
aaaggtctga ctcaggccgc acgtaacgcc aacgacggta tctctctggc gcagaccact    180
gaaggcgcgc tgtctgaaat caacaacaac ttgcagcgtg tgcgtgagtt gaccgttcag    240
gcgacgaccg ggactaactc tgattctgac ctgtcttcta ttcaggacga aatcaaatcc    300
cgtctggatg aaattgatcg cgtttccggt cagacccagt tcaacggcgt gaatgtgctg    360
gcgaaagatg gttcgatgaa gattcaggtt ggcgcgaatg atgggcagac tattagcatt    420
gatttgcaga agattgactc ttctacatta ggactgaacg gtttctccgt ttcgggtcag    480
tcacttaacg ttagtgattc cattactcaa attaccggtg ccgccgggac aaaacctgtt    540
ggtgttgatt tcactgctgt tgcgaaagat ctgactactg cgacaggtaa aacagtcgat    600
gtttctagcc tgacgttaca caacactctg gatgcgaaag gggctgctac atcacagttc    660
gtcgttcaat ccggcaatga tttctactcc gcgtcgatta atcatacaga cggcaaagtc    720
acgttgaata agccgatgt cgaatacaca gacaccgata atggactaac gactgcggct    780
actcagaaag atcaactgat taaagttgcc gctgactctg acggctcggc tgcgggatat    840
gtaacattcc aagtaaaaa ctacgctaca acgtttcaa cggcacttga tgataatact     900
gcggcaaaag caacagataa taaagttgtt gttgaattat caacagcaaa accgactgca    960
cagttctcag gggcttcttc tgctgatcca ctggcacttt tagacaaagc tattgcacag   1020
gttgatactt tccgctcctc cctcggtgcg gtgcaaaacc gtctggattc cgcagtaacc   1080
aacctgaaca acaccaccac caacctgtct gaagcgcagt cccgtattca ggacgccgac   1140
tatgctacag aagtgtccaa catgtcgaaa gcgcagatca tccagcaggc aggtaactcg   1200
gtgctgtcca aa                                                      1212
```

<210> SEQ ID NO 8
<211> LENGTH: 1647
<212> TYPE: DNA
<213> ORGANISM: Escherichia coli

<400> SEQUENCE: 8

```
atggcacaag tcattaatac caacagcctc tcgctgatca ctcaaaataa tatcaacaag     60
aaccagtctg cgctgtcgag ttctatcgag cgtctgtctt ctggcttgcg tattaacagc    120
gcgaaggatg acgccgcggg tcaggcgatt gctaaccgtt ttacttctaa cattaaaggc    180
ctgactcagg ctgcacgtaa cgccaacgac ggtatttctg ttgcgcagac caccgaaggc    240
gcgctgtccg aaattaacaa caacttacag cgtattcgtg aactgacggt tcaggcttct    300
accgggacta actctgattc ggatctggac tccattcagg acgaaatcaa atcccgtctc    360
gacgaaattg accgcgtatc cggtcagacc cagttcaacg gcgtgaacgt actggcaaaa    420
gacggttcga tgaaaattca ggttggtgcg aatgacggcc agactatcac tattgatctg    480
aagaaaattg actctgatac gctggggctg aatgggttta atgtgaacgg caaaggggaa    540
acggctaata cggcagcaac cctgaaagat atgtctggat tcacagctgc ggcggcacca    600
gggggaactg ttggtgtaac tcaatatact gacaaatcgg ctgtagcaag tagcgtagat    660
attctaaatg ctgttgctgg cgcagatgga aataaagtta caactagcgc cgatgttggt    720
tttggtacac cagccgctgc tgtaacctat acctacaata aagacactaa ttcatattcc    780
gccgcttctg atgatatttc cagcgctaac ctggctgctt cctcaatcc tcaggccgga    840
```

-continued

| | |
|---|---|
| gatacgacta aagctacagt tacaattggt ggcaaagatc aagatgtaaa catcgataaa | 900 |
| tccggtaatt taactgctgc tgatgatggc gcagtacttt atatggatgc taccggtaac | 960 |
| ttaactaaaa ataatgctgg tggtgataca caagctactt tggctaaact tgctactgct | 1020 |
| actggtgcta aagccgcgac catccaaact gataaaggaa cattcaccag tgacggtaca | 1080 |
| gcgtttgatg gtgcatcaat gtccattgat accaatacat ttgcaaatgc agtaaaaaat | 1140 |
| gacacttata ctgccactgt aggtgctaag acttatagcg taacaacagg ttctgctgct | 1200 |
| gcagacaccg cttatatgag caatggggtt ctcagtgata ctccgccaac ttactatgca | 1260 |
| caagctgatg aagtatcac aactactgag gatgcggctg ccggtaaact ggtctacaaa | 1320 |
| ggttccgatg gtaagttaac aacggatacg actagcaaag cagaatcaac atcagatccg | 1380 |
| ctggcagctc ttgacgacgc tatcagccag atcgacaaat tccgctcctc cctgggtgcg | 1440 |
| gtgcaaaacc gtctggattc cgcagtgacc aacctgaaca acaccactac caacctgtct | 1500 |
| gaagcgcagt cccgtattca ggacgccgac tatgcgaccg aagtgtccaa catgtcgaaa | 1560 |
| gcgcagatta tccagcaggc cggtaactcc gtgctggcaa aagctaacca ggttccgcag | 1620 |
| caggttctgt ctctgctgca gggttaa | 1647 |

<210> SEQ ID NO 9
<211> LENGTH: 1758
<212> TYPE: DNA
<213> ORGANISM: Escherichia coli

<400> SEQUENCE: 9

| | |
|---|---|
| atggcacaag tcattaatac caacagcctc tcgctgatca ctcaaaataa tatcaacaag | 60 |
| aaccagtctg cgctgtcgag ttctatcgag cgtctgtctt ctggcttgcg tattaacagc | 120 |
| gcgaaggatg acgccgcggg tcaggcgatt gctaaccgtt ttacttctaa cattaaaggc | 180 |
| ctgactcagg ctgcacgtaa cgccaacgac ggtatttctg ttgcacagac caccgaaggc | 240 |
| gcgctgtctg aaatcaacaa caacttacag cgtatccgtg agctgacggt tcaggcttct | 300 |
| accggaacta actctgattc ggatctggac tccattcagg acgaaatcaa atcccgtctt | 360 |
| gatgaaattg accgcgtatc cggccagacc cagttcaacg gcgtgaacgt actggcaaaa | 420 |
| gacggttcga tgaaaattca ggttggtgcg aatgacggtg aaactatcac tatcgacctg | 480 |
| aagaaaatcg attctgatac tctgggtctg aatggttta acgtaaatgg taaaggtact | 540 |
| attaccaaca agctgcaac ggtaagtgat ttaacttctg ctggcgcgaa gttaaacacc | 600 |
| acgacaggtc tttatgatct gaaaaccgaa ataccttgt taactaccga tgctgcattc | 660 |
| gataaattag ggaatggcga taagtcacc gttggcggcg tagattatac ttacaacgct | 720 |
| aaatctggtg atttttactac caccaaatct actgctggta cgggtgtaga cgccgcggcg | 780 |
| caggctactg attcagctaa aaaacgtgat gcgttagctg ccacccttca tgctgatgtg | 840 |
| ggtaaatctg ttaatggttc ttacaccaca aaagatggta ctgtttcttt cgaaacggat | 900 |
| tcagcaggta atatcaccat cggtggaagc caggcatacg tagacgatgc aggcaacttg | 960 |
| acgactaaca acgctggtag cgcagctaaa gctgatatga aagcgctgct taaagccgcg | 1020 |
| agcgaaggta gtgacggtgc ttctctgaca ttcaatggca ctgaatatac tatcgcaaaa | 1080 |
| gcaactcctg cgacaacctc tccagtagct ccgttaatcc ctggtgggat tacttatcag | 1140 |
| gctacagtga gtaaagatgt agtattgagc gaaaccaaag cggctgccgc gacatcttca | 1200 |
| attccctta attccggtgt actgagcaaa actattgggt ttaccgcggg tgaatccagt | 1260 |
| gatgctgcga agtcttatgt ggatgataaa ggtggtatta ctaacgttgc cgactataca | 1320 |

```
gtctcttaca gcgttaacaa ggataacggc tctgtgactg ttgccgggta tgcttcagcg   1380
actgatacca ataaagatta tgctccagca attggtactg ctgtaaatgt gaactccgcg   1440
ggtaaaatca ctactgagac taccagtgct ggttctgcaa cgaccaaccc gcttgctgcc   1500
ctggacgacg ctatcagctc catcgacaaa ttccgttctt ccctgggtgc tatccagaac   1560
cgtctggatt ccgcagtcac caacctgaac aacaccacta ccaacctgtc tgaagcgcag   1620
tcccgtattc aggacgccga ctatgcgacc gaagtgtcca acatgtcgaa agcgcagatt   1680
atccagcagg ccggtaactc cgtgctggca aaagccaacc aggtaccgca gcaggttctg   1740
tctctgctgc agggttaa                                                 1758

<210> SEQ ID NO 10
<211> LENGTH: 1383
<212> TYPE: DNA
<213> ORGANISM: Escherichia coli

<400> SEQUENCE: 10
aacaaatctc agtcttctct tagctctgct attgagcgtc tgtcttctgg tctgcgtatt     60
aacagcgcaa agacgatgc agcaggtcag gcgattgcta accgttttac ggcaaatatt    120
aaaggtctga cccaggcttc ccgtaacgca atgatggta tttctgttgc gcagaccact    180
gaaggtgcgc tgaatgaaat taacaacaac ctgcagcgta ttcgtgaact ttctgttcag    240
gcaactaacg gtactaactc tgacagcgat ctttcttcta tccaggctga aattactcaa    300
cgtctggaag aaattgaccg tgtatctgag caaaactcagt ttaacggcgt gaaagtcctt    360
gctgaaaata tgaaatgaa aattcaggtt ggtgctaatg atggtgaaac catcactatc    420
aatctggcaa aaattgatgc gaaaactctc ggcctggacg gttttaatat cgatggcgcg    480
cagaaagcaa caggcagtga cctgatttct aaatttaaag cgacaggtac tgataattat    540
gatgttggcg gtaaaactta taccgtgaat gtggagagcg cgcgcgttaa gaatgatgct    600
aataaagatg ttttttgtaag cgcagctgat ggatcgctga cgaccagtag tgatactaaa    660
gtatccggtg aaagtattga tgcaacgaaa ctagcgaaac ttgcaataaa attagctgac    720
aaaggctcca ttgaatacaa gggcattaca tttactaaca cactggcgc agagcttgat    780 gctaatggta aagtgttttt gaccgcaaat attgatggtc aagatgttca atttactatt    840
gacagtaatg cacccacggg tgccggcgca acaataacta cagacacagc tgtttacaaa    900
aacagtgcgg gccagttcac cactacaaaa gtggaaaata aagccgcaac actctctgat    960
ctggatctta atgcagccaa gaaaacaggt agcactttag ttgtaaatgg cgccacctac   1020
aatgtcagcg cagatggtaa aacggtaact gatactactc ctggtgcccc taaagtgatg   1080
tatctgagca aatcagaagg tggtagcccg attctggtaa acgaagatgc agcaaaatcg   1140
ttgcaatcta ccaccaaccc gctcgaaact atcgacaagg cattggctaa agttgacaat   1200
ctgcgttctg acctcggtgc agtacaaaac cgtttcgact ctgccatcac caaccttggc   1260
aacaccgtaa caacctgtc ttctgcccgt agccgtatcg aagatgctga ctacgcgacc   1320
gaagtgtcta acatgtctcg tgcgcagatc ctgcaacaag cgggtacctc tgttctggcg   1380
cag                                                                1383

<210> SEQ ID NO 11
<211> LENGTH: 2013
<212> TYPE: DNA
<213> ORGANISM: Escherichia coli
```

-continued

```
<400> SEQUENCE: 11
atggcacaag tcattaatac caacagcctc tcgctgatca ctcaaaataa tatcaacaag    60
aaccagtctg cgctgtcgag ttctatcgag cgtctgtctt ctggcttgcg tattaacagc   120
gcgaaggatg acgccgcggg tcaggcgatt gctaaccgtt ttacttctaa cattaaaggc   180
ctgactcagg ctgcacgtaa cgccaacgac ggtatttccg ttgcacagac cactgaaggc   240
gcgctgtccg aaattaacaa caacttacag cgtattcgtg aactgacggt tcaggcttct   300
accgggacta actccgattc ggatctggac tccattcagg acgaaatcaa atcccgtctg   360
gacgaaattg accgcgtatc cggccagacc cagttcaacg gcgtgaacgt gctgtccaaa   420
gatggctcga tgaaaattca ggtcggcgcg aacgatggcg aaacgattac tattgatctg   480
aagaaaattg actctgatac gctgaatctg gctggtttta cgttaacgg taaaggttct    540 gtagcgaata cagctgcgac aagcgacgat ttaaaactgg ctggtttcac taagggcacc   600
acagatacca atggcgtgac cgcgtataca aacacaatta gtaatgacaa agccaaagct   660
tccgatctgt tagctaatat caccgatgga tcagtgatca ctgggggagg ggcaaacgct   720
tttggcgtgg ctgcaaagaa tggttacacc tatgatgcag caagtaaatc ttatagtttt   780
gctgcagatg gtgccgattc agcgaagacg ttaagcatca ttaatccaaa caccggtgat   840
tcgtcgcagg cgacagtgac tattggtggt aaagagcaga agttaatat tcccaggat    900 ggaaaaatta ctgcggcaga tgataatgcg acgctgtatt tagataaaca gggaaacttg   960
acaaaaacga atgcaggtaa cgataccgca gcgacttggg atggtttaat ttccaacagc  1020
gattctaccg gtgcggttcc agttggggtt gcaactacaa ttacaattac ttctggtaca  1080
gcttccggaa tgtctgttca gtccgcagga gcaggaattc agacctcaac aaattctcag  1140
attcttgcag gtggtgcatt tgcggctaag gtaagtattg agggaggcgc tgctacagac  1200
attttggtag caagtaatgg aaacataaca gcggctgatg gtagtgcact ttatcttgat  1260
gcgactactg gtggattcac tacaacggct ggaggaaata cagctgcttc gttagataat  1320
ttaattgcta acagtaagga tgctacctta accgtaactt caggtaccgg ccagaacact  1380
gtttatagca caacaggaag tggcgctcag ttcaccagtt tagcaaaagt agacacagtc  1440
aatgtcacca acgcacatgt cagtgccgaa ggtatggcaa atctgacaaa aagcaatttt  1500
accattgata tgggcggtac aggtacagta acttacacag tttccaatgg ggatgtgaaa  1560
gctgctgcaa atgctgatgt ttatgtcgaa gatggtgcac tttcagccaa tgctacaaaa  1620
gatgtaacct actttgaaca aaaaatggg gctattacca cagcaccgg tggtaccatc   1680 tatgaaacag ctgatggtaa gttaacaaca gaagctacta ctgcatccag ttccaccgcc  1740
gatcccctga agctctgga cgaagccatc agctccatcg acaaattccg ctcctccctc  1800
ggtgcggtgc aaaaccgtct ggattccgcg gtcaccaacc tgaacaacac cactaccaac  1860
ctgtccgaag cgcagtcccg tattcaggac gccgactatg cgaccgaagt gtccaacatg  1920
tcgaaagcgc agatcatcca gcaggccggt aactccgtgc tggcaaaagc taaccaggta  1980
ccgcagcagg ttctgtctct gctgcagggt taa                              2013

<210> SEQ ID NO 12
<211> LENGTH: 1263
<212> TYPE: DNA
<213> ORGANISM: Escherichia coli

<400> SEQUENCE: 12
atggcacaag tcattaatac caacagcctc tcgctgatca ctcaaaataa tatcaacaag    60
```

```
aaccagtctg cgctgtcgag ttctatcgag cgtctgtctt ctggcttgcg tattaacagc    120
gcgaaggatg acgccgcggg tcaggcgatt gctaaccgtt ttacttctaa cattaaaggc    180
ctgactcagg ctgcacgtaa cgccaacgac ggtatttctg ttgcgcagac caccgaaggc    240
gcgctgtccg aaattaacaa caacttacag cgtgtgcgtg agctgactgt tcaggcgacc    300
accggtacta actctgagtc tgacctgtct tctatccagg acgaaatcaa atctcgcctg    360
gaagagattg atcgtgtttc aagtcagact caatttaacg gcgtgaatgt tttggctaaa    420
gatgggaaaa tgaacattca ggttggggca aatgatggac agactatcac tattgatctg    480
aaaaagatcg attcatctac actaaacctc tccagttttg atgctacaaa cttgggcacc    540
agtgttaaag atggggccac catcaataag caagtggcag taggtgctgg cgactttaaa    600
gataaagctt caggatcgtt aggtacccta aaattagttg agaaagacgg taagtactat    660
gtaaatgaca ctaaaagtag taagtactac gatgccgaag tagatactag taagggtaaa    720
attaacttca actctacaaa tgaaagtgga actactccta ctgcagcgac ggaagtaact    780
actgttggcc gcgatgtaaa attggatgct tctgcactta agccaaccaa tcgcttgtc     840
gtgtataaag ataaaagcgg caatgatgct tatatcattc agaccaaaga tgtaacaact    900
aatcaatcaa ctttcaatgc cgctaatatc agtgatgctg gtgttttatc tattggtgca    960
tctacaaccg cgccaagcaa tttaacagct aacccgctta aggctcttga tgatgcaatt    1020
gcatctgttg ataaattccg ctcttctctc ggtgccgttc agaaccgtct ggattctgcc    1080
attgccaacc tgaacaacac cactaccaac ctgtctgaag cgcagtcccg tattcaggac    1140
gctgactatg cgaccgaagt gtccaacatg tcgaaagcgc agattatcca gcaggccggt    1200
aactccgtgc tggcaaaagc caaccaggta ccgcagcagg ttctgtctct gctgcagggt    1260
taa                                                                 1263

<210> SEQ ID NO 13
<211> LENGTH: 1368
<212> TYPE: DNA
<213> ORGANISM: Escherichia coli

<400> SEQUENCE: 13
aacaaatctc agtcttctct gagctccgcc attgaacgtc tctcttctgg cctgcgtatt     60
aacagtgcta agatgacgc agcaggtcag gcgattgcta accgttttac agcaaatatt    120
aaaggtctga ctcaggcttc ccgtaacgcg aatgatggta tttctgttgc gcagaccact    180
gaaggtgcgc tgaatgaaat taacaacaac ctgcagcgtg tacgtgaact gactgttcag    240
gcaactaacg gtactaactc tgacagcgat cttctcttcta tccaggctga aattactcaa    300
cgtctggaag aaattgaccg tgtatctgag caaactcagt ttaacggcgt gaaagtcctt    360
gctgaaaata tgaaatgaa aattcaggtt ggtgctaatg atggtgaaac catcactatc    420
aatctggcaa aaattgatgc gaaaactctc ggcctggacg ttttaatat cgatggcgcg    480
cagaaagcaa ctggcagtga cctgatttct aaatttaaag cgacaggtac tgataactat    540
gatgttggcg gtgatgctta tactgttaac gtagatagcg gagctgttaa agatactaca    600
gggaatgata ttttttgttag tgcagcgat ggttcactga caactaaatc tgacacaaac    660
atagctggta cagggattga tgctacagca ctcgcagcag cggctaagaa taaagcacag    720
aatgataaat tcacgtttaa tggagttgaa ttcacaacaa caactgcagc ggatggcaat    780
gggaatggtg tatattctgc agaaattgat ggtaagtcag tgacatttac tgtgacagat    840
```

```
gctgacaaaa aagcttcttt gattacgagt gagacagttt acaaaaatag cgctggcctt      900
tatacgacaa ccaaagttga taacaaggct gccacacttt ccgatcttga tctcaatgca      960
gctaagaaaa caggaagcac gttagttgtt aacggtgcaa cttacgatgt tagtgcagat     1020
ggtaaaacga taacggagac tgcttctggt aacaataaag tcatgtatct gagcaaatca     1080
gaaggtggta gcccgattct ggtaaacgaa gatgcagcaa atcgttgca atctaccacc      1140 aacccgctcg aaactatcga caaagcattg gctaagttg acaatctgcg ttctgacctc      1200
ggtgcagtac aaaaccgttt cgactctgct atcaccaacc ttggcaacac cgtaaacaac     1260
ctgtcttctg cccgtagccg tatcgaagat gctgactacg cgaccgaagt gtctaacatg     1320
tctcgtgcgc agatcctgca caagcgggt acctctgttc tggcgcag                   1368
```

<210> SEQ ID NO 14
<211> LENGTH: 1788
<212> TYPE: DNA
<213> ORGANISM: Escherichia coli

<400> SEQUENCE: 14

```
atggcacaag tcattaatac caacagcctc tcgctgatca ctcaaaataa tatcaacaag       60
aaccagtctg cgctgtcgag ttctatcgag cgtctgtctt ctggcttgcg tattaacagc      120
gcgaaggatg acgcagcggg tcaggcgatt gctaaccgtt tcacctctaa cattaaaggc      180
ctgactcagg cggcccgtaa cgccaacgac ggtatctccg ttgcgcagac caccgaaggc      240
gcgctgtccg aaatcaacaa caacttacag cgtatccgtg aactgacggt tcaggcttct      300
accgggacta actccgattc ggatctggac tccattcagg acgaaatcaa atcccgtctg      360
gacgaaattg accgcgtatc tggccagacc cagttcaacg gcgtgaacgt actggcgaaa      420
gacggttcaa tgaaaattca ggttggtgcg aatgacggcc agactatcac gattgatctg      480
aagaaaattg actcagatac gctggggctg aatggttta acgtgaatgg ttccggtacg      540
atagccaata agcggcgac cattagcgac ctgacagcag cgaaaatgga tgctgcaact      600
aatactataa ctacaacaaa taatgcgctg actgcatcaa aggcgcttga tcaactgaaa      660
gatggtgaca ctgttactat caaagcagat gctgctcaaa ctgccacggt ttatacatac      720
aatgcatcag ctggtaactt ctcattcagt aatgtatcga ataatacttc agcaaaagca      780
ggtgatgtag cagctagcct tctcccgccg gctgggcaaa ctgctagtgg tgtttataaa      840
gcagcaagcg gtgaagtgaa ctttgatgtt gatgcgaatg gtaaaatcac aatcggagga      900
cagaaagcat atttaactag tgatggtaac ttaactacaa cgatgctgg tggtgcgact      960 gcggctacgc ttgatggttt attcaagaaa gctggtgatg gtcaatcaat cgggtttaag     1020
aagactgcat cagtcacgat gggggaaca acttataact ttaaaacggg tgctgatgct     1080
gatgctgcaa ctgctaacgc aggggtatcg ttcactgata cagctagcaa agaaaccgtt     1140
ttaaataaag tggctacagc taaacaaggc aaagcagttg cagctgacgg tgatacatcc     1200
gcaacaatta cctataaatc tggcgttcag acgtatcagg ctgtatttgc cgcaggtgac     1260
ggtactgcta gcgcaaaata tgccgataaa gctgacgttt ctaatgcaac agcaacatac     1320
actgatgctg atggtgaaat gactacaatt ggttcataca ccacgaagta ttcaatcgat     1380
gctaacaacg gcaaggtaac tgttgattct ggaactggta cgggtaaata tgcgccgaaa     1440
gtaggggctg aagtatatgt tagtgctaat ggtactttaa caacagatgc aactagcgaa     1500
ggcacagtaa caaaagatcc actgaaagct ctggatgaag ctatcagctc catcgacaaa     1560
ttccgttctt ccctgggtgc tatccagaac cgtctggatt ccgcagtcac caacctgaac     1620
```

```
aacaccacta ccaacctgtc cgaagcgcag tcccgtattc aggacgccga ctatgcgacc    1680
gaagtgtcca acatgtcgaa agcgcagatc attcagcagg ccggtaactc cgtgctggca    1740
aaagccaacc aggtaccgca gcaggttctg tctctgctgc agggttaa                 1788
```

<210> SEQ ID NO 15
<211> LENGTH: 1653
<212> TYPE: DNA
<213> ORGANISM: Escherichia coli

<400> SEQUENCE: 15

```
atggcacaag tcattaatac aacagcctc tcgctgatca ctcaaaataa tatcaacaag       60
aaccagtctg cgctgtcgag ttctatcgag cgtctgtctt ctggcttgcg tattaacagc    120
gcgaaggatg acgccgcagg tcaggcgatt gctaaccgtt ttacttctaa cattaaaggc    180
ctgactcagg ctgcacgtaa cgccaacgac ggtatttccg ttgcgcagac cactgaaggt    240
gcgctgtccg aaatcaacaa caacttacag cgtattcgtg agctgacggt tcaggcttct    300
accgggacta actccgattc tgacctggac tccatccagg acgaaatcaa gtctcgtctg    360
gacgaaattg accgcgtatc cggtcagacc cagttcaacg gcgtgaacgt gctggcgaaa    420
gacggttcga tgaaaattca ggttggtgcg aatgacggcc agactatcac gattgatctg    480
aagaaaattg actcagatac gctggggctg agtgggttta atgtgaatgg tgcggggct    540 gttgctaaca ctgctgcatc taaagctgac ttggtagctg ctaatgcaac tgtggtaggc    600
aacaaatata ctgtgagtgc gggttacgat gctgctaaag cgtctgattt gctggctgga    660
gttagtgatg gtgatactgt tcaggcaacc attaataacg gcttcggaac ggcggctagt    720
gcaacgaatt acaagtatga cagtgcaagt aagtcttact cttttgatac cacaacggct    780
tcagctgccg atgttcagaa atatttgacc ccgggcgttg gtgataccgc taagggcact    840
attactatcg atggttctgc acaggatgtt cagatcagca gtgatggtaa aattacgtca    900
agcaatggag ataaacttta cattgataca actgggcgct taacgaaaaa cggctttagt    960
gcttctttga ctgaggctag tctgtccaca cttgcagcca ataataccaa agcgacaacc   1020
attgacattg gcggtaccct tatctccttt accggtaata gtactacgcc gaacactatt   1080
acttattcag taacaggtgc aaaagttgat caggcagctt cgataaagc tgtatcaacc   1140 tctggaaacg atgttgattt cactaccgca ggttatagcg tcgacggcgc aactggcgct   1200
gtaacaaaag tgttgctcc ggtttatatt gataacaacg gggcgttgac cacatctgat   1260
actgtagatt tttatctaca ggatgatggt tcagtgacta acggcagcgg taaggcagtt   1320 tataagatg ctgacggtaa attgacgaca atgctgaaa ctaaagctgc aaccaccgcc    1380 gatccctga aagctctgga cgaagccatc agctccatcg acaaattccg ctcctccctc    1440
ggtgcggtgc agaaccgtct ggattccgcg gtcaccaacc tgaacaacac cactaccaac   1500
ctgtctgaag cgcagtcccg tattcaggac gctgactatg cgaccgaagt atccaacatg   1560
tcgaaagcgc agatcatcca gcaggccggt aactccgtgc tggcaaaagc taaccaggta   1620
ccacagcagg ttctgtctct gctgcagggt taa                                1653
```

<210> SEQ ID NO 16
<211> LENGTH: 1689
<212> TYPE: DNA
<213> ORGANISM: Escherichia coli

<400> SEQUENCE: 16

-continued

```
atggcacaag tcattaatac caacagcctc tcgctgatca ctcaaaataa tatcaacaag      60
aaccagtctg cgctgtcgag ttctatcgag cgtctgtctt ctggcttgcg tattaacagc     120
gcgaaggatg acgccgcagg tcaggcgatt gctaaccgtt ttacttctaa cattaaaggc     180
ctgactcagg ctgcacgtaa cgccaacgac ggtatttctg ttgcacagac cactgaaggc     240
gcgctgtccg aaatcaacaa caacttacag cgtgtgcgtg aactgaccgt tcaggcaacc     300
accggtacca actcccagtc tgacctggac tctatccagg acgaaattaa atcccgtctg     360
gacgaaattg atcgcgtatc cggtcagacc cagttcaacg gcgtgaacgt gctggcaaaa     420
gacggttcca tgaaaattca ggttggcgcg aacgatggcc agaccatcac tatcgacctg     480
aagaagattg actcttctac cttgaacctg acaggtttta acgttaacgg ttctggttct     540
gtggcgaata ctgcagcaac taaagctgat ttaaccgctc tcaactctc tgcaccgggt      600 gcagcagacg caaatggtac agttacttat actgtcagtg ctggttataa agaatccact     660
gctgcagatg ttattgctag catcaaagac ggcagtgctc cgacttctgc aattactgca     720
accattaata atggcttcgg tgattccagt gcgctgactt ccaatgacta tacttatgac     780
ccagcaaaag gcgacttcac ttacgacgta gcttcaagcg ccaataatac tgctgcccag     840
gttcagtcct tcctgacgcc gaaagcaggt gataccgcaa atctgaaagt aaccgttggt     900
acgacatcgc ttgatgtcgt tctggccagt gatggtaaga ttacagcaaa gatggttct      960 gcattatata tcgacagtac aggtaacctg actcagaaca gtgctggctt gacctctgct    1020
aaactggcta ctctgactgg ccttcagggc tctggtgttg cttcaaccat cactactgaa    1080
gatggcacta atattgatat tgctgctaac ggtaatattg gtctgaccgg tgttcgtatc    1140
agtgctgatt ctctgcagtc agcgactaaa tctacgggct ttactgttgg tactggcgct    1200
acaggtctga ccgtaggtac tgatggtaaa gtgactatcg gcgggactac tgctcagtcc    1260
tacaccagca agatggttc cctgactact gataacacca ctaaactgta tctgcagaaa    1320
gatggctctg taaccaacgg ttcaggtaaa gcggtctatg tagaagcgga tggtgatttc    1380
actaccgacg ctgcaaccaa agccgcaacc accaccgatc cgctgaaagc cctggatgag    1440
gcaatcagcc agatcgataa gttccgttca tccctgggtg ctatccagaa ccgtctggat    1500
tccgcggtca ccaacctgaa caacaccact accaacctgt ctgaagcgca gtcccgtatt    1560
caggacgccg actatgcgac cgaagtgtcc aacatgtcga aagcgcagat cattcagcag    1620
gccggtaact ccgtgctggc aaaagccaac caggtaccgc aacaggttct gtctctgctg    1680
cagggctaa                                                            1689
```

<210> SEQ ID NO 17
<211> LENGTH: 915
<212> TYPE: DNA
<213> ORGANISM: Escherichia coli

<400> SEQUENCE: 17

```
gcgctgtcga cttctatcga gcgcctctct tctggtctgc gtattaacag cgctaaagat      60
gacgctgcgg gccaggcgat tgctaaccgc ttcacttcta acatcaaagg tctgactcag     120
gccgcacgta acgccaacga cggtatttct ctggcgcaga cggctgaagg cgcgctgtca     180
gagattaaca caacttgca gcgtattcgt gaactgaccg ttcaggcctc taccggcacg     240
aactctgatt ccgacctgtc ttctattcag gacgaaatca aatcccgtct tgatgaaatt     300
gaccgtgtat ctggtcagac ccagttcaac ggtgtgaacg tgctgtcgaa aaacgattcg     360
atgaagattc agattggtgc caatgataac cagacgatca gcattggctt gcaacaaatc    420
```

-continued

```
gacagtacca ctttgaatct gaaaggattt accgtgtccg gcatggcgga tttcagcgcg      480
gcgaaactga cggctgctga tggtacagca attgctgctg cggatgtcaa ggatgctggg      540
ggtaaacaag tcaatttact gtcttacact gacaccgcgt ctaacagtac taaatatgcg      600
gtcgttgatt ctgcaaccgg taaatacatg gcagccactg tagtcattac cagtacggcg      660
gcggcggtaa ctgttggtgc aacggaagtg gcgggagccg ctacagccga accgttaaaa      720
gcactggatg ccgcaatcgc taaagtcgac aaattccgct cctccctcgg tgccgttcaa      780
aaccgtctgg attctgcggt caccaacctg aacaacacca ccaccaacct gtctgaagcg      840
cagtcccgta ttcaggacgc cgactatgcg accgaagtgt ccaacatgtc gaaagcgcag      900
attatccagc aggcg                                                       915

<210> SEQ ID NO 18
<211> LENGTH: 1665
<212> TYPE: DNA
<213> ORGANISM: Escherichia coli

<400> SEQUENCE: 18
atggcacaag tcattaatac caacagcctc tcgctgatca ctcaaaataa tatcaacaag       60
aaccagtctg cgctgtcgag ttctatcgag cgtctgtctt ctggcttgcg tattaacagc      120
gcgaaggatg acgccgcagg tcaggcgatt gctaaccgtt ttacttctaa tattaaaggc      180
ctgactcagg ctgcacgtaa cgccaatgac ggtatttctg ttgcacagac cactgaaggc      240
gcgctgtccg aaatcaacaa caacttacag cgtattcgtg aactgacggt tcaggccact      300
acagggacta actccgattc tgacctggac tccatccagg acgaaatcaa atctcgtctg      360
gacgaaattg accgcgtatc cggtcagacc cagttcaacg gcgtgaacgt gctgtccaaa      420
gatggttcaa tgaaaattca ggtcggcgca aatgatggtg aaaccatcac gattgatctg      480
aagaaaattg actctgatac gctgaatctg gctggtttta cgtgaatgg cgaaggtgaa      540 acagccaata ctgctgcaac acttaaagat atggttggtt taaaactcga taatacgggg      600
gtcactacag ctggagttaa tagatatatt gctgacaaag ccgtcgcaag tagcacggat      660
attttgaatg cggtagctgg tgttgatggc agtaaagttt ccacggaggc agatgttggt      720
tttggtgcag ctgccgctgg tacgccagtg aatatactt atcataaaga tactaacaca      780
tatacggctt ctgcttcagt tgatgcgact caactggcgg cattcctgaa tcctgaagcg      840
ggtggtacca ctgctgcaac agtaagtatt ggcaacggta acagctca agagcaaaaa      900 gtcattattg ctaaagatgg ttcttttaact gctgctgatg acggtgccgc tctctatctt      960
gatgatactg gtaacttaag taaaactaac gcaggcactg atactcaagc taaactgtct     1020
gacttaatgg caaacaatgc taatgccaaa acagtcatta acacagataa aggtacattt     1080
actgctaata cgacaaagtt tgatgggggta gatatttctg ttgatgcttc aacgtttgct     1140
aacgccgtta aaaatgagac ttacactgca actgttggtg taactttacc tgcgacatat     1200
acagtcaata atggcactgc tgcatcagcg tatttagtcg atggaaaagt gagcaaaact     1260
cctgccgagt attttgctca gctgatggc actattacta gtggtgaaaa tgcggctacc     1320
agtaaagcta tctatgtaag tgccaatggt aacttaacga ctaatacaac tagtgaatct     1380
gaagctacta ccaacccgct ggcagcattg gatgacgcta tcgcgtctat cgacaaattc     1440
cgttcttccc tgggtgctat ccagaaccgt ctggattccg cagtcaccaa cctgaacaac     1500
accactacca acctgtctga agcgcagtcc cgtattcagg acgccgacta tgcgaccgaa     1560
```

```
gtgtccaaca tgtcgaaagc gcagatcatt cagcaggccg gtaactccgt gctggcaaaa      1620
gccaaccagg taccgcagca ggttctgtct ctgctgcagg gttaa                      1665

<210> SEQ ID NO 19
<211> LENGTH: 1842
<212> TYPE: DNA
<213> ORGANISM: Escherichia coli

<400> SEQUENCE: 19
atggcacaag tcattaatac caacagcctc tcgctgatca ctcaaaataa tatcaacaag        60
aaccagtctg cgctgtcgag ttctatcgag cgtctgtctt ctggcttgcg tattaacagc       120
gcgaaggatg acgccgcagg tcaggcgatt gctaaccgtt ttacttctaa cattaaaggc       180
ctgactcagg ctgcacgtaa cgccaacgac ggtatttctg ttgcgcagac cactgaaggc       240
gcgctgtccg aaattaacaa caacttacag cgtattcgtg aactgacggt tcaggcgacg       300
accggaacta actccacctc tgacctggac tccatccagg acgaaatcaa atcccgtctt       360
gacgaaattg accgcgtatc tggtcagacc cagttcaacg gcgtgaacgt gctgtctaaa       420
gatggctcga tgaaaattca ggtcggcgcg aacgatggcg aaacgattac tattgatctg       480
aagaaaattg actctgatac gctgaatctg gctggtttta cgttaacgg taaaggttct       540 gtagcgaata ccgctgcgac tacagataat ctgacattgg ctggttttac agcgggtact       600
aaagctgctg atggcaccgt aacttatagc aaaaatgtcc agtttgccgc cgcgactgca       660
agcaatgtac tggctgctgc taaagatggc gacgaaatta cgttcgctgg taataacggc       720
acaggtatag ctgcaactgg ggggacttat acttatcata aggactctaa ctcatacagc       780
tttagcgcaa cggctgcatc taaagattct ctgttgagca cactggcacc aaacgctggc       840
gatacattta ccgctaaagt gactattggt tctaaatcgc aagaagttaa cgttagcaaa       900
gatggtacga ttcatcccag cgatggtaag gcgctgtatt tagatgagaa gggcaacctg       960
acccaaacag gtagtggcac aaccaaagct gcaacctggg ataacctgat ggccaataca      1020
gatactacag gcaaagatgc ctatggtaac tctgcggcag cagctgttgg gacagtaatc      1080
gaagcaaaag gaatgaccat cacttctgct ggtggtaatg ctcaggtgtt aaaagacgcg      1140
gcttataatg ccgcatatgc gacctcaatt actactggta ctccgggtga tgcgggagcc      1200
gcgggagccg ctgcaactgc gggtaatgcc gcggtgggag cgctgggcgc aacggcagtt      1260
gataatacca cggcagatgt tgccgatatc tctatctcag cttcgcaaat ggcgagcatc      1320
cttcaggata aagatttcac cttaagtgat ggtagtgata cttacaacgt gaccagcaat      1380
gctgtcacta tcaatggcaa agcagcaaac attgatgaca cggcgcaat cacagaccaa      1440 accagtaaag ttgtcaatta tttcgctcat actaacggta gcgtgactaa cgatacaggc      1500
tccactattt atgcgacaga agatggtagc ctgaccaccg atgcagcaac caaagccgaa      1560
accaccgccg atccctgaa agctctggac gaagccatcg ctccatcga caattccgc       1620 tcctccctcg gtgcggtgca aaaccgtctg gattccgcgg tcaccaacct gaacaacacc      1680
accaccaacc tgtctgaagc gcagtcccgt attcaggacg ccgactatgc gaccgaagtg      1740
tccaacatgt cgaaagcgca gattatccag caggccggta actccgtgct ggcaaaagct      1800
aaccaggtac acagcaggt tctgtctctg ctgcagggtt aa                         1842

<210> SEQ ID NO 20
<211> LENGTH: 1731
<212> TYPE: DNA
<213> ORGANISM: Escherichia coli
```

<400> SEQUENCE: 20

```
atggcacaag tcattaatac caacagcctc tcgctgatca ctcaaaataa tatcaacaag      60
aaccagtctg cgctgtcgag ttctatcgag cgtctgtctt ctggcttgcg tattaacagc     120
gcgaaggatg acgccgcagg tcaggcgatt gctaaccgtt ttacttctaa cattaaaggc     180
ctgactcagg cggcccgtaa cgccaacgac ggtatttctg ttgcgcagac caccgaaggc     240
gcgctgtccg aaattaacaa caacttacag cgtgtgcgtg agctgactgt tcaggcgacc     300
accggtacca actcccagtc tgatctggac tctatccagg acgaaatcaa atcccgtctg     360
gacgaaattg accgcgtatc cggtcagacc cagttcaacg gcgtgaacgt gctggcaaaa     420
gacggttcca tgaaaattca ggttggcgcg aatgatggcc agaccatcac tatcgacctg     480
aagaagattg actcttctac gttgaaactg actggtttta acgtgaatgg ttctggttct     540
gtggcgaata ctgcggcgac taaagcggat ttggctgctg ctgcaattgg taccccctggg    600
gcagcagatt ctacaggtgc cattgcttac acagtaagtg ctgggctgac taaaactaca     660
gccgcagatg tactgtctag cctcgctgat ggtacgacta ttacagccac aggcgtgaaa     720
aatggctttg ctgcaggagc cacttccaat gcctataaac ttaacaaaga taataataca     780
tttacttatg acacgactgc tacgacagct gagctgcagt cttacctgac tccgaaagcg     840
ggcgacactg caacattcag tgttgaaatt ggtggtacta cacaagacgt cgtgctgtcc     900
agtgatggca aactcactgc taaggatggc tctaagcttt acattgatac aactggtaat     960
ttaactcaga atggtggtaa taacggtgtt ggaacactcg cggaagcgac tctgagtggt    1020
ttagctctga acaaaaatgg tttaacggct gttaaatcca caattactac agctgataac    1080
acttcgattg tactgaatgg ttcaagcgat ggtactggta atgctggtac tgaaggtacg    1140
attgctgtta caggcgctgt aattagttca gctgctctgc aatctgcaag caaaacgact    1200
ggtttcactg ttggtacagt agacacagct ggttatatct ctgtaggtac tgatgggagt    1260
gttcaggcat atgatgctgc gacttctggc aacaaagctt cttacaccaa cactgacggt    1320
acactgacta ctgataacac cactaaactg tatctgcaga agatggctct cgtaaccaac    1380
ggttcaggta agcggtcta tgtagaagcg gatggtgatt tcactaccga cgctgcaacc    1440
aaagccgcaa ccaccaccga tccgctggcc gctctggatg acgcaatcag ccagatcgac    1500
aagttccgtt catccttggg tgctatccag aaccgtctgg attctgcagt caccaacctg    1560
aacaacacca ccaccaacct gtctgaagcg cagtcccgta ttcaggacgc cgactatgcg    1620
accgaagtgt ccaatatgtc gaaagcgcag atcatccagc aggccggtaa ctccgtgctg    1680
gcaaaagcca accaggtacc gcagcaggtt ctgtctctgc tgcagggtta a            1731
```

<210> SEQ ID NO 21
<211> LENGTH: 1380
<212> TYPE: DNA
<213> ORGANISM: Escherichia coli

<400> SEQUENCE: 21

```
aacaaatctc agtcttctct gagctccgcc attgaacgtc tctcttctgg cctgcgtatt      60
aacagtgcta agatgacgc agcaggtcag gcgattgcta accgttttac agcaaatatt      120
aaaggtctga ctcaggcttc ccgtaacgcg aatgatggta tttctgttgc gcagaccact     180
gaaggtgcgc tgaatgaaat taacaacaac ctgcagcgta ttcgtgaact ttctgttcag     240
gcaactaacg gtactaactc tgacagcgat ctttcttcta tccaggctga aattactcaa     300
```

-continued

| | |
|---|---|
| cgtctggaag aaattgaccg tgtatctgag caaactcagt ttaacggcgt gaaagtcctt | 360 |
| gctgaaaata atgaaatgaa aattcaggtt ggtgctaatg atggtgaaac catcactatc | 420 |
| aatctggcaa aaattgatgc gaaaactctc ggcctggacg ttttaatat cgatggcgcg | 480 |
| cagaaagcaa ccggcagtga cctgatttct aaatttaaag cgacaggtac tgataattat | 540 |
| caaattaacg gtactgataa ctatactgtt aatgtagata gtggcgtagt acaggataaa | 600 |
| gatggcaaac aagtttatgt gagtactgcg gatggttcac ttacgaccag cagtgatact | 660 |
| caattcaaga ttgatgcaac taagcttgca gtggctgcta agatttagc tcaagggaat | 720 |
| aagattgtct acgaaggtat cgaatttaca ataccggcac tgtcgctat agatgccaaa | 780 |
| ggtaatggta aattaaccgc caatgttgat ggtaaggctg ttgaattcac tatttcgggg | 840 |
| agtactgata catcaggtac tagtgcaacc gttgcccta cgacagccct atacaaaaat | 900 |
| agtgcagggc aattgactgc aacaaaagtt gaaataaag cagcgacact atctgatctt | 960 |
| gatctgaacg ctgccaagaa aacaggaagc acgttagttg ttaacggtgc aacttacgat | 1020 |
| gttagtgcag atggtaaaac gataacggag actgcttctg gtaacaataa agtcatgtat | 1080 |
| ctgagcaaat cagaaggtgg tagcccgatt ctggtaaacg aagatgcagc aaaatcgttg | 1140 |
| caatctacca ccaacccgct cgaaactatc gacaaagcat ggctaaagt tgacaatctg | 1200 |
| cgttctgacc tcggtgcagt acaaaaccgt ttcgactctg ccatcaccaa ccttggcaac | 1260 |
| accgtaaaca acctgtcttc tgcccgtagc cgtatcgaag atgctgacta cgcgaccgaa | 1320 |
| gtgtctaaca tgtctcgtgc gcagatcctg caacaagcgg gtacctctgt tctggcacag | 1380 |

<210> SEQ ID NO 22
<211> LENGTH: 1767
<212> TYPE: DNA
<213> ORGANISM: Escherichia coli

<400> SEQUENCE: 22

| | |
|---|---|
| atggcacaag tcattaatac caacagcctc tcgctgatca ctcaaaataa tatcaacaag | 60 |
| aaccagtctg cgctgtcgag ttctatcgag cgtctgtctt ctggcttgcg tattaacagc | 120 |
| gcgaaggatg acgcagcggg tcaggcgatt gctaaccgtt ttacttctaa cattaaaggc | 180 |
| ctgactcagg cggcacgtaa cgccaacgac ggtatctctc tggcgcagac caccgaaggt | 240 |
| gcgctgtctg aaatcaacaa caacttacag cgtgtacgtg aactgaccgt tcaggcaacc | 300 |
| accggtacta actccgactc cgacctggct tctattcagg acgaaatcaa atcccgtctg | 360 |
| gatgaaattg accgcgtatc tggtcagact cagttcaacg gcgtgaacgt gctggcaaaa | 420 |
| gacggttcca tgaaaattca ggtaggtgct aacgacggcc agactatcac tattgacctg | 480 |
| aaaaaaatcg actctgatac tctgggcctg aatggtttta acgtgaatgg ttctgggacg | 540 |
| attaccaaca aagcagcaac tgtcagtgat gttactcgcg caggcggtac attggtgaat | 600 |
| ggtgcctatg atataaaaac cactaacaca gcgctgacta caactgatgc cttcgcgaaa | 660 |
| ttgaatgatg gtgatgttgt tactatcaat aatggtaagg atactgccta taatataat | 720 |
| gctgctacag gtgggtttac gacggatgtc tccatctccg gggatcctac cgctgctgac | 780 |
| gctactgcta ataaaactgc ccgtgatgca cttgcggcgt cttttacatg tgagccgggt | 840 |
| aaaactgtta tggttcttg gactacgaat gatggtacgg taaatttga taccgatgcc | 900 |
| gatggtaaga tttctattgg tggtgttgct gcttatgtag atgcagcagg caacctgacc | 960 |
| actaacgcag caggtatgac gactcaagca acaactaccg atttggttac tgctgctgca | 1020 |
| tctgctactg gtaagggtgg atccctgacc tttggtgaca cgacgtataa aattggtcag | 1080 |

-continued

```
ggtacggctg gggttgatcc tgatgacgct tcagatgatg tactgggcac catttcttac     1140
tctaaatcag taagcaagga tgttgttctt gctgatacta aagcaactgg taacacgaca     1200
acagttgatt tcaactccgg tatcatgact tcaaaggtta gtttcgatgc aggtacatca     1260
actgatacat tcaaagatgc agatggtgct atcaccaaaa ctaaagaata caccacttct     1320
tatgctgtaa ataaagatac tggtgaagtt accgttgctg attatgctgc ggtagatagc     1380
gccgataagg ctgttgatga tactaaatat aaaccgacta tcggcgcgac agttaacctg     1440
aattctgcag gtaaattgac cactgatacc accagtgcag gcacagcaac caaagatcct     1500
ctggctgccc tggacgctgc tatcagctcc atcgacaaat tccgttcatc cctgggtgct     1560
atccagaacc gtctggattc cgcagtcacc aacctgaaca acaccactac caacctgtcc     1620
gaagcgcagt cccgtattca ggacgccgac tatgcgaccg aagtgtccaa catgtcgaaa     1680
gcgcagatta tccagcaggc cggtaactcc gtgctggcaa aagccaacca ggtaccgcag     1740
caggttctgt ctctgctaca gggttaa                                        1767
```

<210> SEQ ID NO 23
<211> LENGTH: 1383
<212> TYPE: DNA
<213> ORGANISM: Escherichia coli

<400> SEQUENCE: 23

```
aacaaaaacc agtctgcgct gtcgacttct atcgagcgcc tttcttctgg tctgcgtatt       60
aacagcgcta aagatgacgc tgcgggccag gcgattgcta accgcttcac ttctaacatc      120
aaaggtctga ctcaggccgc acgtaacgcc aacgacggta tttctctggc gcagaccact      180
gaaggcgcgc tgtctgagat taacaacaac ttgcagcgtg tgcgtgagtt gactgtacag      240
gcgacgaccg ggactaactc tgattctgac ctgtcttcta tccaggatga aatcaaatcc      300
cgtttaagcg aaattgaccg tgtatctggt cagactcagt ttaacggcgt gaacgtactg      360
gctaagaatg acaccctgtc tattcaggta ggtgcaaatg acggtcagac tatcaatatt      420
gacctgcagc aaatcgattc tcatacactg ggtctggatg gtttcagcgt taaaaataat      480
gatgcagtga aaaccagtgc tgccgtgaat actcttgggg gggggcagg ttctgttgct      540 gtcgacttcg caacaaccag tttgactgct atcactggtc tcggtagcgg tgctatcagc      600
gaaattgcta agacgataa tggtgattac tacgcgcatg tcacagggac tacgggtaat      660
actgctgatg gttactatgc tgtcgatatc gacaaggcta ccggtgaggt cgctctgaaa      720
gatggtaacg tagatacacc gacaggtacg ccaacgacga caagcacata tgacttcaca      780
gacgctggtc aaaccgtttc ctttggcact gatgctgcaa cagccggtat cagcactggt      840
gcttctctcg ttaaacttca ggatgagaaa ggcaatgata ctgctactta tgcaatcaaa      900
gcacaagatg gcagcctgta tgccgccaac gttgatgagg ctaccggtaa agtcactgtc      960
aaaaccgcca gctatactga tgctgacggc aaagcagtga ccgatgccgc tgtaaaactg     1020
ggtggtgaca atggcacaac cgaaattgtt gtcgatgctg cgtcaggtaa aacttacgat     1080
gctggtgcac tgcaaaacgt tgatctctcc agtgcaacca acacggtaac cgcaatcccg     1140
aacggtaaaa ccacgtctcc gctggctgcc cttgacgacg caatcagcca gatcgacaaa     1200
ttccgctcct ccctcggtgc ggtgcagaac cgtctggatt ccgcggtcac caacctgaac     1260
aacaccacta ccaacctgtc tgaagcgcag tcccgtattc aggacgctga ctatgcgacc     1320
gaagtatcca acatgtcgaa agcgcagatc atccagcagg caggtaactc cgtgctgtcc     1380
```

```
aaa                                                                  1383

<210> SEQ ID NO 24
<211> LENGTH: 1197
<212> TYPE: DNA
<213> ORGANISM: Escherichia coli

<400> SEQUENCE: 24
gcgctgtcga cttctatcga gcgcctctct tctggtctgc gcattaacag cgctaaagat      60
gacgctgcgg gccaagcgat tgctaaccgc ttcacttcta acatcaaagg tctgactcag     120
gccgcacgta acgccaacga cggtatttct ctggcgcaga ccactgaagg cgcactgtct     180
gaaatcaaca caacttgca gcgtgttcgt gaactgaccg ttcaggccac taccggtact     240
aactctgatt ctgacctgtc ttcaatacag gacgaaatca atcccgtct cgatgaaatt     300
gaccgcgtat ccggtcagac tcagttcaac ggcgttaatg ttctttccaa agatggttca     360
atgaaaattc aggttggtgc gaatgatggt caaactatct ccatcgatct gaagaaaatt     420
gattcttcaa ctttggggct gaatggcttc tcagtttcta aaaactctct taatgtcagc     480
aatgctatca catctatccc gcaagccgct agcaatgaac tgttgatgt aacttcggt     540
gatactgatg agtctgcagc aatcgcagcc aaattggggg tttccgatac gtcaagcctg     600
tcgctgcaca acatccttga taagatggt aaggcaacag ctgattatgt tgttcagtca     660
ggtaaagact tctatgctgc ttctgttaat gccgcttcag gtaaagtaac cttaaacacc     720
attgatgtta cttatgatga ttatgcgaac ggtgttgacg atgccaagca aacaggtcag     780
ctgatcaaag tttcagcaga taaagacggc gcagctcaag gttttgtcac acttcaaggc     840
aaaaactatt ctgctggtga tgcggcagac attcttaaga atggagcaac agctcttaag     900
ttaactgatc tgaatttaag tgatgttact gatactaatg gtaaggtaac cacaactgcg     960
actgagcaat ttgaaggtgc ttcaactgag gatccgctgg cgcttctgga taaagctatt    1020
gcatcagtcg acaaattccg gtcttctcta ggtgccgtgc agaaccgtct cgattccgct    1080
atcaccaacc tgaacaacac caccaccaac ctgtctgaag cgcagtcccg tattcaggac    1140
gccgactatg cgaccgaagt gtccaacatg tcgaaagcgc agatcatcca gcaggca       1197

<210> SEQ ID NO 25
<211> LENGTH: 1674
<212> TYPE: DNA
<213> ORGANISM: Escherichia coli

<400> SEQUENCE: 25
atggcacaag tcattaatac caacagcctc tcgctgatca ctcaaaataa tatcaacaag      60
aaccagtctg cgctgtcgag ttctatcgag cgtctgtctt ctggcttgcg tattaacagc     120
gcgaaggatg acgccgcagg tcaggcgatt gctaaccgtt ttacttctaa cattaaaggc     180
ctgactcagg ctgcacgtaa cgccaacgac ggtatttctg ttgcacagac cactgaaggc     240
gcgctgtccg aaatcaacaa caacttacag cgtattcgtg aactgacggt tcaggccact     300
acagggacta ctccgattc tgacctggac tccatccagg acgaaatcaa atctcgtctg     360
gacgaaattg accgcgtatc tggtcagacc cagttcaacg gcgtgaacgt gctgtctaaa     420
gatggctcga tgaaaattca ggtcggcgcg aacgatggcg aaacgattac tattgatctg     480
aagaaaattg actctgatac gctaaatctg gctggtttta acgtgaatgg tgctggctct     540
gttgataatg ccaaggcgac tggcaaagat cttactgatg ctggttttac ggcaagcgca     600
gctgatgcta atggcaaaat cacttatacc aaagacaccg ttactaaatt cgacaaagcg     660
```

```
acagcggctg atgtattggg caaagcggct gctggcgata gcattaccta tgcgggcact      720
gatactggct taggagtcgc tgctgatgcc tcgacttaca cctacaatgc agccaataag      780
tcttacactt tgatgctac tggtgttgcc aaggcggatg ctggaacggc actgaaaggg      840
tacttaggcg catctaacac cggtaaaatt aatatcggtg gtaccgagca agaagttaac      900
attgccaaag atggctccat caccgatacc aatggcgatg cgctgtatct cgatagtacc      960
ggcaacttaa ccaaaaatac cgcgaatttg ggggctgctg ataaagcaac tgtagataaa     1020
ctgtttgctg gtgctcagga tgcaacgatc accttcgata gcggcatgac agctaaattc     1080
gatcaaactg ctggtaccgt tgatttcaaa ggcgcgtcta tttctgctga tgcaatggca     1140
tcaaccttaa ataatggttc ctatacagcc aacgtaggtg gtaaggctta tgccgtaacc     1200
gctggcgcag ttcagacagg tggcgcagat gtgtataaag ataccactgg cgcactgacg     1260
actgaagatg acgaaaccgt taccgcgacc tactacggtt ttgctgatgg taaagttttct     1320 gacggtgaag gttctactgt ctataaagct gctgatggtt ccatcactaa agatgcgact     1380
accaagtctg aagcaaccac tgaccctctg aaagcccttg acgacgcaat cagccagatc     1440
gacaaattcc gctcctccct cggtgccgtt caaaaccgtc tggattccgc cgtcaccaac     1500
ctgaacaaca ccactaccaa cctgtctgaa gcgcagtccc gtattcagga cgccgactat     1560
gcgaccgaag tgtccaacat gtcgaaagcg cagatcattc agcaggccgg taactccgtg     1620
ctggcaaaag ccaaccaggt accgcagcag gttctgtctc tgctgcaggg ttaa          1674

<210> SEQ ID NO 26
<211> LENGTH: 1365
<212> TYPE: DNA
<213> ORGANISM: Escherichia coli

<400> SEQUENCE: 26
aacaaatctc agtcttctct tagctctgct attgagcgtc tctcttctgg cctgcgtatt       60
aacagtgcta agatgacgc agcaggtcag gcgattgcta accgttttac ggcaaatatt      120
aaaggtctga ctcaggcttc ccgtaacgcg aatgatggta tttctgttgc gcagactact      180
gaaggtgcgc tgaatgaaat taacaacaac ctgcagcgtg tacgtgaact gactgttcag      240
gcaactaacg gtactaactc tgacagcgat ctttcttcta ttcaggcaga aattactcaa      300
cgtctggaag aaattgaccg tgtatctgag caaactcagt ttaacggcgt gaaagtcctt      360
gccgaaaata tgaaatgaa aattcaggtt ggtgctaatg atggggaaac catcactatc      420
aatctggcaa aaattgatgc gaaaactctc ggcctggacg gctttaatat cgatggcgcg      480
cagaaagcaa ctggcagtga cctgatttct aaatttaaag cgacaggtac tgataattat      540
caaattaacg gtactgataa ctatactgtt aatgtagata gtggagcagt tcaaaatgag      600
gatggtgacg caattttgt tagcgctacc gatggttctc tgactactaa gagtgataca      660
aaagtcggtg gtacaggtat tgatgcgact gggcttgcaa aagccgcagt ttctttagct      720
aaagatgcct caattaaata ccaaggtatt actttcacca acaaaggcac tgatgcattt      780
gatggcagtg gtaacggcac tctaaccgct aatattgatg gcaaagatgt aacctttact      840
attgatgcga cagggaagga cgcaacatta aaaacgtctg atcctgttta caaaaatagt      900
gcaggtcagt tcactacaac taaggttgaa aacaaagccg ctacagcatc ggatctggac      960
ttaaataacg ctaaaaaagt gggtagttct ttagttgtaa atggcgctga ttatgaagtt     1020
agcgctgatg gtaagacagt aactgggctt ggcaaaacta tgtatctgag caaatcagaa     1080
```

-continued

| | |
|---|---|
| ggtggtagcc cgattctggt aaaagaagat gcagcaaaat cgttgcaatc tactaccaac | 1140 |
| ccgctcgaaa ccatcgacaa ggcattggct aaagttgaca atctgcgttc tgacctcggt | 1200 |
| gcagtacaaa accgtttcga ctctgctatc accaaccttg caacaccgt aaacaacctg | 1260 |
| tcttctgccc gtagccgtat cgaagatgct gactacgcga ccgaagtgtc taacatgtct | 1320 |
| cgtgcgcaga tcctgcaaca agcgggtacc tctgttctgg cgcag | 1365 |

<210> SEQ ID NO 27
<211> LENGTH: 1740
<212> TYPE: DNA
<213> ORGANISM: Escherichia coli

<400> SEQUENCE: 27

| | |
|---|---|
| atggcacaag tcattaatac caacagcctc tcgctgatca ctcaaaataa tatcaacaag | 60 |
| aaccagtctg cgctgtcgag ttctatcgag cgtctgtctt ctggcttgcg tattaacagc | 120 |
| gcgaaggatg acgccgcagg tcaggcgatt gctaaccgtt ttacttctaa cattaaaggc | 180 |
| ctgactcagg ctgcacgtaa cgccaacgat ggtatttctg ttgcacagac cactgaaggc | 240 |
| gcgctgtccg aaatcaacaa caacttacag cgtatccgtg aactgacggt tcaggcttct | 300 |
| accgggacta actccgattc ggatctggac tccattcagg acgaaatcaa atcccgtctg | 360 |
| gacgaaattg accgcgtatc tggccagacc cagttcaacg gcgtgaacgt actggcgaaa | 420 |
| gacggttcaa tgaaaattca ggttggtgcg aatgacggcc agactatcac gattgatctg | 480 |
| aagaaaattg actctgatac gctggggctg agtgggttta atgtgaatgg tagcggggct | 540 |
| gtggctaata ctgcagcgac taaatctgat ttggcagcag ctcaactctt ggctccaggt | 600 |
| actgctgatg ctaatggtac agttacctat actgttggcg caggcctgaa acatctaca | 660 |
| gctgcagatg taattgcgag tttggctaat aacgcaaaag ttaatgccac aattgcaaat | 720 |
| ggttttggat cgccaacagc tacagattat acatacaaca gcgctacagg cgatttaca | 780 |
| tatagtgcaa ctattgcagc tggtacaaat tctggtgata gtaacagtgc tcagttacaa | 840 |
| tccttcctga caccaaaagc gggcgatact gctaacttaa acgttaaaat tggttctacg | 900 |
| tcaattgacg ttgtattggc tagcgacggt aaaattaccg cgaaagatgg ttcagaacta | 960 |
| tttattgacg tagatggtaa cctcactcaa aacaatgctg ggactgtcaa agcagccact | 1020 |
| cttgatgcac tgactaaaaa ctggcataca acaggcacac cgagtgccgt atctacggta | 1080 |
| attacaactg aagatgaaac aaccttcact ctggctggcg gtactgatgc tactacttct | 1140 |
| ggtgcaatca ctgtagcaaa tgcaagaatg agtgctgagt ctcttcaatc ggcaactaag | 1200 |
| tccacaggat tcagagttga tgttggagct actggtacca gcgcaggcga tattaaagtt | 1260 |
| gatagtaaag gtatagtaca acaacacaca ggtacaggtt ttgaagacgc ttacaccaaa | 1320 |
| gctgatggtt cactgactac cgataataca accaatctgt ttttgcaaaa agacggaact | 1380 |
| gtgaccaatg gttcaggtaa agcagtctat gtttcagcgg atggtaattt tactactgac | 1440 |
| gctgaaacta agctgcaac caccgccgat ccactgaaag ctctggacga agcgatcagc | 1500 |
| tccatcgaca aattccgttc ttccctcggt gcggtgcaaa accgtctgga ttccgcagtc | 1560 |
| accaacctga acaacaccac tactaacctg tctgaagcgc agtcccgtat tcaggacgct | 1620 |
| gactatgcga ccgaagtgtc caatatgtcg aaagcgcaga tcatccagca ggccggtaac | 1680 |
| tccgtgctgg caaaagctaa ccaggtaccg cagcaggttc tgtctctgct gcagggttaa | 1740 |

<210> SEQ ID NO 28
<211> LENGTH: 1233

<212> TYPE: DNA
<213> ORGANISM: Escherichia coli

<400> SEQUENCE: 28

```
aacaaaaacc agtctgcgct gtcgacttct atcgagcgcc tctcttctgg tctgcgcatt      60
aacagcgcta agatgacgc tgcgggccag gcgattgcta accgcttcac ttctaacatc      120
aaaggtctga ctcaggccgc acgtaacgcc aacgacggta tctctctggc gcagaccact     180
gaaggcgcac tgtctgaaat caacaacaac ttgcagcgtg ttcgtgagct gaccgttcag     240
gccactaccg gtactaactc tgattctgac ctgtcttcaa tccaggacga atcaaatcc      300
cgtctcgatg aaattgaccg tatccggt cagactcagt tcaacggcgt gaacgtactg       360
gcaaaagata caccatgaa gattcaggtt ggtgcgaacg atggtcagac tatatccatc      420
gacctgcaaa aaatcgactc ttctactctt ggtttgaacg gtttctccgt ttctaaaaat     480
gctctcgaaa ctagcgaagc gatcactcag ttgccgaacg gtgcgaatgc accaatcgct    540
gtgaagatgg atgcgtctgt tctgaccgat cttaacatta ctgatgcttc cgctgtttcg     600
ctgcacaacg taactaaagg tggtgtcgca acgtctactt atgttgttca gtatggcgat     660
aagagctatg cagcatctgt tgatgcggga ggtacagtaa aactgaataa agccgacgta    720
acatataacg acgcagcaaa tggtgttacg aatgccaccc agattggtag tctggttcag    780
gttggtgctg atgcaaacaa tgatgcagtt ggttttgtta ccgtgcaggg gaaaaactat    840
gttgctaatg actcattagt caatgctaat ggcgctgctg cgctgcagc aactagagtt     900
acaattgatg gtgatggtag ccttggagct aaccaggcta aaattgaact tagccaaaat    960
ggtgctactg ctgcaacatc agagttcgct ggtgcttcaa ccaacgatcc actgactctg    1020
ctggacaaag ctatcgcatc tgttgataaa ttccgttctt ctttggggc ggtacagaac    1080
cgtctgagct ccgctgtaac caacctgaac aacaccacta ccaacctgtc tgaagcgcag   1140
tcccgtattc aggacgccga ctatgcgacc gaagtgtcca acatgtcgaa agcgcagatc   1200
atccagcagg caggtaactc cgtgctgtcc aaa                                 1233
```

<210> SEQ ID NO 29
<211> LENGTH: 1713
<212> TYPE: DNA
<213> ORGANISM: Escherichia coli

<400> SEQUENCE: 29

```
atggcacaag tcattaatac caacagcctc tcgctgatca ctcaaaataa tatcaacaag     60
aaccagtctg cgctgtcgag ttctatcgag cgtctgtctt ctggcttgcg tattaacagc    120
gcgaaggatg acgccgcagg tcaggcgatt gctaaccgtt ttacttctaa cattaaaggc   180
ctgactcagg ctgcacgtaa cgccaacgac ggtatttctg ttgcacagac cactgaaggc    240
gcgctgtccg aaatcaacaa caacttacag cgtattcgtg aactgacggt tcaggcgacg    300
accggaacta actccaccctc tgacctggac tccattcagg acgaaatcaa atcccgtctt   360
gatgaaattg accgcgtatc cggccaaacc cagttcaacg gcgtgaacgt actgtcaaaa   420
gatggctcga tgaaaattca ggtcggcgca aatgatggtg aaaccatcac gattgatctg   480
aaaaagatcg actcttctac attgaagctg accagcttca atgttaacgg taaaggcgct   540
gttgataatg ctaaagccac tgaagcagat ctgaccgctg cgggcttctc ccaaggtgca   600
gtcgtcagtg gcaacagcac ctggactaaa tctactgtta ctacctttaa tgcagcaaca   660
gctaccgacg tgctggcaag cgttagcggc ggcagcacta ttagcggtta taccggtaca   720
```

-continued

| | |
|---|---|
| aacaatggat taggcgtagc ggcttctact gcatatacct acaacgcaac cagcaagtct | 780 |
| tattcatttg acgcaaccgc acttaccaat ggcgatggta ctggggccac cactaaagtt | 840 |
| gctgatgtgc tgaaagccta tgcagcaaac ggtgataata cggctcagat ctccatcggc | 900 |
| ggaagcgctc aggacgttaa aattgccagc gatggcaccc tgactgacgt caatggtgat | 960 |
| gctttatata ttggttctga cggcaacctg actaaaaacc aggccggcgg tccagatgcg | 1020 |
| gcaacgttgg acggtatttt caacggtgcg aatggtaatg cagcagttga tgcgaagatt | 1080 |
| acattcggca gcggcatgac cgttgatttc acccaggcta gcaaaaaagt ggatattaag | 1140 |
| ggcgcaacgg tatccgccga agatatggac actgcgttaa ctgggcaggc ttataccgta | 1200 |
| gctaacggcg cacagtcttt tgacgttgcc gctggtgggg cagtaaccgc tactacaggt | 1260 |
| ggcgctaccg taaatattgg tgctgatggt gaactgacga ctgcgaccaa caagactgtc | 1320 |
| acagaaactt atcacgaatt tgctaacggc aatattctgg atgatgacgg cgcggctctg | 1380 |
| tacaaagcgc tgacggttc tctgaccact gaagctactg taaatccga agtgaccacg | 1440 |
| gatccgctga aagcgctgga cgatgctatc gcatccgtag acaaattccg ctcctccctc | 1500 |
| ggtgcggtgc agaaccgtct ggattccgca gtcaccaacc tgaacaacac cactaccaac | 1560 |
| ctgtctgaag cgcagtcccg cattcaggac gccgactatg cgaccgaagt gtccaatatg | 1620 |
| tcgaaagcgc agatcatcca gcaggccggt aactccgtgc tggcaaaagc caaccaggta | 1680 |
| ccgcagcagg ttctgtctct gctgcagggt taa | 1713 |

<210> SEQ ID NO 30
<211> LENGTH: 1668
<212> TYPE: DNA
<213> ORGANISM: Escherichia coli

<400> SEQUENCE: 30

| | |
|---|---|
| atggcacaag tcattaatac caacagcctc tcgctgatca ctcaaaataa atcaacaag | 60 |
| aaccagtctg cgctgtcgag ttctatcgag cgtctgtctt ctggcttgcg tattaacagc | 120 |
| gctaaggatg acgccgcggg tcaggcgatt gctaaccgtt ttacttctaa cattaaaggc | 180 |
| ctgactcagg ctgcacgtaa cgccaacgac ggtatttctg ttgcgcagac cactgaaggc | 240 |
| gcgctgtccg aaatcaacaa caacttacag cgtatccgtg aactgacggt tcaggcttct | 300 |
| accgggacta actccgattc ggatctggac tccattcagg acgaaatcaa atcccgtctg | 360 |
| gacgaaattg accgcgtatc tggccagacc cagttcaacg gcgtgaacgt actggcgaaa | 420 |
| gacggttcaa tgaaaattca ggttggtgcg aatgacggcc agactatcac tattgatctg | 480 |
| aagaaaattg actcagatac gctggggctg agtgggttta atgtgaatgg tggcgggggct | 540 |
| gttgctaata ctgcagcgac taaagatgat ttggtcgctg catcagtttc agctgcggta | 600 |
| ggtaatgaat acactgtctc tgctggcctg tcgaaatcaa ctgctgctga tgttattgct | 660 |
| agtctcacag atggtgcgac agtaactgcg gctggtgtaa gcaatggttt tgctgcaggg | 720 |
| gcaactggag atgcttataa attcaatcaa gcaaacaaca cttttactta caataccacc | 780 |
| tcaacagcgg cagaactcca atcttacctc acgcctaagg cggggatac cgcaactttc | 840 |
| tccgttgaaa ttggtggcac caagcaggat gttgttctgg ctagtgatgg caaaatcaca | 900 |
| gcaaagacg gtctaaaact ttatattgac accacaggga attaaccca aaacggtgga | 960 |
| ggtactttag aagaagctac cctcaatggc ttagctttca accactctgg tccagccgct | 1020 |
| gctgtacaat ctactattac tactgcggat ggaacttcaa tagttctagc aggttctggc | 1080 |
| gactttggaa caacaaaaac tgctgggggct attaatgtca caggagcagt gatcagtgct | 1140 |

-continued

```
gatgcacttc tttccgccag taaagcgact gggtttactt ctggcactta taccgtaggt   1200
acagatggag ttgttaaatc tggtggcaat gacgtttata caaagctga cgggacggga    1260 ttaactactg acaataccac aaaatattat ttacaagatg acgggtctgt aactaatggt   1320
tctggtaaag ctgtgtatgc tgatgcaaca ggaaaactaa ctactgacgc tgaaactaaa   1380
gccgaaacca ccgccgatcc cctgaaagct ctggacgaag cgatcagctc catcgacaaa   1440
ttccgttctt ccctcggtgc ggtgcaaaac cgtctggatt ccgcggtcac caacctgaac   1500
aacaccacta ccaacctgtc cgaagcgcag tcccgtattc aggacgccga ctatgcgacc   1560
gaagtgtcca acatgtcgaa agcgcagatc atccagcagg ccggtaactc cgtgctggca   1620
aaagctaacc aggtaccgca gcaggttctg tctctgctgc agggttaa               1668
```

<210> SEQ ID NO 31
<211> LENGTH: 1713
<212> TYPE: DNA
<213> ORGANISM: Escherichia coli

<400> SEQUENCE: 31

```
atggcacaag tcattaatac caacagcctc tcgctgatca ctcaaaataa tatcaacaag    60
aaccagtctg cgctgtcgag ttctatcgag cgtctgtctt ctggcttgcg tattaacagc   120
gcgaaggatg acgccgcggg tcaggcgatt gctaaccgtt ttacttctaa cattaaaggc   180
ctgactcagg ctgcacgtaa cgccaacgac ggtatttccg ttgcgcagac caccgaaggc   240
gcgctgtccg aaatcaacaa caacttacag cgtatccgtg aactgacggt tcaggccact   300
accggtacta actccgattc tgacctggac tccatccagg acgaaatcaa atctcgtctt   360
gatgaaattg accgcgtatc tggtcagacc cagttcaatg gcgtgaatgt gttgtccaaa   420
gacggttcaa tgaaaattca ggtgggcgca aatgatggtg aaaccatcac gattgacctg   480
aaaaaaatcg actcttctac actgaagctg accagcttca cgtcaacgg taaggcgct    540 gttgataatg caaaagccac tgaagcagat ctgaccgctg cgggcttctc ccaaagtgca   600
gttgtcagtg gcaatagcac ctggactaaa tctactgtta ctacctttaa tgcagcaaca   660
gctaccgatg tgctggctag cgttagtggc ggcagcacta ttagcggtta tgctggcaca   720
aacaatgggt taggcgtagc ggcttctact gcatatacct acaacgcaac cagcaagtct   780
tattcatttg acgcaaccgc acttactaat ggtgatggta ctgcgggctc aactaaagtt   840
gctgatgttc tgaaagccta tgcagcaaac ggcgataaca cggctcagat ctccatcggt   900
ggtagcgctc aggaagttaa aattgccagc gatggtaccc tgacggatac taatggcgat   960
gcttatacaa ttggtgctga cggtaacctg acgaaaaacc aggccggcgg cccagccgcg  1020
gcaacgttgg acggtatttt caacggtgcg aatggtcatg atgcagttga tgcgaagatt  1080
accttcggca gcggcatgac cgttgacttc acccaggtta gcaacaatgt ggatattaag  1140
ggcgcgacgg tatccgccga agatatgaac actgcgttaa ccggtcaggc ttataccgta  1200
gctaacggcg cacagtctta tgacgttgcc gctgatggtg cagtaactgc tactacaggt  1260
ggagcgaccg taaatattgg tgctgagggt gaactgacga ctgcggccaa caagactgtc  1320
acagaaactt atcacgaatt tgctaacggc aatattctgg atgatgacgg cgcggctctg  1380
tataaagcgg ctgacggctc tctgaccact gaagctacag taaatctga agcgaccacg  1440 gatccgctga agcgctgga cgatgctatc gcatccgtag acaaattccg ttcttccctg  1500
ggtgccgtgc agaaccgtct ggattccgca gtcaccaacc tgaacaacac cactaccaac  1560
```

| | |
|---|---|
| ctgtccgaag cgcagtcccg tattcaggac gccgactatg cgaccgaagt gtccaacatg | 1620 |
| tcgaaagcgc agattattca gcaggcaggt aactccgtgc tggcaaaagc taaccaggta | 1680 |
| ccgcagcagg ttctgtctct gctgcagggt taa | 1713 |

```
<210> SEQ ID NO 32
<211> LENGTH: 1188
<212> TYPE: DNA
<213> ORGANISM: Escherichia coli

<400> SEQUENCE: 32
```

| | |
|---|---|
| aacaaaaacc agtctgcgct gtcgacttct atcgagcgcc tctcttctgg tctgcgcatt | 60 |
| aacagcgcta agatgacgc tgcgggccag gcgattgcta accgcttcac ttctaacatc | 120 |
| aaaggtctga ctcaggccgc acgtaacgcc aacgacggta tctctctggc gcagaccact | 180 |
| gaaggcgcac tgtctgaaat caacaacaac ttgcagcgtg tgcgtgagtt gactgttcag | 240 |
| gcgacgaccg ggactaactc tgattctgac ctgtcttcta ttcaggacga aatcaaatcc | 300 |
| cgtctggatg aaattgaccg tgtttccggt cagacccagt tcaacggcgt gaacgtgctg | 360 |
| gctaaaaacg gttctatggc gattcaggtt ggcgcgaatg atgggcagac catcaacatc | 420 |
| gacctgcaga aaatcgactc ttctactctg ggcctgggcg cttctccgt atctaacaat | 480 |
| gcactgaaac tgagcgattc tatcactcag gttggtgcga gtggttcact ggcagatgtg | 540 |
| aaactgagct ctgttgcctc ggctctgggt gtagacgcaa gcactctgac tctgcacaac | 600 |
| gtacagaccc cagctggcgc agcaacagct aactatgttg tctcttctgg ttctgacaac | 660 |
| tactcagtat ctgttgaaga tagctccggt acagttacgc tgaacaccac tgatataggt | 720 |
| tataccgata ccgctaatgg cgttactacc ggttccatga ctggtaagta cgttaaagtt | 780 |
| ggagctgatg cattgggtgc tgctgtaggt tatgtcaccg tacagggaca aaacttcaaa | 840 |
| gctgatgctg cgcgctggt taactccaag aatgctgctg gtagtcagaa tgttacttct | 900 |
| gcaattggcg atattgctaa taaagcgaat gctaacattt acactggaac ctcttctgca | 960 |
| gatccactgg ctctgctgga caaagctatc gcatctgttg ataaattccg ttcttctcta | 1020 |
| ggggcggtgc agaaccgtct gagctctgct gtaaccaacc tgaacaacac cactaccaac | 1080 |
| ctgtccgaag cgcagtcccg tattcaggac gccgactatg cgaccgaagt gtccaacatg | 1140 |
| tcgaaagcgc agatcatcca gcaggcgggt aactccgtgc tgtctaaa | 1188 |

```
<210> SEQ ID NO 33
<211> LENGTH: 1638
<212> TYPE: DNA
<213> ORGANISM: Escherichia coli

<400> SEQUENCE: 33
```

| | |
|---|---|
| atggcacaag tcattaatac caacagcctc tcgctgatca ctcaaaataa tatcaacaag | 60 |
| aaccagtctg cgctgtcgag ttctatcgag cgtctgtctt ctggcttgcg tattaacagc | 120 |
| gcgaaggatg acgccgccgg tcaggcgatt gctaaccgtt ttacttctaa cattaaaggc | 180 |
| ctgactcagg ctgcacgtaa cgccaatgac ggtatttctg ttgcacagac cactgaaggc | 240 |
| gcgctgtccg aaatcaacaa caacttacag cgtattcgtg aactgacggt tcaggcttct | 300 |
| accgggacta ctctgattc ggatctggac tccattcagg acgaaatcaa atcccgtctc | 360 |
| gacgaaattg accgcgtatc cggtcagacc cagttcaacg gcgtgaacgt actggcaaaa | 420 |
| gacggttcga tgaaaattca ggttggtgcg aacgacggcc agactatcac tattgatctg | 480 |
| aagaaaattg actctgatac gctggggctg agtgggttta acgtaaatgg tagcgcagat | 540 |

```
aaggcaagtg tcgcggcgac agctgacgga atggttaaag acggatatat caaagggtta    600
acttcatctg acggcagcac tgcatatact aaaactacag caaatactgc agcaaaagga    660
tctgatattc ttgcggcgct taagactggc gataaaatta ccgcaacagg tgcaaatagc    720
cttgctgata atgcgacatc gacaacttat acttataatg caaccagcaa taccttctcc    780
tatacggctg acggtgtaaa ccaaacgaat gctgcagcaa atctcatacc tgcagcaggg    840
aaaacgacag ctgcatcagt tactattggt gggacagcac agaatgtaaa tattgatgat    900
tcgggcaata ttacttcaag tgatggcgat caactttatc tggattcaac aggtaacctg    960
actaaaaacc aggccggcaa cccgaaaaaa gcaaccgttt ctgggcttct cggaaatacg   1020
gatgcgaaag gtactgctgt taaaacaacc atcaagacag aggctggtgt aacagttaca   1080
gctgaaggta atacaggtac tgtaaaaatt gaaggtgcta ctgtttcagc atctgcattt   1140 acggcattg catattccgc caacaccggt gggaatactt atgctgttgc cgcaaataat   1200
actacaaatg gtttcctggc gggggatgac ttaacccagg atgctcaaac tgtttcaacc   1260
tactactcgc aagccgatgg cacggtcacg aatagcgcag gcaaagaaat ctataaagac   1320
gctgatggtg tctacagcac agagaataaa acatcgaaga cgtccgatcc attggctgcg   1380
cttgacgacg caatcagctc catcgacaaa ttccgttcat ccttgggtgc tatccagaac   1440
cgtctggatt ccgcggtcac caacctgaac aacaccacta ccaacctgtc cgaagcgcag   1500
tcccgtattc aggacgccga ctatgcgacc gaagtgtcca acatgtcgaa agcgcagatc   1560
atccagcagg ccggtaactc cgtgctggca aaagctaacc aggtaccgca gcaggttctg   1620
tctctgctgc agggctaa                                                 1638

<210> SEQ ID NO 34
<211> LENGTH: 2145
<212> TYPE: DNA
<213> ORGANISM: Escherichia coli

<400> SEQUENCE: 34
aacaaatctc agtcttctct gagctccgcc attgaacgtc tctcttctgg cctgcgtatt     60
aacagtgcta agatgacgc agcaggtcag gcgattgcta accgttttac agcaaatatt    120
aaaggtctga ctcaggcttc ccgtaacgcg aatgatggta tttctgttgc gcagaccact    180
gaaggtgcgc tgaatgaaat taacaacaac ctgcagcgtg tacgtgaact gactgttcag    240
gcaactaacg gtactaactc tgacagcgat ctttcttcta tccaggctga aattactcaa    300
cgtctggaag aaattgaccg tgtatctgag caaactcagt taacggcgt gaaagtcctt    360 gctgaaaata tgaaatgaa aattcaggtt ggtgctaatg atggtgaaac catcactatc    420
aatctggcaa aaattgatgc gaaaactctc ggcctggacg ttttaatat cgatggcgcg    480 cagaaagcaa ctggcagtga cctgatttct aaatttaaag cgacaggtac tgataactat    540
gatgttggcg gtgatgctta tactgttaac gtagatagcg gagctgggta atgactccaa    600
cttattgata gtgtttttatg ttcagataat gcccgatgac tttgtcatgc agctccaccg    660 atttgagaa cgacagcgac ttccgtccca gccgtgccag gtgctgcctc agattcaggt    720
tatgccgctc aattcgctgc gtatatcgct tgctgattac gtgcagcttt cccttcaggc    780
gggattcata cagcggccag ccatccgtca tccatatcac cacgtcaaag ggtgacagca    840
ggctcataag acgccccagc gtcgcctag tgcgttcacc gaatacgtgc gcaacaaccg    900
tcttccggag cctgtcatac gcgtaaaaca gccagcgctg gcgcgattta gccccgacat    960
```

-continued

```
agtcccactg ttcgtccatt tccgcgcaga cgatgacgtc actgcccggc tgtatgcgcg    1020
aggttaccga ctgcggcctg agtttttaa gtgacgtaaa atcgtgttga ggccaacgcc    1080
cataatgcgg gcagttgccc ggcatccaac gccattcatg ccatatcaa tgattttctg    1140 gtgcgtaccg ggttgagaag cggtgtaagt gaactgcagt tgccatgttt tacggcagtg    1200
agagcagaga tagcgctgat gtccggcggt gcttttgccg ttacgcacca ccccgtcagt    1260
agctgaacag gagggacagc tgatagaaac agaagccact ggagcacctc aaaaacacca    1320
tcatacacta aatcagtaag ttggcagcat taccgcggag ctgttaaaga tactacaggg    1380
aatgatattt ttgttagtgc agcagatggt tcactgacaa ctaaatctga cacaaacata    1440
gctggtacag ggattgatgc tacagcactc gcagcagcgg ctaagaataa agcacagaat    1500
gataaattca cgtttaatgg agttgaattc acaacaacaa ctgcagcgga tggcaatggg    1560
aatggtgtat attctgcaga aattgatggt aagtcagtga catttactgt gacagatgct    1620
gacaaaaaag cttctttgat tacgagtgag acagtttaca aaaatagcgc tggcctttat    1680
acgacaacca agttgataa caaggctgcc acactttccg atcttgatct caatgcagct    1740
aagaaaacag gaagcacgtt agttgttaac ggtgcaactt acgatgttag tgcagatggt    1800
aaaacgataa cggagactgc ttctggtaac aataaagtca tgtatctgag caaatcagaa    1860
ggtggtagcc cgattctggt aaacgaagat gcagcaaaat cgttgcaatc taccaccaac    1920
ccgctcgaaa ctatcgacaa agcattggct aaagttgaca atctgcgttc tgacctcggt    1980
gcagtacaaa accgtttcga ctctgctatc accaaccttg caacaccgt aaacaacctg    2040 tcttctgccc gtagccgtat cgaagatgct gactacgcga ccgaagtgtc taacatgtct    2100
cgtgcgcaga tcctgcaaca agcgggtacc tctgttctgg cgcag               2145
```

<210> SEQ ID NO 35
<211> LENGTH: 1587
<212> TYPE: DNA
<213> ORGANISM: Escherichia coli

<400> SEQUENCE: 35

```
aacaagaacc agtctgcgct gtcgagttct atcgagcgtc tgtcttctgg cttgcgtatt      60
aacagcgcga aggatgacgc cgcaggtcag gcgattgcta accgttttac ttctaacatt     120
aaaggcctga ctcaggctgc acgtaacgcc aacgacggta tttctgttgc gcagaccacc     180
gaaggcgcgc tgtccgaaat caacaacaac ttacagcgtg tgcgtgaact gaccgttcag     240
gcaaccaccg gtaccaactc ccagtctgac ctggactcta tccaggacga aattaaatcc     300
cgtctggacg aaattgaccg cgtatccggt cagacccagt tcaacggcgt gaacgtactg     360
gcaaaagacg gttccatgaa aattcaggtt ggcgcgaacg atggccagac catcactatc     420
gacctgaaga gattgactc ttctacgctg aaactgactg gttttaacgt gaatggcaaa     480
gcagcggttg ataatgctaa agcgacggat gcaaatctga ctaccgccgg ttttacacaa     540
ggcgttgtgg attcaaatgg taatagtact tggactaaat caactacgac taatttcgat     600
gcggcaactc agtaaacgt actagcagca gttaaagatg gcagcacaat caattacacc     660
ggtactggta atggtttagg gattgctgca acaagtgctt atacatatca cgatagcact     720
aaatcctata cctttgattc tacggggct gcagtagctg tgccgcgtc cagcctgcaa     780 ggtacttttg gtacagatac gaatactgca aaaatcacca tcgatggttc tgctcaagaa     840
gtaaacatcg ctaagatgg gaaaattact gatactgatg gtaaagcttt atatatcgat     900
tccactggta attttgactaa gaacggctct gatactttaa ctcaggcaac attgaatgat     960
```

```
gtccttactg gtgctaattc agttgatgat acaaggattg acttcgatag cggcatgtct    1020
gtcacccttg ataaagtgaa cagcactgta gatatcactg gcgcatctat ttcagccgct    1080
gcaatgacta atgagttgac aggtaaggcc tataccgtag taaatggtgc agaatcttac    1140
gctgtagcta ctaataacac agtaaaaacg actgctgatg ctaaaaatgt ttatgttgat    1200
gctagtggta aattaactac tgatgacaaa gccactgtta cagaaactta tcatgaattt    1260
gcgaatggca atatctatga tgataaaggc gctgctgttt atgcggcggc ggatggttct    1320
ctgactacag aaactacaag taaatcagaa gctacagcta acccgctggc cgctctggac    1380
gacgcaatca gccagatcga caaattccgt tcatccctgg gtgctatcca gaaccgtctg    1440
gattccgcag tcaccaacct gaacaacacc actaccaatc tgtctgaagc gcagtcccgt    1500
attcaggacg ccgactatgc gaccgaagtg tccaatatgt cgaaagcgca gatcatccag    1560
caggcaggca actccgtgct ggcaaaa                                        1587

<210> SEQ ID NO 36
<211> LENGTH: 1245
<212> TYPE: DNA
<213> ORGANISM: Escherichia coli

<400> SEQUENCE: 36
aacaaaaacc agtctgcgct gtcgacttct atcgagcgcc tctcttctgg tctgcgcatt      60
aacagcgcta aagatgacgc tgcgggccag gcgattgcta accgcttcac ttctaacatc     120
aaaggtctga ctcaggccgc acgtaacgcc aacgacggta tctctctggc gcagaccact     180
gaaggcgcac tgtctgaaat caacaacaac ttgcagcgtg ttcgtgaact gaccgttcag     240
gccactaccg gtactaactc tgattctgac ctgtcttcaa tccaggacga aatcaaatcc     300
cgtctcgatg aaattgaccg cgtatccggt cagactcagt tcaacggcgt gaacgtactg     360
gcaaaagatg gctcgatgaa aattcaggtc ggtgcaaatg atggtcagac aatcagcatt     420
gatttgcaga gattgattc ttctactttta gggttaaatg gtttttctgt ttccaaaaat     480
gcagtatctg ttggtgatgc tattactcaa ttgcctggcg agacggcagc cgatgccacca    540 gtaaccatca gtttgatga ttcagtaaaa actgatttaa aactgaccga tgcttcaggg      600
ttaagtctgc ataaccctcaa agatgaaaat ggtaatttaa ctaaccagta tgttgtacag    660
aatggcggaa atcttacgc tgctacagtc gctgccaatg gtaatgttac gctgaacaaa     720
gcaaatgtaa cctacagcga tgtcgcaaac ggtattgata ccgcaacgca gtcaggccag     780
ttagttcagg ttggtgcaga ttctaccggt acgccaaaag cattcgtgtc tgtccaaggt     840
aaaagctttg gcattgatga cgccgccttg aagaataaca ctggtgatgc taccgctact     900
caaccgggaa catctgggac aacagttgtc gcagcgtcaa ttcatctgag tacgggcaaa     960
aactctgtag acgctgatgt aacggcttcc actgaattca caggtgcttc aaccaacgat    1020
ccactgactc tgctggacaa agctatcgca tctgttgata aattccgttc ttctttgggg    1080
gcggtacaga accgtctgag ctccgctgta accaacctga caacaccac caccaacctg    1140 tctgaagcgc agtcccgtat tcaggacgcc gactatgcga ccgaagtgtc caacatgtcg    1200
aaagcgcaga ttatccagca ggcaggtaac tccgtgctgt ccaaa                    1245

<210> SEQ ID NO 37
<211> LENGTH: 1185
<212> TYPE: DNA
<213> ORGANISM: Escherichia coli
```

```
<400> SEQUENCE: 37
aacaaaaacc agtctgcgct gtcgacttct atcgagcgcc tctcttctgg tctgcgcatt      60
aacagcgcta aagatgacgc tgcgggccag gcgattgcta accgcttcac ttctaacatc     120
aaaggtctga ctcaggctgc acgtaacgcc aatgacggta tttctctagc acagacagcg    180
gaaggcgcgc tgtcagagat taacaacaac ttgcagcgtg tgcgtgagtt gaccgtgcag    240
gcaaccactg gtaccaactc tgattccgat ctctcttcta ttcaggatga aattaaatct    300
cgtctggatg aaattgaccg cgtctctggt cagacccagt ttaacggcgt gaacgtactg    360
gctaaaaacg gttctatggc aattcaggtt ggcgcgaacg atggccagac tatctctatc    420
gacctgcaga aaatagactc ttctactctg gtctgagcg gcttctctgt ttctcagaac     480
tccctgaaac tgagcgattc tatcactacg atcggcaata ctactgctgc atcgaagaac    540
gtggacctga gcgcagtagc aactaaactg ggcgtgaatg caagcaccct gagcctgcac    600
gaagttcagg actctgctgg tgacggtact ggtaccttcg ttgtttcttc tggcagcgac    660
aactatgctg tgtctgtaga cgcggcctct ggtgcagtta acctgaacac cactgacgtc    720
acctatgatg acgctactaa tggtgttact ggcgcgactc agaacggtca gctgatcaaa    780
gtaacttctg acgccaacgg tgcagctgtt ggttacgtaa ccattcaggg taaaaactat    840
caggctggtc gaccggtgt tgacgttctg gcgaacagcg tgttgcagc tccaactaca      900 gctgttgata ccggtactct gcaactgagc ggtactggtg caactactga gctgaaaggt    960
actgcaactc agaacccact ggcactattg gacaaagcta tcgcttctgt tgataaattc   1020
cgttcttctc tgggtgcggt acagaatcgt ctgagctctg ctgtaaccaa cctgaataac   1080
accaccacta acctgtctga agcgcagtcc cgtattcagg atgccgacta tgcgaccgaa   1140
gtgtcaaata tgtctaaagc gcagatcgtt cagcaggccg gtaac                    1185

<210> SEQ ID NO 38
<211> LENGTH: 1383
<212> TYPE: DNA
<213> ORGANISM: Escherichia coli

<400> SEQUENCE: 38
aacaaatctc agtcttctct tagctctgct attgagcgtc tgtcttctgg tctgcgtatt     60
aacagcgcaa agacgatgc agcaggtcag gcgattgcta accgttttac ggcaaatatt    120
aaaggtctga cccaggcttc ccgtaacgca aatgatggta tttctgttgc gcagaccact    180
gaaggtgcgc tgaatgaaat taacaacaac ctgcagcgta ttcgtgaact ttctgttcag    240
gcaactaacg gtactaactc tgacagcgat cttctcttcta tccaggctga aattactcaa   300
cgtctggaag aaattgaccg tgtatctgag caaactcagt ttaacggcgt gaaagtcctt    360
gctgaaaata tgaaatgaa aattcaggtt ggtgctaatg atggtgaaac catcactatc      420
aatctggcaa aaattgatgc gaaaactctc ggcctggacg gttttaatat cgatggcgcg    480
cagaaagcaa caggcagtga cctgatttct aaatttaaag cgacaggtac tgataattat    540
gatgttggcg gtaaaactta taccgtgaat gtggagagcg gcgcggttaa gaatgatgct    600
aataaagatg ttttttgtaag cgcagctgat ggatcgctga cgaccagtag tgatactaaa   660
gtatccggtg aaagtattga tgcaacgaaa ctagcgaaac ttgcaataaa attagctgac    720
aaaggctcca ttgaatacaa gggcattaca tttactaaca acactggcgc agagcttgat    780
gctaatggta aagtgttttt gaccgcaaat attgatggtc aagatgttca atttactatt    840
gacagtaatg cacccacggg tgccggcgca acaataacta cagacacagc tgtttacaaa    900
```

```
aacagtgcgg gccagttcac cactacaaaa gtggaaaata agccgcaac actctctgat      960
ctggatctta atgcagccaa gaaaacaggt agcactttag ttgtaaatgg cgccacctac     1020
aatgtcagcg cagatggtaa aacgtaact gatactactc ctggtgcccc taaagtgatg      1080
tatctgagca atcagaagg tggtagcccg attctggtaa acgaagatgc agcaaaatcg      1140
ttgcaatcta ccaccaaccc gctcgaaact atcgacaagg cattggctaa agttgacaat     1200
ctgcgttctg acctcggtgc agtacaaaac cgtttcgact ctgccatcac caaccttggc    1260
aacaccgtaa acaacctgtc ttctgcccgt agccgtatcg aagatgctga ctacgcgacc    1320
gaagtgtcta acatgtctcg tgcgcagatc ctgcaacaag cgggtacctc tgttctggcg    1380
cag                                                                   1383
```

<210> SEQ ID NO 39
<211> LENGTH: 1680
<212> TYPE: DNA
<213> ORGANISM: Escherichia coli

<400> SEQUENCE: 39

```
atggcacaag tcattaatac caacagcctc tcgctgatca ctcaaaataa tatcaacaag      60
aaccagtctg cgctgtcgag ttctatcgag cgtctgtctt ctggcttgcg tattaacagc     120
gcgaaggatg acgccgcagg tcaggcgatt gctaaccgtt tcacctctaa cattaaaggc     180
ctgactcagg ctgcacgtaa cgccaacgac ggtatttctg ttgcacagac caccgaaggc    240
gcgctgtccg aaatcaacaa caacttacag cgtatccgtg aactgaccgt tcaggcttct    300
accgggacta actctgattc ggatctggac tccattcagg acgaaatcaa atcccgtctg    360
gacgaaattg accgcgtatc cggccagacc cagttcaacg gcgtgaacgt gctggcgaaa    420
gacggttcaa tgaaaattca ggttggtgcg aatgacggcc agactatcac tattgatctg    480
aagaaaattg actctgatac tctgggtttg agtggattta atgtgaatgg caaaggggct    540
gtggctaacg caaaagcgac cgaagcagat ttaacggggg ctggtttctc tcaaggagcg    600
gtggatacaa acgaaaatag tacttggaca aaatcaacca ccaccaatta ctcagctgca    660
acaactgctg acttgttatc gaccattaag gatggctcta ctgttacata tgcagggaca    720
gacaccggat taggggtcgc agcagcagga aattatactt atgatgcgaa cagtaaatct    780
tattccttca atgccaatgg tctgacgggc gcaaataccg caactgcact caaaggttac    840
ttggggacag tgctaacac cgctaaaatt tctatcggtg gtacagagca ggaagtgaat    900
attgccaaag atggcactat tacagatacg aatggtgatg cgctctatct ggatattacc    960
ggcaacctga ctaagaacta tgcgggttca ccacctgcag caacgctgga taacgtatta   1020
gcttccgcaa ctgtaaatgc cactatcaag tttgatagcg gtatgacggt tgattacact   1080
gcaggtactg cgcgaatat tacaggtgca tccatttctg cagatgacat ggccgcaaaa   1140
ctgagcggaa aggcgtacac tgttgccaat ggtgctgagt cttatgacgt tgctgcagtt   1200
acggggggctg taacaactac agcaggtaat tcacctgtgt atgccgatgc agacggtaaa   1260
ttaacgacga gtgccagtaa tacggttact cagacttatc acgagtttgc taatggtaac   1320
atttatgatg acaaaggctc gtcactgtat aaagctgcag atggctctct gacttctgaa   1380
gctaaaggga atctgaagc aaccgccgat cccctgaaag ctctggacga agccatcagc   1440
tccatcgaca aattccgctc ctccctcggt gccgttcaaa accgtctgga ttctgcggtg   1500
accaacctga acaacaccac taccaacctg tctgaagcgc agtcccgtat tcaggacgcc   1560
```

| | |
|---|---|
| gactatgcga ccgaagtgtc caatatgtcg aaagcgcaga tcatccagca ggccggtaac | 1620 |
| tccgtgttgg caaaagctaa ccaggtaccg cagcaggttc tgtctctgct gcaggttaa | 1680 |

<210> SEQ ID NO 40
<211> LENGTH: 1146
<212> TYPE: DNA
<213> ORGANISM: Escherichia coli

<400> SEQUENCE: 40

| | |
|---|---|
| gcgctgtcga cttctatcga gcgcctctct tctggtttgc gcattaacag cgctaaagat | 60 |
| gacgctgcgg gccaggcgat tgctaaccgc ttcacttcta acatcaaagg tctgactcag | 120 |
| gccgcacgta acgccaacga cggtatctct ctggcgcaga ccactgaagg cgcactgtct | 180 |
| gaaatcaaca caacttgca gcgtgttcgt gaactgaccg ttcaggccac taccggtact | 240 |
| aactctgatt ctgacctgtc ttcaatccag gacgaaatca atcccgctt ggctgaaatc | 300 |
| gatcgtgtct ctggtcagac ccagttcaac ggcgtgaacg tgctggctaa aaacggttct | 360 |
| ctgaatattc aggttggcgc gaatgatggg cagaccatct ctatcgattt gcagaaaata | 420 |
| gactcttctg cccttggttt aagtggtttt agtgttgccg gtgggggcgct aaaattaagc | 480 |
| gatacagtga cgcaggtcgg cgatggttca gccgcgccag ttaaagtgga tctggatgca | 540 |
| gcagcaacag atattggtac tgctttgggg caaaaggtta atgcaagttc tttaacgttg | 600 |
| cacaatatct tagacaaaga tggtgcggca actgagaact atgttgttag ctatggtagt | 660 |
| gataattacg ctgcatctgt tgcagatgac gggactgtaa ctcttaataa aacgatatt | 720 |
| acttattcag gcggtgatat taccggcgct accaaagatg atacgttgat taaagttgct | 780 |
| gctaattctg acggagaggc cgttggtttc gctaccgttc agggtaagaa ttatgaaatt | 840 |
| acagatggtg taaaaaacca gtccactgct gcaccaaccg atattgctca gaccattgat | 900 |
| ctggatacgg ctgatgaatt tactgggggct tccactgctg atccactggc acttttagac | 960 |
| aaagctattg cacaggttga tactttccgc tcctccctcg gtgccgttca aaaccgtctg | 1020 |
| gattccgcag tcaccaacct gaacaacact actaccaacc tgtctgaagc gcagtcccgt | 1080 |
| attcaggacg ccgactatgc gaccgaagtg tccaatatgt cgaaagcgca gatcatccag | 1140 |
| caggcc | 1146 |

<210> SEQ ID NO 41
<211> LENGTH: 1506
<212> TYPE: DNA
<213> ORGANISM: Escherichia coli

<400> SEQUENCE: 41

| | |
|---|---|
| atggcacaag tcattaatac caacagcctc tcgctgatca ctcaaaataa tatcaacaag | 60 |
| aaccagtctg cgctgtcgag ttctatcgag cgtctgtctt ctggcttgcg tattaacagc | 120 |
| gcgaaggatg acgcagcggg tcaggcgatt gctaaccgtt ttacttctaa tattaaaggc | 180 |
| ctgactcagg ctgcacgtaa cgccaatgac ggtatttctc tggcgcagac cactgaaggc | 240 |
| gcactgtctg aaatcaacaa caacttgcag cgtgtgcgtg aactgaccgt acaggcgaca | 300 |
| accggaacga actccgaatc tgacctgtcc tctatccagg acgaaatcaa atcccgtctg | 360 |
| gaagagattg accgcgtatc cggccagact cagttcaacg gcgtgaatgt gctggcaaaa | 420 |
| gacggcacca tgaaaattca ggtaggcgcg aacgatggtc agactatctc tatcgatctg | 480 |
| aaaaaaatcg actcttcaac cctgggcctg accggttttg atgtttcgac gaaagcgaat | 540 |
| atttctacga cagcagtaac gggggcggca acgaccactt atgctgatag cgccgttgca | 600 |

```
attgatatcg aacggatat tagcggtatt gctgctgatg ctgcgttagg aacgatcaat    660
ttcgataata caacaggcaa gtactacgca cagattacca gtgcggccaa tccgggcctt   720
gatggtgctt atgaaatcca tgttaatgac gcggatggtt ccttcactgt agcagcgagt   780
gataaacaag cggtgctgc tccgggtact gctctgacaa gcggtaaagt tcagactgca    840
accaccacgc caggtacggc tgttgatgtc actgcggcta aaactgctct ggctgcagca   900
ggtgctgaca cgagtggcct gaaactggtt caactgtcca acacggattc cgcaggtaaa   960
gtgaccaacg tgggttacgg cctgcagaat gacagcggca ctatctttgc aaccgactac  1020
gatggcacca ctgtgaccac gccgggcgca gagactgtga cttacaaaga tgcttccggt  1080 aacagccacca ctgcggctgt cacactgggt ggctctgatg gcaaaaccaa tctggttacc  1140
gccgctgacg gcaaaacgta cggtgcgact gcactgaatg gtgctgatct gtccgatcct  1200
aataacaccg ttaaatctgt tgcagacaac gctaaaccgt tggctgccct ggatgatgca  1260
attgcgatgg tcgacaaatt ccgctcctcc ctcggtgcgg tgcaaaaccg tctggattcc  1320
gcagtcacca acctgaacaa caccactacc aacctgtctg aagcgcagtc ccgtattcag  1380
gacgccgact atgcgaccga agtgtccaac atgtcgaaag cgcagattat ccagcaggca  1440
ggtaactccg tgctgtccaa agctaaccag gttccgcagc aggttctgtc tctgctgcag  1500
ggttaa                                                             1506

<210> SEQ ID NO 42
<211> LENGTH: 950
<212> TYPE: DNA
<213> ORGANISM: Escherichia coli

<400> SEQUENCE: 42
aacaaaaacc agtctgcgct gtcgacttct atcgagcgcc tctcttctgg tctgcgtatt    60
aacagcgcta aagatgacgc cgcgggccag gcgattgcta accgctttac ttctaacatc   120
aaaggtctga ctcaggccgc acgtaacgcc aacgacggta tttctctggc gcagacggct   180
gaaggcgcgc tgtcagagat taacaacaac ttgcagcgta ttcgtgaact gaccgttcag   240
gcctctaccg gcacgaactc tgattccgac ctgtcttcta ttcaggacga aatcaaatcc   300
cgtcttgatg aaattgaccg tgtatctggt cagacccagt tcaacggtgt gaacgtgctg   360
tcgaaaaacg attcgatgaa gattcagatt ggtgccaatg ataaccagac gatcagcatt   420
ggcttgcaac aaatcgacag taccactttg aatctgaaag gatttaccgt gtccggcatg   480
gcggatttca gcgcggcgaa actgacggct gctgatggta cagcaattgc tgctgcggat   540
gtcaaggatg ctgggggtaa acaagtcaat ttactgtctt acactgacac cgcgtctaac   600
agtactaaat atgcggtcgt tgattctgca accggtaaat acatggaagc cactgtagcc   660
attaccggta cggcggcggc ggtaactgtt ggtgcagcgg aagtggcggg agccgctaca   720
gccgatccgt aaaagcact ggatgccgca atcgctaaag tcgacaaatt ccgctcctcc   780
ctcggtgccg ttcaaaaccg tctggattct gcggtcacca acctgaacaa caccaccacc   840
aacctgtctg aagcgcagtc ccgtattcag gacgccgact atgcgaccga agtgtccaac   900
atgtcgaaag cgcagattat ccagcaggcc ggtaactccg tgctggcaaa               950

<210> SEQ ID NO 43
<211> LENGTH: 1707
<212> TYPE: DNA
<213> ORGANISM: Escherichia coli
```

<400> SEQUENCE: 43

```
atggcacaag tcattaatac caacagcctc tcgctgatca ctcaaaataa tatcaacaag      60
aaccagtctg cgctgtcgag ttctatcgag cgtctgtctt ctggcttgcg tattaacagc     120
gcgaaggatg acgcagcggg tcaggcgatt gctaaccgtt ttacctctaa cattaaaggt     180
ctgactcagg ctgcacgtaa cgccaacgac ggtatttctg ttgcacagac cactgaaggc     240
gcgctgtccg aaatcaacaa caacttacag cgtatccgtg aactgacggt tcaggcttct     300
accgggacta actccgattc ggatctggac tccattcagg acgaaatcaa atcccgtctg     360
gacgaaattg accgcgtatc cggtcaaacc cagttcaacg tgtgaacgt actggcgaaa      420
gacggttcga tgaaaattca ggttggtgcg aatgacggcc agactatcac gattgatctg     480
aagaaaattg actcagatac gctggggctg aatggtttca cgttaatgg caaaggcact      540
attgcgaaca agctgctac agtcagcgat ctgaccgctg ctggtgcaac gggaacaggt      600
ccttatgctg tgaccacaaa caatacagca ctcagcgcta cgatgcact gtctcgcctg      660
aaaaccggag atacagttac tactactggc tcgagtgctg cgatctatac ttatgatgcg     720
gctaaaggga acttcaccac tcaagcaaca gttgcagatg cgatgttgt taactttgcg      780
aatactctga accagcggc tggcactact gcatcaggtg tttatactcg tagtactggt      840
gatgtgaagt tgatgtaga tgctaatggc gatgtgacca tcggtggtaa agccgcgtac      900
ctggacgcca ctggtaacct atctacaaac aaccccggca ttgcatcttc agcgaaattg     960
tccgatctgt ttgctagcgg tagtaccta gcgacaactg ttctatcca gctgtctggc     1020
acaacttata actttggtgc agcggcaact tctggcgtaa cctacaccaa actgtaagc     1080
gctgatactg tactgagcac agtgcagagt gctgcaacgg ctaacacagc agttactggt    1140
gcgacaatta agtataatac aggtattcag tctgcaacgg cgtccttcgg tggtgtgaat    1200
actaatggtg ctggtaattc gaatgacacc tatactgatg cagacaaaga gctcaccaca    1260
accgcatctt acactatcaa ctacaacgtc gataaggata ccggtacagt aactgtagct    1320
tcaaatggcg caggtgcaac tggtaaattt gcagctactg ttggggcaca ggcttatgtt    1380
aactctacag gcaaactgac cactgaaacc accagtgcag gcactgcaac caaagatcct    1440
ctggctgccc tggatgaagc tatcagctcc atcgacaaat ccgttcatc cctgggtgct    1500
atccagaacc gtctggattc cgcggttacc aacctgaaca caccactac caacctgtcc    1560
gaagcgcagt cccgtattca ggacgccgac tatgcgaccg aagtgtccaa catgtcgaaa    1620
gcgcagatta ccagcaggc cggtaactcc gtgctggcaa aagccaacca ggtaccgcag    1680
caggttctgt ctctgctgca gggttaa                                      1707
```

<210> SEQ ID NO 44
<211> LENGTH: 1720
<212> TYPE: DNA
<213> ORGANISM: Escherichia coli

<400> SEQUENCE: 44

```
atggcacaag tcattaatac caacagcctc tcgctgatca ctcaaaataa tatcaacaag      60
aaccagtctg cgctgtcgag ttctatcgag cgtctgtctt ctggcttgcg tattaacagc     120
gcgaaggatg acgccgcagg tcaggcgatt gctaaccgtt ttacttctaa tattaaaggc     180
ctgactcagg ctgcacgtaa cgccaatgac ggtatttctg ttgcacagac cactgaaggc     240
gcgctgtccg aaatcaacaa caacttacag cgtgtgcgtg aactgaccgt tcaggcgacc     300
accggtacca actcccagtc tgatctggac tctatccagg acgaaatcaa atcccgtctg     360
```

-continued

```
gacgaaattg accgcgtatc cggtcagact cagttcaacg gcgtgaacgt actggcaaaa    420
gacggttcca tgaaaattca ggttggcgcg aatgatggcc agaccatcac tatcgacctg    480
aagaagattg actcttctac gttgaaactg actggtttta acgtgaatgg ttctggttct    540
gtggcgaata ctgcggcgac taaagacgaa ctggctgctg ctgctgcggc ggcgggtaca    600
actcctgctg tcggtactga cggcgtgacc aaatataccg tagacgcagg gcttaacaaa    660
gccacagcag caaacgtgtt tgcaaacctt gcagatggtg ctgttgttga tgctagcatt    720
tccaacggtt ttggtgcagc agcagccaca gactacacct acaataaagc tacaaatgat    780
ttcactttca atgccagcat tgctgctggt gctgcggccg tgatagtaa cagcgcagct    840 ctgcaatcct tcctgactcc aaaagcaggt gatacagcta acctgagcgt caaaatcggt    900
acgacatctg ttaatgttgt tctggcgagc gatggcaaaa ttacagcgaa agatggctca    960
gctctgtata tcgactcaac gggtaacctg actcagaaca gcgcaggcac tgtaacagca   1020
gcaaccctgg atggactgac caaaaaccat gatgcgacag gagctgttgg tgttgatatc   1080
acgaccgcag atgcgcaac tatctctctg gcaggctctg ctaacgcggc aacaggtact   1140
caatcaggtg caattacact gaaaaatgtt cgtatcagtg ctgatgctct gcagtctgct   1200
gcgaaaggta ctgttatcaa tgttgataat ggtgctgatg atatttctgt tagtaaaacc   1260
gggtgtcgtt actaccggag gtgcgcctac ttatactgat gctgatggta aattaacgac   1320
aaccaacacc gttgattatt tcctgcaaac tgatggcagc gtaaccaatg gttctggtaa   1380
aggggtttac accgatgcag ctggtaaatt cactaccgac gctgcaacca aagccgcaac   1440
caccaccgat ccgctgaaag cccttgatga cgcaatcagc cagatcgata agttccgttc   1500
atccctgggt gctatccaga accgtctgga ttccgcggtt accaacctga caacaccac    1560 taccaacctg tccgaagcgc agtcccgtat tcaggacgcc gactatgcga ccgaagtgtc   1620
caatatgtcg aaagcgcaga tcatccagca ggccggtaac tccgtgttgg caaaagctaa   1680
ccaggtaccg cagcaggttc tgtctctgct gcagggttaa                         1720
```

<210> SEQ ID NO 45
<211> LENGTH: 14516
<212> TYPE: DNA
<213> ORGANISM: Escherichia coli

<400> SEQUENCE: 45

```
gatctgatgg ccgtagggcg ctacgtgctt tctgctgata tctgggctga gttggaaaaa    60
actgctccag gtgcctgggg acgtattcaa ctgactgatg ctattgcaga gttggctaaa   120
aaacagtctg ttgatgccat gctgatgacc ggcgacagct acgactgcgg taagaagatg   180
ggctatatgc aggcattcgt taagtatggg ctgcgcaacc ttaaagaagg ggcgaagttc   240
cgtaagagca tcaagaagct actgagtgag tagagattta cacgtctttg tgacgataag   300
ccagaaaaaa tagcggcagt aacatccag gcttctatgc tttaagcaat ggaatgttac   360
tgccgttttt tatgaaaaat gaccaataat aacaagttaa cctaccaagt ttaatctgct   420
ttttgttgga ttttttcttg tttctggtcg catttggtaa gacaattagc gtgagtttta   480
gagagttttg cgggatctcg cggaactgct cacatctttg gcatttagtt agtgcactgg   540
tagctgttaa gccaggggcg gtagcttgcc taattaattt ttaacgtata catttattct   600
tgccgcttat agcaaataaa gtcaatcgga ttaaacttct tttccattag gtaaaagagt   660
gtttgtagtc gctcagggaa attggttttg gtagtagtac ttttcaaatt atccattttc   720
```

```
cgatttagat ggcagttgat gttactatgc tgcatacata tcaatgtata ttatttactt      780
ttagaatgtg atatgaaaaa aatagtgatc ataggcaatg tagcgtcaat gatgttaagg      840
ttcaggaaag aattaatcat gaatttagtg aggcaaggtg ataatgtata ttgtctagca      900
aatgattttt ccactgaaga tcttaaagta ctttcgtcat ggggcgttaa ggggttaaa       960 ttctctctta actcaaaggg tattaatcct tttaaggata taattgctgt ttatgaacta     1020
aaaaaaattc ttaaggatat ttccccagat attgtatttt catattttgt aaagccagta     1080
atatttggaa ctattgcttc aaagttgtca aaagtgccaa ggattgttgg aatgattgaa     1140
ggtctaggta atgccttcac ttattataag ggaaagcaga ccacaaaaac taaaatgata     1200
aagtggatac aaattctttt atataagtta gcattaccga tgcttgatga tttgattcta     1260
ttaaatcatg atgataaaaa agatttaatc gatcagtata atattaaagc taaggtaaca     1320
gtgttaggtg ggattggatt ggatcttaat gagttttcat ataaagagcc accgaaagag     1380
aaaattacct ttatttttat agcaaggtta ttaagagaga aagggatatt tgagtttatt     1440
gaagccgcaa agttcgttaa gacaacttat ccaagttctg aatttgtaat tttaggaggt     1500
tttgagagta ataatccttt ctcattacaa aaaaatgaaa ttgaatcgct aagaaaagaa     1560
catgatctta tttatcctgg tcatgtggaa aatgttcaag attggttaga gaaaagttct     1620
gtttttgttt tacctacatc atatcgagaa ggcgtaccaa gggtgatcca agaagctatg     1680
gctattggta gacctgtaat aacaactaat gtacctgggt gtagggatat aataaatgat     1740
ggggtcaatg gctttttgat acctccattt gaaattaatt tactggcaga aaaaatgaaa     1800
tattttattg agaataaaga taaagtactc gaaatggggc ttgctggaag gaagtttgca     1860
gaaaaaaact ttgatgcttt tgaaaaaaat aatagactag catcaataat aaaatcaaat     1920
aatgattttt gacttgagca gaaattattt atatttcaat ctgaaaaata aaggctgtta     1980
ttatgaataa agtggcatta attactggta tcactgggca agatggctcc tatttggcag     2040
aattattgtt agaaaaaggt tatgaagttc atggtattaa acgccgtgca tcttcattta     2100
atactgagcg agtggatcac atctatcagg attcacattt agctaatcct aaacttttc      2160 tacactatgg cgatttgaca gatacttcca atctgacccg tattttaaaa gaagttcaac     2220
cagatgaagt ttacaatttg ggggcgatga gccatagc ggtatcattt gagtcaccag        2280
aatacactgc tgatgttgat gcgataggaa cattgcgtct tcttgaagct atcaggatat     2340
tggggctgga aaaaagaca aaatttatc aggcttcaac ttcagagctt tatggtttgg        2400
ttcaagaaat tccacaaaaa gagactacgc cattttatcc acgttcgcct tatgctgttg     2460
caaaattata tgcctattgg atcactgtta attatcgtga gtcttatggt atgtttgcct     2520
gcaatggtat tctctttaac cacgaatcac ctcgccgtgg cgagaccttt gttactcgta     2580
aaataacacg cgggatagca atattgctc aaggtcttga taaatgctta tacttgggaa      2640
atatggattc tctgcgtgat tggggacatg ctaaggatta tgtcaaaatg caatggatga     2700
tgctgcagca agaaactcca gaagattttg taattgctac aggaattcaa tattctgtcc     2760
gtgagtttgt cacaatggcg gcagagcaag taggcataga gttagcattt gaaggtgagg     2820
gagtaaatga aaaggtgtt gttgtttcgg tcaatggcac tgatgctaaa gctgtaaacc      2880
cgggcgatgt aattatatct gtagatccaa ggtattttag gcctgcagaa gttgaaacct     2940
tgcttggcga tcctactaat gcgcataaaa aattaggatg gagccctgaa attacattgc     3000
gtgaaatggt aaaagaaatg gtttccagcg atttagcaat agcgaaaaag aacgtcttgc     3060
tgaaagctaa taacattgcc actaatattc cgcaagaata aaaaagataa tacattaaat     3120
```

-continued

```
aattaaaaat ggtgctagat ttattagtac cattattttt ttttgggtga ctaatgttta    3180
ttacatcaga taaatttaga gaaattatca agttagttcc attagtatca attgatctgc    3240
taattgaaaa cgagaatggt gaatatttat ttggtcttag gaataatcga ccggccaaaa    3300
attattttt tgttccaggt ggtaggattc gcaaaaatga atctattaaa aatgctttta     3360
aaagaatatc atctatggaa ttaggtaaag agtatggtat ttcaggaagt gtttttaatg    3420
gtgtatggga acatttctat gatgatggtt ttttttctga aggcgaggca acacattata    3480
tagtgctttg ttacacactg aaagttctta aaagtgaatt gaatctccca gatgatcaac    3540
atcgtgaata cctttggcta actaaacacc aaataaatgc taaacaagat gttcataact    3600
attcaaaaaa ttattttttg taattttat taaaaattaa tatgcgagag aattgtatgt     3660
ctcaatgtct ttaccctgta attattgccg gaggaaccgg aagccgtcta tggccgttgt    3720
ctcgagtatt taccctaaa caattttaa atttagttgg ggattctaca atgttgcaaa      3780
caacaattac gcgtttggat ggcatcgaat gcgaaaatcc aattgttatc tgcaatgaag    3840
atcaccgatt tattgtagca gagcaattac gacagattgg taagctaacc aagaatatta    3900
tacttgagcc gaaaggccgt aatactgcac ctgccatagc tttagctgct tttatcgctc    3960
agaagaataa tcctaatgac gacccttat tattagtact tgcggcagac cactctataa     4020
ataatgaaaa agcatttcga gagtcaataa taaaagctat gccgtatgca acttctggga    4080
agttagtaac atttggaatt attccggaca cggcaaatac tggttatgga tatattaaga    4140
gaagttcttc agctgatcct aataaagaat tcccagcata taatgttgcg gagtttgtag    4200
aaaaaccaga tgttaaaaca gcacaggaat atatttcgag tgggaattat tactggaata    4260
gcggaatgtt tttatttcgc gccagtaaat atcttgatga actacggaaa tttagaccag    4320
atatttatca tagctgtgaa tgtgcaaccg ctacagcaaa tatagatatg gactttgtcc    4380
gaattaacga ggctgagttt attaattgtc ctgaagagtc tatcgattat gctgtgatgg    4440
aaaaaacaaa agacgctgta gttcttccga tagatattgg ctggaatgac gtgggttctt    4500
ggtcatcact ttgggatata agccaaaagg attgccatgg taatgtgtgc catggggatg    4560
tgctcaatca tgatggagaa aatagtttta tttactctga gtcaagtctg gttgcgacag    4620
tcggagtaag taatttagta attgtccaaa ccaaggatgc tgtactggtt gcggaccgtg    4680
ataaagtcca aaatgttaaa acatagttg acgatctaaa aaagagaaaa cgtgctgaat     4740
actacatgca tcgtgcagtt tttcgccctt ggggtaaatt cgatgcaata gaccaaggcg    4800
atagatatag agtaaaaaaa ataatagtta aaccaggaga agggttagat ttaaggatgc    4860
atcatcatag ggcagagcat tggattgttg tatccggtac tgctaaagtt tcactaggta    4920
gtgaagttaa actattagtt tctaatgagt ctatatatat ccctcaggga gcaaaatata    4980
gtcttgagaa tccaggcgta ataccttgc atcaattga agtaagttct ggtgattacc      5040
ttgaatcaga tgatatagtg cgttttactg acagatataa cagtaaacaa ttcctaaagc    5100
gagattgata aatatgaata aaataacttg cttcaaagca tatgatatac gtgggcgtct    5160
tggtgctgaa ttgaatgatg aaatagcata tagaattggt cgcgcttatg gtgagttttt    5220
taaacctcaa actgtagttg tgggaggaga tgctcgctta acaagtgaga gtttaaagaa    5280
atcactctca aatgggctat gtgatgcagg cgtaaatgtc ttagatcttg gaatgtgtgg    5340
tactgaagag atatattttt ccacttggta tttaggaatt gatggtggaa tcgaggtaac    5400
tgcaagccat aatccaattg attataatgg aatgaaatta gtaaccaaag gtgctcgacc    5460
```

```
aatcagcagt gacacaggtc tcaaagatat acaacaatta gtagagagta ataattttga    5520
agagctcaac ctagaaaaaa aagggaatat taccaaatat tccacccgag atgcctacat    5580
aaatcatttg atgggctatg ctaatctgca aaaaataaaa aaaatcaaaa tagttgtgaa    5640
ttctgggaat ggtgcagctg gtcctgttat tgatgctatt gaggaatgct ttttacggaa    5700
caatattccg attcagtttg taaaaataaa taatacaccc gatggtaatt ttccacatgg    5760
tatccctaat ccattactac ctgagtgcag agaagatacc agcagtgcgg ttataagaca    5820
tagtgctgat tttggtattg catttgatgg tgattttgat aggtgttttt tctttgatga    5880
aaatggacaa tttattgaag gatactacat tgttggttta ttagcggaag ttttttttagg   5940
gaaatatcca aacgcaaaaa tcattcatga tcctcgcctt atatggaata ctattgatat    6000
cgtagaaagt catggtggta tacctataat gactaaaacc ggtcatgctt acattaagca    6060
agaatgcgt gaagaggatg ccgtatatgg cggcgaaatg agtgcgcatc attattttaa     6120
agattttgca tactgcgata gtggaatgat tccttggatt ttaatttgtg aacttttgag    6180
tctgacaaat aaaaaattag gtgaactggt ttgtggttgt ataaacgact ggccggcaag    6240
tggagaaata aactgtacac tagacaatcc gcaaaatgaa atagataaat tatttaatcg    6300
ttacaaagat agtgccttag ctgttgatta cactgatgga ttaactatgg agttctctga    6360
ttggcgtttt aatgttagat gctcaaatac agaacctgta gtacgattga atgtagaatc    6420
taggaataat gctattctta tgcaggaaaa aacagaagaa attctgaatt ttatatcaaa    6480
ataaatttgc acctgagttc ataatgggaa caagaaatat atgaaagtac ttctgactgg    6540
ctcaactggc atggttggta agaatatatt agagcatgat agtgcaagta aatataatat    6600
acttactcca accagctctg atttgaattt attagataaa aatgaaatag aaaaattcat    6660
gcttatcaac atgccagact gtattataca tgcagcggga ttagttggag gcattcatgc    6720
aaatataagc aggccgtttg attttctgga aaaaaatttg cagatgggtt taaatttagt    6780
ttccgtcgca aaaaaactag gtatcaagaa agtgcttaac ttgggtagtt catgcatgta    6840
ccccaaaaac tttgaagagg ctattcctga gaaagctctg ttaactggtg agctagaaga    6900
aactaatgag ggatatgcta ttgcgaaaat tgctgtagca aaagcatgcg aatatatatc    6960
aagagaaaac tctaattatt tttataaaac aattatccca tgtaatttat atgggaaata    7020
tgataaattt gatgataact cgtcacatat gattccggca gttataaaaa aaatccatca    7080
tgcgaaaatt aataatgtcc cagagatcga aatttggggg gatggtaatt cgcgccgtga    7140
gtttatgtat gcagaagatt tagctgatct tatttttat gttattccta aaatagaatt     7200
catgcctaat atggtaaatg ctggtttagg ttacgattat tcaattaatg actattataa    7260
gataattgca gaagaaattg gttatactgg gagttttttct catgatttaa caaaaccaac    7320
aggaatgaaa cggaagctag tagatatttc attgcttaat aaaattggtt ggtcaagtca    7380
ctttgaactc agagatggca tcagaaagac ctataattat tacttggaga atcaaaataa    7440
atgattacat acccacttgc tagtaatact tgggatgaat atgagtatgc agcaatacag    7500
tcagtaattg actcaaaaat gtttaccatg ggtaaaaagg ttgagttata tgagaaaaat    7560
tttgctgatt tgtttggtag caaatatgcc gtaatggtta gctctggttc tacagctaat    7620
ctgttaatga ttgctgccct tttcttcact aataaaccaa aacttaaaag aggtgatgaa    7680
ataatagtac ctgcagtgtc atggtctacg acatattacc ctctgcaaca gtatggctta    7740
aaggtgaagt ttgtcgatat caataaagaa actttaaata ttgatatcga tagttttgaaa   7800
aatgctattt cagataaaac aaaagcaata ttgacagtaa atttattagg taatcctaat    7860
```

```
gattttgcaa aaataaatga gataataaat aataggaata ttatcttact agaagataac    7920
tgtgagtcga tgggcgcggt cttttcaaaat aagcaggcag gcacattcgg agttatgggt    7980
acctttagtt cttttttactc tcatcatata gctacaatgg aaggggggctg cgtagttact    8040
gatgatgaag agctgtatca tgtattgttg tgccttcgag ctcatggttg acaagaaat     8100
ttaccaaaag agaatatggt tacaggcact aagagtgatg atattttcga agagtcgttt    8160
aagtttgttt taccaggata caatgttcgc ccacttgaaa tgagtggtgc tattgggata    8220
gagcaactta aaaagttacc aggttttata tccaccagac gttccaatgc acaatatttt    8280
gtagataaat ttaaagatca tccattcctt gatatacaaa agaagttgg tgaaagtagc     8340
tggtttggtt tttccttcgt tataaaggag ggagctgcta ttgagaggaa gagtttagta    8400
aataatctga tctcagcagg cattgaatgc cgaccaattg ttactgggaa ttttctcaaa    8460
aatgaacgtg ttttgagtta ttttgattac tctgtacatg atacggtagc aaatgccgaa    8520
tatatagata agaatggttt ttttgtcgga aaccaccaga tacctttgtt taatgaaata    8580
gattatctac gaaaagtatt aaaataacta acgaggcact ctatttcgaa tagagtgcct    8640
ttaagatggt attaacagtg aaaaaaattt tagcgtttgg ctattctaaa gtactaccac    8700
cggttattga acagtttgtc aatccaattt gcatcttcat tatcacacca ctaatactca    8760
accacctggg taagcaaagc tatggtaatt ggattttatt aattactatt gtatctttttt   8820
ctcagttaat atgtggagga tgttccgcat ggattgcaaa aatcattgca gaacagagaa    8880
ttcttagtga tttatcaaaa aaaaatgctt tacgtcaaat ttcctataat ttttcaattg    8940
ttattatcgc atttgcggta ttgatttctt ttcttatatt aagtatttgt ttcttcgatg    9000
ttgcgaggaa taattcttca ttcttattcg cgattattat ttgtggtttt tttcaggaag    9060
ttgataattt atttagtggt gcgctaaaag gttttgaaaa atttaatgta tcatgttttt    9120
ttgaagtaat tacaagagtg ctctgggctt ctatagtaat atatggcatt tacggaaatg    9180
cactcttata ttttacatgt ttagccttta ccattaaagg tatgctaaaa tatattcttg    9240
tatgtctgaa tattaccggt tgtttcatca atcctaattt taatagagtt gggattgtta    9300
atttgttaaa tgagtcaaaa tggatgtttc ttcaattaac tggtggcgtc tcacttagtt    9360
tgtttgatag gctcgtaata ccattgatt tatctgtcag taaactggct tcttatgtcc     9420
cttgccttca actagctcaa ttgatgttca ctctttctgc gtctgcaaat caaatattac    9480
taccaatgtt tgctagaatg aaagcatcta acacatttcc ctctaattgt ttttttaaaa    9540
ttctgcttgt atcactaatt tctgttttgc cttgtcttgc gttattcttt tttggtcgtg    9600
atatattatc aatatggata aaccctacat ttgcaactga aaattataaa ttaatgcaaa    9660
ttttagctat aagttacatt ttattgtcaa tgatgacatc ttttcatttc ttgttattag    9720
gaattggtaa atctaagctt gttgcaaatt taaatctggt tgcagggctc gcacttgctg    9780
cttcaacgtt aatcgcagct cattatggcc tttatgcaat atctatggta aaaataatat    9840
atccggcttt tcaattttat tacctttatg tagcttttgt ctatttttaat agagcgaaaa   9900
atgtctattg atttactttt ttcaattact gaaatcgcaa ttgttttttc ttgcactatt    9960
tacatattta ctcaatgttt gttaatgcgg aggatctatt tagataaaag tattttaatt   10020
ctttttatgct tgctcttttt tttagtaatc attcaacttc ctgagcttaa tgtaaacggt    10080
ttggtcgatt ctttaaagtt atcactgcct ttattgatgg tctttatcgc ttttcaaaaa    10140
ccgaaattat gcttgtgggt tattattgca ttgttgtttt tgaactctgc atttaatttt    10200
```

```
ttatatttaa agacattcga taagtttagc tcatttcctt ttactttttt tatattgctg    10260
ttttacttgt ttagattggg aattggtaat ttaccggttt ataaaaataa aaaattttac    10320
gcgttgattt ttctctttat attaatagac ataatgcagt cattgttaat aaattataag    10380
gggcagattt tatattccgt aatttgcatc ctgatacttg tgtttaaagt taatttaaga    10440
aaaaagattc catactttt tttaatgctg ccagttttat atgtaattat tatggcttat     10500
attggtttta attatttcaa taaaggcgta actttttttg aacctacagc aagtaatatt    10560
gaacgtacgg ggatgatata ttatttggtt tcacagcttg gtgattatat attccatggt    10620
atggggacat taaatttctt aaataacggc ggacaatata agacgttata tggacttcca    10680
tcattaattc ctaatgaccc tcatgatttt ttattacggt tctttataag tattggtgtg    10740
ataggagcat tggtttatca ttctatattt tttgttttt ttaggagaat atctttctta     10800
ttatatgaga gaaatgctcc tttcattgtt gtaagttgtt tgttactgtt acaagttgtg    10860
ttaatttata cattaaaccc ttttgatgct tttaatcgat tgatttgcgg gcttacagtt    10920
ggagttgttt atggatttgc aaaaattaga taagtatacc tgtaatggaa atttagacgc    10980
tccacttgtt tcaataatca ttgcaactta taattctgaa cttgatatag ctaagtgttt    11040
gcaatcggta actaatcaat cttataagaa tattgaaatc ataataatgg atggaggatc    11100
ttctgataaa acgcttgata ttgcaaaatc gtttaaagac gaccgaataa aaatagtttc    11160
agagaaagat cgtggaattt atgatgcctg gaataaagca gttgatttat ccattggtga    11220
ttgggtagca tttattggtt cagatgatgt ttactatcat acagatgcaa ttgcttcatt    11280
gatgaagggg gttatggtat ctaatggcgc ccctgtggtt tatgggagga cagcgcacga    11340
aggtcccgat aggaacatat ctggattttc aggcagtgaa tggtacaacc taacaggatt    11400
taagtttaat tattacaaat gtaatttacc attgcccatt atgagcgcaa tatattctcg    11460
tgatttcttc agaaacgaac gttttgatat taaattaaaa attgttgctg acgctgattg    11520
gtttctgaga tgtttcatca aatggagtaa agagaagtca ccttattta ttaatgacac      11580
gaccctatt gttagaatgg gatatggtgg ggtttcgact gatatttctt ctcaagttaa     11640
aactacgcta gaaagtttca ttgtacgcaa aaagaataat atatcctgtt taaacataca    11700
gctgattctt agatatgcta aaattctggt gatggtagcg atcaaaata ttttggcaa      11760
taatgtttat aaattaatgc ataacgggta tcattcccta aagaaaatca agaataaaat    11820
atgaagattg tttatataat aaccgggctt acttgtggtg gagccgaaca ccttatgacg    11880
cagttagcag accaaatgtt tatacgcggg catgatgtta atattatttg tctaactggt    11940
atatctgagg taaagccaac acaaaatatt aatattcatt atgttaatat ggataaaaat    12000
tttagaagct tttttagagc tttatttcaa gtaaaaaaaa taattgtcgc cttaaagcca    12060
gatataatac atagtcatat gtttcatgct aatatttta gtcgttttat taggatgctg     12120
attccagcgg tgcccctgat atgtaccgca cacaacaaaa atgaaggtgg caatgcaagg    12180
atgttttgtt atcgactgag tgatttttta gcttctatta ctacaaatgt aagtaaagag    12240
gctgttcaag agtttatagc aagaaaggct acacctaaaa ataaaatagt agagattccg    12300
aattttatta atacaaataa atttgatttt gatattaatg tcagaaagaa aacgcgagat    12360
gcttttaatt tgaaagacag tacagcagta ctgctcgcag taggaagact tgttgaagca    12420
aaagactatc cgaacttatt aaatgcaata aatcatttga ttccttcaaa aacatcaaat    12480
tgtaatgatt ttatttttgct tattgctggc gatggcgcat taagaaataa attattggat    12540
ttggtttgtc aattgaatct tgtggataaa gttttcttct tggggcaaag aagtgatatt    12600
```

```
aaagaattaa tgtgtgctgc agatctttt gttttgagtt ctgagtggga aggttttggt      12660
ctcgttgttg cagaagctat ggcgtgtgaa cgtcccgttg ttgctaccga ttctggtgga      12720
gttaaagaag tcgttggacc tcataatgat gttatccctg tcagtaatca tattctgttg      12780
gcagagaaaa tcgctgagac acttaaaata gatgataacg caagaaaaat aataggtatg      12840
aaaaatagag aatatattgt ttccaatttt tcaattaaaa cgatagtgag tgagtgggag      12900
cgcttatatt ttaaatattc caagcgtaat aatataattg attgaaaata taagtttgta      12960
ctctggatgc aatagtttct ctatgctgtt tttttactgg ctccgtattt ttacttatag      13020
ctggattttg ttatatatca gtattaatct gtctcaactt catctagact acattcaagc      13080
cgcgcatgcg tcgcgcggtg actacacctg acaggagtat gtaatgtcca agcaacagat      13140
cggcgtcgtc ggtatggcag tgatggggcg caacctggcg ctcaacatcg aaagccgcgg      13200
ttataccgtc tccatcttca accgctcccg cgagaaaact gaagaagttg ttgccgagaa      13260
cccggataag aaactggttc cttattacac ggtgaaagag ttcgtcgagt ctcttgaaac      13320
cccacgtcgt atcctgttaa tggtaaaagc aggggcggga actgatgctg ctatcgattc      13380
cctgaagccg tatctggata aggcgacat cattattgat ggtggcaaca ccttcttcca      13440
ggacactatc cgtcgtaacc gtgaactgtc cgcggaaggc tttaacttca tcggtaccgg      13500
cgtgtccggc ggtgaagagg gcgccctgaa aggcccatct atcatgccag gtggccagaa      13560
agaagcgtat gagctggttg cgcctatcct gaccaagatt gctgcggttg ctgaagatgg      13620
cgaaccatgt ataacttaca tcggtgctga cggtgcgggt cactacgtga agatggtgca      13680
caacggtatc gaatatggcg atatgcagct gattgctgaa gcctattctc tgcttaaagg      13740
cggccttaat ctgtctaacg aagagctggc aaccacttt accgagtgga atgaaggcga      13800
gctaagtagc tacctgattg acatcaccaa agacatcttc accaaaaaag atgaagaggg      13860
taaatacctg gttgatgtga tcctggacga agctgcgaac aaaggcaccg gtaaatggac      13920
cagccagagc tctctggatc tgggtgaacc gctgtcgctg atcaccgaat ccgtattcgc      13980
tcgctacatc tcttctctga agaccagcg cattgcggca tctaaagtgc tgtctggtcc      14040
gcaggctaaa ctggctggtg ataaagcaga gttcgttgag aaagtccgtc gcgcgctgta      14100
cctgggtaaa atcgtctctt atgcccaagg cttctctcaa ctgcgtgccg cgtctgacga      14160
atacaactgg gatctgaact acggcgaaat cgcgaagatc ttccgcgcgg gctgcatcat      14220
tcgtgcgcag ttcctgcaga aaattactga gcgtatgct gaaaacaaag gcattgctaa      14280
cctgttgctg gctccgtact tcaaaaatat cgctgatgaa tatcagcaag cgctgcgtga      14340
tgtagtggct tatgctgtgc agaacggtat tccggtaccg accttctctg cagcggtagc      14400
ctactacgac agctaccgtt ctgcggtact gccggctaat ctgattcagg cacagcgtga      14460
ttacttcggt gcgcacacgt ataaacgcac tgataaagaa ggtgtgttcc acaccg           14516

<210> SEQ ID NO 46
<211> LENGTH: 1380
<212> TYPE: DNA
<213> ORGANISM: Escherichia coli

<400> SEQUENCE: 46
aacaaatctc agtcttctct tagctctgct attgagcgtc tgtcttctgg tctgcgtatt         60
aacagcgcaa aagacgatgc agcaggtcag gcgattgcta accgttttac ggcaaatatt        120
aaaggtctga cccaggcttc ccgtaacgcg aatgatggta tttctgttgc gcagaccact        180
```

-continued

| | |
|---|---|
| gaaggtgcgc tgaatgaaat taacaacaac ctgcagcgta ttcgtgaact ttctgttcag | 240 |
| gcaactaacg gtactaactc tgacagcgat ctttcttcta tccaggctga aattactcaa | 300 |
| cgtctggaag aaattgaccg tgtatctgag caaactcagt ttaacggcgt gaaagtcctt | 360 |
| gctgaaaata atgaaatgaa aattcaggtt ggtgctaatg atggtgaaac catcactatc | 420 |
| aatctggcaa aaattgatgc gaaaactctc ggcctggacg ttttaatat cgatggcgcg | 480 |
| cagaaagcaa ccggcagtga cctgatttct aaatttaaag cgacaggtac tgataattat | 540 |
| caaattaacg gtactgataa ctatactgtt aatgtagata gtggagtagt acaggataaa | 600 |
| gatggcaaac aagtttatgt gagtgctgcg atggttcac ttacgaccag cagtgatact | 660 |
| caattcaaga ttgatgcaac taagcttgca gtggctgcta agatttagc tcaaggtaat | 720 |
| aagattgtct acgaaggtat cgaatttaca aataccggca ctggcgctat acctgccaca | 780 |
| ggtaatggtg aattaaccgc caatgttgat ggtaaggctg ttgaattcac tatttcgggg | 840 |
| agtgctgata catcaggtac tagtgcaacc gttgcccta cgacagccct atacaaaaat | 900 |
| agtgcagggc aattgactgc aacaaaagtt gaaaataaag cagcgacact atctgatctt | 960 |
| gatctgaacg ctgccaagaa aacaggaagc acgttagttg ttaacggtgc aacttacgat | 1020 |
| gttagtgcag atggtaaaac gataacggag actgcttctg gtaacaataa agtcatgtat | 1080 |
| ctgagcaaat cagaaggtgg tagcccgatt ctggtaaacg aagatgcagc aaaatcgttg | 1140 |
| caatctacca ccaacccgct cgaaactatc gacaaagcat ggctaaagt tgacaatctg | 1200 |
| cgttctgacc tcggtgcagt acaaaaccgt ttcgactctg ccatcaccaa ccttggcaac | 1260 |
| accgtaaaca acctgtcttc tgcccgtagc cgtatcgaag atgctgacta cgcgaccgaa | 1320 |
| gtgtctaaca tgtctcgtgc gcagatcctg caacaagcgg gtacctctgt tctggcacag | 1380 |

<210> SEQ ID NO 47
<211> LENGTH: 1497
<212> TYPE: DNA
<213> ORGANISM: Escherichia coli

<400> SEQUENCE: 47

| | |
|---|---|
| atggcacaag tcattaatac caacagcctc tcgctgatca ctcaaaataa tatcaacaag | 60 |
| aaccagtctg cgctgtcgag ttctatcgag cgtctgtctt ctggcttgcg tattaacagc | 120 |
| gcgaaggatg acgcagcggg tcaggcgatt gctaaccgtt tcacctctaa cattaaaggc | 180 |
| ctgactcagg cggcccgtaa cgccaacgac ggtatctccg ttgcgcagac caccgaaggc | 240 |
| gcgctgtccg aaatcaacaa caacttacag cgtgtgcgtg aactgacggt acaggccact | 300 |
| accggtacta ctctgagtc tgatctgtct tctatccagg acgaaattaa atcccgtctg | 360 |
| gatgaaattg accgcgtatc tggtcagacc cagttcaacg gcgtgaacgt gctggcaaaa | 420 |
| aatggctcca tgaaaatcca ggttggcgca aatgataacc agactatcac tatcgatctg | 480 |
| aagcagattg atgctaaaac tcttggcctt gatggttta gcgttaaaa taacgataca | 540 |
| gttaccacta gtgctccagt aactgctttt ggtgctacca ccacaaacaa tattaaactt | 600 |
| actggaatta ccctttctac ggaagcagcc actgatactg cggaactaa cccagcttca | 660 |
| attgagggtg tttatactga taatggtaat gattactatg cgaaaatcac cggtggtgat | 720 |
| aacgatggga agtattacgc agtaacagtt gctaatgatg gtacagtgac aatggcgact | 780 |
| ggagcaacgg caaatgcaac tgtaactgat gcaaatacta ctaaagctac aactatcact | 840 |
| tcaggcggta cacctgttca gattgataat actgcaggtt ccgcaactgc caaccttggt | 900 |
| gctgttagct tagtaaaact gcaggattcc aagggtaatg ataccgatac atatgcgctt | 960 |

-continued

```
aaagatacaa atggcaatct ttacgctgcg gatgtgaatg aaactactgg tgctgtttct    1020
gttaaaacta ttacctatac tgactcttcc ggtgccgcca gttctccaac cgcggtcaaa    1080
ctgggcggag atgatggcaa aacagaagtg gtcgatattg atggtaaaac atacgattct    1140
gccgatttaa atggcggtaa tctgcaaaca ggtttgactg ctggtggtga ggctctgact    1200
gctgttgcaa atggtaaaac cacggatccg ctgaaagcgc tggacgatgc tatcgcatct    1260
gtagacaaat tccgttcttc cctcggtgcg gtgcaaaacc gtctggattc cgcggttacc    1320
aacctgaaca acaccactac caacctgtct gaagcgcagt cccgtattca ggacgccgac    1380
tatgcgaccg aagtgtccaa tatgtcgaaa gcgcagatca tccagcaggc cggtaactcc    1440
gtgttggcaa aagctaacca ggtaccgcag caggttctgt ctctgctgca gggttaa      1497
```

<210> SEQ ID NO 48
<211> LENGTH: 1695
<212> TYPE: DNA
<213> ORGANISM: Escherichia coli

<400> SEQUENCE: 48

```
atggcacaag tcattaatac caacagcctc tcgctgatca ctcaaaataa tatcaacaag      60
aaccagtctg cgctgtcgag ttctatcgag cgtctgtctt ctggcttgcg tattaacagc     120
gcgaaggatg acgccgcagg tcaggcgatt gctaaccgtt ttacttctaa cattaaaggc     180
ctgactcagg ctgcacgtaa cgccaacgac ggtatttctg ttgcgcagac caccgaaggc     240
gcgctgtctg aaatcaacaa caacttacag cgtattcgtg aactgaccgt tcaggcttct     300
accgggacta actctgattc ggatctggac tccattcagg acgaaatcaa atcccgtctg     360
gacgaaattg accgcgtatc cggtcaaacc cagttcaacg gtgtgaacgt actggcgaaa     420
gacggttcga tgaaaattca ggttggtgcg aatgacggcc agactatcac tattgatctg     480
aagaaaattg actctgatac gctggggctg aatggtttta acgttaacgg caaaggtact     540
attgcgaaca agcggcaaca cattagtgat ctggcggcga cggggcgaa tgttactaac     600 tcaagcaata ttgttgtcac gacaaagttc aatgccttgg atgcagcgac tgcatttagc     660
aaactcaaag atggtgattc tgttgccgtt gctgctcaga atatactta taacgcatcg     720 accaatgatt ttcgacaga aaatacagta gcgacaggca ctgcaacgac agatcttggc     780
gctactctga aggctgctgc tgggcagagt caatcaggta catataccct tgcaaatggt     840
aaagttaact ttgatgttga tgcaagcggt aatatcacta ttggcggcga aaaggctttc     900
ttggttggtg gagcgctgac tactaacgat cccaccggct ccactccagc aacgatgtct     960
tccctgttta aggccgcgga tgacaaagat gccgctcaat cctcgattga ttttggcggg    1020
aaaaaatacg aatttgctgg tggcaattct actaatggtg gcggcgttaa attcaaagac    1080
acggtgtctt ctgacgcgct tttggctcag gttaaagcgg atagtactgc taataatgta    1140
aaaatcacct ttaacaatgg tcctctgtca ttcactgcat cgttccaaaa tggtgtatct    1200
ggctccgcgg catcgaatgc agcctacatt gatagcgaag cgaactgac aactactgaa    1260 tcctacaaca caaattattc cgtagacaaa gacacggggg ctgtaagtgt tacagggggg    1320
agcggtacgg gtaaatacgc cgcaaacgtg ggtgctcagg cttatgtagg tgcagatggt    1380
aaattaacca cgaatactac tagtaccggc tctgcaacca agatccact aaatgcgctg    1440 gatgaggcaa ttcatccat cgacaaattc cgttcttccc tggggctat ccagaaccgt    1500 ctggattccg cagtcaccaa cctgaacaac accactacca acctgtctga agcgcagtcc    1560
```

| | |
|---|---:|
| cgtattcagg acgccgacta tgcgaccgaa gtgtccaaca tgtcgaaagc gcagatcatc | 1620 |
| cagcaggccg gtaactccgt gttggcaaaa gctaaccagg taccgcagca ggttctgtct | 1680 |
| ctgctgcagg gttaa | 1695 |

<210> SEQ ID NO 49
<211> LENGTH: 1164
<212> TYPE: DNA
<213> ORGANISM: Escherichia coli

<400> SEQUENCE: 49

| | |
|---|---:|
| aacaagaacc agtctgcgct gtcgagttct atcgagcgtc tgtcttctgg cttgcgtatt | 60 |
| aacagcgcga aggatgacgc cgcgggtcag gcgattgcta accgttttac ttctaacatt | 120 |
| aaaggcctga ctcaggctgc acgtaacgcc aacgacggta tttctgttgc gcagaccacc | 180 |
| gaaggcgcgc tgtccgaaat taacaacaac ttacagcgtg tgcgtgagct gactgttcag | 240 |
| gcgaccaccg gtactaactc tgagtctgac ctgtcttcta tccaggacga aatcaaatct | 300 |
| cgcctggaag agattgatcg tgtttcaagt cagactcaat ttaacggcgt gaatgttttg | 360 |
| gctaaagatg ggaaaatgaa cattcaggtt ggggcaagtg atggacagac tatcactatt | 420 |
| gatctgaaaa agatcgattc atctacacta aacctctcca gttttgatgc tacaaacttg | 480 |
| ggcaccagtt ttaaagatgg ggccaccatc aataagcaag tggcagtaga tgctggcgac | 540 |
| tttaaagata aagcttcagg atcgttaggt accctaaaat tagttgagaa agacggtaag | 600 |
| tactatgtaa atgacactaa agtagtaagt actacgatg ccgaagtaga tactagtaag | 660 |
| ggtgaaatta acttcaactc tacaaatgaa agtggaacta ctcctactgc agcgacggaa | 720 |
| gtaactactg ttggccgcga tgtaaaattg gatgcttctg cacttaaagc caaccaatcg | 780 |
| cttgtcgtgt ataaagataa agcggcaat gatgcttata tcattcagac caaagatgta | 840 |
| acaactaatc aatcaacttt caatgccgct aatatcagtg atgctggtgt tttatctatt | 900 |
| ggtgcatcta caaccgcgcc aagcaattta acagctgacc cgcttaaggc tcttgatgat | 960 |
| gcaattgcat ctgttgataa attccgctct tctctcggtg ccgttcagaa ccgtctggat | 1020 |
| tctgccattg ccaacctgaa caacaccact accaacctgt ctgaagcgca gtcccgtatt | 1080 |
| caggacgctg actatgcgac cgaagtgtcc aacatgtcga aagcgcagat tatccagcag | 1140 |
| gccggtaact ccgtgctggc aaaa | 1164 |

<210> SEQ ID NO 50
<211> LENGTH: 1818
<212> TYPE: DNA
<213> ORGANISM: Escherichia coli

<400> SEQUENCE: 50

| | |
|---|---:|
| atggcacaag tcattaatac caacagcctc tcgctgatca ctcaaaataa tatcaacaag | 60 |
| aaccagtctg cgctgtcgag ttctatcgag cgtctgtctt ctggcttgcg tattaacagc | 120 |
| gcgaaggatg acgcagcggg tcaggcgatt gctaaccgtt tcacctctaa cattaaaggc | 180 |
| ctgactcagg ctgcacgtaa cgctaacgat ggtatctctc tggcgcagac cactgaaggc | 240 |
| gcactgtctg agattaacaa caacttacaa cgtgtgcgtg agttgactgt acaggcgacc | 300 |
| accggtacta ctctgattc tgacctggct tctattcagg acgaaatcaa atcccgtttg | 360 |
| tctgaaattg accgcgtatc cggcagacc cagttcaacg gcgtgaacgt attgtctaaa | 420 |
| gatggctccc tgaaaattca ggttggcgca aatgatggtc agactatctc tatcgacctg | 480 |
| aagaaaattg actctgatac tctgggtttg aatggtttca cgttaatgg ttctggtacc | 540 |

-continued

| | |
|---|---|
| attgcaaaca aagcggccac aatcagtgac ttgactgctc agaaagccgt tgacaacggt | 600 |
| aatggtactt ataaagttac aactagcaac gctgcactta ctgcatctca ggcattaagt | 660 |
| aagctgagtg atggcgatac tgtagatatt gcaacctatg ctggtggtac aagttcaaca | 720 |
| gttagttata aatacgacgc agatgcaggt aacttcagtt ataacaatac tgcaaacaaa | 780 |
| acaagtgctg cggctggaac tctggcagat actcttctcc cggcagctgg ccagactaaa | 840 |
| accggtactt acaaggctgc tactggtgat gttaacttta atgttgacgc aactggtaat | 900 |
| ctgacaattg gcggacagca agcctacctg actactgatg gtaaccttac aacaaacaac | 960 |
| tccggtggtg cggctactgc aactcttaaa gagctgttta ctcttgctgg cgatggtaaa | 1020 |
| tctctgggga acggcggtac tgctaccgtt actctggata atactacgta taatttcaaa | 1080 |
| gctgctgcga acgttactga tggtgctggt gtcatcgctg ctgctggtgt aacttataca | 1140 |
| gccactgttt ctaaagatgt cattctggca caactgcaat ctgcaagtca ggcagcagca | 1200 |
| accgctaccg acggtgatac tgtcgcaacg atcaactata atctggtgt catgatcggt | 1260 |
| tccgctacct ttaccaatgg taaaggtact gccgatggta tgacttctgg tacaactcca | 1320 |
| gtcgtagcta caggtgctaa agctgtatat gttgatggca acaatgaact gacttccact | 1380 |
| gcatcttacg atacgactta ctctgtcaac gcagatacag gcgcagtaaa agtggtatca | 1440 |
| ggtactggta ctggtaaatt tgaagctgtt gctggtgcgg atgcttatgt aagcaaagat | 1500 |
| ggcaaattaa cgacagaaac caccagtgca ggcactgcaa ccaaagatcc tttggctgcc | 1560 |
| ctggatgctg ctatcagctc catcgacaaa ttccgttcct ccctgggtgc tatccagaac | 1620 |
| cgtctggatt ccgcagtcac caacctgaac aacaccacta ctaacctgtc tgaagcgcag | 1680 |
| tcccgtattc aggacgccga ctatgcgacc gaagtgtcca atatgtcgaa agcgcagatc | 1740 |
| atccagcagg ccggtaactc tgtgttggca aaagctaacc aggtaccgca gcaggttctg | 1800 |
| tctctgctgc agggttaa | 1818 |

<210> SEQ ID NO 51
<211> LENGTH: 1344
<212> TYPE: DNA
<213> ORGANISM: Escherichia coli

<400> SEQUENCE: 51

| | |
|---|---|
| atggcacaag tcattaatac caacagcctc tcgctgatca ctcaaaataa tatcaacaag | 60 |
| aaccagtctg cgctgtcgag ttctatcgag cgtctgtctt ctggcttgcg tattaacagc | 120 |
| gcgaaggatg acgccgcagg tcaggcgatt gctaaccgtt ttacttctaa cattaaaggc | 180 |
| ctgactcagg ctgcacgtaa cgccaacgac ggtatttctg ttgcacagac cactgaaggc | 240 |
| gcgctgtccg aaatcaacaa caacttacag cgtattcgtg aactgacggt tcaggcttct | 300 |
| accgggacta ctctgattc ggatctggac tccattcagg acgaaatcaa atcccgtctc | 360 |
| gacgaaattg accgcgtttc cggtcagacc cagttcaacg gcgtgaacgt gctggcgaaa | 420 |
| gacggttcga tgaagattca ggttggcgcg aatgacgggc agaccatctc tatcgatttg | 480 |
| cagaaaattg attcttcaac gctgggattg aaaggtttct cggtatcagg aacgcatta | 540 |
| aaagttagcg atgcgataac tacagttcct ggtgctaatg ctggcgatgc cccggttacg | 600 |
| gttaaatttg gtgcgaacga taccgctgct gccgcaatgg ctaaaacatt gggaataagt | 660 |
| gatacatcag gcttgtccct acataacgta caaagcgcgg atggtaaagc gacaggaacc | 720 |
| tatgttgttc aatctggtaa tgacttctat tcggcttccg ttaatgctgg tggcgttgtt | 780 |

-continued

| | |
|---|---|
| acgcttaata ccaccaatgt tactttcact gatcctgcga acgtgttac cacagcaaca | 840 |
| cagacaggtc agcctatcaa ggtcacgacg aatagtgctg gcgcggctgt tggctatgtt | 900 |
| actattcaag gcaaagatta ccttgctggt gcagacggta aggatgcaat tgaaaacggt | 960 |
| ggtgacgctg caacaaatga agacacaaaa atccaactta ccgatgaact cgatgttgat | 1020 |
| ggttctgtaa aaacagcggc aacagcaaca ttttctggta ctgcaaccaa cgatccgctg | 1080 |
| gcacttttag acaaagctat ctcgcaagtt gatactttcc gctcctccct cggtgccgta | 1140 |
| caaaaccgtc tggattctgc ggtcaccaac ctgaataaca ccaccaccaa cctgtctgaa | 1200 |
| gcgcagtccc gtattcagga cgccgactat gcgaccgaag tgtccaacat gtcgaaagcg | 1260 |
| cagatcatcc agcaggcggg taactctgtg ctgtctaaag ctaaccaggt accgcagcag | 1320 |
| gttctgtctc tgctgcaggg ttaa | 1344 |

<210> SEQ ID NO 52
<211> LENGTH: 2599
<212> TYPE: DNA
<213> ORGANISM: Escherichia coli

<400> SEQUENCE: 52

| | |
|---|---|
| cttctcttag ctctgctatt gagcgtctgt cttctggtct gcgtattaac agcgcaaaag | 60 |
| acgatgcagc aggtcaggcg attgctaacc gttttacggc aaatattaaa ggtctgaccc | 120 |
| aggcttcccg taacgcgaat gatggtattt ctgttgcgca gaccactgaa ggtgcgctga | 180 |
| atgaaattaa caacaacctg cagcgtattc gtgaactttc tgttcaggca actaacggta | 240 |
| ctaactctga cagcgatctt tcttctatcc aggctgaaat tactcaacgt ctggaagaaa | 300 |
| ttgaccgtgt atctgagcaa actcagttta acggcgtgaa agtccttgct gaaaataatg | 360 |
| aaatgaaaat tcaggttggt gctaatgatg gtgaaaccat tgacctgccc ccacgattag | 420 |
| atacaacact cagttagtaa cgtcggaatc ttcattctca gaatgaccct ttctccagcc | 480 |
| cgctgcaaat tcagacggtg tctgataatt cagcgtggag tgcgggcggc attcgttata | 540 |
| atcctgccgc cagtcattaa taattttcct ggcatgaacg atatcgctga accagtgctc | 600 |
| attcaaacat tcatcgcgaa atcgtccgtt aaagctctca ataaatccgt tctgcgttgg | 660 |
| cttgcccggc tggattaagc gcaactcaac accatgctca aaggcccatt gatccagtgc | 720 |
| acggcaagtg aactccggcc cctggtcagt tcttatcgtc gccggatagc ctcgaaacag | 780 |
| tgcaatgctg tccagaatac gcgtgacctg aacgcctgaa atcccaaagg caacagtgac | 840 |
| cgtcaggcat tccttttgtga aatcatcgac gcaggtaaga cacttgatcc tgcgaccggt | 900 |
| ggaaagtgcg tccatgacga aatccatcga ccaggtcaga ttgggcgccg ccggacggag | 960 |
| cagcggcaga cgttctgttg ccagccctttt acgacgtctt ctgcgttta cgcccaggcc | 1020 |
| actgaggtga taaagccggt acacgcgctt atgattaaca tgaagccctt cacggcgcag | 1080 |
| caactgccaa atacgacggt agccaaaacg cctgcgctcc agtgccagct cagtgatgcg | 1140 |
| ccctgataaa tgcgcatcag cagccggacg gtgagcctca tagcggcagg tcgacaggga | 1200 |
| taaacctgta agcctgcagg cacgacgttg cgacagaccg gtcgcatcac acatcaacat | 1260 |
| cacggcttcc cgcttctggt ctgtcgtcag tactttcgcc caagagccac ctgaagcgcc | 1320 |
| tctttatcca gcatggcttc ggcaagcagc ttcttgagtc tggtgttctc ttcctcaagc | 1380 |
| gacttcaggc gcttaacttc aggcacctcc ataccgccat acttcttacg ccaggtgtaa | 1440 |
| aacgtggcat cggaaatggc atgcttgcgg cagagttcac gggcgggtac cccagcttcg | 1500 |
| gcttcgcgga gaatactgat gatctgttcg tcggaaaaac gcttcttcat ggggatgtcc | 1560 |

-continued

```
tcatgtggct tatgaagaca ttactaacat cggggtgtac taatcaacgg ggagcaggtc    1620
accatcacta tcaatctggc aaaaattgat gcgaaaactc tcggcctgga cggttttaat    1680
atcgatggcg cgcagaaagc aaccggcagt gacctgattt ctaaatttaa agcgacaggt    1740
actgataatt atcaaattaa cggtactgat aactatactg ttaatgtaga tagtggagta    1800
gtacaggata aagatggcaa acaagtttat gtgagtgctg cggatggttc acttacgacc    1860
agcagtgata ctcaattcaa gattgatgca actaagcttg cagtggctgc taaagattta    1920
gctcaaggta ataagattgt ctacgaaggt atcgaattta caaataccgg cactggcgct    1980
atacctgcca caggtaatgg taaattaacc gccaatgttg atggtaaggc tgttgaattc    2040
actatttcgg ggagtgctga tacatcaggt actagtgcaa ccgttgcccc tacgacagcc    2100
ctatacaaaa atagtgcagg gcaattgact gcaacaaaag ttgaaaataa agcagcgaca    2160
ctatctgatc ttgatctgaa cgctgccaag aaaacaggaa gcacgttagt tgttaacggt    2220
gcaacttacg atgttagtgc agatggtaaa acgataacgg agactgcttc tggtaacaat    2280
aaagtcatgt atctgagcaa atcagaaggt ggtagcccga ttctggtaaa cgaagatgca    2340
gcaaaatcgt tgcaatctac caccaacccg ctcgaaacta tcgacaaagc attggctaaa    2400
gttgacaatc tgcgttctga cctcggtgca gtacaaaacc gtttcgactc tgccatcacc    2460
aaccttggca caccgtaaa caacctgtct tctgcccgta gccgtatcga agatgctgac    2520
tacgcgaccg aagtgtctaa catgtctcgt gcgcagatcc tgcaacaagc gggtacctct    2580
gttctggcac aggctaacc                                                 2599
```

<210> SEQ ID NO 53
<211> LENGTH: 1245
<212> TYPE: DNA
<213> ORGANISM: Escherichia coli

<400> SEQUENCE: 53

```
aacaaaaacc agtctgcgct gtcgacttct atcgagcgcc tctcttctgg tctgcgcatt      60
aacagcgcta aagatgacgc tgcgggccag gcgattgcta accgcttcac ttctaacatc     120
aaaggtctga ctcaggccgc acgtaacgcc aacgacggta tctctctggc gcagaccact     180
gaaggcgcac tgtctgaaat caacaacaac ttgcagcgtg ttcgtgaact gaccgttcag     240
gccactaccg gtactaactc tgattctgac ctgtcttcaa tccaggacga aatcaaatcc     300
cgtctcgatg aaattgaccg cgtatccggt cagactcagt tcaacggcgt gaacgtactg     360
gcaaaagatg gctcgatgaa aattcaggtc ggtgcaaatg atggtcagac aatcagcatt     420
gatttgcaga agattgattc ttctacttta gggttaaatg ttttttctgt ttccaaaaat     480
gcagtatctg ttggtgatgc tattactcaa ttgcctggcg agacggcagc cgatgcacca     540
gtaaccatca gtttgatga ttcagtaaaa actgatttaa aactgaccga tgcttcaggg     600
ttaagtctgc ataacctcaa agatgaaaat ggtaatttaa ctaaccagta tgttgtacag     660
aatggcggaa atcttacgc tgctacagtc gctgccaatg gtaatgttac gctgaacaaa     720
gcaaatgtaa cctacagcga tgtcgcaaac ggtattgata ccgcaacgca gtcaggccag     780
ttagttcagg ttggtgcaga ttctaccggt acgccaaaag cattcgtgtc tgtccaaggt     840
aaaagctttg gcattgatga cgccgccttg aagaataaca ctggtgatgc taccgctact     900
ccaccgggaa catctgggac aacagttgtc gcagcgtcaa ttcatctgag tacgggcaaa     960
aactctgtag acgctgatgt aacggcttcc actgaattca caggtgcttc aaccaacgat    1020
```

```
ccactgactc tgctggacaa agctatcgca tctgttgata aattccgttc ttctttgggg    1080
gcggtacaga accgtctgag ctccgctgta accaacctga caacaccac caccaacctg    1140 tctgaagcgc agtcccgtat tcaggacgcc gactatgcga ccgaagtgtc caacatgtcg    1200
aaagcgcaga ttatccagca ggcaggtaac tccgtgctgt ccaaa                   1245
```

<210> SEQ ID NO 54
<211> LENGTH: 1212
<212> TYPE: DNA
<213> ORGANISM: Escherichia coli

<400> SEQUENCE: 54

```
aacaaaaacc agtctgcgct gtcgacttct atcgaacgcc tctcttctgg cctgcgtatt     60
aacagtgcga aagatgacgc tgccggtcag gcgatagcta accgtttcac ctctaacatt    120
aaaggcctga ctcaggctgc gcgtaacgcc aacgacggta tttctctggc gcagaccaca    180
gaaggtgcgt tgtctgaaat caacaacaac ttgcaacgtg tgcgtgagtt gaccgttcag    240
gcgacgaccg gtactaactc tgattctgac ctgtcatcta ttcaggacga aatcaaatcc    300
cgtctggatg agattgaccg tgtttccggt cagacccagt tcaacggcgt gaatgtactg    360
gcaaaagacg gttcgatgaa gattcaggtt ggcgcgaatg atggccagac tattagcatt    420
gatttacaga aaattgactc ttctacatta gggttgaatg gtttctccgt ttctgctcaa    480
tcacttaacg ttggtgattc aattactcaa attacaggag ccgctgggac aaaacctgtt    540
ggtgttgatt tcactgctgt tgcgaaagat ctgactactg cgacaggtaa aactgtcgat    600
gtttccagcc tgacgttaca caacaccctg gatgcgaaag gggctgccac cgcacagttc    660
gtcgttcaat ccggtagtga tttctactcc gcgtccattg accatgcaag tggtgaagtg    720
acgttgaata agccgatgt cgaatacaaa gacaccgata atggactaac gactgcagct    780
actcagaaag atcagctgat taaagttgcc gctgactctg acggcgcggc tgcgggatat    840
gtaacattcc agggtaaaaa ctacgctaca acggctccag cggcgcttaa tgatgacact    900
acggcaacag ccacagcgaa caagttgtt gttgaattat ctacagcaac tccgactgcg    960
cagttctcag gggcttcttc tgctgatcca ctggcacttt tagacaaagc cattgcacag    1020
gttgatactt tccgctcctc cctcggtgcc gttcaaaacc gtctggactc tgcggtaacc    1080
aacctgaaca acaccaccac caacctgtct gaagcgcagt cccgtattca ggacgccgac    1140
tatgcgaccg aagtgtctaa catgtcgaaa gcgcagatca tccagcaggc gggtaactct    1200
gtgctgtcta aa                                                        1212
```

<210> SEQ ID NO 55
<211> LENGTH: 1758
<212> TYPE: DNA
<213> ORGANISM: Escherichia coli

<400> SEQUENCE: 55

```
atggcacaag tcattaatac caacagcctc tcgctgatca ctcaaaataa tatcaacaag     60
aaccagtctg cgctgtcgag ttctatcgag cgtctgtctt ctggcttgcg tattaacagc    120
gcgaaggatg acgccgcggg tcaggcgatt gctaaccgtt ttacttctaa cattaaaggc    180
ctgactcagg ctgcacgtaa cgccaacgac ggtatttctg ttgcagacac cactgaaggc    240
gcgctgtccg aaatcaacaa caacttacag cgtatccgtg agctgacggt tcaggcttct    300
accgggacta ctctgattcc ggatctggac tccattcagg acgaaatcaa atccgtctc    360 gacgaaattg accgcgtatc cggtcagacc cagttcaacg gcgtgaacgt actggcaaaa    420
```

```
gacggttcga tgaaaattca ggttggtgcg aatgacggtg aaactatcac tatcgacctg    480
aagaaaatcg attctgatac tctgggtctg aatggtttta acgtaaatgg taaaggtact    540
attaccaaca aagctgcaac ggtaagtgat ttaacttctg ctggcgcgaa gttaaacacc    600
acgacaggtc tttatgatct gaaaaccgaa ataccttgt taactaccga tgctgcattc     660
gataaattag ggaatggcga taaagtcacc gttggcggcg tagattatac ttacaacgct    720
aaatctggtg atttttactac caccaaatct actgctggta cgggtgtaga cgccgcggcg   780
caggctactg attcagctaa aaacgtgat gcgttagctg ccacccttca tgctgatgtg     840
ggtaaatctg ttaatggttc ttacaccaca aaagatggta ctgtttcttt cgaaacggat    900
tcagcaggta atatcaccat cggtggaagc caggcatacg tagacgatgc aggcaacttg    960
acgactaaca acgctggtag cgcagctaaa gctgatatga aagcgctgct taaagccgcg   1020
agcgaaggta gtgacggtgc ctctctgaca ttcaatggca ctgaatatac tatcgcaaaa   1080
gcaactcctg cgacaaccct ccagtagct ccgttaatcc ctggtgggat tacttatcag    1140
gctacagtga gtaaagatgt agtattgagc gaaaccaaag cggctgccgc gacatcttca   1200
attaccttta attccggtgt actgagcaaa actattgggt ttaccgcggg tgaatccagt   1260
gatgctgcga gtcttatgt ggatgataaa ggtggtatta ctaacgttgc cgactataca    1320
gtctcttaca gcgttaacaa ggataacggc tctgtgactg ttgccgggta tgcttcagcg   1380
actgatacca ataaagatta tgctccagca attggtactg ctgtaaatgt gaactccgcg   1440
ggtaaaatca ctactgagac taccagtgct ggttctgcaa cgaccaaccc gcttgctgcc   1500
ctggacgacg ctatcagctc catcgacaaa ttccgttctt ccctgggtgc tatccagaac   1560
cgtctggatt ccgcagtcac caacctgaac aacaccacta ccaacctgtc tgaagcgcag   1620
tcccgtattc aggacgccga ctatgcgacc gaagtgtcca acatgtcgaa agcgcagatt   1680
atccagcagg ccgtaactc cgtgctggca aaagccaacc aggtaccgca gcaggttctg   1740
tctctgctgc agggttaa                                                  1758
```

<210> SEQ ID NO 56
<211> LENGTH: 14024
<212> TYPE: DNA
<213> ORGANISM: Escherichia coli

<400> SEQUENCE: 56

```
gtaaccaagg gcggtacgtg cataaatttt aatgcttatc aaaactatta gcattaaaaa     60
tatataagaa attctcaaat gaacaaagaa accgtttcaa taattatgcc cgtttacaat    120
ggggccaaaa ctataatctc atcagtagaa tcaattatac atcaatctta tcaagatttt    180
gttttgtata tcattgacga ttgtagcacc gatgatacat tttcattaat caacagtcga    240
tacaaaaaca atcagaaaat aagaatattg cgtaacaaga caatttagg tgttgcagaa    300 agtcgaaatt atggaataga aatggccacg gggaaatata tttctttttg tgatgcggat   360
gatttgtggc acgagaaaaa attagagcgt caaatcgaag tgttaaataa tgaatgtgta    420
gatgtggtat gttctaatta ttatgttata gataacaata gaaatattgt tggcgaagtt    480
aatgctcctc atgtgataaa ttatagaaaa atgctcatga aaactacat agggaatttg     540 acaggaatct ataatgccaa caattgggt aagtttatc aaaaaaagat tggtcacgag     600
gattatttga tgtggctgga ataattaat aaaacaaatg gtgctatttg tattcaagat     660
aatctggcgt attacatgcg ttcaaataat tcactatcgg gtaataaaat taagctgca    720
```

-continued

```
aaatggacat ggagtatata tagagaacat ttacatttgt cctttccaaa aacattatat      780 tatttttat tatatgcttc aaatggagtc atgaaaaaaa taacacattc actattaagg       840
agaaaggaga ctaaaaagtg aagtcagcgg ctaagttgat ttttttattc ctatttacac      900
tttatagtct ccagttgtat ggggttatca tagatgatcg tataacaaat tttgatacaa      960
aggtattaac tagtattata attatatttc agatttttt tgttttatta ttttatctaa     1020
cgattataaa tgaagaaaa cagcagaaaa aatttatcgt gaactgggag ctaaagttaa      1080
tactcgtttt cctttttgtg actatagaaa ttgctgctgt agtttatttt cttaaagaag     1140
gtattcctat atttgatgat gatccagggg gggctaaact tagaatagct gaaggtaatg     1200
gactttacat tagatatatt aagtattttg gtaatatagt tgtgtttgca ttaattattc     1260
tttatgatga gcataaattc aaacagagga ccatcatatt tgtatatttt acaacgattg     1320
ctttatttgg ttatcgttct gaattggtgt tgctcattct tcaatatata ttgattacca     1380
atatcctgtc aaaggataac cgtaatccta aaataaaaag aataataggg tatttttat      1440 tggtagggt tgtatgctcg ttgttttatc taagtttagg acaagacgga gaacaaaatg      1500
actcatataa taatatgtta aggataatta ataggttaac aatagagcaa gttgaaggtg     1560
ttccatatgt tgtttctgaa tctattaaga acgatttctt tccgacacca gagttagaaa     1620
aggaattaaa agcaataata aatagaatac agggaataaa gcatcaagac ttatttatg      1680 gagaacggtt acataaacaa gtatttggag acatgggagc aaattttta tcagttacta     1740 cgtatggagc agaactgtta gtttttttg gttttctctg tgtattcatt atcccttag      1800 ggatatatat accttttat cttttaaaga gaatgaaaaa aacccatagc tcgataaatt     1860
gcgcattcta ttcatatatc attatgattt tattgcaata cttagtggct gggaatgcat     1920
cggccttctt ttttggtcct tttctctccg tattgataat gtgtactcct ctgatcttat     1980
tgcatgatac gttaaagaga ttatcacgaa atgaaaatat cagttataac tgtgacttat     2040
aataatgctg aagggttaga aaaaacttta agtagtttat caattttaaa aataaaacct     2100
tttgagatta ttatagttga tggcggctct acagatggaa cgaatcgtgt cattagtaga     2160
tttactagta tgaatattac acatgtttat gaaaagatg aagggatata tgatgcgatg      2220
aataagggcc gaatgttggc caaaggcgac ttaatacatt atttaaacgc cggcgatagc     2280
gtaattggag atatatataa aaatatcaaa gagccatgtt tgattaaagt tggccttttc     2340
gaaaatgata aacttctggg attttcttct ataacccatt caaatacagg gtattgtcat     2400 caagggtga ttttcccaaa gaatcattca gaatatgatc taagtataa aatatgtgct      2460 gattataagc ttattcaaga ggtgtttcct gaagggttaa gatctctatc tttgattact     2520
tcgggttatg taaaatatga tatggggga gtatcttcaa aaaaagaat tttaagagat     2580 aaagagcttg ccaaaattat gtttgaaaaa aataaaaaa accttattaa gtttattcca     2640
atttcaataa tcaaaatttt attccctgaa cgtttaagaa gagtattgcg gaaaatgcaa     2700
tatatttgtc taactttatt cttcatgaag aatagttcac catatgataa tgaataaaat     2760
caaaaaaata cttaaatttt gcactttaaa aaaatatgat acatcaagtg ctttaggtag     2820
agaacaggaa aggtacagga ttatatcctt gtctgttatt tcaagtttga ttagtaaaat     2880
actctcacta ctttctctta tattaactgt aagtttaact ttaccttatt taggacaaga     2940
gagatttggt gtatggatga ctattaccag tcttggtgct gctctgacat ttttggactt     3000
aggtatagga aatgcattaa caaacaggat cgcacattca tttgcgtgtg gcaaaaattt     3060
aaagatgagt cggcaaatta gtggtgggct cactttgctg gctggattat cgtttgtcat     3120
```

```
aactgcaata tgctatatta cttctggcat gattgattgg caactagtaa taaaaggtat    3180
aaacgagaat gtgtatgcag agttacaaca ctcaattaaa gtctttgtaa tcatatttgg    3240
acttggaatt tattcaaatg gtgtgcaaaa agtttatatg ggaatacaaa aagcctatat    3300
aagtaatatt gttaatgcca tatttatatt gttatctatt attactctag taatatcgtc    3360
gaaactacat gcgggactac cagttttaat tgtcagcact cttggtattc aatacatatc    3420
gggaatctat ttaacaatta atcttattat aaagcgatta ataaagttta caaaagttaa    3480
catacatgct aaaagagaag ctccatattt gatattaaac ggttttttct tttttatttt    3540
acagttaggc actctggcaa catggagtgg tgataacttt ataatatcta taacattggg    3600
tgttacttat gttgctgttt ttagcattac acagagatta tttcaaatat ctacggtccc    3660
tcttacgatt tataacatcc cgttatgggc tgcttatgca gatgctcatg cacgcaatga    3720
tactcaattt ataaaaaaga cgctcagaac atcattgaaa atagtgggta tttcatcatt    3780
cttattggcc ttcatattag tagtgttcgg tagtgaagtc gttaatattt ggacagaagg    3840
aaagattcag gtacctcgaa cattcataat agcttatgct ttatggtctg ttattgatgc    3900
tttttcgaat acatttgcaa gctttttaaa tggtttgaac atagttaaac aacaaatgct    3960
tgctgttgta acattgatat tgatcgcaat tccagcaaaa tacatcatag ttagccattt    4020
tgggttaact gttatgttgt actgcttcat ttttatatat attgtaaatt actttatatg    4080
gtataaatgt agttttaaaa acatatcga tagacagtta aatataagag gatgaaaatg    4140
aaatatatac cagtttacca accgtcattg acaggaaaag aaaaagaata tgtaaatgaa    4200
tgtctggact caacgtggat ttcatcaaaa ggaaactata ttcagaagtt tgaaaataaa    4260
tttgcggaac aaaaccatgt gcaatatgca actactgtaa gtaatggaac ggttgctctt    4320
catttagctt tgttagcgtt aggtatatcg gaaggagatg aagttattgt tccaacactg    4380
acatatatag catcagttaa tgctataaaa tacacaggag ccacccccat tttcgttgat    4440
tcagataatg aaacttggca aatgtctgtt agtgacatag aacaaaaaat cactaataaa    4500
actaaagcta ttatgtgtgt ccatttatac ggacatccat gtgatatgga acaaattgta    4560
gaactggcca aaagtagaaa tttgtttgta attgaagatt gcgctgaagc ctttggttct    4620 aaaatataaag gtaaatatgt gggaacattt ggagatattt ctacttttag cttttttgga    4680
aataaaacta ttactacagg tgaaggtgga atggttgtca cgaatgacaa aacactttat    4740
gaccgttgtt tacattttaa aggccaagga ttagctgtac ataggcaata ttggcatgac    4800
gttataggct acaattatag gatgacaaat atctgcgctg ctataggatt agcccagtta    4860
gaacaagctg atgattttat atcacgaaaa cgtgaaattg ctgatattta taaaaaaaat    4920
atcaacagtc ttgtacaagt ccacaaggaa agtaaagatg ttttttcacac ttattggatg    4980 gtctcaattc taactaggac cgcagaggaa agagaggaat taaggaatca ccttgcagat    5040
aaactcatcg aaacaaggcc agttttttac cctgtccaca cgatgccaat gtactcggaa    5100
aaatatcaaa agcaccctat agctgaggat cttggttggc gtggaattaa tttacctagt    5160
ttccccagcc tatcgaatga gcaagttatt tatatttgtg aatctattaa cgaattttat    5220
agtgataaat agcctaaaat attgtaaagg tcattcatga aaattgcgtt gaattcagat    5280 ggatttttacg agtgggcgg tggaattgat tttattaaat atattctgtc aatattagaa    5340
acgaaaccag aaatatgtat cgatattctt ttaccgagaa atgatataca ttctctttata    5400 agagaaaaag catttccttt taaaagtata ttaaaagcaa ttttaaagag ggaaaggcct    5460
```

-continued

```
cgatggattt cattaaatag atttaatgag caatactata gagatgcctt tacacaaaat   5520
aatatagaga cgaatcttac ctttattaaa agtaagagct ctgccttta ttcatatttt    5580 gatagtagcg attgtgatgt tattcttcct tgcatgcgtg ttccttcggg aaatttgaat   5640
aaaaaagcat ggattggtta tatttatgac tttcaacact gttactatcc ttcattttt   5700 agtaagcgag aaatagatca aaggaatgtg ttttttaaat tgatgctcaa ttgcgctaac   5760
aatattattg ttaatgcaca ttcagttatt accgatgcaa ataaatatgt tgggaattat   5820
tctgcaaaac tacattctct tccatttagt ccatgccctc aattaaaatg gttcgctgat   5880
tactctggta atattgccaa ataataatatt gacaaggatt atttataat ttgcaatcaa    5940 ttttggaaac ataaagatca tgcaactgct tttagggcat ttaaaattta tactgaatat   6000
aatcctgatg tttatttagt atgcacggga gctactcaag attatcgatt ccctggatat   6060
tttaatgaat tgatggtttt ggcaaaaaag ctcggaattg aatcgaaaat taagatatta   6120
gggcatatac ctaaacttga acaaattgaa ttaatcaaaa attgcattgc tgtaatacaa   6180
ccaaccttat ttgaaggcgg gcctggaggg ggggtaacat ttgacgctat tgcattaggg   6240
aaaaaagtta tactatctga catagatgtc aataaagaag ttaattgcgg tgatgtatat   6300
ttctttcagg caaaaaacca ttattcatta aatgacgcga tggtaaaagc tgatgaatct   6360 aaaattttt atgaacctac aactctgata gaattgggtc tcaaaagacg caatgcgtgt   6420
gcagattttc ttttagatgt tgtgaaacaa gaaattgaat cccgatctta atatattcaa   6480
gaggtatata atgactaaag tcgctcttat tacaggtgta actggacaag atggatctta   6540
tctagctgag ttttttgcttg ataaagggta tgaagttcat ggtatcaaac gccgagcctc   6600 atctttaat acagaacgca tagaccatat ttatcaagat ccacatggtt ctaacccaaa   6660
ttttcacttg cactatggag atctgactga ttcatctaac ctcactagaa ttctaaagga   6720
ggtacagcca gatgaagtat ataatttagc tgctatgagt cacgtagcag tttcttttga   6780
gtctccagaa tatacagccg atgtcgatgc aattggtaca ttacgtttac tggaagcaat   6840
tcgcttttta ggattggaaa acaaaacgcg tttctatcaa gcttcaacct cagaattata   6900
tggacttgtt caggaaatcc ctcaaaaaga atccacccct ttttatcctc gttcccctta   6960
tgcagttgca aaactttacg catattggat cacggtaaat tatcgagagt catatggtat   7020
ttatgcatgt aatggtatat tgttcaatca tgaatctcca cgccgtggag aaacgtttgt   7080
aacaaggaaa attactcgag gacttgcaaa tattgcacaa ggcttggaat catgtttgta   7140
tttagggaat atggattcgt tacgagattg gggacatgca aaagattatg ttagaatgca   7200
atggttgatg ttacaacagg agcaacccga agattttgtg attgcaacag gagtccaata   7260
ctcagtccgt cagtttgtcg aaatggcagc agcacaactt ggtattaaga tgagctttgt   7320
tggtaaagga atcgaagaaa aaggcattgt agattcggtt gaaggacagg atgctccagg   7380
tgtgaaacca ggtgatgtca ttgttgctgt tgatcctcgt tatttccgac cagctgaagt   7440
tgatactttg cttggagatc cgagcaaagc taatctcaaa cttggttgga gaccagaaat   7500
tactcttgct gaaatgattt ctgaaatggt tgccaaagat cttgaagccg ctaaaaaaca   7560 ttctcttta aaatcgcatg gttttttctgt aagcttagct ctggaatgat gatgaataag   7620
caacgtattt ttattgctgg tcaccaagga atggttggat cagctattac ccgacgcctc   7680
aaacaacgtg atgatgttga gttggttta cgtactcggg atgaattgaa cttgttggat   7740
agtagcgctg ttttggattt tttttcttca cagaaaatcg accaggttta tttggcagca   7800
gcaaaagtcg gaggtatttt agctaacagt tcttatcctg ccgattttat atatgagaat   7860
```

```
ataatgatag aggcgaatgt cattcatgct gcccacaaaa ataatgtaaa taaactgctt    7920
ttcctcggtt cgtcgtgtat ttatcctaag ttagcacacc aaccgattat ggaagacgaa    7980
ttattacaag ggaaacttga gccaacaaat gaaccttatg ctatcgcaaa aattgcaggt    8040
attaaattat gtgaatctta taaccgtcag tttgggcgtg attaccgttc agtaatgcca    8100
accaatcttt atggtccaaa tgacaatttt catccaagta attctcatgt gattccggcg    8160
cttttgcgcc gctttcatga tgctgtggaa acaattctc cgaatgttgt tgtttgggga    8220
agtggtactc caaagcgtga attcttacat gtagatgata tggcttctgc aagcatttat    8280
gtcatggaga tgccatacga tatatggcaa aaaaatacta agtaatgtt gtctcatatc    8340
aatattggaa caggtattga ctgcacgatt tgtgagcttg cggaaacaat agcaaaagtt    8400
gtaggttata aagggcatat tacgttcgat acaacaaagc ccgatggagc ccctcgaaaa    8460
ctacttgatg taacgcttct tcatcaacta ggttggaatc ataaaattac ccttcacaag    8520
ggtcttgaaa atacatacaa ctggtttctt gaaaaccaac ttcaatatcg ggggtaataa    8580
tgttttttaca ttcccaagac tttgccacaa ttgtaaggtc tactcctctt atttctatag    8640
atttgattgt ggaaaacgag tttggcgaaa ttttgctagg aaaacgaatc aaccgcccgg    8700
cacagggcta ttggttcgtt cctggtggta gggtgttgaa agatgaaaaa ttgcagacag    8760
cctttgaacg attgacagaa attgaactag gaattcgttt gcctctctct gtgggtaagt    8820
tttatggtat ctggcagcac ttctacgaag acaatagtat gggggggagac ttttcaacgc    8880
attatatagt tatagcattc cttcttaaat tacaaccaaa cattttgaaa ttaccgaagt    8940
cacaacataa tgcttattgc tggctatcgc gagcaaagct gataaatgat gacgatgtgc    9000
attataattg tcgcgcatat tttaacaata aaacaaatga tgcgattggc ttagataata    9060
aggatataat atgtctgatg cgccaataat tgctgtagtt atggccggtg gtacaggcag    9120
tcgtcttttgg ccactttctc gtgaactata tccaaagcag ttttttacaac tctctggtga    9180
taacaccttg ttacaaacga ctttgctacg actttcaggc ctatcatgtc aaaaaccatt    9240
agtgataaca aatgaacagc atcgctttgt tgtggctgaa cagttaaggg aaataaataa    9300
attaaatggt aatattattc tagaaccatg cgggcgaaat actgcaccag caatagcgat    9360
atctgcgttt catgcgttaa aacgtaatcc tcaggaagat ccattgcttc tagttcttgc    9420
ggcagaccac gttatagcta aagaaagtgt tttctgtgat gctattaaaa atgcaactcc    9480
catcgctaat caaggtaaaa ttgtaacgtt tggaattata ccagaatatg ctgaaactgg    9540
ttatgggtat attgagagag gtgaactatc tgtaccgctt caagggcatg aaaatactgg    9600
tttttattat gtaaataagt ttgtcgaaaa gcctaatcgt gaaaccgcag aattgtatat    9660
gacttctggt aatcactatt ggaatagtgg aatattcatg tttaaggcat ctgtttatct    9720
tgaggaattg agaaaattta gacctgacat ttacaatgtt tgtgaacagg ttgcctcatc    9780
ctcatacatt gatctagatt ttattcgatt atcaaaagaa caatttcaag attgtcctgc    9840
tgaatctatt gattttgctg taatggaaaa aacagaaaaa tgtgttgtat gccctgttga    9900
tattggttgg agtgacgttg gatcttggca atcgttatgg gacattagtc taaaatcgaa    9960
aacaggagat gtatgtaaag gtgatatatt aacctatgat actaagaata ttatatctta    10020
ctctgagtca gcgttggtag ccgccattgg aattgaagat atggttatcg tgcaaactaa    10080
agatgccgtt cttgtgtcta aaaagagtga tgtacagcat gtaaaaaaaa tagtcgaaat    10140
gcttaaattg cagcaacgta cagagtatat tagtcatcgt gaagttttcc gaccatgggg    10200
```

```
aaaatttgat tcgattgacc aaggtgagcg atacaaagtc aagaaaatta ttgtgaaacc  10260
tggtgagggg cttctcttaa ggatgcatca ccatcgttct gaacattgga tcgtgctttc  10320
tggtacagca aaagtaaccc ttggcgataa aactaaacta gtcaccgcaa atgaatcgat  10380
atacattccc cttggcgcag cgtatagtct tgagaatccg gcataatcc ctcttaatct   10440
tattgaagtc agttcagggg attatttggg agaggatgat attataagac agaaagaacg  10500
ttacaaacat gaagattaac atatgaaatc tttaacctgc tttaaagcct atgatattcg  10560
cgggaaatta ggcgaagaac tgaatgaaga tattgcctgg cgcattgggc gtgcctatgg  10620
cgaatttctc aaaccgaaaa ccattgtttt aggcggtgat gtccgcctca ccagcgaagc  10680
gttaaaactg gcgcttgcga aggtttaca ggatgcgggc gtcgatgtgc tggatatcgg   10740
tatgtccggc accgaagaga tctatttcgc cacgttccat ctcggagtgg atggcggcat  10800
cgaagttacc gccagccata acccgatgga ttacaacggc atgaagctgg tgcgcgaagg  10860
ggctcgcccg atcagcggtg ataccggact gcgcgatgtc cagcgtctgg cagaagccaa  10920
tgacttccct cctgtcgatg aaaccaaacg tggtcgctat cagcaaatca atctgcgtga  10980
cgcttacgtt gatcacctgt tcggttatat caacgtcaaa aacctcacgc cgctcaagct  11040
ggtgatcaac tccgggaacg gcgcagcggg tccggtggtg gacgccattg aagcccgatt  11100
taaagccctc ggcgcaccgg tggaattaat caaagtacac aacacgccgg acggcaattt  11160
ccccaacggt attcctaacc cgctgctgcc ggaatgccgc gacgacaccc gtaatgcggt  11220
catcaaacac ggcgcggata tgggcattgc ctttgatggc gattttgacc gctgtttcct  11280
gtttgacgaa aaagggcagt ttatcgaggg ctactacatt gtcggcctgc tggcagaagc  11340
gttcctcgaa aaaatcccg gcgcgaagat catccacgat ccacgtctct cctggaacac   11400
cgttgatgtg gtgactgccg caggcggcac cccggtaatg tcgaaaaccg gacacgcctt  11460
tattaaagaa cgtatgcgca aggaagacgc catctacggt ggcgaaatga gcgctcacca  11520
ttacttccgt gatttcgctt actgcgacag cggcatgatc ccgtggctgc tggtcgccga  11580
actggtgtgc ctgaaaggaa aaacgctggg cgaaatggtg cgcgaccgga tggcggcgtt  11640
tccggcaagc ggtgagatca acagcaaact ggcgcaaccc gttgaggcaa ttaatcgcgt  11700
ggaacagcat tttagccgcg aggcgctggc ggtggatcgc accgatggca tcagcatgac  11760
cttttgccgac tggcgcttta acctgcgctc ctccaacacc gaaccggtgg tgcggttgaa  11820
tgtggaatca cgcggtgatg taaagctaat ggaaaagaaa actaaagctc ttcttaaatt  11880
gctaagtgag tgattattta cattaatcat taagcgtatt taagattata ttaaagtaat  11940
gttattgcgg tatatgatga atatgtgggc tttttttatgt ataacgacta taccgcaact  12000
ttatctagga aaagattaat agaaataaag ttttgtactg accaatttgc atttcacgtc  12060
acgattgaga cgttcctttg cttaagacat ttttttcatcg cttatgtaat aacaaatgtg  12120
ccttatataa aaaggagaac aaaatggaac ttaaaataat tgagacaata gatttttatt  12180
atccctgttt acgatattat agccaaagtt gtatcctgca tcagtcctgc aatatttcac  12240
gagtgctttg ttaactgaat acatgtctgc cattttccag atgataacga cgtcatcgca  12300
attgatggta aaacacttcg gcacacttat gacaagagtc gtcgcagagg agtggttcat  12360
gtcattagtc cgtttcagca atgcacagtc tggtcctcgg atagatcaag acggatgaga  12420
aacctaatgc gttcacagtt attcatgaac tttctaaaat gatgggtatt aaaggaaaaa  12480
taatcataac tgatgcgatg gcttgccaga aagatattgc agagaagata taaaaacaga  12540
gatgtgatta tttattcgct gtaaaaggaa ataagagtcg gcttaataga gtctttgagg  12600
```

```
agatatttac gctgaaagaa ttaaataatc caaaacatga cagttacgca attagtgaaa    12660
agaggcacgg cagagacgat gtccgtcttc atattgtttg agatgctcct gatgagctta    12720
ttgatttcac gtttgaatgg aaagggctgc agaatttatg aatggcagtc cactttctct    12780
caataatagc agagcaaaag aaagaatccg aaatgacgat caaatattat attagatctg    12840
ctgctttaac cgcagagaag ttcgccacag taaatcgaaa tcactggcgc atggagaata    12900
agttgcacag tagcctgatg tggtaatgaa tgaaatcgac tataatataa aaggcgagt     12960 tgcattcgaa tgatttccta gaatgcggca catcgctatt aatatctgac aatgataatg    13020
tattcaaggc aggattatca tgtaagatgc gaaaagcagt catggacaga aacttcctag    13080
cgtcaggcat tgcagcgtgc gggctttcat aatcttgcat tggttttgat aagatatttc    13140
tttggagatg ggaaaatgaa tttgtatggt attttttggtg ctggaagtta tggtagagaa    13200 acaatacccca ttctaaatca acaaataaag caagaatgtg ttctgacta tgctctggtt     13260 tttgtggatg atgttttggc aggaaagaaa gttaatggtt ttgaagtgct ttcaaccaac    13320
tgctttctaa aagccccta tttaaaaaag tatttaatg ttgctattgc taatgataag     13380
atacgacaga gagtgtctga gtcaatatta ttacacgggg ttgaaccaat aactataaaa    13440
catccaaata gcgttgttta tgatcatact atgataggta gtggcgctat tatttctccc    13500
tttgttacaa tatctactaa tactcatata gggaggtttt ttcatgcaaa catatactca    13560
tacgttgcac atgattgtca ataggagac tatgttacat ttgctcctgg ggctaaatgt      13620
aatggatatg ttgttattga agacaatgca tatataggct cgggtgcagt aattaagcag    13680
ggtgttccta atcgcccact tattattggc gcgggagcca ttataggtat gggggctgtt    13740
gtcactaaaa gtgttcctgc cggtataact gtgtgcggaa atccagcaag agaaatgaaa    13800
agatcgccaa catctatta atgggaatgc gaaaacacgt tccaaatggg actaatgttt    13860
aaaatatata taatttcgct aatttactaa attatggctt cttttttaagc tatccttac    13920 ttagttatta ctgatacagc atgaaattta taatactctg atacattttt atacgttatt    13980
caagccgcat atctagcggt aaccccctgac aggagtaaac aatg                    14024

<210> SEQ ID NO 57
<211> LENGTH: 1758
<212> TYPE: DNA
<213> ORGANISM: Escherichia coli

<400> SEQUENCE: 57
atggcacaag tcattaatac caacagcctc tcgctgatca ctcaaaataa tatcaacaag      60
aaccagtctg cgctgtcgag ttctatcgag cgtctgtctt ctggcttgcg tattaacagc     120
gcgaaggatg acgccgcagg tcaggcgatt gctaaccgtt ttacttctaa cattaaaggc     180
ctgactcagg cggcccgtaa cgccaacgac ggtatttctg ttgcgcagac caccgaaggc     240
gcgctgtccg aaatcaacaa caacttacag cgtattcgtg aactgacggt tcaggccact     300
acagggacta ctccgattc tgacctggac tccatccagg acgaaatcaa atctcgtctt     360
gatgaaattg accgcgtatc cggccagacc cagttcaacg gcgtgaacgt gctggcgaaa     420
gacggttcaa tgaaaattca ggttggtgcg aatgacggcg aaaccatcac gatcgacctg     480
aaaaaaatcg attctgatac tctgggtctg aatggcttta acgtaaatgg taaaggtact     540
attaccaaca aagctgcaac ggtaagtgat ttaacttctg ctggcgcgaa gttaaacacc     600
acgacaggtc tttatgatct gaaaaccgaa atccttgt taactaccga tgctgcattc     660
```

-continued

```
gataaattag ggaatggcga taaagtcaca gttggcggcg tagattatac ttacaacgct    720
aaatctggtg attttactac cactaaatct actgctggta cgggtgtaga cgccgcggcg    780
caggctgctg attcagcttc aaaacgtgat gcgttagctg ccaccccttca tgctgatgtg    840 ggtaaatctg ttaatggttc ttacaccaca aaagatggta ctgtttcttt cgaaacggat    900
tcagcaggta atatcaccat cggtggaagc caggcatacg tagacgatgc aggcaacttg    960
acgactaaca acgctggtag cgcagctaaa gctgatatga aagcgctgct caaagcagcg   1020
agcgaaggta gtgacggtgc ctctctgaca ttcaatggca cagaatatac catcgcaaaa   1080
gcaactcctg cgacaaccac tccagtagct ccgttaatcc ctggtgggat tacttatcag   1140
gctacagtga gtaaagatgt agtattgagc gaaaccaaag cggctgccgc gacatcttca   1200
attaccttta attccggtgt actgagcaaa actattgggt ttaccgcggg tgaatccagt   1260
gatgctgcga agtcttatgt ggatgataaa ggtggtatca ctaacgttgc cgactataca   1320
gtctcttaca gcgttaacaa ggataacggc tctgtgactg ttgccgggta tgcttcagcg   1380
actgatacca ataaagatta tgctccagca attggtactg ctgtaaatgt gaactccgcg   1440
ggtaaaatca ctactgagac taccagtgct ggttctgcaa cgaccaaccc gcttgctgcc   1500
ctggacgacg caatcagctc catcgacaaa ttccgttctt ccctgggtgc tatccagaac   1560
cgtctggatt ccgcagtcac caacctgaac aacaccacta ccaacctgtc cgaagcgcag   1620
tcccgtattc aggacgccga ctatgcgacc gaagtgtcca acatgtcgaa agcgcagatc   1680
attcagcagg ccggtaactc cgtgctggca aaagctaacc aggtaccgca gcaggttctg   1740
tctctgctgc agggttaa                                                  1758
```

<210> SEQ ID NO 58
<211> LENGTH: 1758
<212> TYPE: DNA
<213> ORGANISM: Escherichia coli
<400> SEQUENCE: 58

```
atggcacaag tcattaatac caacagcctc tcgctgatca ctcaaaataa tatcaacaag     60
aaccagtctg cgctgtcgag ttctatcgag cgtctgtctt ctggcttgcg tattaacagc    120
gcgaaggatg acgcagcggg tcaggcgatt gctaaccgtt ttacttctaa cattaaaggc    180
ctgactcagg ctgcacgtaa cgccaacgac ggtatttctg ttgcgcagac caccgaaggc    240
gcgctgtccg aaatcaacaa caacttacag cgtattcgtg aactgacggt tcaggccact    300
acagggacta actccgattc tgacctggac tccatccagg acgaaatcaa atctcgtctt    360
gatgaaattg accgcgtatc cggccagacc cagttcaacg gcgtgaacgt gctggcgaaa    420
gacggttcaa tgaaaattca ggttggtgcg aatgacggca aaaccatcac gatcgacctg    480
aaaaaaatcg attctgatac tctgggtctg aatggctttaa acgtaaatgg taaaggtact    540
attaccaaca aagctgcaac ggtaagtgat ttaacttctg ctggcgcgaa gttaaacacc    600
acgacaggtc tttatgatct gaaaaccgaa ataccttgt taactaccga tgctgcattc    660
gataaattag ggaatggcga taaagtcaca gttggcggcg tagattatac ttacaacgct    720
aaatctggtg attttactac cactaaatct actgctggta cgggtgtaaa cgccgcggcg    780
caggctgctg attcagcttc aaaacgtgat gcgttagctg ccaccccttca tgctgatgtg    840 ggtaaatctg ttaatggttc ttacaccaca aaagatggta ctgtttcttt cgaaacggat    900
tcagcaggta atatcaccat cggtggaagc caggcatacg tagacgatgc aggcaacttg    960
acgactaaca acgctggtag cgcagctaaa gctgatatga aagcgctgct caaagcagcg   1020
```

```
agcgaaggta gtgacggtgc ctctctgaca ttcaatggca cagaatatac catcgcaaaa    1080
gcaactcctg cgacaaccac tccagtagct ccgttaatcc ctggtgggat tacttatcag    1140
gctacagtga gtaaagatgt agtattgagc gaaaccaaag cggctgccgc gacatcttca    1200
attaccttta attccggtgt actgagcaaa actattgggt ttaccgcggg tgaatccagt    1260
gatgctgcga agtcttatgt ggatgataaa ggtggtatca ctaacgttgc cgactataca    1320
gtctcttaca gcgttaacaa ggataacggc tctgtgactg ttgccgggta tgcttcagcg    1380
actgatacca ataaagatta tgctccagca attggcactg ctgtaaatgt gaactccgcg    1440
ggtaaaatca ctactgagac taccagtgct ggttctgcaa cgaccaaccc gcttgctgcc    1500
ctggacgacg caatcagctc catcgacaaa ttccgttctt ccctgggtgc tatccagaac    1560
cgtctggatt ccgcggtcac caacctgaac aacaccacta ccaacctgtc cgaagcgcag    1620
tcccgtattc aggacgccga ctatgcgacc gaagtgtcca acatgtcgaa agcgcagatc    1680
atccagcagg ccggtaactc cgtgctggca aaagctaacc aggtaccgca gcaggttctg    1740
tctctgctgc agggttaa                                                  1758

<210> SEQ ID NO 59
<211> LENGTH: 1758
<212> TYPE: DNA
<213> ORGANISM: Escherichia coli

<400> SEQUENCE: 59
atggcacaag tcattaatac caacagcctc tcgctgatca ctcaaaataa tatcaacaag      60
aaccagtctg cgctgtcgag ttctatcgag cgtctgtctt ctggcttgcg tattaacagc     120
gcgaaggatg acgccgcggg tcaggcgatt gctaaccgtt ttacttctaa cattaaaggc     180
ctgactcagg ctgcacgtaa cgccaacgac ggtatttctg ttgcacagac cactgaaggc     240
gcgctgtccg aaatcaacaa caacttacag cgtatccgtg agctgaccgt tcaggcttct     300
accgggacta actctgattc ggatctggac tccattcagg acgaaatcaa atcccgtctc     360
gacgaaattg accgcgtatc cggtcagacc cagttcaacg gcgtgaacgt actggcaaaa     420
gacggttcga tgaaaattca ggttggtgcg aatgacggtg aaactatcac tatcgacctg     480
aagaaaatcg attctgatac tctgggtctg aatggtttta acgtaaatgg taaaggtact     540
attaccaaca aagctgcaac ggtaagtgat ttaacttctg ctggcgcgaa gttaaacacc     600
acgacaggtc tttatgatct gaaaaccgaa ataccttgta actaccga tgctgcattc     660 gataaaattag ggaatggcga taaagtcacc gttggcggcg tagattatac ttacaacgct     720
aaatctggtg atttactac caccaaatct actgctggta cgggtgtaga cgccgcggcg     780
caggctactg attcagctaa aaaacgtgat gcgttagctg ccaccccttca tgctgatgtg     840 ggtaaatctg ttaatggttc ttacaccaca aaagatggta ctgtttcttt cgaaacggat     900
tcagcaggta atatcaccat cggtggaagc caggcatacg tagacgatgc aggcaacttg     960
acgactaaca acgctggtag cgcagctaaa gctgatatga aagcgctgct taaagccgcg    1020
agcgaaggta gtgacggtgc ctctctgaca ttcaatggca ctgaatatac tatcgcaaaa    1080
gcaactcctg cgacaacctc tccagtagct ccgttaatcc ctggtgggat tacttatcag    1140
gctacagtga gtaaagatgt agtattgagc gaaaccaaag cggctgccgc gacatcttca    1200
attaccttta attccggtgt actgagcaaa actattgggt ttaccgcggg tgaatccagt    1260
gatgctgcga agtcttatgt ggatgataaa ggtggtatta ctaacgttgc cgactataca    1320
```

-continued

```
gtctcttaca gcgttaacaa ggataacggc tctgtgactg ttgccgggta tgcttcagcg   1380
actgatacca ataaagatta tgctccagca attggtactg ctgtaaatgt gaactccgcg   1440
ggtaaaatca ctactgagac taccagtgct ggttctgcaa cgaccaaccc gcttgctgcc   1500
ctggacgacg ctatcagctc catcgacaaa ttccgttctt ccctgggtgc tatccagaac   1560
cgtctggatt ccgcagtcac caacctgaac aacaccacta ccaacctgtc tgaagcgcag   1620
tcccgtattc aggacgccga ctatgcgacc gaagtgtcca acatgtcgaa agcgcagatt   1680
atccagcagg ccgtaactc cgtgctggca aaagccaacc aggtaccgca gcaggttctg    1740
tctctgctgc agggttaa                                                 1758

<210> SEQ ID NO 60
<211> LENGTH: 1758
<212> TYPE: DNA
<213> ORGANISM: Escherichia coli

<400> SEQUENCE: 60
atggcacaag tcattaatac caacagcctc tcgctgatca ctcaaaataa tatcaacaag     60
aaccagtctg cgctgtcgag ttctatcgag cgtctgtctt ctggcttgcg tattaacagc   120
gcgaaggatg acgccgcagg tcaggcgatt gctaaccgtt ttacttctaa cattaaaggc   180
ctgactcagg cggcccgtaa cgccaacgac ggtatttctg ttgcgcagac caccgaaggc   240
gcgctgtccg aaatcaacaa caacttacag cgtattcgtg aactgacggt tcaggccact   300
acagggacta ctccgattc tgacctggac tccatccagg acgaaatcaa atctcgtctt   360
gatgaaattg accgcgtatc cggccagacc cagttcaacg gcgtgaacgt gctggcgaaa   420
gacggttcaa tgaaaattca ggttggtgcg aatgacggcg aaaccatcac gatcgacctg   480
aaaaaaatcg attctgatac tctgggtctg aatggctta acgtaaatgg taaaggtact   540
attaccaaca aagctgcaac ggtaagtgat ttaacttctg ctggcgcgaa gttaaacacc   600
acgacaggtc tttatgatct gaaaaccgaa ataccttgt aactaccga tgctgcattc   660 gataaattag ggaatggcga taagtcaca gttggcggcg tagattatac ttacaacgct   720
aaatctggtg attttactac cactaaatct actgctggta cgggtgtaga cgccgcggcg   780
caggctgctg attcagcttc aaaacgtgat gcgttagctg ccaccttca tgctgatgtg   840 ggtaaatctg ttaatggttc ttacaccaca aaagatggta ctgttctttt cgaaacggat   900
tcagcaggta atatcaccat cggtggaagc caggcatacg tagacgatgc aggcaacttg   960
acgactaaca acgctggtag cgcagctaaa gctgatatga aagcgctgct caaagcagcg   1020
agcgaaggta gtgacggtgc ctctctgaca ttcaatggca cagaatatac catcgcaaaa   1080
gcaactcctg cgacaaccac tccagtagct ccgttaatcc ctggtgggat tacttatcag   1140
gctacagtga gtaaagatgt agtattgagc gaaaccaaag cggctgccgc gacatcttca   1200 attccttta attccggtgt actgagcaaa actattgggt ttaccgcggg tgaatccagt   1260
gatgctgcga agtcttatgt ggatgataaa ggtggtatca ctaacgttgc cgactataca   1320
gtctcttaca gcgttaacaa ggataacggc tctgtgactg ttgccgggta tgcttcagcg   1380
actgatacca ataaagatta tgctccagca attggtactg ctgtaaatgt gaactccgcg   1440
ggtaaaatca ctactgagac taccagtgct ggttctgcaa cgaccaaccc gcttgctgcc   1500
ctggacgacg caatcagctc catcgacaaa ttccgttctt ccctgggtgc tatccagaac   1560
cgtctggatt ccgcagtcac caacctgaac aacaccacta ccaacctgtc cgaagcgcag   1620
tcccgtattc aggacgccga ctatgcgacc gaagtgtcca acatgtcgaa agcgcagatc   1680
```

```
attcagcagg ccggtaactc cgtgctggca aaagctaacc aggtaccgca gcaggttctg    1740
tctctgctgc agggttaa                                                  1758

<210> SEQ ID NO 61
<211> LENGTH: 1758
<212> TYPE: DNA
<213> ORGANISM: Escherichia coli

<400> SEQUENCE: 61
atggcacaag tcattaatac caacagcctc tcgctgatca ctcaaaataa tatcaacaag      60
aaccagtctg cgctgtcgag ttctatcgag cgtctgtctt ctggcttgcg tattaacagc    120
gcgaaggatg acgccgcagg tcaggcgatt gctaaccgtt ttacttctaa cattaaaggc    180
ctgactcagg ctgcacgtaa cgccaacgac ggtatttctg ttgcgcagac caccgaaggc    240
gcgctgtccg aaatcaacaa caacttacag cgtattcgtg aactgaccgt tcaggccact    300
acagggacta actccgattc tgacctggac tccatccagg acgaaatcaa atctcgtctt    360
gatgaaattg accgcgtatc cggccagacc cagttcaacg gcgtgaacgt gctggcgaaa    420
gacggttcaa tgaaaattca ggttggtgcg aatgacggcg aaaccatcac gatcgacctg    480
aaaaaaatcg attctgatac tctgggtctg aatggcttta cgtaaatgg taaaggtact    540 attaccaaca aagctgcaac ggtaagtgat ttaacttctg ctggcgcgaa gttaaacacc    600
acgacaggtc tttatgatct gaaaaccgaa ataccttgt taactaccga tgctgcattc    660
gataaattag ggaatggcga taagtcaca gttggcggcg tagattatac ttacaacgct    720
aaatctggtg attttactac cactaaatct actgctggta cgggtgtaga cgccgcggcg    780
caggctgctg attcagcttc aaaacgtgat gcgttagctg ccaccctcca tgctgatgtg    840
ggtaaatctg ttaatggttc ttacaccaca aaagatggta ctgtttcttt cgaaacggat    900
tcagcaggta atatccaccat cggtggaagc caggcatacg tagacgatgc aggcaacttg    960
acgactaaca acgctggtag cgcagctaaa gctgatatga agcgctgct caaagcagcg   1020 agcgaaggta gtgacggtgc ctctctgaca ttcaatggca cagaatatac catcgcaaaa   1080
gcaactcctg cgacaaccac tccagtagct ccgttaatcc ctggtgggat tacttatcag   1140
gctacagtga gtaaagatgt agtattgagc gaaaccaaag cggctgccgc gacatcttca   1200
attcccttta attccggtgt actgagcaaa actattgggt ttaccgcggg tgaatccagt   1260
gatgctgcga gtcttatgt ggatgataaa ggtggtatca ctaacgttgc cgactataca   1320
gtctcttaca gcgttaacaa ggataacggc tctgtgactg ttgccgggta tgcttcagcg   1380
actgatacca ataagagatta tgctccagca attggcactg ctgtaaatgt gaactccgcg   1440
ggtaaaatca ctactgagac taccagtgct ggttctgcaa cgaccaaccc gcttgctgcc   1500
ctggacgacg caatcagctc catcgacaaa ttccgttctt ccctgggtgc tatccagaac   1560
cgtctggatt ccgcggtcac caacctgaac aacaccacta ccaacctgtc cgaagcgcag   1620
tcccgtattc aggacgccga ctatgcgacc gaagtgtcca acatgtcgaa agcgcagatc   1680
atccagcagg ccggtaactc cgtgctggca aaagctaacc aggtaccgca gcaggttctg   1740
tctctgctgc agggttaa                                                 1758

<210> SEQ ID NO 62
<211> LENGTH: 1758
<212> TYPE: DNA
<213> ORGANISM: Escherichia coli
```

<400> SEQUENCE: 62

```
atggcacaag tcattaatac caacagcctc tcgctgatca ctcaaaataa tatcaacaag      60
aaccagtctg cgctgtcgag ttctatcgag cgtctgtctt ctggcttgcg tattaacagc     120
gcgaaggatg acgccgcggg tcaggcgatt gctaaccgtt ttacttctaa cattaaaggc     180
ctgactcagg ctgcacgtaa cgccaacgac ggtatttctg ttgcacagac cactgaaggc     240
gcgctgtccg aaatcaacaa caacttacag cgtatccgtg agctgacggt tcaggcttct     300
accgggacta actctgattc ggatctggac tccattcagg acgaaatcaa atcccgtctc     360
gacgaaattg accgcgtatc cggtcagacc cagttcaacg gcgtgaacgt actggcaaaa     420
gacggttcga tgaaaattca ggttggtgcg aatgacggtg aaactatcac tatcgacctg     480
aagaaaatcg attctgatac tctgggtctg aatggtttta cgtaaatgg taaaggtact     540
attaccaaca aagctgcaac ggtaagtgat ttaacttctg ctggcgcgaa gttaaacacc     600
acgacaggtc tttatgatct gaaaaccgaa atacccttgt taactaccga tgctgcattc     660
gataaattag ggaatggcga taaagtcacc gttggcggcg tagattatac ttacaacgct     720
aaatctggtg atttctactac caccaaatct actgctggta cgggtgtaga cgccgcggcg     780
caggctactg attcagctaa aaacgtgat gcgttagctg ccaccttca tgctgatgtg     840
ggtaaatctg ttaatggttc ttacaccaca aaagatggta ctgtttcttt cgaaacggat     900
tcagcaggta atatcaccat cggtggaagc caggcatacg tagacgatgc aggcaacttg     960
acgactaaca acgctggtag cgcagctaaa gctgatatga agcgctgct taaagccgcg    1020
agcgaaggta gtgacggtgc ctctctgaca ttcaatggca ctgaatatac tatcgcaaaa    1080
gcaactcctg cgacaacctc tccagtagct ccgttaatcc ctggtgggat ttcttatcag    1140
gctacagtga gtaaagatgt agtattgagc gaaaccaaag cggctgccgc gacatcttca    1200
attaccttta attccggtgt actgagcaaa actattgggt ttaccgcggg tgaatccagt    1260
gatgctgcga agtcttatgt ggatgataaa ggtggtatta ctaacgttgc cgactataca    1320
gtctcttaca gcgttaacaa ggataacggc tctgtgactg ttgccgggta tgcttcagcg    1380
actgatacca ataaagatta tgctccagca attggtactg ctgtaaatgt gaactccgcg    1440
ggtaaaatca ctactgagac taccagtgct ggttctgcaa cgaccaaccc gcttgctgcc    1500
ctggacgacg ctatcagctc catcgacaaa ttccgttctt ccctgggtgc tatccagaac    1560
cgtctggatt ccgcagtcac caacctgaac aacaccacta ccaacctgtc tgaagcgcag    1620
tcccgtattc aggacgccga ctatgcgacc gaagtgtcca acatgtcgaa agcgcagatt    1680
atccagcagg ccgtaactc cgtgctggca aaagccaacc aggtaccgca gcaggttctg    1740
tctctgctgc agggttaa                                                  1758
```

<210> SEQ ID NO 63
<211> LENGTH: 1758
<212> TYPE: DNA
<213> ORGANISM: Escherichia coli

<400> SEQUENCE: 63

```
atggcacaag tcattaatac caacagcctc tcgctgatca ctcaaaataa tatcaacaag      60
aaccagtctg cgctgtcgag ttctatcgag cgtctgtctt ctggcttgcg tattaacagc     120
gcgaaggatg acgccgcagg tcaggcgatt gctaaccgtt ttacttctaa cattaaaggc     180
ctgactcagg cggcccgtaa cgccaacgac ggtatttctg ttgcgcagac caccgaaggc     240
gcgctgtccg aaatcaacaa caacttacag cgtattcgtg aactgacggt tcaggccact     300
```

```
acagggacta actccgattc tgacctggac tccatccagg acgaaatcaa atctcgtctt      360
gatgaaattg accgcgtatc cggccagacc cagttcaacg gcgtgaacgt gctggcgaaa      420
gacggttcaa tgaaaattca ggttggtgcg aatgacggcg aaaccatcac gatcgacctg      480
aaaaaaatcg attctgatac tctgggtctg aatggcttta acgtaaatgg taaaggtact      540
attaccaaca aagctgcaac ggtaagtgat ttaacttctg ctggcgcgaa gttaaacacc      600
acgacaggtc tttatgatct gaaaaccgaa ataccttgt taactaccga tgctgcattc       660
gataaattag ggaatggcga taagtcaca gttggcggcg tagattatac ttacaacgct       720
aaatctggtg attttactac cactaaatct actgctggta cgggtgtaga cgccgcggcg      780
caggctgctg attcagcttc aaaacgtgat gcgttagctg ccaccttca tgctgatgtg       840 ggtaaatctg ttaatggttc ttacaccaca aaagatggta ctgtttcttt cgaaacggat      900
tcagcaggta atatcaccat cggtggaagc caggcatacg tagacgatgc aggcaacttg      960
acgactaaca acgctggtag cgcagctaaa gctgatatga agcgctgct caaagcagcg      1020 agcgaaggta gtgacggtgc ctctctgaca ttcaatggca cagaatatac catcgcaaaa      1080
gcaactcctg cgacaaccac tccagtagct ccgttaatcc ctggtgggat tacttatcag      1140
gctacagtga gtaaagatgt agtattgagc gaaaccaaag cggctgccgc gacatcttca      1200
attcctttta attccggtgt actgagcaaa actattgggt ttaccgcggg tgaatccagt      1260
gatgctgcga agtcttatgt ggatgataaa ggtggtatca ctaacgttgc cgactataca      1320
gtctcttaca gcgttaacaa ggataacggc tctgtgactg ttgccgggta tgcttcagcg      1380
actgatacca ataaagatta tgctccagca attggtactg ctgtaaatgt gaactccgcg      1440
ggtaaaatca ctactgagac taccagtgct ggttctgcaa cgaccaaccc gcttgctgcc      1500
ctggacgacg caatcagctc catcgacaaa ttccgttctt ccctgggtgc tatccagaac      1560
cgtctggatt ccgcagtcac caacctgaac aacaccacta ccaacctgtc cgaagcgcag      1620
tcccgtattc aggacgccga ctatgcgacc gaagtgtcca acatgtcgaa agcgcagatc      1680
attcagcagg ccggtaactc cgtgctggca aaagctaacc aggtaccgca gcaggttctg      1740
tctctgctgc agggttaa                                                    1758
```

<210> SEQ ID NO 64  
<211> LENGTH: 1758  
<212> TYPE: DNA  
<213> ORGANISM: Escherichia coli

<400> SEQUENCE: 64

```
atggcacaag tcattaatac caacagcctc tcgctgatca ctcaaaataa tatcaacaag       60
aaccagtctg cgctgtcgag ttctatcgag cgtctgtctt ctggcttgcg tattaacagc      120
gcgaaggatg acgccgcggg tcaggcgatt gctaaccgtt ttacttctaa cattaaaggc      180
ctgactcagg ctgcacgtaa cgccaacgac ggtatttctg ttgcacagac caccgaaggc      240
gcgctgtctg aaatcaacaa caacttacag cgtatccgtg agctgaccgt tcaggcttct      300
accggaacta actctgattc ggatctggac tccattcagg acgaaatcaa atcccgtctt      360
gatgaaattg accgcgtatc cggccagacc cagttcaacg gcgtgaacgt actggcaaaa      420
gacggttcga tgaaaattca ggttggtgcg aatgacggtg aaactatcac tatcgacctg      480
aagaaaatcg attctgatac tctgggtctg aatggttta acgtaaatgg taaaggtact      540
attaccaaca aagctgcaac ggtaagtgat ttaacttctg ctggcgcgaa gttaaacacc      600
```

-continued

```
acgacaggtc tttatgatct gaaaaccgaa ataccttgt taactaccga tgctgcattc    660
gataaattag ggaatggcga taaagtcacc gttggcggcg tagattatac ttacaacgct    720
aaatctggtg attttactac caccaaatct actgctggta cgggtgtaga cgccgcggcg    780
caggctactg attcagctaa aaacgtgat gcgttagctg ccaccccttca tgctgatgtg    840 ggtaaatctg ttaatggttc ttacaccaca aaagatggta ctgtttcttt cgaaacggat    900
tcagcaggta atatcaccat cggtggaagc caggcatacg tagacgatgc aggcaacttg    960
acgactaaca acgctggtag cgcagctaaa gctgatatga aagcgctgct taaagccgcg   1020
agcgaaggta gtgacggtgc ttctctgaca ttcaatggca ctgaatatac tatcgcaaaa   1080
gcaactcctg cgacaacctc tccagtagct ccgttaatcc ctggtgggat tacttatcag   1140
gctacagtga gtaaagatgt agtattgagc gaaaccaaag cggctgccgc gacatcttca   1200 attacccttta attccggtgt actgagcaaa actattgggt ttaccgcggg tgaatccagt   1260
gatgctgcga agtcttatgt ggatgataaa gtggtatta ctaacgttgc cgactataca   1320
gtctcttaca gcgttaacaa ggataacggc tctgtgactg ttgccgggta tgcttcagcg   1380
actgatacca ataagatta tgctccagca attggtactg ctgtaaatgt gaactccgcg   1440
ggtaaaatca ctactgagac taccagtgct ggttctgcaa cgaccaaccc gcttgctgcc   1500
ctggacgacg ctatcagctc catcgacaaa ttccgttctt ccctgggtgc tatccagaac   1560
cgtctggatt ccgcagtcac caacctgaac aacaccacta ccaacctgtc tgaagcgcag   1620
tcccgtattc aggacgccga ctatgcgacc gaagtgtcca acatgtcgaa agcgcagatt   1680
atccagcagg ccggtaactc cgtgctggca aaagccaacc aggtaccgca gcaggttctg   1740
tctctgctgc agggttaa                                                1758
```

<210> SEQ ID NO 65
<211> LENGTH: 1758
<212> TYPE: DNA
<213> ORGANISM: Escherichia coli

<400> SEQUENCE: 65

```
atggcacaag tcattaatac caacagcctc tcgctgatca ctcaaaataa tatcaacaag     60
aaccagtctg cgctgtcgag ttctatcgag cgtctgtctt ctggcttgcg tattaacagc    120
gcgaaggatg acgccgcggg tcaggcgatt gctaaccgtt ttacttctaa cattaaaggc    180
ctgactcagg ctgcacgtaa cgccaacgac ggtatttctg ttgcacagac cactgaaggc    240
gcgctgtccg aaatcaacaa caacttacag cgtatccgtg agctgacggt tcaggcttct    300
accgggacta actctgattc ggatctggac tccattcagg acgaaatcaa atcccgtctc    360
gacgaaattg accgcgtatc cggtcagacc cagttcaacg gcgtgaacgt actggcaaaa    420
gacggttcga tgaaaattca ggttggtgcg aatgacggtg aaactatcac tatcgacctg    480
aagaaaatcg attctgatac tctgggtctg aatggtttta cgtaaatgg taaaggtact    540 attaccaaca aagctgcaac ggtaagtgat ttaacttctg ctggcgcgaa gttaaacacc    600
acgacaggtc tttatgatct gaaaaccgaa ataccttgt taactaccga tgctgcattc    660
gataaattag ggaatggcga taaagtcacc gttggcggcg tagattatac ttacaacgct    720
aaatctggtg attttactac caccaaatct actgctggta cgggtgtaga cgccgcggcg    780
caggctactg attcagctaa aaacgtgat gcgttagctg ccaccccttca tgctgatgtg    840 ggtaaatctg ttaatggttc ttacaccaca aaagatggta ctgtttcttt cgaaacggat    900
tcagcaggta atatcaccat cggtggaagc caggcatacg tagacgatgc aggcaacttg    960
```

-continued

```
acgactaaca acgctggtag cgcagctaaa gctgatatga aagcgctgct taaagccgcg    1020
agcgaaggta gtgacggtgc ctctctgaca ttcaatggca ctgaatatac tatcgcaaaa    1080
gcaactcctg cgacaacctc tccagtagct ccgttaatcc ctggtgggat ttcttatcag    1140
gctacagtga gtaaagatgt agtattgagc gaaaccaaag cggctgccgc gacatcttca    1200
attaccttta attccggtgt actgagcaaa actattgggt ttaccgcggg tgaatccagt    1260
gatgctgcga agtcttatgt ggatgataaa ggtggtatta ctaacgttgc cgactataca    1320
gtctcttaca gcgttaacaa ggataacggc tctgtgactg ttgccgggta tgcttcagcg    1380
actgatacca ataaagatta tgctccagca attggtactg ctgtaaatgt gaactccgcg    1440
ggtaaaatca ctactgagac taccagtgct ggttctgcaa cgaccaaccc gcttgctgcc    1500
ctggacgacg ctatcagctc catcgacaaa ttccgttctt ccctgggtgc tatccagaac    1560
cgtctggatt ccgcagtcac caacctgaac aacaccacta ccaacctgtc tgaagcgcag    1620
tcccgtattc aggacgccga ctatgcgacc gaagtgtcca acatgtcgaa agcgcagatt    1680
atccagcagg ccggtaactc cgtgctggca aaagccaacc aggtaccgca gcaggttctg    1740
tctctgctgc agggttaa                                                  1758
```

<210> SEQ ID NO 66
<211> LENGTH: 1788
<212> TYPE: DNA
<213> ORGANISM: Escherichia coli

<400> SEQUENCE: 66

```
atggcacaag tcattaatac caacagcctc tcgctgatca ctcaaaataa tatcaacaag      60
aaccagtctg cgctgtcgag ttctatcgag cgtctgtctt ctggcttgcg tattaacagc     120
gcgaaggatg acgccgcggg tcaggcgatt gctaaccgtt ttacttctaa cattaaaggc     180
ctgactcagg ctgcacgtaa cgccaacgac ggtatttctg ttgcacagac cactgaaggc     240
gcgctgtccg aaatcaacaa caacttacag cgtatccgtg agctgactgg tcaggcttct     300
accgggacta ctctgattcc ggatctggac tccattcagg acgaaatcaa atcccgtctc     360
gacgaaattg accgcgtatc cggtcagacc cagttcaacg gcgtgaacgt actggcaaaa     420 gacgggttcga tgaaaattca ggtaggtgcg aacgacggcc agactatcac tattgatctg     480
aagaaaattg actctgatac gctggggctg aatggtttta cgtgaatgg ttccggtacg      540 atagccaata aagcggcgac cattagcgac ctgacagcag cgaaaatgga tgctgcaact     600
aatactataa ctacaacaaa taatgcgctg actgcatcaa aggcccttga tcaactgaaa     660
gatggtgaca ctgttactat caaagcagat gcagctcaaa ctgccacggt ctatacatac     720
aatgcatctg ctggtaactt ctcattcagt aatgtatcga ataatacttc agcaaaagca     780
ggtgatgtag cagctagcct tctcccgccg gctgggcaaa ctgctagtgg tgtttacaaa     840
gcagcaagcg gtgaagtgaa ctttgatgtt gatgcgaatg taaaattac aatcggagga     900 caggaagcct atttaactag tgatggtaac ttaactacaa cgatgctgg tgtgcgact      960 gcggctacgc ttgatggttt attcaagaaa gctggtgatg gtcaatcaat cgggtttaat    1020
aagactgcat cagtcacgat ggggggaaca acttataact ttaaaacggg tgctgatgct    1080
ggtgctgcaa ctgctaacgc aggggtatcg ttcactgata cagctagcaa agaaaccgtt    1140
ttaaataaag tggctacagc taaacaaggc acagcagttg cagctaacgg tgatacatcc    1200
gcaacaatta cctataaatc tggcgttcag acgtatcagg cggtatttgc cgcaggtgac    1260
```

-continued

| | |
|---|---|
| ggtactgcta gcgcaaaata tgccgataat actgacgttt ctaatgcaac agcaacatac | 1320 |
| acagatgctg atggtgaaat gactacaatt ggttcataca ccacgaagta ttcaatcgat | 1380 |
| gctaacaacg gcaaggtaac tgttgattct ggaactggtt cggtaaaata tgcgccgaaa | 1440 |
| gtcggggctg aagtatatgt tagtgctaat ggtactttaa caacagatgc aactagcgaa | 1500 |
| ggcacagtaa caaagatcc actgaaagct ctggatgaag ctatcagctc catcgacaaa | 1560 |
| ttccgttcat ccctggggc tatccaaaac cgtttggatt ccgccgtcac caacctgaac | 1620 |
| aacaccacta ccaacctgtc tgaagcgcag tcccgtattc aggacgccga ctatgcgacc | 1680 |
| gaagtgtcca acatgtcgaa agcgcagatt atccagcagg ccgtaactc cgtgctggca | 1740 |
| aaagccaacc aggtaccgca gcaggttctg tctctactgc agggttaa | 1788 |

<210> SEQ ID NO 67
<211> LENGTH: 1398
<212> TYPE: DNA
<213> ORGANISM: Escherichia coli

<400> SEQUENCE: 67

| | |
|---|---|
| aacaaatctc agtcttctct tagctctgct attgagcgtc tgtcttctgg tctgcgtatt | 60 |
| aacagcgcaa aagacgatgc agcaggtcag gcgattgcta accgttttac ggcaaatatt | 120 |
| aaaggtctga cccaggcttc ccgtaacgca atgatggta tttctgttgc gcagaccact | 180 |
| gaaggtgcgc tgaatgaaat taacaacaac ctgcagcgta ttcgtgaact ttctgttcag | 240 |
| gcaactaacg gtactaactc tgacagtgac ctgacctcca tccagtccga aatccagcag | 300 |
| cgtctgagtg aaattgaccg tgtttctggt cagactcagt ttaacggcgt taaagtgctg | 360 |
| gcttctgatc aggatatgac tattcaggtt ggtgcaaacg acggcgaaac aattactatt | 420 |
| aaactgcagg aaattaattc cgacacactg ggattatctg gttttggtat taaagatcct | 480 |
| actaaattaa aagccgcaac ggctgaaaca acctattttg gatcgacagt taagcttgct | 540 |
| gacgctaata cacttgatgc agatattaca gctacagtta aaggcactac gactccgggc | 600 |
| caacgtgacg gtaatattat gtctgatgct aacggtaagt tgtacgttaa agttgccggt | 660 |
| tcagataaac ccgctgaaaa tggttattat gaagttactg tggaggatga tccgacatct | 720 |
| cctgatgcag gtaagctgaa gctgggggct ctagcgggta cccagcctca agctggtaat | 780 |
| ttaaaggaag tcacaacggt gaaagggaag ggggctattg atgttcagtt gggtactgat | 840 |
| accgcaaccg cttctatcac aggtgcaaaa ctctttaagt tagaagacgc caatggcaaa | 900 |
| gatactggtt catttgcgtt gattggtgat gacggtaaac agtatgcagc gaatgttgat | 960 |
| cagaaaacag gagcagtttc cgttaaaaca atgtcttaca ctgatgctga cggtgtcaaa | 1020 |
| cacgacaatg ttaaagttga actgggtgga agcgatggca aaccgaagt tgtaactgca | 1080 |
| accgatggca aaacttacag tgttagtgat ttacaaggta agagcctgaa aactgattct | 1140 |
| attgcagcaa tttctacgca gaaaacagaa gatcctttgg ctgctatcga taagcactg | 1200 |
| tctcaggttg actcgttgcg ttctaaccta ggtgcaattc aaaatcgttt cgactctgcc | 1260 |
| atcaccaacc ttggcaacac cgtaaacaac ctgtcttctg cccgtagccg tatcgaagat | 1320 |
| gctgactacg cgaccgaagt gtctaacatg tctcgtgcgc agatcctgca acaagcgggt | 1380 |
| acctctgttc tggcgcag | 1398 |

<210> SEQ ID NO 68
<211> LENGTH: 1479
<212> TYPE: DNA
<213> ORGANISM: Escherichia coli

<400> SEQUENCE: 68

```
aacaaatctc agtcttctct gagctccgcc attgaacgtc tctcttctgg cctgcgtatt      60
aacagtgcta aagatgacgc agcaggtcag gcgattgcta accgttttac agcaaatatt     120
aaaggtctga ctcaggcttc ccgtaacgcg aatgatggta tttctgttgc gcagaccact     180
gaaggtgcgc tttctgaaat caacaataac ttacagcgta ttcgtgaatt gtcagtacag     240
gccactaatg gtacaaactc tgactccgac ctgaattcaa ttcaggatga aattacacaa     300
cgccttagtg aaattgatcg tgtttctaac cagacacaat ttaatggtgt aaaagttctg     360
gcttctgatc agactatgaa aattcaagta ggtgcgaacg atggtgaaac cattgagatt     420
gcccttgata aaattgatgc taaaaccttg gggcttgata actttagcgt agcaccagga     480
aaagttccaa tgtcctctgc ggttgcactt aagagcgaag ccgctcctga cttaactaag     540
gtaaatgcaa ctgatggtag tgtgggaggt gctaaagcat tcggtagcaa ttataaaaat     600
gctgatgttg aaacttattt tggtaccggt aatgtacaag atacaaagga tacaactgat     660
gcgaccggta ctgcaggaac aaaagtttat caagtacagg tggaagggca gacttatttt     720
gttggtcaag ataataatac caacacgaac ggttttacat tattgaaaca aaactctaca     780
ggttatgaaa agttcaggt gggtggtaag gatgttcagt tagcaaactt tggtggtcgt      840
gtaactgcat ttgttgaaga taatggttct gccacatcag ttgatttagc tgcgggtaaa     900
atgggtaaag cattagctta taatgatgca ccaatgtctg tttattttgg gggaaaaaac     960
ctagatgtcc accaagtaca agatacccaa gggaatcctg tacctaattc atttgctgct    1020
aaaacatcag acggcaccta cattgcagta aatgtagatg ccgctacagg taacacgtct    1080
gttattactg atcctaatgg taaggcagtt gaatgggcag taaaaaatga tggttctgca    1140
caggcaatta tgcgtgaaga tgataaggtt tatacagcca atatcacgaa taagacggca    1200
accaaaggtg ctgaactcag tgcctcagat ttgaaagcct tagcaaccac aaatccatta    1260
tccacattag acgaagcttt ggcaaaagtt gataagttgc gcagttcttt gggtgcagta    1320
caaaaccgtt tcgactctgc catcaccaac cttggcaaca ccgtaaacaa cctgtcttct    1380
gcccgtagcc gtatagaaga tgctgactac gcaaccgaag tgtctaacat gtctcgtgcg    1440
cagatcctgc aacaagcggg tacctctgtt ctggcacag                           1479
```

<210> SEQ ID NO 69
<211> LENGTH: 27
<212> TYPE: DNA
<213> ORGANISM: Artificial Sequence
<220> FEATURE:
<223> OTHER INFORMATION: Primer with restriction endonuclease site

<400> SEQUENCE: 69

```
catgccatgg cacaagtcat taatacc                                          27
```

<210> SEQ ID NO 70
<211> LENGTH: 31
<212> TYPE: DNA
<213> ORGANISM: Artificial Sequence
<220> FEATURE:
<223> OTHER INFORMATION: Primer with restriction endonuclease site

<400> SEQUENCE: 70

```
atatgtcgac ttaaccctgc agcagagaca g                                     31
```

<210> SEQ ID NO 71

```
<211> LENGTH: 29
<212> TYPE: DNA
<213> ORGANISM: Artificial Sequence
<220> FEATURE:
<223> OTHER INFORMATION: Primer with restriction endonuclease site

<400> SEQUENCE: 71
atggatcctt aaccctgcag cagagacag                                            29

<210> SEQ ID NO 72
<211> LENGTH: 29
<212> TYPE: DNA
<213> ORGANISM: Artificial Sequence
<220> FEATURE:
<223> OTHER INFORMATION: Primer with restriction endonuclease site

<400> SEQUENCE: 72
aactgcagtt aaccctgtag cagagacag                                            29

<210> SEQ ID NO 73
<211> LENGTH: 29
<212> TYPE: DNA
<213> ORGANISM: Artificial Sequence
<220> FEATURE:
<223> OTHER INFORMATION: Primer with restriction endonuclease site

<400> SEQUENCE: 73
cgggatcccg cagactggtt cttgttgat                                            29

<210> SEQ ID NO 74
<211> LENGTH: 29
<212> TYPE: DNA
<213> ORGANISM: Artificial Sequence
<220> FEATURE:
<223> OTHER INFORMATION: Primer with restriction endonuclease site

<400> SEQUENCE: 74
cgggatccac ttctatcgag cgcctctct                                            29

<210> SEQ ID NO 75
<211> LENGTH: 29
<212> TYPE: DNA
<213> ORGANISM: Artificial Sequence
<220> FEATURE:
<223> OTHER INFORMATION: Primer with restriction endonuclease site

<400> SEQUENCE: 75
gctctagagc gcagatcatt cagcaggcc                                            29

<210> SEQ ID NO 76
<211> LENGTH: 29
<212> TYPE: DNA
<213> ORGANISM: Artificial Sequence
<220> FEATURE:
<223> OTHER INFORMATION: Primer with restriction endonuclease site

<400> SEQUENCE: 76
gctctagaca tgttggacac ttcggtcgc                                            29

<210> SEQ ID NO 77
<211> LENGTH: 20
<212> TYPE: DNA
<213> ORGANISM: Escherichia coli
```

<400> SEQUENCE: 77
atggcacaag tcattaatac                                                     20

<210> SEQ ID NO 78
<211> LENGTH: 20
<212> TYPE: DNA
<213> ORGANISM: Escherichia coli

<400> SEQUENCE: 78
ttaaccctgc agtagagaca                                                     20

<210> SEQ ID NO 79
<211> LENGTH: 24
<212> TYPE: DNA
<213> ORGANISM: Escherichia coli

<400> SEQUENCE: 79
ctgatcactc aaaataatat caac                                                24

<210> SEQ ID NO 80
<211> LENGTH: 18
<212> TYPE: DNA
<213> ORGANISM: Escherichia coli

<400> SEQUENCE: 80
ctgcggtacc tggttggc                                                       18

<210> SEQ ID NO 81
<211> LENGTH: 25
<212> TYPE: DNA
<213> ORGANISM: Escherichia coli

<400> SEQUENCE: 81
atggcacaag tcattaatac ccaac                                               25

<210> SEQ ID NO 82
<211> LENGTH: 20
<212> TYPE: DNA
<213> ORGANISM: Escherichia coli

<400> SEQUENCE: 82
ctaaccctgc agcagagaca                                                     20

<210> SEQ ID NO 83
<211> LENGTH: 18
<212> TYPE: DNA
<213> ORGANISM: Escherichia coli

<400> SEQUENCE: 83
gggtggaaac ccaatacg                                                       18

<210> SEQ ID NO 84
<211> LENGTH: 18
<212> TYPE: DNA
<213> ORGANISM: Escherichia coli

<400> SEQUENCE: 84
gcgcatcagg caatttgg                                                       18

<210> SEQ ID NO 85
<211> LENGTH: 18
<212> TYPE: DNA

-continued

<213> ORGANISM: Escherichia coli

<400> SEQUENCE: 85
ggcctgactc aggcggcc                                           18

<210> SEQ ID NO 86
<211> LENGTH: 18
<212> TYPE: DNA
<213> ORGANISM: Escherichia coli

<400> SEQUENCE: 86
gagttaccgg cctgctga                                           18

<210> SEQ ID NO 87
<211> LENGTH: 21
<212> TYPE: DNA
<213> ORGANISM: Escherichia coli

<400> SEQUENCE: 87
cagcgatgaa atacttgcca t                                       21

<210> SEQ ID NO 88
<211> LENGTH: 18
<212> TYPE: DNA
<213> ORGANISM: Escherichia coli

<400> SEQUENCE: 88
caatgcttcg tgacgcac                                           18

<210> SEQ ID NO 89
<211> LENGTH: 18
<212> TYPE: DNA
<213> ORGANISM: Escherichia coli

<400> SEQUENCE: 89
gcctgagtca gacctttg                                           18

<210> SEQ ID NO 90
<211> LENGTH: 18
<212> TYPE: DNA
<213> ORGANISM: Escherichia coli

<400> SEQUENCE: 90
aacctgtctg aagcgcag                                           18

<210> SEQ ID NO 91
<211> LENGTH: 31
<212> TYPE: DNA
<213> ORGANISM: Escherichia coli

<400> SEQUENCE: 91
attggtagct gtaagccaag ggcggtagcg t                            31

<210> SEQ ID NO 92
<211> LENGTH: 35
<212> TYPE: DNA
<213> ORGANISM: Escherichia coli

<400> SEQUENCE: 92
cactgccata ccgacgacgc cgatctgttg cttgg                        35

SEQUENCES FOR THE DETECTION OF *ESCHERICHIA COLI*

TECHNICAL FIELD

The invention relates to novel nucleotide sequences located in a gene which encodes a bacterial flagellin antigen, and the use of those nucleotide sequences for the detection of bacteria which express particular flagellin antigens, on the basis of that antigen alone, or in conjunction with the O antigen expressed by that strain.

BACKGROUND ART

The flagellum of many bacteria appears to be made up of a single protein known as flagellin. The serotyping schemes of *E. coli* and *Salmonella enterica* are based on highly variable antigenic surface structures which include the lipopolysaccharide which carries the O antigen and flagellin which is now known to be the carrier of the classical H antigen. In many strains of *S. enterica* there are two loci (fliC and fljB) which encode flagellin, and a regulatory system which allows one only to be expressed at any time; and which also provides for expression to rapidly alternate between the two forms first identified as two phases (H1 and H2) for the H antigen of most strains. In *E. coli* there are 54 forms of H antigen recognised and until recently they were all thought to be encoded at the fliC locus, as has been shown for *E. coli* K-12. However in the 1980s Ratiner [Ratiner Y A "Phase variation of the H antigen in *Escherichia coli* strain Bi327-41, the standard strain for *Escherichia coli* flagellin antigen H3" FEMS Microbiol. Lett 15 (1982) 33–36; Ratiner Y A "Presence of two structural genes determining antigenically different phase-specific flagellins in some *Escherichia coli* strains" FEMS Microbiol. Lett. 19 (1983) 37–41; Ratiner Y A "Two genetic arrangements determining flagellin antigen specificities in two diphasic *Escherichia coli* strains" FEMS Microbiol. Lett. 29 (1985) 317–323; Ratiner Y A "Different alleles of the flagellin gene hagB in *Escherichia coli* standard H test strains" FEMS Microbiol Lett. 48 (1987) 97–104] showed that in some cases there are two loci and that expression can alternate. The matter was further complicated by a recent paper by Ratiner [Ratiner Y A (1998) "New flagellin-specifying genes in some *Escherichia coli* strains" J. Bacteriol. 180 979–984] showing three loci (flk, fll and flm) for flagellin in addition to fliC although the fljB locus has not been found in *E. coli*. However *E. coli* strains are normally identified by the combination of one O antigen and one H antigen [and K antigen when present as a capsule (K) antigen], with no problems reported for the vast majority of cases with alternate phases, while *S. enterica* strains are normally identified by the combination of O, H1 and H2 antigens. It is still not clear how widespread in *E. coli* H antigens determined by flagellin genes other than fliC are.

Typing is typically carried out using specific antisera. The incidence of pathogenic *E. coli* in association with human and animal disease supports the need for suitable and rapid typing techniques.

DESCRIPTION OF THE INVENTION

In a first aspect, the present invention provides a novel nucleic acid molecule encoding all or part of an *E. coli* flagellin protein.

The present invention provides, for the first time, full length sequence for a flagellin gene for the following *E. coli* type strains: H6 (SEQ ID NO:8), H9(SEQ ID NO:11), H10(SEQ ID NO:12), H14(SEQ ID NO:15), H18(SEQ ID NO:18), H23(SEQ ID NO:22), H51(SEQ ID NO:50), H45 (SEQ ID NO:43), H49(SEQ ID NO:48), H19(SEQ ID NO:19), H30(SEQ ID NO:29), H32(SEQ ID NO:31), H26 (SEQ ID NO:25), H41(SEQ ID NO:39), H15(SEQ ID NO:16), H20(SEQ ID NO:20), H28(SEQ ID NO:27), H46 (SEQ ID NO:44), H31(SEQ ID NO:30), H34(SEQ ID NO:33), H43(SEQ ID NO:41) and H52(SEQ ID NO:51). Corrected full length sequences have been obtained for H7 (SEQ ID NO:9) and H12(SEQ ID NO:14) type strains.

Partial flagellin gene sequence, including the central variable region, has been obtained for the following *E. coli* H type strains: H40 (SEQ ID NO:38), H8(SEQ ID NO:10), H21(SEQ ID NO:21), H47(SEQ ID NO:46), H11(SEQ ID NO:13), H17(SEQ ID NO:17), H25(SEQ ID NO:24), H42 (SEQ ID NO:40), H27(SEQ ID NO:26), H35(SEQ ID NO:34), H2(SEQ ID NO:67), H3(SEQ ID NO:68), H24 (SEQ ID NO:23), H37(SEQ ID NO:35), H50(SEQ ID NO:49), H4(SEQ ID NO:6), H44(SEQ ID NO:42), H38 (SEQ ID NO:36), H39(SEQ ID NO:37), H55(SEQ ID NO:53), H29(SEQ ID NO:28), H33(SEQ ID NO:32), H5(SEQ ID NO:7), H54(SEQ ID NO:52) and H56(SEQ ID NO:54).

Comparison of sequences demonstrates that unique flagellin genes have now been sequenced (partially or completely) for the following *E. coli* H type strains: H1, H2, H3, H5, H6, H7, H9, H11, H12, H14, H15, H18, H19, H20, H21, H23, H24, H25, H26, H27, H28, H29, H30, H31, H32, H33, H34, H35, H37, H38, H39, H41, H42, H43, H45, H46, H48, H49, H51, H52, H54, and H56 and either H8 or H40, H10 or H50 and H4 or H17.

By comparison of these sequences, the present inventors were able to identify specific sequences for each of the above H serotypes.

The present invention also provides fliC sequences from 10 different H7 strains, in addition to that from the H7 type strain, and two sequences specific to H7 of O157 and O55 *E. coli* strains.

The present invention encompasses all or part of the flagellin genes sequenced for H2, H3, H5, H6, H9, H11, H14, H18, H19, H20, H21, H23, H24, H25, H26, H27, H28, H29, H30, H31, H32, H33, H34, H35, H37, H38, H39, H41, H42, H43, H44, H45, H46, H47, H48, H49, H51, H52, H54, H55, H56, H8, H40, H15, H10, or H50, H4 and H17 type strains. Of these flagellin genes sequenced, those from the type strains for H8 and H40 are identical, those from type strains H10 and H50, H1 and H12, H38 and H55, H21 and H47, and H4, H17 and H44 type strains are highly similar.

The invention also encompasses newly provided sequence for H7 and H12 as well as novel primers for the specific amplification of H1, H7, H12 and H48 as well as for the other above mentioned newly sequenced flagellin genes.

By cloning and expression of these sequenced flagellin genes in a fliC deletion *E. coli* K-12 strain, and use of anti-H antiserum, we have confirmed the H specificities encoded by 39 flagellin genes. The 39 H specificities are H1, H2, H4, H5, H6, H7, H9, H10, H11, H12, H14, H15, H16, H18, H19, H20, H21, H23, H24, H26, H27, H28, H29, H30, H31, H32, H33, H34, H38, H39, H41, H42, H43, H45, H46, H49, H51, H52, and H56, encoded by flagellin genes obtained from H type strains for H1, H2, H4, H5, H6, H7, H9, H10, H11, H12, H14, H15, H16, H18, H19, H20, H21, H23, H24, H26, H27, H28, H29, H30, H31, H32, H33, H34, H38, H39, H41, H42, H43, H45, H46, H49, H51, H52, and H56 respectively.

The nucleic acid molecules of the invention may be variable in length. In one embodiment they are oligonucleotides of from about 10 to about 20 nucleotides in length. The oligonucleotides of the invention are specific for the flagellin gene from which they are derived and are derived from the central region of the gene. In one embodiment, oligonucleotides in accordance with the present invention, which also include oligonucleotides from the previously sequenced *E. coli* H1, H7, H12 and H48 genes, are those shown in Table 3.

The 45 sequences (see Table 3) provide a panel to which newly sequenced genes can be compared to select specific oligonucleotides for those newly sequenced genes.

In a second aspect the invention provides a method of detecting the presence of *E. coli* of a particular H serotype in a sample, the method comprising the step of specifically hybridising at least one nucleic acid molecule derived from a flagellin gene, wherein the at least one nucleic acid molecule is specific for a particular flagellin gene associated with the H serotype, to any *E. coli* in the sample which contain the gene, and detecting any specifically hybridised nucleic acid molecules, wherein the presence of specifically hybridised nucleic acid molecules identifies the presence of the H serotype in the sample.

In one preferred embodiment the detection method is a Southern blot method. More preferably, the nucleic acid molecule is labelled and hybridisation of the nucleic acid molecule is detected by autoradiography or detection of fluorescence.

Preferred nucleic acid molecules for the detection of particular flagellin genes are listed in Table 3.

In a third aspect the invention provides a method of detecting the presence of *E. coli* of a particular H serotype in a sample, the method comprising the step of specifically hybridising at least one pair of nucleic acid molecules to any *E. coli* in the sample which contains the flagellin gene for the particular H serotype, wherein at least one of the nucleic acid molecules is specific for the particular flagellin gene associated with the H serotype, and detecting any specifically hybridised nucleic acid molecules, wherein the presence of specifically hybridised nucleic acid molecules identifies the presence of the H serotype in the sample.

In one preferred embodiment the detection method is a polymerase chain reaction method. More preferably, the nucleic acid molecules are labelled and hybridisation of the nucleic acid molecule is detected by electrophoresis.

It is recognised that there may be instances where spurious hybridisation will arise through the initial selection of a sequence found in many different genes but this is typically recognisable by, for instance, comparison of band sizes against controls in PCR gels, and an alternative sequence can be selected.

In a fourth aspect the invention provides a method for detecting the presence of a particular O serotype and H serotype of *E. coli* in a sample, the method comprising the following steps:

(a) specifically hybridising at least one nucleic acid molecule, derived from and specific for a gene encoding a transferase or a gene encoding an enzyme for the transport or processing of a polysaccharide or oligosaccharide unit, the gene being involved in the synthesis of a particular *E. coli* O antigen, to any *E. coli* in the sample which contain the gene;

(b) specifically hybridising at least one nucleic acid molecule derived from and specific for a particular flagellin gene associated with that H serotype, to any *E. coli* in the sample which contain the gene; and (c) detecting any specifically hybridised nucleic acid molecules.

Preferred nucleic acid molecules for the detection of particular flagellin genes are listed in Table 3.

In one preferred embodiment, the sequence of the nucleic acid molecule specific for the O antigen is specific to the nucleotide sequence encoding the O111 antigen. More preferably, the sequence is derived from a gene selected from the group consisting of wbdH (nucleotide position 739 to 1932 of FIG. 5), wzx (nucleotide position 8646 to 9911 of FIG. 5), wzy (nucleotide position 9901 to 10953 of FIG. 5), wbdM (nucleotide position 11821 to 12945 of FIG. 5) and fragments of those molecules of at least 10–12 nucleotides in length. Particularly preferred nucleic acid molecules are those set out in Tables 8 and 8A, with respect to the above mentioned genes.

In another preferred embodiment, the sequence of the nucleic acid molecule specific for the O antigen is specific to the nucleotide sequence encoding the O157 antigen. More preferably, the sequence is derived from a gene selected from the group consisting of wbdN (nucleotide position 79 to 861 of FIG. 6), wbdO (nucleotide position 2011 to 2757 of FIG. 6), wbdP (nucleotide position 5257 to 6471 of FIG. 6), wbdR (nucleotide position 13156 to 13821 of FIG. 6), wzx (nucleotide position 2744 to 4135 of FIG. 6) and wzy (nucleotide position 858 to 2042 of FIG. 6) and fragments of those molecules of at least 10–12 nucleotides in length. Particularly preferred nucleic acid molecules are those set out in Tables 9 and 9A, with respect to the above mentioned genes.

In one preferred embodiment the detection method is a Southern blot method. More preferably, the nucleic acid molecule is labelled and hybridisation of the nucleic acid molecule is detected by autoradiography or detection of fluorescence.

In a fifth aspect the invention provides a method for detecting the presence of a particular O serotype and H serotype of *E. coli* in a sample, the method comprising the following steps:

(a) specifically hybridising at least one pair of nucleic acid molecules, at least one of which is derived from and specific for a gene encoding a transferase or a gene encoding an enzyme for the transport or processing of a polysaccharide or oligosaccharide unit, the gene being involved in the synthesis of the particular *E. coli* O antigen, to any *E. coli* in the sample which contain the gene;

(b) specifically hybridising at least one pair of nucleic acid molecules, at least one of which is derived from and specific for a particular flagellin gene associated with the particular H serotype, to any *E. coli* in the sample which contain the gene; and (c) detecting any specifically hybridised nucleic acid molecules.

Preferred nucleic acid molecules for the detection of particular flagellin genes are listed in Table 3.

In one preferred embodiment, the sequence of the nucleic acid molecule specific for the O antigen is specific to the nucleotide sequence encoding the O111 antigen. More preferably, the sequence is derived from a gene selected from the group consisting of wbdH (nucleotide position 739 to 1932 of FIG. 5), wzx (nucleotide position 8646 to 9911 of FIG. 5), wzy (nucleotide position 9901 to 10953 of FIG. 5), wbdM (nucleotide position 11821 to 12945 of FIG. 5) and fragments of those molecules of at least 10–12 nucleotides in length. Particularly preferred nucleic acid molecules are those set out in Tables 8 and 8A, with respect to the above mentioned genes.

In another preferred embodiment, the sequence of the nucleic acid molecule specific for the O antigen is specific to the nucleotide sequence encoding the O157 antigen. More preferably, the sequence is derived from a gene selected from the group consisting of wbdN (nucleotide position 79 to 861 of FIG. 6), wbdO (nucleotide position 2011 to 2757 of FIG. 6), wbdP (nucleotide position 5257 to 6471 of FIG. 6), wbdR (nucleotide position 13156 to 13821 of FIG. 6), wzx (nucleotide position 2744 to 4135 of FIG. 6) and wzy (nucleotide position 858 to 2042 of FIG. 6) and fragments of those molecules of at least 10–12 nucleotides in length. Particularly preferred nucleic acid molecules are those set out in Tables 9 and 9A, with respect to the above mentioned genes.

In one preferred embodiment the detection method is a polymerase chain reaction method. More preferably, the nucleic acid molecules are labelled and hybridisation of the nucleic acid molecule is detected by electrophoresis.

The present inventors believe that based on the teachings of the present invention and available information concerning O antigen gene clusters, and through use of experimental analysis, comparison of nucleic acid sequences or predicted protein structures, nucleic acid molecules in accordance with the invention can be readily derived for any particular O antigen of interest. Suitable bacterial strains can typically be acquired commercially from depositary institutions.

There are currently 166 defined *E. coli* O antigens.

Samples of the 166 different *E. coli* O antigen serotypes are available from Statens Serum Institut, Copenhagen, Denmark.

The inventors envisage rare circumstances whereby two genetically similar gene clusters encoding serologically different O antigens have arisen through recombination of genes or mutation so as to generate polymorphic variants. In these circumstances multiple pairs of oligonucleotides may be selected to provide hybridisation to the specific combination of genes. The invention thus envisages the use of a panel containing multiple nucleic acid molecules for use in the method of testing for O antigen in conjunction with H antigen, wherein the nucleic acid molecules are derived from genes encoding transferases and/or enzymes for the transport or processing of a polysaccharide or oligosaccharide unit including wzx or wzy genes, wherein the panel of nucleic acid molecules is specific to a particular O antigen. The panel of nucleic acid molecules can include nucleic acid molecules derived from O antigen sugar pathway genes where necessary.

The inventors also found two mutated flagellin genes from H type strains for H35 and H54 which have insertion sequences inserted into normal flagellar genes identical or near identical to that that of the H11 and H21 type strains respectively. Thus, primers for H11 and H21 (listed in Table 3) would also amplify fragments in H35 and H54, which differ in sizes to those in H11 and H21 respectively. The inventors also provide two pairs of primers each for H35 and H54 based on the insertion sequence (see H35 and H54 columns in Table 3). The use of one of them in combination with one of the H11 or H21 primers will generate a PCR band only in H35 or H54 respectively, and this will also differentiate H35 and H54 from H11 and H21 respectively.

The present invention also relates to methods of detecting the presence of particular *E. coli* H antigens or H antigen and O antigen combinations where one or more nucleic acid molecules which generate a particular size fragment indicative of the presence of that H antigen are used or in which the combination of one antigen specific primer for that H antigen with another primer for a related H antigen provides for the detection of the particular H antigen by hybridisation to the relevant gene. Preferably, the H antigen is H11, H21, H35 or H54.

The pairs of nucleic acid molecules where the method of the fifth aspect is used may both hybridise to the relevant H or O antigen gene or alternatively only one may hybridise to the relevant gene and the other to another site.

The inventors recognise in applying the methods of the invention for detecting combinations of O and H antigens to samples, that the methods do not indicate whether a positive result for a particular O and H antigen combination arises because the O and H antigen are present on a single *E. coli* strain present in the sample or are present on different *E. coli* strains present in the sample. Because the ability to identify the presence of *E. coli* strains with particular O and H antigen combinations is highly desirable (due to the relationship between particular combinations and pathogenicity) the determination that a particular combination is present in a sample can be followed by isolation of single colonies and checking whether the they contain the relevant combination by using the same method again or using antibody labelled magnetic beads to separate cells expressing the particular O or H antigen and then testing the isolated cells for the other serotype.

In addition, as mentioned above, the present inventors have established the existence of H7 primers specific to the O157 and O55 serotypes. Using such primers it is possible to detect particular O and H antigen combinations with the use of H specific nucleic acid molecules.

In a sixth aspect the invention provides a method for detecting the presence of a particular O serotype and H serotype of *E. coli* in a sample, the method comprising the following steps:

(a) specifically hybridising at least one nucleic acid molecule, derived from and specific for a gene encoding a flagellin associated with a particular *E. coli* H antigen serotype to any *E. coli* carrying the gene and present in the sample; and (b) detecting the at least one specifically hybridised nucleic acid molecule, wherein the at least one nucleic acid molecule is specific for the particular combination of O and H antigen.

Preferably the combination is O55:H7 or O157:H7.

The ability to detect the O157:H7 combination from a particular H7 primer or pair is of particular use given the association of this combination with pathogenic strains.

In a seventh aspect the present invention provides a method for testing a food derived sample for the presence of one or more particular *E. coli* O antigens and H antigens comprising testing the sample by a method of the fourth, fifth or sixth aspect the invention.

In an eighth aspect the present invention provides a method for testing a faecal derived sample for the presence of one or more particular *E. coli* O antigens and H antigens comprising testing the sample by a method of the fourth, fifth or sixth aspect the invention.

In a ninth aspect the present invention provides a method for testing a patient or animal derived sample for the presence of one or more particular *E. coli* O antigens and H antigens comprising testing the sample by a method of the fourth, fifth or sixth aspect the invention.

Preferably, the method of the seventh, eighth or ninth aspect of the invention is a polymerase chain reaction method. More preferably the oligonucleotide molecules for use in the method are labelled. Even more preferably the hybridised nucleic acid molecules are detected by electrophoresis.

In the above described methods it will be understood that where pairs of nucleic acid molecules are used one of the nucleic acid molecules may hybridise to a sequence that is not from the O antigen transferase, wzx or wzy gene or the flagellin gene. Further where both hybridise to these genes the O antigen molecules may hybridise to the same or a different one of these genes.

In a tenth aspect the present invention provides a kit for identifying the H serotype of *E. coli*, the kit comprising:

at least one nucleic acid molecule derived from and specific for an *E. coli* flagellin gene.

In an eleventh aspect the present invention provides a kit for identifying the H and O serotype of *E. coli*, the kit comprising:

(a) at least one nucleic acid molecule derived from and specific for an *E. coli* flagellin gene; and (b) at least one nucleic acid molecule derived from and specific for a gene encoding a transferase or a gene encoding an enzyme for the transport or processing of a polysaccharide or oligosaccharide unit, the gene being involved in the synthesis of a particular *E. coli* O antigen.

The nucleic acid molecules may be provided in the same or different vials. The kit may also provide in the same or separate vials a second set of specific nucleic acid molecules.

Particularly preferred nucleic acid molecules for inclusion in the kits are those specified in Tables 3, 8, 8A, 9 and 9A as described above.

Definitions

In this specification, we have used term "flagellin gene" in many cases where previously one would have used "fliC", to allow for the uncertainty as to locus introduced by recent observations. However, uncertainty as to the locus does not alter the fact that most *E. coli* strains express a single H antigen and that a single flagellin gene sequence per strain is required to give the genetic basis for H antigen variation. Any use of the name fliC in this specification where a different locus is later shown to be involved would not affect the validity of conclusions drawn regarding application of information based on the sequence, where the conclusions do not relate to the map position. Thus it is generally the nucleic acid molecule itself which is of importance rather than the name attributed to the gene. When it is known or suspected that the gene encoding the H antigen is not in the fliC locus, we use the term flagellin rather than fliC.

The phrase, "a nucleic acid molecule derived from a gene" means that the nucleic acid molecule has a nucleotide sequence which is either identical or substantially similar to all or part of the identified gene. Thus a nucleic acid molecule derived from a gene can be a molecule which is isolated from the identified gene by physical separation from that gene, or a molecule which is artificially synthesised and has a nucleotide sequence which is either identical or substantially similar to all or part of the identified gene. While some workers consider only the DNA strand with the same sequence as the mRNA transcribed from the gene, here either strand is intended.

Transferase genes are regions of nucleic acid which have a nucleotide sequence which encodes gene products that transfer monomeric sugar units.

Flippase or wzx genes are regions of nucleic acid which have a nucleotide sequence which encodes a gene product that flips oligosaccharide repeat units generally composed of three to six monomeric sugar units to the external surface of the membrane.

Polymerase or wzy genes are regions of nucleic acid which have a nucleotide sequence which encodes gene products that polymerise repeating oligosaccharide units generally composed of 3–6 monomeric sugar units.

The nucleotide sequences provided in this specification are described as anti-sense sequences. This term is used in the same manner as it is used in Glossary of Biochemistry and Molecular Biology Revised Edition, David M. Glick, 1997 Portland Press Ltd., London on page 11 where the term is described as referring to one of the two strands of double-stranded DNA usually that which has the same sequence as the mRNA. We use it to describe this strand which has the same sequence as the mRNA.

| NOMENCLATURE Synonyms for *E. coli* O111 rfb | | |
|---|---|---|
| Current names | Our names | Bastin et al. 1991 |
| wbdH | orf1 | |
| gmd | orf2 | |
| wbdI | orf3 | orf3.4* |
| manC | orf4 | rfbM* |
| manB | orf5 | rfbK* |
| wbdJ | orf6 | orf6.7* |
| wbdK | orf7 | orf7.7* |
| wzx | orf8 | orf8.9 and rfbX* |
| wzy | orf9 | |
| wbdL | orf10 | |
| wbdM | orf11 | |

*Nomenclature according to Bastin D. A., et al. 1991 "Molecular cloning and expression in *Escherichia coli* K-12 of the rfb gene cluster determining the O antigen of an *E. coli* O111 strain". Mol. Microbiol. 5:9 2223–2231.

| Other Synonyms | |
|---|---|
| wzy | rfc |
| wzx | rfbX |
| rmlA | rfbA |
| rmlB | rfbB |
| rmlC | rfbC |
| rmlD | rfbD |
| glf | orf6* |
| wbbI | orf3#, orf8* of *E. coli* K-12 |
| wbbJ | orf2#, orf9* of *E. coli* K-12 |
| wbbK | orf1#, orf10* of *E. coli* K-12 |
| wbbL | orf5#, orf11* of *E. coli* K-12 |

Nomenclature according to Yao, Z. And M. A. Valvano 1994. "Genetic analysis of the O-specific lipopolysaccharide biosynthesis region (rfb) of *Eschericia coli* K-12 W3110: identification of genes the confer groups-specificty to *Shigella flexineri* serotypes Y and 4a". J. Bacteriol. 176: 4133–4143.

*Nomenclature according to Stevenson et al. 1994. "Structure of the O-antigen of *E. coli* K-12 and the sequence of its rfb gene cluster". J. Bacteriol 176: 4144–4156.

• The O antigen genes of many species were given rfb names (rfbA etc) and the O antigen gene cluster was often referred to as the rfb cluster. There are now new names for the rfb genes as shown in the table. Both terminologies haven been used herein, depending on the source of the information.

In the claims that follow and in the summary of the invention, except where the context requires otherwise due to express language or necessary implication, the word "comprising" is used in the sense of "including", i.e. the features specified may be associated with further features in various embodiments of the invention.

BRIEF DESCRIPTION OF THE DRAWINGS

FIG. 5 shows the nucleotide sequence (SEQ ID NO:45) of the *E. coli* O111 O antigen gene cluster. Note: (1) The first and last three bases of a gene are underlined and of italic respectively; (2) The region which was previously sequenced by Bastin and Reeves 1995 "Sequence and anlysis of the O antigen gene (rfb) cluster of *Escherichia coli* O111" Gene 164: 17–23 is marked.

FIG. 6 shows the nucleotide sequence (SEQ ID NO:56) of the *E. coli* O157 O antigen gene cluster. Note: (1) The first and last three bases of a gene (region) are underlined and of italic respectively (2) The region previously sequenced by Bilge et al. 1996 "Role of the *Escherichia coli* O157-H7 O side chain in adherence and analysis of an rfb locus". Inf. and Immun 64:4795–4801 is marked.

FIGS. 7 to 9 show the nucleotide sequences (SEQ ID NOS:66 to 68 respectively) obtained for flagellin genes from *E. coli* type strains for H1 to H3 respectively. The primer positions listed in Table 3 are based on treating the first nucleotide of each of these sequences as No. 1.

FIGS. 10 to 18 show the nucleotide sequences (SEQ ID NOS:6 to 14 respectively) obtained for flagellin genes from *E. coli* type strains for H4 to H12 respectively. The primer positions listed in Table 3 are based on treating the first nucleotide of each of these sequences as No. 1.

FIGS. 19 and 20 show the nucleotide sequences (SEQ ID NOS:15 to 16 respectively) obtained for flagellin genes from *E. coli* type strains for H14 and H15 respectively. The primer positions listed in Table 3 are based on treating the first nucleotide of each of these sequences as No. 1.

FIGS. 22 to 26 show the nucleotide sequences (SEQ ID NOS:17 to 21 respectively) obtained for flagellin genes from *E. coli* type strains for H17 to H21 respectively. The primer positions listed in Table 3 are based on treating the first nucleotide of each of these sequences as No. 1.

FIGS. 27 to 39 show the nucleotide sequences (SEQ ID NOS:22 to 34) obtained for flagellin genes from *E. coli* type strains for H23 to H35 respectively. The primer positions listed in Table 3 are based on treating the first nucleotide of each of these sequences as No. 1.

FIGS. 40 to 49 show the nucleotide sequences (SEQ ID NOS:35 to 44) obtained for flagellin genes from *E. coli* type strains for H37 to H46 respectively. The primer positions listed in Table 3 are based on treating the first nucleotide of each of these sequences as No. 1.

FIGS. 50 to 55 show the nucleotide sequences (SEQ ID NOS:46 to 51) obtained for flagellin genes from *E. coli* type strains for H47 to H52 respectively. The primer positions listed in Table 3 are based on treating the first nucleotide of each of these sequences as No. 1.

FIGS. 56 to 58 show the nucleotide sequences (SEQ ID NOS:52 to 54) obtained for flagellin genes from *E. coli* type strains for H54 to H56 respectively. The primer positions listed in Table 3 are based on treating the first nucleotide of each of these sequences as No. 1.

FIG. 59 shows the nucleotide sequence (SEQ ID NO:55) obtained for the flagellin gene from *E. coli* H7 strain M1179. The primer positions listed in Table 3 are based on treating the first nucleotide of each of these sequences as No. 1.

FIGS. 60 to 68 show the nucleotide sequences (SEQ ID NOS:57 to 65 respectively) obtained for flagellin genes from *E. coli* strains M1004, M1211, M1200, M1686, M1328, M917, M527, M973, and M918 respectively. The primer positions listed in Table 3 are based on treating the first nucleotide of each of these sequences as No. 1.

FIG. 69 shows the nucleotide sequence (SEQ ID NO:1) of the fliC gene and DNA flanking the fliC gene from the H25 type strain.

FIG. 70A shows the nucleotide sequence (SEQ ID NO:2) obtained from the 5' end of the insert of plasmid pPR1989. The insert of plasmid pPR1989 encodes the second flagellin gene of the H55 type strain.

FIG. 70B shows the nucleotide sequence (SEQ ID NO:3) obtained from the 3' end of the insert of plasmid pPR1989. The insert of plasmid pPR1989 encodes the second flagellin gene of the H55 type strain.

FIG. 71 shows the nucleotide sequence (SEQ ID NO:4) obtained from the 5' end of the insert of plasmid pPR1993. The insert of plasmid pPR1993 encodes the second flagellin gene of the H36 strain.

FIG. 72 shows the nucleotide sequence (SEQ ID NO:5) obtained from the 3' end of the insert of plasmid pPR1993. The insert of plasmid pPR1993 encodes the second flagellin gene of the H36 type strain.

FIG. 73 A shows the sequence of polylinker and the SD sequence of plasmid pTrc99A.

FIG. 73B shows the sequence of the junction region between the SD sequence and the start of flagellin gene in the plasmids used for the expression of flagellin genes.

EXAMPLES OF THE INVENTION

Figure 1:
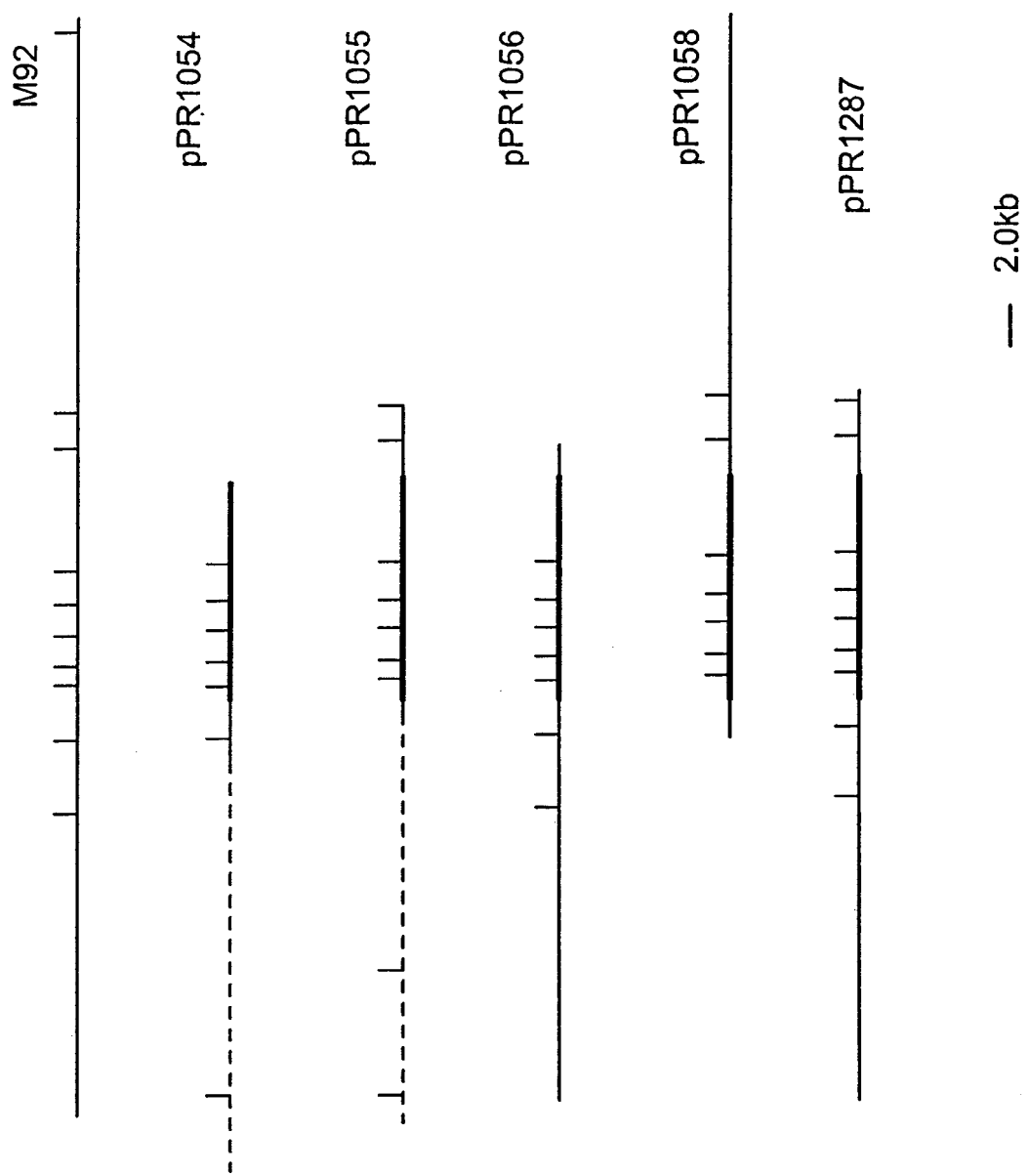
FIG. 1 shows a sequence of the XREM region of the CYP3A4 gene (SEQ ID NO: 1). Base numbering is relative and does not indicate location within the CYP3A4 gene structure.

In carrying out the methods of the invention with respect to the testing of particular sample types including samples from food, patients, animals and faeces the samples are prepared by routine techniques routinely used in the preparation of such samples for DNA based testing. The steps for testing the samples using particular nucleic acid molecules in assay formats such as Southern blots and PCR are performed under routinely determined conditions appropriate to the sample and the nucleic acid molecules.

H Antigen

Materials and Methods

1. Bacterial strains and plasmid:

There are 54 H types in *E. coli* [Ewing, W. H.: Edwards and Ewing's identification of the Enterobacteriaceae., Elsevier Science Publishers, Amsterdam, The Netherlands, 1986]: note H antigens from 1 to 57 were listed and that 13, 22 and 57 are not valid. All the standard H type strains except H16 were obtained from the Institute of Medical and Veterinary Science, Adelaide, Australia. The primary stocks are hold at the Statens Serum Institut, Copenhagen, Denmark.

The additional H7 strains used are listed in Table 1.

We do not have the type strain for H16. It is known that the H3 type strain is biphasic and can also express the H16 flagellin gene [Ratiner, Y. A. (1985) "Two genetic arrangements determining flagellar antigen specificities in two diphasic E. coli strains. FEMS Microbiol Lett 19: 317–323]. We have sequenced and cloned the H16 flagellin gene from the H3 type strain (see below).

E. coli K-12 strain C600 hsm hsr fliC::Tn10 [Kuwajiwa, G. (1988) "Flagellin domain that affects H antigenicity of E. coli K-12" J. Bacteriol. 170; 485–488] (laboratory stock no. M2126) was obtained from Dr Benita Westerlund-Wikstrom of the Department of Biosciences, University of Helsinkin, Finland. E. coli K-12 strain EJ2282 (laboratory no. P5560) is a fliC deletion strain, and was obtained from Dr Masatoshi Enomoto of the Department of Biology, Okayama University, Japan [Tominaga, A. M. A.-H. Mahmound, T. Mokaihara and M. Enomoto (1994) "Molecular characterization of intact but cryptic, flagellin genes in the genus Shigella.: Mol. Microbiol. 12: 277–285].

Plasmid pTrc99A was purchased from Pharmacia LKB (Melbourne, VIC, Australia).

2. Antisera

Antisera against H1, H3, H8, H14, H15, H17, H23, H24, H25, H26, H29, H30, H31, H32, H33, H35, H36, H37, H38, H39, H43, H44, H46, H47, H48, H49, H52, H53, H54, H55, and H56 were obtained from the Institute of Medical and veterinary Science, Adelaide, Australia. Antisera against H2, H4, H5, H6, H7, H9, H10, H11, H12, H16, H18, H19, H20, H21, H27, H28, H34, H40, H41, H42, H45, and H51 were obtained from Denka Seiken Co., Ltd, Tokyo, Japan.

Antisera to type H50 was not available from any known source.

The antisera available were checked against the appropriate type strains to confirm the specificities of both flagellin H antigen and H antisera: 52 sera (all those except anti-H16 serum listed above) gave a positive reaction with the corresponding type strains for that serum.

3. Agglutination test:

Bacteria from 1 ml of an overnight culture grown in Luria broth (Difco Tryptone, 10 g/l; Difco yeast extract, 5 g/l; NaCl, 0.5 g/l; pH 7.2) at 30° C. was centrifuged (4000 rpm/10 min) and the bacteria pellet resuspended in 100 ml of saline. The agglutination test was carried out by mixing equal volumes (5 ml) of both the cells and antiserum on a slide. The slide was rocked for 1 minute and then observed for agglutination. For all agglutination tests, saline containing no antiserum was mixed with cells to be used as a negative control.

For testing the H specificities of strain M2126 or strain P5560 carrying plasmid containing cloned flagellin genes, cells of M2126 or P5560 were used as an additional negative control.

All agglutination tests were first carried out using undiluted antisera (note that the antisera we used have been diluted before reaching our hands), except for anti-H11, anti-H34, anti-H52 and anti-H26 serum for which we used 1:10 dilutions to avoid background agglutination. In cases for which cross-reactions have been reported, we carried out agglutination tests using serial dilutions of sera (see section 10.1)

4. Motility test:

The motility of strain M2126 or strain P5560 carrying cloned flagellin genes was examined microscopically. 1 ml of overnight culture grown in Luria broth (Difco Tryptone, 10 g/l; Difco yeast extract, 5 g/l; NaCl, 0.5 g/l; pH 7.2) at 30° C. was inoculated into 10 ml of Luria broth, and the culture was shaken at 100 rpm at 30° C. to early log phase (OD 625=0.2). A loopful of culture was placed on a slide and examined under a microscope. Motility of individual cells was easily distinguished from Brownian movement and streaming, and presence or absence of motility recorded.

5. Isolation of chromosomal DNA:

Chromosomal DNA from all the 53 H type strains and the strains listed in Table 1 was isolated using the Promega Genomic isolation kit (Madison Wis. USA). Each chromosomal DNA sample was checked by gel electrophoresis of the DNA and by PCR amplification of the mdh gene using oligonucleotides based on the E. coli K-12 mdh gene [Boyd, E. F., Nelson, K., Wang, F.-S., Whittam, T. S. and Selander, R. K.: Molecular genetic basis of allelic polymorphism in malate dehydrogenase (mdh) in natural populations of Escherichia coli and Salmonella enterica. Proc. Natl. Acad. Sci. USA 91 (1994) 1280–1284].

6. PCR amplification of flagellin gene:

Flagellin genes from different strains were first PCR amplified using one of the following four pairs of oligonucleotides:

1285 (SEQ ID NO:77) (5'-atggcacaagtcattaatac)

and

1286 (SEQ ID NO:78) (5'-ttaaccctgcagtagagaca);

1417 (SEQ ID NO:79) (5'-ctgatcactcaaaataatatcaac)

and

1418 (SEQ ID NO:80) (5'-ctgcggtacctggttggc);

1431 (SEQ ID NO:81) (5'-atggcacaagtcattaatacccaac)

and

1432 (SEQ ID NO:82) (5'-ctaaccctgcagcagagaca):

1575 (SEQ ID NO:83) (5'-gggtggaaacccaatacg)

and

1576 (SEQ ID NO:84) (5'-gcgcatcaggcaatttgg)

PCR reactions were carried out under the following conditions: denaturing, 94° C./30'; annealing, temperature varies (refer to Table 2)/30'; extension, 72° C./1'; 30 cycles. The PCR product was purified using the Promega Wizard PCR purification kit (Madison Wis. USA) before being sequenced.

The H36 and H53 type strains gave two PCR bands using primer pairs #1431/#1432 (SEQ ID NOS:81/82) and #1417/#1418 (SEQ ID NOS:79/80) respectively, and were not sequenced.

7. Enzymes and buffers:

Restriction endonucleases and DNA T4 ligase were purchased from Boehringer Mannheim (Castle Hill, NSW, Australia). Restriction enzymes were used in the recommended commercial buffer.

8. Sequencing of the flagellin genes:

Each PCR product was first sequenced using the oligonucleotide primers used for the PCR amplification. Primers based on the obtained sequence were then used to sequence further, and this procedure was repeated until the entire PCR product was sequenced.

The sequencing reactions were performed using the DyeDeoxy Terminator Cycle Sequencing method (Applied Biosystems, CA, USA), and reaction products were analysed using fluorescent dye and an ABI377 automated sequencer (CA, USA).

Sequence data were processed and analysed using Staden programs [Sacchi C T, Zanella R C, Caugant D A, Frasch C E, Hidalgo N T, Milagres L G, Pessoa L L, Ramos S R, Camargo M C C and Melles C E A "Emergence of a new clone of serogroup C *Neisseria meningitidis* in Sao Paulo, Brazil" J. Clin. Microbiol. 30 (1992) 1282–1286; Staden, R.: Automation of the computer handling of gel reading data produced by the shotgun method of DNA sequencing. Nucl. Acids Res. 10 (1982a) 4731–4751; Staden, R.: An interactive graphics program for comparing and aligning nucleic acid and amino acid sequences. Nucl. Acids Res. 10 (1982b) 2951–2961;

Staden, R.: Computer methods to locate signals in nucleic acid sequences. Nucl. Acids Res. 12 (1984a) 505–519;

Staden, R.: Graphic methods to determine the function of nucleic acid sequences. A summary of ANALYSEQ options. Nucl. Acids Res. 12 (1984b) 521–538;

Staden, R.: The current status and portability of our sequence handling software. Nucl. Acids Res. 14 (1986) 217–231].

We were able to PCR amplify flagellin genes from H type strains for H7, 23, 12, 51, 45, 49, 19, 9, 30, 32, 26, 41, 15, 20, 28, 46, 31, 14, 18, 6, 34, 48, 43, 10, 52, and also from H7 strains m1004, m527, m1686, m1211, m1328, m973, m1179, m1200, m917, and m918 using primers #1575 (SEQ ID NO:83) and #1576 (SEQ ID NO:84) which are based on sequences 51–34 bp upstream and 37–54 bp downstream of start and end of the *E. coli* K-12 fliC gene respectively. Thus, the full sequence of the flagellin gene from these strains was obtained and the use of flanking sequence for primers makes it highly likely that they are at the fliC locus.

For other strains, we were only able to amplify the flagellin gene using one or more of the other three pairs of primers, which are based on sequence within the fliC gene, and thus only partial sequence was obtained. These amplicons may be of the fliC gene or one of the alternative flagellin genes. The flagellin gene sequences from H type strains for H40, 8, 21, 47, 11, 27, 35, 2, 3, 24, 37, 50, 4, 44, 38, 55, 29, 33, 5, and 56 obtained are lacking 18 and 14 codons at 5' and 3' ends respectively. The flagellin gene sequence of H39 obtained using primers #1285/#1286 (SEQ ID NOS:77/78) lacks 18 and 19 codons at 5' and 3' ends respectively. The flagellin gene sequence of H type strains of H17, 25 and 42 lack 23 and 21 codons at 5' and 3' ends respectively. The flagellin gene sequence of the H type strain for H54 lacks 23 and 12 codons at the 5' and 3' ends respectively. There is very little variation in the sequence at the two ends of flagellin genes and antigenic variation is due to variation in the central region of the gene. The absence of sequence for the ends of some of the flagellin genes is not important for the purpose of the present invention relating to the detection of antigenic variation by DNA sequence based means.

The fliC genes from H type strains of H1, H7 and H12 have been sequenced previously [Schoenhals, G. and Whitfield, C.: Comparative analysis of flagellin sequences from *Escherichia coli* strains possessing serologically distinct flagellar filaments with a shared complex surface pattern. J. Bacteriol. 175 (1993) 5395–5402] and we did not sequence the gene from the H1 strain.

We have sequenced fliC genes from a set of H7 strains with different O antigens, including that of fliC from the H7 type strain as one of the set: we have found four differences from the published H7 sequence (GenBank accession number L07388) which we believe are due to errors in the published sequence.

We have also re-sequenced the fliC gene from the H12 type strain, and have found one difference from the published H12 sequence (GenBank accession number L07389) which we believe is due to an error in the published sequence.

The flagellin genes from type strains H35 and H54 were also amplified using primers #1431/#1432, which are based on sequence within the fliC gene. Sequence data revealed that these two genes would be non-functional due to insertion sequence inserted in the middle of them. We have sequenced them to facilitate selection of primers for the functional flagellin genes.

9. Cloning of flagellin genes

DNA was digested for 2 hr at 37° C. with appropriate restriction enzyme(s). The reaction product was then extracted once with phenol, and twice with ether. DNA was precipitated with 2 vols of ethanol and resuspended in water before the ligation reaction was carried out. Ligation was carried out O/N at 4° C. and the ligated DNA was electroporated into one of the *E. coli* fliC mutant strains.

9.1. Cloning of flagellin genes from type strains for H1, H2, H3, H5, H6, H7, H9, H10, H11, H12, H14, H15, H18, H19, H20, H21, H24, H26, H27, H28, H29, H31, H34, H38, H39, H41, H42, H43, H45, H46, H49, H51, H52, and H56:

The full flagellin gene was PCR amplified using primers #1868 (SEQ ID NO:69) and #1870 (SEQ ID NO:71) (Table 3A). Both these primers are based on the sequences of the H7 flagellin gene of the H7 type strain. #1868 (SEQ ID NO:69) is the 5' primer: there is an NcoI site incorporated into the primer (Table 3B) and the flagellin gene starts at base 3 of the NcoI site. The 3' primer #1870 (SEQ ID NO:71) has a BamHI site incorporated downstream of the stop codon of the flagellin gene (Table 3B). PCR reactions were carried out under the following conditions: denaturing, 94° C./30'; annealing, temperature varies (refer to Table 3A)/30'; extension, 72° C./1'; 30 cycles. The PCR product was purified using the Promega Wizard PCR purification kit (Madison Wis. USA) before being digested by restriction enzymes NcoI and BamHI and cloned into the NcoI/BamHI sites of plasmid pTrc99A.

Plasmid pTrc99A has a strong trc promoter upstream of the polylinker. Downstream of the promoter, it contains the ribosome binding site (SD sequence, see FIG. 73) which is located 8 bp upstream of the ATG site within the NcoI site. The polylinker and the SD sequence of pTrc99A are shown in FIG. 73.

The plasmids generated were given pPR numbers, and they are listed in Table 3A. In these plasmids, the expression module consists of the trc promoter, the SD sequence, and the full flagellin gene. The sequence of the junction region between the SD sequence and the start of flagellin gene is shown in FIG. 73.

For flagellin genes from type strains for H6, H7, H9, H10, H12, H14, H18, H19, H20, H26, H28, H31, H41, H43, H45, H46, H49, H51, and H52, we have the full sequence for each gene and the primer sequences (#1868 (SEQ ID NO:69) and #1870 (SEQ ID NO:71)) are conserved among them. The cloned genes therefore have the same sequence as those from the type strains.

For flagellin genes from type strains for H1, H15 and H34, we also have the full sequence. The previously published sequence of the flagellin gene from the H1 type strain was extracted from GenBank (accession number L07387) and used. Primer #1868 (SEQ ID NO:69) is conserved in all three. But, primer #1870 (SEQ ID NO:71) has the third base of the fifth last codon in the H1 sequence changed from A to G, and the third base of the second last codon changed from C to T in the H15 and H34 sequences: these changes did not change the amino acid coded, so the cloned genes encode the same gene products as those of the type strains.

For flagellin genes from type strains for H2, H3, H5, H11, H21, H24, H27, H29, H38, H39, H42, and H56, we do not have the full sequences. In the plasmids carrying genes from these type strains, the expression module consists of the trc promoter, the SD sequence, and the full flagellin gene with the first and the last 21 base pairs being determined by the primer sequences which are based on the H7 flagellin gene of the H7 type strain. The sequence of the junction region between the SD sequence and the start of flagellin gene is shown in FIG. 73.

9.2. Cloning of the flagellin gene from type strain of H23:

The full flagellin gene was PCR amplified using primers #1868 (SEQ ID NO:69) and #1869 (SEQ ID NO:70)(Table 3A). #1868 (SEQ ID NO:69) is the 5' primer: there is an NcoI site incorporated into the primer (Table 3B) and the flagellin gene starts at base 3 of the NcoI site. The 3' primer #1869 (SEQ ID NO:70) has a SalI site incorporated downstream of the stop codon of the flagellin gene (Table 3B). PCR reactions were carried out under the following conditions: denaturing, 94° C./30'; annealing, 55° C./30'; extension, 72° C./1'; 30 cycles. The PCR product was purified using the Promega Wizard PCR purification kit (Madison Wis. USA) before being digested by restriction enzymes NcoI and SalI and cloned into the NcoI/SalI sites of plasmid pTrc99A to give plasmid pPR1942.

Plasmid pTrc99A has a strong trc promoter upstream of the polylinker. Downstream of the promoter, it contains the ribosome binding site (SD sequence, see FIG. 73) which is located 8 bp upstream of the ATG site within the NcoI site. The polylinker and the SD sequence of pTrc99A are shown in FIG. 73.

The expression module of pPR1942 consists of the trc promoter, the SD sequence, and the full flagellin gene. The sequence of the junction region between the SD sequence and the start of flagellin gene is shown in FIG. 73.

9.3. Cloning of flagellin genes from type strains of H30, H32 and H33:

The full flagellin gene was PCR amplified using primers #1868 (SEQ ID NO:69) and #1871 (SEQ ID NO:72)(Table 3A). #1868 (SEQ ID NO:69) is the 5' primer: there is an NcoI site incorporated into the primer (Table 3B) and the flagellin gene starts at base 3 of the NcoI site. The 3' primer #1871 (SEQ ID NO:72) has a PstI site incorporated downstream of the stop codon of the flagellin gene (Table 3B). PCR reactions were carried out under the following conditions: denaturing, 94° C./30'; annealing, temperature varies (refer to Table 3A)/30'; extension, 72° C./1'; 30 cycles. The PCR product was purified using the Promega Wizard PCR purification kit (Madison Wis. USA) before being digested by restriction enzymes NcoI and PstI and cloned into the NcoI/PstI sites of plasmid pTrc99A.

Plasmid pTrc99A has a strong trc promoter upstream of the polylinker. Downstream of the promoter, it contains the ribosome binding site (SD sequence, see FIG. 73) which is located 8 bp upstream of the ATG site within the NcoI site. The polylinker and the SD sequence of pTrc99A are shown in FIG. 73.

For flagellin genes from type strains for H30 and H32, we have the full sequence. Primer #1868 (SEQ ID NO:69) sequence is conserved in both of them. But, primer #1871 (SEQ ID NO:72) has the third base of the fourth last codon in both sequences changed from G to A to remove a PstI site (see Table 3B): this change did not change the amino acid coded. The expression module consists of the trc promoter, the SD sequence, and the full flagellin gene coding for a gene product which is same as that of the type strain. The sequence of the junction region between the SD sequence and the start of flagellin gene is shown in FIG. 73.

We do not have the full sequence for the flagellin gene from the H33 type strain. In the plasmid containing the H33 type strain gene, the expression module consists of the trc promoter, the SD sequence, and the full flagellin gene with the first and the last 21 base pairs been determined by the primer sequences which were used for the cloning of H30 and H32. The sequence of the junction region between the SD and the start of flagellin gene is shown in FIG. 73.

9.4. Flagellin genes from type strains for H4 and H17:

For the flagellin genes of H4 and H17 type strains the full sequence was not obtained, and the sequenced parts were PCR amplified and cloned into plasmid pPR1951 to give in each case a gene in which the first 26 and the last 31 codons are based on the sequence of the H7 flagellin gene of the H7 type strain.

9.4.1 Construction of expression plasmid vector pPR1951:

The first 26 codons of the H7 flagellin gene was first PCR amplified using primers #1868 (SEQ ID NO:69) and #1872 (SEQ ID NO:73)(Table 3B). #1868 (SEQ ID NO:69) is the 5' primer: there is an NcoI site incorporated into the primer (Table 3B) and the flagellin gene starts at base 3 of the NcoI site. Primer #1872 (SEQ ID NO:73) was made to have the last two codons (codons 25 and 26) changed from CTG TCG (Leucine and Serine) to GGA TCC (Glycine and Serine) to generate a BamHI site. This PCR fragment was digested with NcoI and BamHI before being cloned into the NcoI/BamHI sites of pTrc99A to make plasmid pPR1949.

The last 31 codons (including the stop codon) of the H7 flagellin gene was PCR amplified using primers #1884 (SEQ ID NO:75) and #1871 (SEQ ID NO:72) (Table 3A). The 5' primer, #1884 (SEQ ID NO:75), has the first two of the 31 codons changed from TCG AAA (Serine and Lysine) to TCT AGA (Serine and Arginine) to generate a XbaI site (Table 3B). The 3' primer #1871 (SEQ ID NO:72) has a PstI site incorporated downstream of the stop codon (Table 3B). This PCR fragment was digested with XbaI and PstI, and then cloned into the XbaI/PstI sites of pPR1949 to make plasmid pPR1951.

9.4.2 Cloning of flagellin genes from the H4 and H17 type strains:

The central regions of flagellin genes from type strains H4 and H17 were PCR amplified using primers #1878 (SEQ ID NO:74) and #1885 (SEQ ID NO:76) (Table 3B), which have a BamHI and a XbaI incorporated at their ends respectively. PCR reactions were carried out under the following conditions: denaturing, 94° C./30'; annealing, 65° C./30'; extension, 72° C./1'; 30 cycles. The PCR product was purified using the Promega Wizard PCR purification kit (Madison Wis. USA) before being digested by restriction enzymes BamHI and XbaI and cloned into the XbaI/BamHI sites of plasmid pPR1951 to make plasmids pPR1955 (H4) and pPR1957 (H17).

The expression module of plasmids pPR1955 and pPR1957 consists of the trc promoter, the SD sequence, the first 24 codons of the H7 flagellin gene (of the H7 type strain), 2 codons encoding Glycine and Serine, 292 or 293 codons of the central region based on the flagellin gene obtained from the H4 or H17 type strain respectively, 2 codons encoding Serine and Arginine, and then the last 29 codons of the H7 flagellin gene (of the H7 type strain).

10. Expression of flagellin gene plasmids in *E. coli* strains lacking the fliC gene, and identification of the H antigens encoded by these plasmids:

Plasmids carrying flagellin genes as described in section 9 (see Table 3A for a list) were electroporated into strains M2126 or P5560. Strains M2126 and P5560 do not have functional fliC genes, and are not motile when examined under a microscope. Transformants carrying any of the plasmids listed in Table 3A are motile when examined under a microscope. Thus, the flagellin genes in all of the plasmids are expressed.

The antigenic specificity of the flagellin of each transformant was then determined by slide agglutination.

10.1 Flagellin genes from type strains for H2, H5, H6, H7, H9, H11, H14, H15, H18, H19, H20, H21, H23, H24, H26, H27, H28, H29, H30, H31, H32, H33, H34, H39, H41, H42, H43, H45, H46, H49, H51, H52, and H56:

As shown in Table 3A, strains with plasmids carrying these flagellin genes expressed the same H antigen as their respective flagellin parent strain.

For flagellin specificities H2, H5, H6, H7, H9, H14, H15, H18, H19, H20, H23, H24, H26, H27, H28, H29, H31, H33, H39, H51, H52, and H56, there was no cross reaction reported between these flagellins and flagellin antisera for other H antigens [Ewing, W. H.: Edwards and Ewing's identification of the Enterobacteriaceae., Elsevier Science Publishers, Amsterdam, The Netherlands, 1986], and we conclude that we have in each case sequenced the gene encoding the flagellin of the expected specificity from the respective type strain.

It has been observed that cross reactions exist between some type strains and certain antisera at different levels of dilution (of the antisera), being H11 with anti-H21 and anti-H40, H21 with anti-H11, H30 with anti-H32, H32 with anti-H30, H34 with anti-H24 and anti-H31, H41 with anti-H37 and anti-H39, H42 with anti-H6, H43 with anti-H37, H45 with anti-H20, H46 with anti-H17, and H49 with anti-H39 [Ewing, W. H.: Edwards and Ewing's identification of the Enterobacteriaceae., Elsevier Science Publishers, Amsterdam, The Netherlands, 1986]. We have tested strain M2126 or strain P5560 carrying plasmids containing flagellin genes obtained from each of these type strains (H11, H21, H30, H32, H34, H41, H42, H43, H45, H46, and H49) with the appropriate cross-reacting antisera.

For strain M2126 or strain P5560 carrying plasmids containing flagellin genes obtained from type strains H11, H34, H41, H42, H43, H45, H46, and H49, no cross reaction was found. We conclude that we have in each case sequenced the gene coding the flagellin of the expected specificity from the respective type strain.

Cross reaction was observed for strain P5560 carrying plasmid pPR1948 (containing the flagellin gene obtained from the H30 type strain) with anti-H32 serum, strain P5560 carrying pPR1940 (containing the flagellin gene obtained from the H32 type strain) with anti-H30 serum, and strain M2126 carrying plasmid pPR1995 (containing the flagellin gene obtained from the H21 type strain) with anti-H11 serum.

We note that the reported cross reactions between the H30 type strain and anti-H32, the H32 type strain and anti-H30, and the H21 type strain and anti-H11 happened at a higher level of dilution (of antisera) than for all other type strains with the antisera mentioned above [Ewing, W. H.: Edwards and Ewing's identification of the Enterobacteriaceae., Elsevier Science Publishers, Amsterdam, The Netherlands, 1986]. We conclude that except for these three cases, the antiserum used were supplied at a dilution which did not exhibit cross reactions. For the three strains carrying flagellin genes cloned form type strains for H30, H32, and H21, it was necessary to further dilute the antiserum.

Strain P5560 carrying plasmid pPR1948 (containing the flagellin gene obtained from the H30 type strain) agglutinates with anti-H30 serum when the antiserum is diluted to 1:60, but agglutinates with anti-H32 serum only at a dilution of 1:10 and not at a 1:20 dilution (note that the antisera we used have been diluted before reaching our hands). In contrast, strain P5560 carrying plasmid pPR1940 (containing flagellin gene obtained from the H32 type strain) agglutinates with anti-H32 serum when the antiserum is diluted at 1:100, but agglutinates with anti-H30 serum only at a 1:10 dilution and not at a 1:10 dilution. Thus, we conclude that the flagellin genes we sequenced from type strains for H30 and H32 encode flagellins of H30 and H32 specificities respectively.

Strain M2126 carrying plasmid pPR1995 (containing the flagellin gene obtained from the H21 type strain) agglutinates with anti-H21 serum when the antiserum is diluted to 1:40, but agglutinates only with undiluted anti-H11 serum and not at a 1:10 dilution (note that the antisera we used have been diluted before reaching our hands). In contrast, strain M2126 carrying plasmid pPR1981 (containing flagellin gene obtained from the H11 type strain) did not agglutinate with anti-H21 serum. Thus, we conclude that the flagellin genes we sequenced from type strains for H21 encodes flagellin of H21 specificity.

10.2 Flagellin genes from type strains of H1 and H12:

These two genes are very similar in sequence, with 8 a.a difference between the gene products. It has been known that some cross-reaction exists between anti-H12 serum and the H1 type strain and between anti-H1 serum and the H12 type strain [Ewing, W. H.: Edwards and Ewing's identification of the Enterobacteriaceae., Elsevier Science Publishers, Amsterdam, The Netherlands, 1986]. Strain M2126 carrying pPR1920 (carrying a flagellin gene from the H1 type strain, Table 3A) agglutinates with anti-H1 serum when the antiserum is diluted to 1:100, but agglutinates only with undiluted anti-H12 serum and not at a 1:10 dilution (please note that the antisera we used have been diluted before reaching our hands). In contrast, strain M2126 carrying plasmid pPR1990 (carrying a flagellin gene from the H12 type strain, Table 3A) agglutinates with anti-H12 serum when the antiserum is diluted at 1:100, but agglutinates only with undiluted anti-H1 serum and not at a 1:10 dilution. Thus, we conclude that the flagellin genes we sequenced from type strains for H1 and H12 encode flagellins of H1 and H12 specificities respectively.

10.3. Flagellin gene coding for H16:

Strain P5560 carrying plasmid pPR1969 agglutinated with anti-H16 serum. pPR1969 carries a flagellin gene amplified from the H3 type strain. It has been shown that this H3 type strain is a biphasic strain which can express H3 and H16 specificities [Ratiner, Y. A. (1985) "Two genetic arrangements determining flagellar antigen specificities in two diphasic *E. coli* strains. FEMS Microbiol Lett 19: 317–323]. Thus, the H3 type strain has two flagellin genes coding for H3 and H16 specificities. We conclude that we have cloned and sequenced the H16 flagellin gene from this H3 type strain.

10.4 Flagellin gene coding for H4:

The flagellin genes obtained from type strains for H4 and H17 are nearly identical, with 4 a.a. difference in the gene products. Plasmid pPR1955 carries a flagellin gene from the H4 type strain, and plasmid pPR1957 carries a flagellin gene from the H17 type strain. Strain P5560 carrying plasmid pPR1955 or plasmid pPR1957 agglutinated with anti-H4 serum, but not with anti-H17 serum. It has been shown that the type strain for H17 is a biphasic strain which can express H17 and H4 [Ratiner, Y. A. (1985) "Two genetic arrangements determining flagellar antigen specificities in two diphasic *E. coli* strains. FEMS Microbiol Lett 19: 317–323]. The flagellin gene obtained from type strain for H44 is also highly similar to that obtained from the H4 type strain, with 2 a.a. difference in the gene products. It has been shown that the H44 type strain has two complete flagellin genes, being H4 and H44 [Ratiner, Y. A. (1998) "New flagellin specifying genes in some *E. coli* strains" J. Bacteriol 180: 979–984]. Thus, we conclude that all the three flagellin genes (obtained from type strains for H4, H17 and H44, and sequenced) encode the H4 flagellin, and that the flagellin genes for H17 and H44 specificities have not yet been cloned.

10.5 Flagellin gene coding for H10:

The flagellin genes obtained from type strains for H10 and H50 are nearly identical, with 3 a.a. difference in the gene products. Strain P5560 carrying plasmid pPR1923 (which carries a flagellin gene from the H10 type strain) agglutinated with anti-H10 serum. We conclude that the sequence obtained from the H10 type strain encodes the H10 flagellin. It is not clear if the sequence obtained from the H50 type strain encodes H10 or H50 (see below section for H50).

10.6 Flagellin gene coding for H38:

The flagellin genes obtained from type strains for H38 and H55 are nearly identical, with only 1 a.a. difference in the gene products. Strain M2126 carrying plasmid pPR1984 (carrying the flagellin gene from the type strain H38) agglutinated with anti-H38 serum, but not with anti-H55 serum. It also has been shown that the type strain for H55 has two complete flagellin genes coding for H55 and H38 specificities [Ratiner, Y. A. (1998) "New flagellin specifying genes in some *E. coli* strains" J. Bacteriol 180: 979–984]. Thus, we conclude that both cloned genes encode the H38 flagellin.

10.7 Summary:

Flagellin genes coding for 39 H antigens have been identified, being those for specificities H1, H2, H4, H5, H6, H7, H9, H10, H11, H12, H14, H15, H16, H18, H19, H20, H21, H23, H24, H26, H27, H28, H29, H30, H31, H32, H33, H34, H38, H39, H41, H42, H43, H45, H46, H49, H51, H52, and H56.

11. Comparison and alignment of the flagellin genes:

Programs Pileup [Devereux, J., Haeberli, P. and Smithies, O.: A comprehensive set of sequence analysis programs for the VAX. Nucl. Acids Res. 12 (1984) 387–395] and Multicomp [Reeves, P. R., Farnell, L. and Lan, R.: MULTICOMP: a program for preparing sequence data for phylogenetic analysis. CABIOS 10 (1994) 281–284] were used.

The previously published sequence of H1 (GenBank accession number L07387) was extracted from GenBank and used. Because we did not sequence H36 and H53 flagellin genes and we did not have the H16 type strain, we only compared 51 flagellin genes of H type strains and the fliC genes from the additional 10 H7 strains.

Among the H7 fliC genes, the percentage of DNA difference ranged from 0.0 to 2.39%. The flagellin genes from type strains for H40 and H8 are identical. Some others are nearly identical: H21 and H47 (1.5% difference), H12 and H1 (2.6% difference), H10 and H50 (0.3% difference), H38 and H55 (0.1% difference), H4, H44 and H17 are very similar, the pairwise difference ranging from 0.33% to 0.87%.

For the flagellin genes obtained from type strains for H4, H17 and H44, we have shown that all the three genes encode flagellin with the H4 specificity (see above). For the flagellin genes obtained from type strains for H21 and H47, and H38 and H55, we have confirmed the specificities for one for each pair and have good reason to conclude that both genes of each pair encode the same H specificity (see above section), being that for H21 and H38 specificities respectively.

For the flagellin genes obtained from type strains for H10 and H50, we have confirmed that the one from the H10 type strain encodes H10 specificity. As these two genes are highly similar, we have presumed that they both encode H10 specificity.

In the cases where the flagellin gene from two type strains is near identical, we conclude that both genes code for flagellin of the same H specificity and that one or other strain has an additional locus which carries the functional gene, although the flagellin genes sequenced do not appear to be mutated.

We have shown by cloning and expression that the flagellin genes obtained from the H1 and H12 type strains encode H1 and H12 specificities respectively (see above section). The nucleotide difference between these two genes is higher at 2.6% (see above), but still within the normal range for variation within a gene in *E. coli*. The two antigens cross react, and this cross reaction must be due to the high level similarity of the flagellins encoded by these two genes.

As discussed above, genes encoding some H antigens have been shown to be located at loci other than fliC. H3, H36, H47, H53 have been shown to be at a locus called flkA, H44 and H55 at fllA, and H54 at flmA [Ratiner Y A (1998) "New flagellin-specifying genes in some *Escherichia coli* strains" J. Bacteriol. 180 979–984]. However, these strains may carry a fliC in addition to flkA, fllA or flmA [Ratiner Y A (1998) "New flagellin-specifying genes in some *Escherichia coli* strains" J. Bacteriol. 180 979–984].

The flagellin gene encoding H48 was previously sequenced from *E. coli* strain K-12 [Kuwajima G, Asaka J, Fujiwara T, Node K and Kondo E "Nucleotide sequence of the hag gene encoding flagellin of *Escherichia coli*" J. Bacteriol. 168 (1986) 1479–1483]. We have sequenced the fliC gene from the H48 type strain, and found that it is identical to that from K-12.

The H54 gene is known to be at flmA [Ratiner Y A (1998) "New flagellin-specifying genes in some *Escherichia coli* strains" J. Bacteriol. 180 979–984] and the finding of a non-functional presumptive fliC locus in the H54 strain shows that it is present but not expressed. However, we have not amplified and sequenced the functional flmA gene of this strain.

Using the 43 unique sequences (being the 39 identified genes with confirmed specificities and the flagellin genes obtained from the H8 (or H40), H25, H37, and H48 type strains) and the sequences from the two non-functional flagellin genes (from H type strains H35 and H54)(see Table 3) we have been able to determine antigen specific primers for each of the H antigen specificities and thereby show that it is practicable to detect *E. coli* strains carrying specific H antigens without false positives from strains of other H types. There is no reason to expect that the addition of 11 sequences to the 43 unique sequences obtained will affect the general conclusion, as unlike previous reports, our study covers flagellin sequences for a substantial majority of known *E. coli* H antigen specificities.

Our study of 11 H7 genes from strains of eight different O antigens shows limited variation which was such that the variation within genes for H antigens does not affect the ability to select antigen specific primers. O:H combinations in general define a strain and as some of the strains thus defined were quite distant from each other in a study by Whittam [Whittam T S, wolfe M L, Wachsmuth I K, Orskov I and Wilson R A "Clonal relationships among *Escherichia coli* strains that cause hemorrhagic colitis and infantile diarrhea" Infect. Immun. 61 (1993) 1619–1629] the variation we observe is thought to represent that generally present in H7 genes. We also obtained more than one sequences for flagellin genes for H specificities H4, H10, and H38, and again the level of variation within a given specifities is very low. However, there is a low possibility that primers chosen without knowledge of the variation within genes of each H specificity could fail to give positive results with some isolates due to chance choice of primers which cover a base or bases which contribute to this low level variation. The variation within the H7 genes is in the normal range for variation within a gene in *E. coli* and if this possibility did occur it would be easy to use an alternate primer pair. For example, if a first primer in a primer pair is unable to hybridise to a target region because of low level variation in that region, a positive result may be achieved by using a second primer in that pair together with a third primer, whether or not the third primer is specific for the flagellin gene. Where the third primer is not specific for the flagellin gene, the specificity of the primer pair derives from the specificity of the second primer. The observation that the overall level of variation within gene for a given H specificity is very low making it extremely unlikely that the regions covered by the two primers specific for H specificity would both have undergone change in the same strain.

There are 54 known H antigens for *E. coli* and of these there are 11 H antigen specificities for which we do not as yet have sequence. It will be easy to determine these sequences and determine primer pairs specific for these H antigens by comparing these sequences with the 45 obtained sequences (see Table 3), and also modify the primers selected for any H antigen for which we already know the sequence in the unlikely event that there is a possibility of false positives with the primers selected.

The sequences for the remaining H antigens can be obtained in one of the following ways:

1. where we have two bands by PCR(H36 and H53 type strains), we purify each and sequence, and also clone each into a strain mutated in its fliC gene and determine the H antigen expressed by use of specific sera. In this way a specific sequence can be related to an H antigen specificity. The other band which represents an H antigen gene for a different specificity is expected to include a mutant gene or a gene similar to one of those for a known H specificity, but if not may represent a new specificity for which primer pairs could be selected. It may be difficult to obtain expression of flagellin genes when cloned from *E. coli* due to cloning together with regulatory sequences which prevent expression. This is easily avoided by cloning the major segment of the gene into a functioning fliC gene to replace the equivalent segment of that gene, using standard site directed mutagenesis to give suitable restriction sites within the cloned gene and incorporating those restriction sites into primers used to amplify the major segment of the gene to be studied to facilitate the cloning. We have cloned and sequenced the PCR bands from the H36 and the H55 type strains using this method (see section 16).

2. Where two or more strains have the same flagellin gene sequence, the genes are cloned as above and the H antigen specificity represented by this sequence is determined. This identifies the strain in which the expected gene is expressed and also those strains for which we have sequenced a gene which is not being expressed. We then clone the gene for the antigen expressed in these strains by making a bank of plasmid clones using chromosomal DNA and select for a clone which is expressing an H antigen different from the one represented by the known sequence. This can be done by taking advantage of the fact that the H antigen is on flagellin, the protein of the bacterial flagellum used for movement of the bacteria. In the presence of antibodies specific to that flagellum the bacteria cannot swim. For selection the clones are placed in a situation in which motile cells can swim away from the others and be collected. There are many versions of these techniques and any could be used. One version is to place the bacteria on a nutrient agar plate with reduced agar content such that bacteria can swim away from the site of inoculation. This is easily seen as growth on the plate and a sample of the bacteria which are motile can be recovered and cultivated. In this way bacteria carrying cloned H antigen genes can be selected. If the medium in the plate has antibody added to it only bacteria which express an H antigen different to that recognised by the antiserum will be able to swim. Specifically if the antiserum used is specific for the H antigen expressed by the gene for which we have sequence, only clones which express a different H antigen, such as those expressing the H antigen expressed by the H type strains used to make the plasmid, will be selected. Once the clone is obtained, the H antigen gene can be sequenced.

Our work has shown that there are at least 7 cases where the H antigen type strains carry two H antigen genes which appear to be complete and have the potential to function. However, while *E. coli* does not (in general) have a capacity to express more than one flagellin gene, it is striking that there are several loci for flagellin genes [Ratiner Y A (1998) "New flagellin-specifying genes in some *Escherichia coli* strains" J. Bacteriol. 180 979–984]. Several of the pairs of H type strains with identical or near identical sequence do not include any of the H antigen types shown by Ratiner [Ratiner Y A (1998) "New flagellin-specifying genes in some *Escherichia coli* strains" J. Bacteriol. 180 979–984] to map other than at fliC although these predominate. This suggests that there are additional cases where the expressed gene is not the only flagellin gene present. However the fact that many of the cases where we obtained flagellin genes of identical or near identical sequence and/or two flagellin genes from one strain involve type strains found by Ratiner

[Ratiner Y A (1998) "New flagellin-specifying genes in some *Escherichia coli* strains" J. Bacteriol. 180 979–984] to map away from fliC are among those near identical to others, indicates that the phenomenon is of limited extent. Nonetheless it remains possible even where only one gene has been obtained by PCR, that it is one of a pair of flagellin genes, the other not being amplified by the primers used, and further that it is the one not amplified which is expressing the H antigen of the strain. It will therefore be necessary to clone as described above each of the flagellin genes we have sequenced and confirm that it expresses the expected antigen to ensure that the invention give results corresponding to those of the traditional serotyping scheme. In the event that it does not, the gene for the type antigen can be cloned and sequenced by the means described above.

The 11 H7 fliC sequences fell into three groups, one comprising the genes from the O157:H7 and O55:H7 strains, which were identical, as expected given the proposed relationship between the clones. It has been shown that *E. coli* O157:H7 and O55:H7 clones are closely related [Whittam T S, wolfe M L, Wachsmuth I K, Orskov I and Wilson R A "Clonal relationships among *Escherichia coli* strains that cause hemorrhagic colitis and infantile diarrhea" Infect. Immun. 61 (1993) 1619–1629] thus it was expected that the H7 fliC genes from O157 and O55 would be identical. Among the H7 fliC sequences, we can identify primers specific to the H7 fliC gene for each of the three H7 groups. Two of these primers in combination with an H7 specific primer gave two primer pairs specific for the H7 gene of from the O157:H7 and O55:H7 clones.

13. Specific oligonucleotide primers for each of the 43 flagellin genes

Two oligonucleotide primers were chosen based on each of the 43 sequences. None of them had more than 85% identity with any other of 61 flagellin gene sequences. Thus, these primers are specific for each H type. These primers are listed in Table 3.

The flagellin gene of the H54 type strain is a mutated gene. It has an insertion sequence (IS1222) inserted into a normal flagellin gene of H21. Thus, primers for H21 would amplify a fragment of different size in H54. We also provide 2 primers based on the insertion sequence (see H54 row in Table 3), and the use of one of them in combination with one of the H21 primers will generate a PCR band only in H54, which will also differentiate those strain carrying the mutated H21 gene from those expressing the H21 flagellin gene.

The flic gene of H35 type strain is also a mutated gene. It has an insertion sequence (IS1) inserted into a normal flagellin gene of H11. Thus, primers for H11 would amplify a fragment of different size in H35. We also provide 2 primers based on the insertion sequence (see H35 row in Table 3), and the use of one of them in combination with one of the H11 primers will generate a PCR band only in H35, which will also differentiate those strain carrying the mutated H11 gene from those expressing the H11 flagellin gene.

14. Testing of the H7 specific oligonucleotide primers

Primer pair #1806/#1809 (SEQ ID NO:9) (see Table 3) was used to carry out PCR on chromosomal DNA samples of all the 54 H type strains and the H7 strains listed in Table 1. PCR reactions were carried out under the following conditions: denaturing, 94° C./30'; annealing, 58° C./30'; extension, 72° C./1'; 30 cycles. PCR reaction was carried out in a volume of 50 ul for each of the chromosomal sample.

After the PCR reaction, 5 µl PCR product from each sample was run on an agarose gel to check for amplified DNA.

Primer pairs #1806/#1809 (SEQ ID NO:9) produced a band of predicted size with all the 11 strains expressing H7, but gave no band with other H type strains. Thus, these primers are H7 specific.

15. Testing of oligonucleotide primers specific to H7 of O157 and O55:

Based on a comparison of the fliC sequences of 11 different H7 strains, we have identified two oligonucleotides [#1696 (SEQ ID NO:85) (5'-GGCCTGACTCAGGCG-GCC) at positions 178 to 195 in M527 and #1697 (SEQ ID NO:86) (5'-GAGTTACCGGCCTGCTGA) positions 1700–1683 in M527] which are unique to H7 of O157 and O55. Although not identical to any parts of the fliC sequences of any other H7 strains, these two primers are identical or have high level similarity to fliC genes of some other H types. However a combination of one of these primers with one of the H7 specific primers can give specificity for H7 of O157:H7 and O55:H7 *E. coli*.

Primer pairs #1696/#1809 (SEQ ID NOS:85/9) and #1697/#1806 (SEQ ID NOS:86/9) were used to carry out PCR on chromosomal DNA samples of all the H type strains and the H7 strains listed in Table 1. PCR reactions were carried out under the following conditions: denaturing, 94° C./30'; annealing, 61° C./30' (for #1696/#1809) (SEQ ID NOS:85/9) or 60° C./30' (for#1697/#1806) (SEQ ID NOS: 86/9); extension, 72° C./1'; 30 cycles. PCR reaction was carried out in an volume of 50 µl for each of the chromosomal samples. After the PCR reaction, 50 µl PCR product from each sample was run on an agarose gel to check for amplified DNA.

Both primer pairs produced a band of predicted size with both of the O157:H7 strains (strains M1004 and M527, see Table 1), and the O55:H7 strain (strain M1686, see Table 1), but gave no band with other strains. Thus, these two pairs of primers are specific to H7 genes of O157:H7 and O55:H7 *E. coli* strains.

16. Identification of flagellin genes for the remaining 15 H specificities.

16.1. Sequencing the potential flkA gene coding for the H36 flagellin:

Using primers #1431 (5'-atg gca caa gtc att aat acc caa c) (SEQ ID NO:81) and #1432 (5'-cta acc ctg cag cag aga ca) (SEQ ID NO:82), we have amplified two bands from the H36 type strain. PCR reaction was carried out under the following conditions: denaturing, 94° C./30'; annealing, 57° C./30'; extension, 72° C./1'; 30 cycles. These two PCR fragments were then cloned into the pGEM-T vector using the Promega pGEM-T cloning kit (Madison Wis. USA) to make plasmids pPR1992 and pPR1993. Inserts from both plasmids were first sequenced using the M13 universal primers (which bind to the pGEM-T DNA flanking the insertion site). For pPR1992, primers based on the sequence obtained were then used to sequence further, and this procedure was repeated until the insert was fully sequenced.

The sequence of the insert of pPR1992 is identical to that of the H12 flagellin gene sequence except perhaps for the first 8 and last 7 codons which are encoded by the PCR primers in plasmid pPR1992. We have only sequenced the two ends of the insert of plasmid pPR1993 (FIGS. 71 and 72), and the sequences of the two ends of the insert of pPR1993 are very similar to ends of other sequenced flagellin genes. We conclude that the insert of plasmid pPR1993 encodes a flagellin gene. The full sequence of the insert of plasmid pPR1993 can be obtained using the same method as for the sequencing of the insert of plasmid pPR1992. It is known that flkA gene encodes the H36 flagellin [Ratiner, Y. A. (1998) "New flagellin specifying genes in some *E. coli* strains" J. Bacteriol 180: 979–984], and it is highly likely that plasmid pPR1993 contains the flkA gene of the H36 type strain. H specificities can be confirmed by slide agglutination.

The currently uncharacterised sequence of both ends and of DNA flanking these two sequenced genes can be obtained by PCR walking and sequencing. Methods for PCR walking from a known sequence to an unknown region in chromosomal DNA are available (see [Siebert, P. D., A. Chenchi, D. E. Kellogg, A. Lukyanov and S. A. Lukyanov (1995) "An improved PCR method for walking in uncloned genomic DNA." Nuc. Acids Res. 23: 1087–1088]).

The sequenced genes then can be PCR amplified and cloned using the method(s) described in section 9. Flagellins expressed by strain M2126 carrying these plasmids then can be determined by use of specific sera.

The sequences flanking the flkA gene can then be used to PCR amplify other flkA genes (see below).

16.2 The flkA genes coding for H3, H47 and H53:

It has been shown that flagellins H3, H47 and H53 are encoded by flkA genes in the type strains [Ratiner, Y. A. (1998) "New flagellin specifying genes in some *E. coli* strains" J. Bacteriol 180: 979–984]. These genes can be PCR amplified using primers based on the sequences flanking the flkA gene in the H36 type strain. These PCR fragments can then be sequenced, and the genes expressed in strain M2126 for the identification of these genes.

16.3 The fllA genes coding for H44 and H55:

It is known that flagellins H44 and H55 are coded by fllA genes.

16.3.1 The H55 flagellin gene:

Using primers #1868 (SEQ ID NO:69) and #1870 (SEQ ID NO:71) (Table 3B), we have amplified two bands from the H55 type strain. PCR reaction was carried out under the following conditions: denaturing, 94° C./30'; annealing, 50° C./30'; extension, 72° C./1'; 30 cycles. These two PCR fragments were then cloned into the pGEM-T vector using the Promega pGEM-T cloning kit (Madison Wis. USA) to make plasmids pPR1994 and pPR1989. Inserts from both plasmids were first sequenced using the M13 universal primers (which bind to the pGEM-T DNA flanking the insertion site). Primers based on the sequence obtained were then used to sequence further, and this procedure was repeated until both inserts were fully or partly sequenced.

The sequence of the insert of pPR1994 is highly similar to that of the flagellin gene of the H38 type strain, with 1 amino acid difference in the gene products. We have only sequenced the two ends of the insert of plasmid pPR1989 (FIGS. 70A and 70B), and the sequences of the two ends of the insert of pPR1989 are very similar to ends of other sequenced flagellin genes. We conclude that the insert of plasmid pPR1989 encodes a flagellin gene. The full sequence of the insert of plasmid pPR1989 can be obtained using the same method as for the sequencing of the insert of plasmid pPR1994. It is known that the H55 type strain carries flagellin genes for both H38 and H55, and that the H55 flagellin gene is at the fllA locus [Ratiner, Y. A. (1998) "New flagellin specifying genes in some *E. coli* strains" J. Bacteriol 180: 979–984]. Thus, it is highly likely that plasmid pPR1989 contains the fllA gene of the H55 type strain.

The currently uncharacterised sequence of both ends and of DNA flanking these two sequenced genes can be obtained by PCR walking and sequencing. Methods for PCR walking from a known sequence to an unknown region in chromosomal DNA are available (see [Siebert, P. D., A. Chenchi, D. E. Kellogg, A. Lukyanov and S. A. Lukyanov (1995) "An improved PCR method for walking in uncloned genomic DNA." Nuc. Acids Res. 23: 1087–1088]).

The sequenced genes then can be PCR amplified and cloned using the method(s) described in section 9. Flagellins expressed by strain M2126 carrying these plasmids then can be determined by use of specific sera.

16.3.2 The H44 flagellin gene:

The sequence information for DNA flanking the fllA gene in the H55 type strain can then be used to PCR, sequence and identify the fllA gene in the H44 type strain.

16.4 The flmA gene coding for H54:

This gene can be cloned by making a bank of plasmid clones in strain M2126 using chromosomal DNA of the H54 type strain and selecting for a transformant which is motile on an agar plate. This is done by taking advantage of the fact that the H antigen is on flagellin, the protein of the bacterial flagellum used for movement of the bacteria. Strain M2126 lacks flagellin. Once the clone(s) is obtained and identified by use of anti-H54 serum, the flagellin gene can be sequenced. It is possible that clones expressing different flagellin specificities can be obtained, and each of them can be identified by using different sera.

16.5 The flagellin genes obtained from the H37 and H48 type strains:

We have used primers #1868 (SEQ ID NO:69) and #1869 (SEQ ID NO:70) (both were based on the sequence obtained from the H48 type strain, also see section 9) and primers #1868 (SEQ ID NO:69) and #1870 (SEQ ID NO:71) (both were based on the sequences of the H7 flagellin gene of the H7 type strain, also see section 9) to PCR amplify and clone the sequenced flagellin genes from the H48 and H37 type strains respectively. Strain P5560 carrying the plasmid containing either the cloned gene was not motile and did not react with the appropriate antisera. It is highly likely that mutaions have occured due to PCR errors. This can be resolved by re-amplification and re-cloning of the genes.

16.6 The flagellin gene obtained from the H25 type strain:

The flagellin gene sequence we first obtained from the H25 type strain lacks 23 and 21 codons at 5' and 3' ends respectively. We could not amplify the full gene from the H25 type strain using primers based on the H7 flagellin gene of the H7 type strain, and it was necessary to get the full sequence of this flagellin gene by other means.

We have used primers (#2650 (SEQ ID NO:87) 5'-cag cga tga aat act tgc cat and #2648 (SEQ ID NO:88): 5'-caa tgc ttc gtg acg cac) based on the genes (fliD and fliA respectively) flanking fliC gene in *E. coli* K-12 [Blattner, F. R., G. I. Plunkett, C. A. Bloch, N. T. Perna, V. Burland, M. Riley and et al. (1997) "The complete genome sequence of *E. Coli* Ki12" Science 277: 1453–1474] and primers (#2658 (SEQ ID NO:89): 5'-gcc tga gtc aga cct ttg and # 2653 (SEQ ID NO:90): 5'-aac ctg tct gaa gcg cag) based on the flagellin sequence obtained from the H25 type strain to PCR amplify both ends of the flagellin gene. The PCR product was then sequenced, and we have now obtained the full flagellin gene sequence and sequence for the DNA flanking the flagellin gene from type strain H25 (FIG. 69). Now, it is straightforward to PCR amplify, clone and express, and identify this gene using the methods described in sections 9 and 10.

16.7 The flagellin genes obtained from the H8 and H40 type strains:

The flagellin gene sequences obtained from both the H8 and H40 type strains lack 18 and 15 codons at 5' and 3' ends respectively. We have used primers based on the H7 flagellin gene of the H7 type strain to PCR amplify and clone the full genes from these two strains. Strain M2126 carrying plasmid made this way was not motile under microscope and did not react with the appropriate antisera. This could be due to PCR errors as mentioned in section 16.5 or perhaps the first and last few amino acids encoded by the primers (based on H7 flagellin gene) are uncompatible in this case.

The full sequence of the full gene can be obtained using method described in section 16.6. The flagellin gene can then be PCR amplified, cloned and expressed, and identified using the methods described in sections 9 and 10.

The gene products of the flagellin genes obtained from the H8 and H40 type strains are identical. Thus, one of these two H specificities must be encoded by a unknown gene, and it can be cloned and identified using the method described in the section 16.8.

16.8 Flagellin genes coding for H17, H35, and H50:

As mentioned above, the sequenced flagellin genes from the H17 and H50 type strains encode H4 and H10 specificities respectively. The flagellin gene sequence obtained from the H35 strain has an insertion and encodes a non-functional gene (see section 8). Thus, genes coding for these flagellins have not been identified, and their location is unknown. One can use primers based on DNA flanking fliC, fllA, flkA, and flmA to do PCR on the type strain for each of the flagellin antigen. PCR products can then be sequenced, and possible genes can be cloned, expressed and identified then.

If the target gene is not PCR amplified using primers based on sequence of these loci or sequence flanking these loci, it can be cloned by making a bank of plasmid clones in strain M2126 using chromosomal DNA of the type strain and selecting for a transformant which is motile on an agar plate. This is done by taking advantage of the fact that the H antigen is on flagellin, the protein of the bacterial flagellum used for movement of the bacteria. Strain M2126 lacks flagellin. Once the clone(s) is obtained and identified by use of antisera, the flagellin gene can be sequenced. It is possible that clones expressing different flagellin antigens can be obtained, and each of them can be identified by using different antisera. Antiserum for H50 can be prepared using standard methods [Ewing, W. H.: Edwards and Ewing's identification of the Enterobacteriaceae., Elsevier Science Publishers, Amsterdam, The Netherlands, 1986].

O Antigen

Materials and Methods—Part 1

The experimental procedures for the isolation and characterisation of the *E. coli* O111 O antigen gene cluster (position 3,021–9,981) are according to Bastin D. A., et al. 1991 "Molecular cloning and expression in *Escherichia coli* K-12 of the rfb gene cluster determining the O antigen of an *E. coli* O111 strain". *Mol. Microbiol.* 5:9 2223–2231 and Bastin D. A. and Reeves, P. R. 1995 "Sequence and analysis of the O antigen gene (rfb) cluster of *Escherichia coli* O111". *Gene* 164: 17–23.

A. Bacterial strains and growth media

Bacteria were grown in Luria broth supplemented as required.

B. Cosmids and phage

Cosmids in the host strain x2819 were repackaged in vivo. Cells were grown in 250 mL flasks containing 30 mL of culture, with moderate shaking at 30° C. to an optical density of 0.3 at 580 nm. The defective lambda prophage was induced by heating in a water bath at 45° C. for 15 min followed by an incubation at 37° C. with vigorous shaking for 2 hr. Cells were then lysed by the addition of 0.3 mL chloroform and shaking for a further 10 min. Cell debris were removed from 1 mL of lysate by a 5 min spin in a microcentrifuge, and the supernatant removed to a fresh microfuge tube. One drop of chloroform was added then shaken vigorously through the tube contents.

C. DNA preparation

Chromosomal DNA was prepared from bacteria grown overnight at 37° C. in a volume of 30 mL of Luria broth. After harvesting by centrifugation, cells were washed and resuspended in 10 mL of 50 mMTris-HCl pH 8.0. EDTA was added and the mixture incubated for 20 min. Then lysozyme was added and incubation continued for a further 10 min. Proteinase K, SDS, and ribonuclease were then added and the mixture incubated for up to 2 hr for lysis to occur. All incubations were at 37° C. The mixture was then heated to 65° C. and extracted once with 8 mL of phenol at the same temperature. The mixture was extracted once with 5 mL of phenol/chloroform/iso-amyl alcohol at 4° C. Residual phenol was removed by two ether extractions. DNA was precipitated with 2 vols. of ethanol at 4° C., spooled and washed in 70% ethanol, resuspended in 1–2 mL of TE and dialysed. Plasmid and cosmid DNA was prepared by a modification of the Birnboim and Doly method [Birnboim, H. C. and Doly, J. (1979) "A rapid alkaline extraction procedure for screening recombinant plasmid DNA" *Nucl. Acid Res.* 7:1513–1523]. The volume of culture was 10 mL and the lysate was extracted with phenol/chloroform/iso-amyl alcohol before precipitation with isopropanol. Plasmid DNA to be used as vector was isolated on a continuous caesium chloride gradient following alkaline lysis of cells grown in 1 L of culture.

D. Enzymes and buffers.

Restriction endonucleases and DNA T4 ligase were purchased from Boehringer Mannheim (Castle Hill, NSW, Australia) or Pharmacia LKB (Melbourne, VIC Australia). Restriction enzymes were used in the recommended commercial buffer.

E. Construction of a gene bank.

Individual aliquots of M92 chromosomal DNA (strain Stoke W, from Statens Serum Institut, 5 Artillerivej, 2300 Copenhagen S, Denmark) were partially digested with 0.2U Sau3A1 for 1–15 mins. Aliquots giving the greatest proportion of fragments in the size range of approximately 40–50 kb were selected and ligated to vector pPR691 previously digested with BamH1 and PvuII. Ligation mixtures were packaged in vitro with packaging extract. The host strain for transduction was x2819 and recombinants were selected with kanamycin.

F. Serological procedures.

Colonies were screened for the presence of the O111 antigen by immunoblotting. Colonies were grown overnight, up to 100 per plate then transferred to nitrocellulose discs and lysed with 0.5N HCl. Tween 20 was added to TBS at 0.05% final concentration for blocking, incubating and washing steps. Primary antibody was *E. coli* O group 111 antiserum, diluted 1:800. The secondary antibody was goat anti-rabbit IgG labelled with horseradish peroxidase diluted 1:5000. The staining substrate was 4-chloro-1-napthol. Slide agglutinalion was performed according to the standard procedure.

G. Recombinant DNA methods.

Restriction mapping was based on a combination of standard methods including single and double digests and sub-cloning. Deletion derivatives of entire cosmids were produced as follows: aliquots of 1.8 mg of cosmid DNA were digested in a volume of 20 ml with 0.25U of restriction enzyme for 5–80 min. One half of each aliquot was used to check the degree of digestion on an agarose gel. The sample which appeared to give a representative range of fragments was ligated at 4° C. overnight and transformed by the $CaCl_2$ method into JM109. Selected plasmids were transformed into sf174 by the same method. P4657 was transformed with pPR1244 by electroporation.

H. DNA hybridisation

Probe DNA was extracted from agarose gels by electroelution and was nick-translated using [a-32P]-dCTP. Chromosomal or plasmid DNA was electrophoresed in 0.8% agarose and transferred to a nitrocellulose membrane. The hybridisation and pre-hybridisation buffers contained either 30% or 50% formamide for low and high stringency probing respectively. Incubation temperatures were 42° C. and 37° C. for pre-hybridisation and hybridisation respectively. Low stringency washing of filters consisted of 3×20 min washes in 2×SSC and 0.1% SDS. High-stringency washing consisted of 3×5 min washes in 2×SSC and 0.1% SDS at room temperature, a 1 hr wash in 1×SSC and 0.1% SDS at 58° C. and 15 min wash in 0.1×SSC and 0.1% SDS at 58° C.

I. Nucleotide sequencing of *E. coli* O111 O antigen gene cluster (position 3,021–9,981)

Nucleotide sequencing was performed using an ABI 373 automated sequencer (CA, USA). The region between map positions 3.30 and 7.90 was sequenced using uni-directional exonuclease III digestion of deletion families made in PT7T3190 from clones pPR1270 and pPR1272. Gaps were filled largely by cloning of selected fragments into M13mp18 or M13mp19. The region from map positions 7.90–10.2 was sequenced from restriction fragments in M13mp18 or M13mp19. Remaining gaps in both the regions were filled by priming from synthetic oligonucleotides complementary to determined positions along the sequence, using a single stranded DNA template in M13 or phagemid. The oligonucleotides were designed after analysing the adjacent sequence. All sequencing was performed by the chain termination method. Sequences were aligned using SAP [Staden, R., 1982 "Automation of the computer handling of gel reading data produced by the shotgun method of DNA sequencing". *Nuc. Acid Res.* 10: 4731–4751; Staden, R., 1986 "The current status and portability of our sequence handling software". *Nuc. Acid Res.* 14: 217–231]. The program NIP [Staden, R. 1982 "An interactive graphics program for comparing and aligning nucleic acid and amino acid sequence". *Nuc. Acid Res.* 10: 2951–2961] was used to find open reading frames and translate them into proteins.

J. Isolation of clones carrying *E. coli* O111 O antigen gene cluster

The *E. coli* O antigen gene cluster was isolated according to the method of Bastin D. A., et al. [1991 "Molecular cloning and expression in *Escherichia coli* K-12 of the rfb gene cluster determining the O antigen of an *E. coli* O111 strain". *Mol. Microbiol.* 5(9), 2223–2231]. Cosmid gene banks of M92 chromosomal DNA were established in the in vivo packaging strain x2819. From the genomic bank, $3.3 \times 10^3$ colonies were screened with *E. coli* O111 antiserum using an immuno-blotting procedure: 5 colonies (pPR1054, pPR1055, pPR1056, pPR1058 and pPR1287) were positive. The cosmids from these strains were packaged in vivo into lambda particles and transduced into the *E. coli* deletion mutant Sf174 which lacks all O antigen genes. In this host strain, all plasmids gave positive agglutination with 0111 antiserum. An Eco R1 restriction map of the 5 independent cosmids showed that they have a region of approximately 11.5 kb in common (FIG. 1). Cosmid pPR1058 included sufficient flanking DNA to identify several chromosomal markers linked to O antigen gene cluster and was selected for analysis of the O antigen gene cluster region.

K. Restriction mapping of cosmid pPR1058

Figure 2:
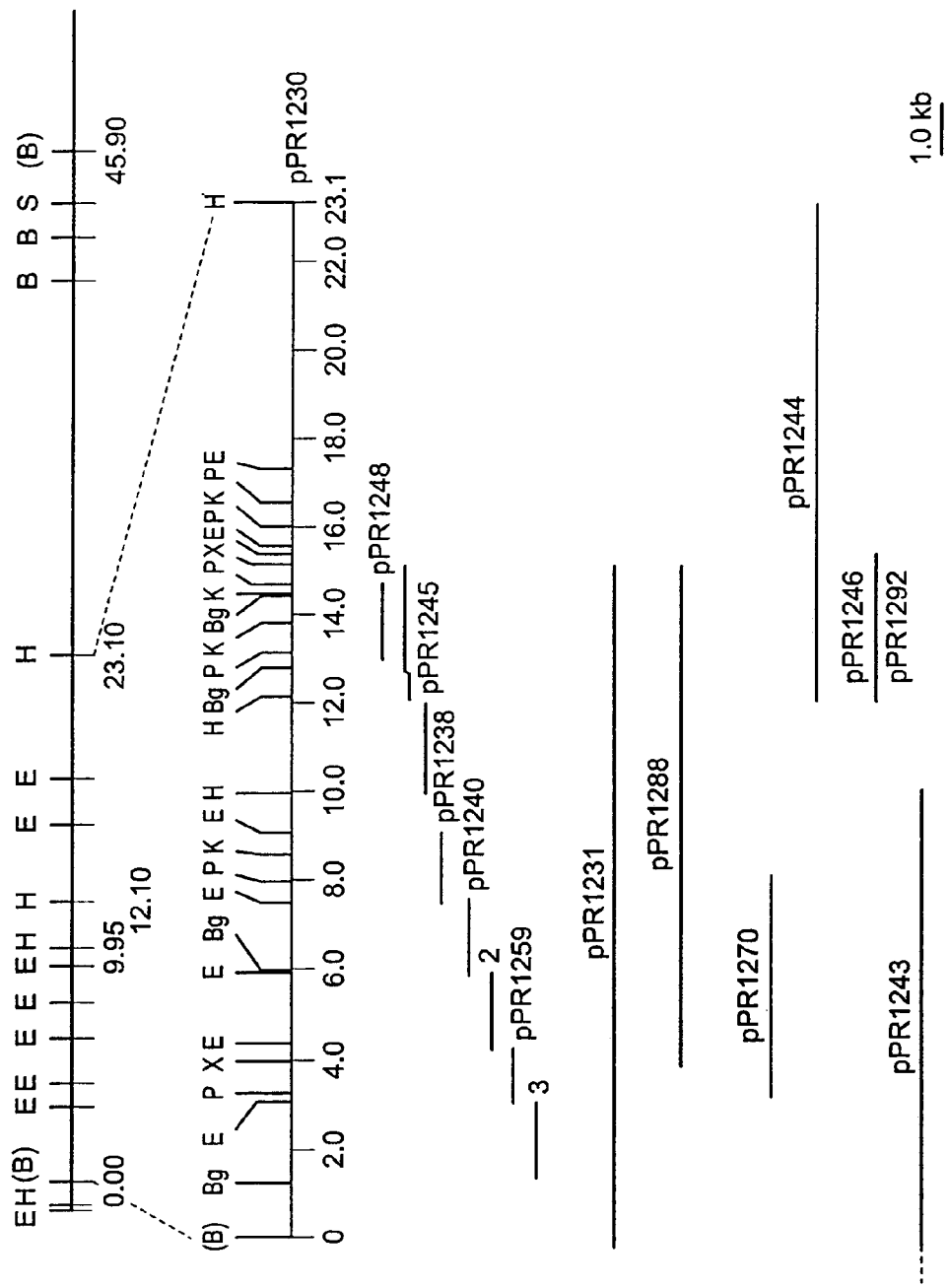
FIG. 2 shows a restriction mapping analysis of *E. coli* O111 O antigen gene cluster within the cosmid clone pPR1058. Restriction enzymes are: (B: BamH1; Bg: BglII, E: EcoR1; H: HindIII; K: KpnI; P: PstI; S: SalI and X: Xho1. Plasmids pPR1230, pPR1231, and pPR1288 are deletion derivatives of pPR1058. Plasmids pPR 1237, pPR1238, pPR1239 and pPR1240 are in pUC19. Plasmids pPR1243, pPR1244, pPR1245, pPR1246 and pPR1248 are in pUC18, and pPR1292 is in pUC19. Plasmid pPR1270 is in pT7T319U. Probes 1, 2 and 3 were isolated as internal fragments of pPR1246, pPR1243 and pPR1237 respectively. Dotted lines indicate that subclone DNA extends to the left of the map into attached vector.

Cosmid pPR1058 was mapped in two stages. A preliminary map was constructed first, and then the region between map positions 0.00 and 23.10 was mapped in detail, since it was shown to be sufficient for O111 antigen expression. Restriction sites for both stages are shown in FIG. 2. The region common to the five cosmid clones was between map positions 1.35 and 12.95 of pPR1058.

To locate the O antigen gene cluster within pPR1058, pPR1058 cosmid was probed with DNA probes covering O antigen gene cluster flanking regions from *S. enterica* LT2 and *E. coli* K-12. Capsular polysaccharide (cps) genes lie upstream of O antigen gene cluster while the gluconate dehydrogenase (gnd) gene and the histidine (his) operon are downstream, the latter being further from the O antigen gene cluster. The probes used were pPR472 (3.35 kb), carrying the gnd gene of LT2, pPR685 (5.3 kb) carrying two genes of the cps cluster, cpsB and cpsG of LT2, and K350 (16.5 kb) carrying all of the his operon of K-12. Probes hybridised as follows: pPR472 hybridised to 1.55 kb and 3.5 kb (including 2.7 kb of vector) fragments of Pst1 and HindIII double digests of pPR1246 (a HindIII/EcoR1 subclone derived from pPR1058, FIG. 2), which could be located at map positions 12.95–15.1; pPR685 hybridised to a 4.4 kb EcoR1 fragment of pPR1058 (including 1.3 kb of vector) located at map position 0.00–3.05; and K350 hybridised with a 32 kb EcoR1 fragment of pPR1058 (including 4.0 kb of vector), located at map position 17.30–45.90. Subclones containing the presumed gnd region complemented a gnd⁻edd⁻ strain GB23152. On gluconate bromothymol blue plates, pPR1244 and pPR1292 in this host strain gave the green colonies expected of a gnd⁺edd⁻ genotype. The his³⁰ phenotype was restored by plasmid pPR1058 in the his deletion strain Sf174 on minimal medium plates, showing that the plasmid carries the entire his operon.

It is likely that the O antigen gene cluster region lies between gnd and cps, as in other *E. coli* and *S. enterica* strains, and hence between the approximate map positions 3.05 and 12.95. To confirm this, deletion derivatives of pPR1058 were made as follows: first, pPR1058 was partially digested with HindIII and self ligated. Transformants were selected for kanamycin resistance and screened for expression of O111 antigen. Two colonies gave a positive reaction. EcoR1 digestion showed that the two colonies hosted identical plasmids, one of which was designated pPR1230, with an insert which extended from map positions 0.00 to 23.10. Second pPR1058 was digested with Sal1 and partially digested with Xho1 and the compatible ends were re-ligated. Transformants were selected with kanamycin and screened for O111 antigen expression. Plasmid DNA of 8 positively reacting clones was checked using EcoR1 and Xho1 digestion and appeared to be identical. The cosmid of one was designated pPR1231. The insert of pPR1231 contained the DNA region between map positions 0.00 and 15.10. Third, pPR1231 was partially digested with Xho1, self-ligated, and transformants selected on spectinomycin/streptomycin plates. Clones were screened for kanamycin sensitivity and of 10 selected, all had the DNA region from the Xho1 site in the vector to the Xho1 site at position 4.00 deleted. These clones did not express the O111 antigen, showing that the Xho1 site at position 4.00 is within the O antigen gene cluster. One clone was selected and named pPR1288. Plasmids pPR1230, pPR1231, and pPR1288 are shown in FIG. 2.

Figure 3:
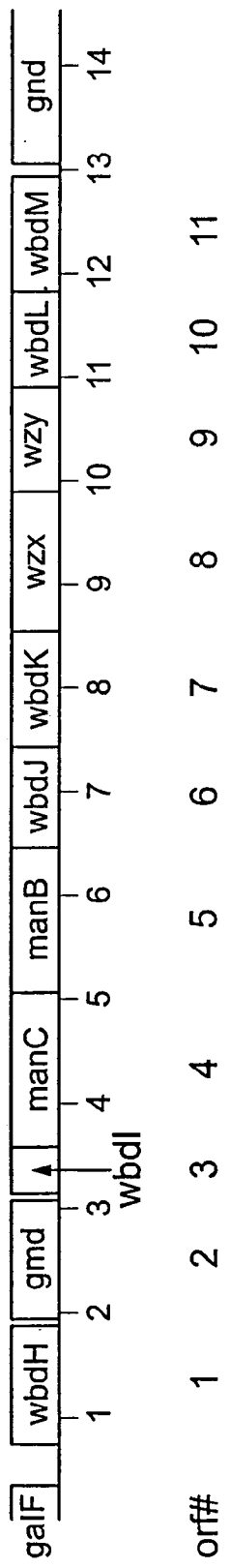
FIG. 3 shows the structure of *E. coli* O111 O antigen gene cluster.

L. Analysis of the *E. coli* O111 O antigen gene cluster (position 3,021–9,981) nucleotide sequence data Bastin and Reeves [1995 "Sequence and analysis of the O antigen gene (rfb) cluster of *Escherichia coli* O111". Gene 164: 17–23] partially characterised the *E. coli* O111 O antigen gene cluster by sequencing a fragment from map position 3,021–9,981. FIG. 3 shows the gene organisation of position 3,021–9,981 of *E. coli* O111 O antigen gene cluster. orf3 and orf6 have high level amino acid identity with wcaH and wcaG (46.3% and 37.2% respectively), and are likely to be similar in function to sugar biosynthetic pathway genes in the *E. coli* K-12 colanic gene cluster. orf4 and orf5 show high levels of amino acid homology to manC and manB genes respectively. orf7 shows high level homology with rfbH which is an abequose pathway gene. orf8 encodes a protein with 12 transmembrane segments and has similarity in secondary structure to other wzx genes and is likely therefore to be the O antigen flippase gene.

Materials and Methods—Part 2

A. Nucleotide sequencing of 1 to 3,020 and 9,982 to 14,516 of the *E. coli* O111 O antigen gene cluster The sub clones which contained novel nucleotide sequences, pPR1231 (map position 0 and 1,510), pPR1237 (map position –300 to 2,744), pPR1239 (map position 2,744 to 4,168), pPR1245 (map position 9,736 to 12,007) and pPR1246 (map position 12,007 to 15,300) (FIG. 2), were characterised as follows: the distal ends of the inserts of pPR1237, pPR1239 and pPR1245 were sequenced using the M13 forward and reverse primers located in the vector. PCR walking was carried out to sequence further into each insert using primers based on the sequence data and the primers were tagged with M13 forward or reverse primer sequences for sequencing. This PCR walking procedure was repeated until the entire insert was sequenced. pPR1246 was characterised from position 12,007 to 14,516. The DNA of these sub clones was sequenced in both directions. The sequencing reactions were performed using the dideoxy termination method and thermocycling and reaction products were analysed using fluorescent dye and an ABI automated sequencer (CA, USA).

B. Analysis of the *E. coli* O111 O antigen gene cluster (positions 1 to 3,020 and 9,982 to 14,516 of FIG. 5) nucleotide sequence data The gene organisation of regions of *E. coli* O111 O antigen gene cluster which were not characterised by Bastin and Reeves [1995 "Sequence and analysis of the O antigen gene (rfb) cluster of *Escherichia coli* O111." Gene 164: 17–23], (positions 1 to 3,020 and 9,982 to 14,516) is shown in FIG. 3. There are two open reading frames in region 1. Four open reading frames are predicted in region 2. The position of each gene is listed in Table 9.

The deduced amino acid sequence of orf1 (wbdH) shares about 64% similarity with that of the rfp gene of *Shigella dysenteriae*. Rfp and WbdH have very similar hydrophobicity plots and both have a very convincing predicted transmembrane segment in a corresponding position. rfp is a galactosyl transferase involved in the synthesis of LPS core, thus wbdH is likely to be a galactosyl transferase gene. orf2 has 85.7% identity at amino acid level to the gmd gene identified in the *E. coli* K-12 colanic acid gene cluster and is likely to be a gmd gene. orf9 encodes a protein with 10 predicted transmembrane segments and a large cytoplasmic loop. This inner membrane topology is a characteristic feature of all known 0 antigen polymerases thus it is likely that orf9 encodes a 0 antigen polymerase gene, wzy. orf10 (wbdL) has a deduced amino acid sequence with low homology with Lsi2 of *Neisseria gonorrhoeae*. Lsi2 is responsible for adding GlcNAc to galactose in the synthesis of lipooligosaccharide. Thus it is likely that wbdL is either a colitose or glucose transferase gene. orf11 (wbdM) shares high level nucleotide and amino acid similarity with TrsE of *Yersinia enterocolitica*. TrsE is a putative sugar transferase thus it is likely that wbdM encodes the colitose or glucose transferase.

In summary three putative transferase genes and an 0 antigen polymerase gene were identified at map position 1 to 3,020 and 9,982 to 14,516 of *E. coli* O111 O antigen gene cluster. A search of GenBank has shown that there are no genes with significant similarity at the nucleotide sequence level for two of the three putative transferase genes or the polymerase gene. FIG. 5 provides the nucleotide sequence of the O111 antigen gene cluster.

Materials and Methods—Part 3

A. PCR amplification of O157 antigen gene cluster from an *E. coli* O157:H7 strain (Strain C664-1992, from Statens Serum Institut, 5 Artillerivej, 2300, Copenhagen S, Denmark):

*E. coli* O157 O antigen gene cluster was amplified by using long PCR [Cheng et al. 1994, "Effective amplification of long targets from cloned inserts and human and genomic DNA" P.N.A.S. USA 91: 5695–569] with one primer (primer #412 (SEQ ID NO:91): att ggt agc tgt aag cca agg gcg gta gcg t) based on the JumpStart sequence usually found in the promoter region of O antigen gene clusters [Hobbs, et al. 1994 "The JumpStart sequence: a 39 bp element common to several polysaccharide gene clusters" Mol. Microbiol. 12: 855–856], and another primer #482 (cac tgc cat acc gac gac gcc gat ctg ttg ctt gg) (SEQ ID NO:92) based on the gnd gene usually found downstream of the O antigen gene cluster. Long PCR was carried out using the Expand Long Template PCR System from Boehringer Mannheim (Castle Hill NSW Australia), and products, 14 kb in length, from several reactions were combined and purified using the Promega Wizard PCR preps DNA purification System (Madison Wis. USA). The PCR product was then extracted with phenol and twice with ether, precipitated with 70% ethanol, and resuspended in 40 mL of water.

B. Construction of a random DNase I bank:

Two aliquots containing about 150 ng of DNA each were subjected to DNase I digestion using the Novagen DNase I Shotgun Cleavage (Madison Wis. USA) with a modified protocol as described. Each aliquot was diluted into 45 ml of 0.05M Tris-HCl (pH7.5), 0.05 mg/mL BSA and 10 mM $MnCl_2$. 5 mL of 1:3000 or 1:4500 dilution of DNaseI (Novagen) (Madison Wis. USA) in the same buffer was added into each tube respectively and 10 ml of stop buffer (100 mM EDTA), 30% glycerol, 0.5% Orange G, 0.075% xylene and cyanol (Novagen) (Madison Wis. USA) was added after incubation at 15° C. for 5 min. The DNA from the two DNaseI reaction tubes were then combined and fractionated on a 0.8% LMT agarose gel, and the gel segment with DNA of about 1 kb in size (about 1.5 mL agarose) was excised. DNA was extracted from agarose using Promega Wizard PCR Preps DNA Purification (Madison Wis. USA) and resuspended in 200 mL water, before being extracted with phenol and twice with ether, and precipitated. The DNA was then resuspended in 17.25 mL water and subjected to T4 DNA polymerase repair and single dA tailing using the Novagen Single dA Tailing Kit (Madison Wis. USA). The reaction product (85 ml containing about 8 ng DNA) was then extracted with chloroform: isoamyl alcohol (24:1) once and ligated to $3\times10^{-3}$ pmol pGEM-T (Promega) (Madison Wis. USA) in a total volume of 100 mL. Ligation was carried out overnight at 4° C. and the ligated DNA was precipitated and resuspended in 20 mL water before being electroporated into E. coli strain JM109 and plated out on BCIG-IPTG plates to give a bank.

C. Sequencing

DNA templates from clones of the bank were prepared for sequencing using the 96-well format plasmid DNA miniprep kit from Advanced Genetic Technologies Corp (Gaithersburg Md. USA). The inserts of these clones were sequenced from one or both ends using the standard M13 sequencing primer sites located in the pGEM-T vector. Sequencing was carried out on an ABI377 automated sequencer (CA USA) as described above, after carrying out the sequencing reaction on an ABI Catalyst (CA USA). Sequence gaps and areas of inadequate coverage were PCR amplified directly from O157 chromosomal DNA using primers based on the already obtained sequencing data and sequenced using the standard M13 sequencing primer sites attached to the PCR primers.

Figure 4:
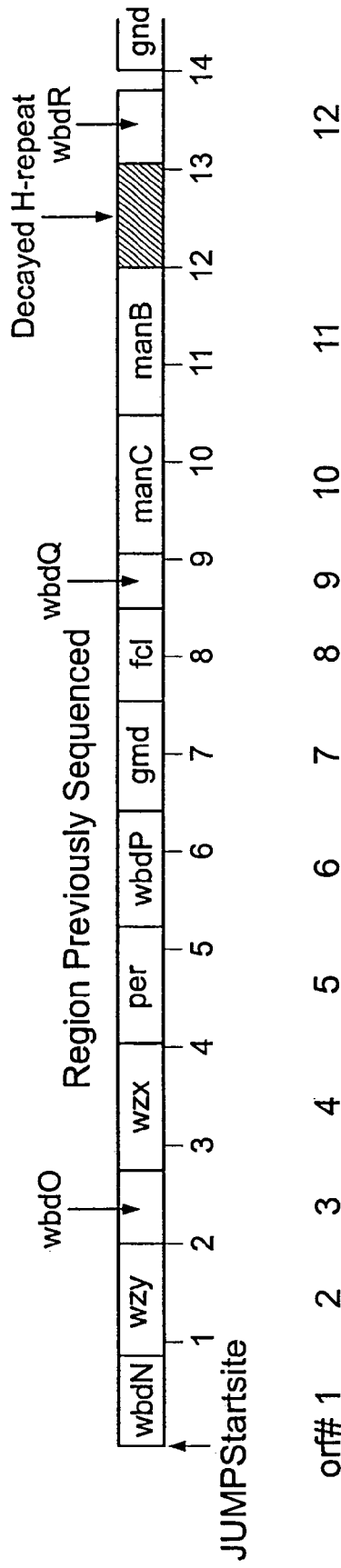
FIG. 4 shows the structure of *E. coli* O157 O antigen gene cluster.

D. Analysis of the *E. coli* O157 O antigen gene cluster nucleotide sequence data Sequence data were processed and analysed using the Staden programs [Staden, R., 1982 "Automation of the computer handling of gel reading data produced by the shotgun method of DNA sequencing." *Nuc. Acid Res.* 10: 4731–4751; Staden, R., 1986 "The current status and portability of our sequence handling software". *Nuc. Acid Res.* 14: 217–231; Staden, R. 1982 "An interactive graphics program for comparing and aligning nucleic acid and amino acid sequence". *Nuc. Acid Res.* 10: 2951–2961]. FIG. 4 shows the structure of *E. coli* O157 O antigen gene cluster. Twelve open reading frames were predicted from the sequence data, and the nucleotide and amino acid sequences of all these genes were then used to search the GenBank database for indication of possible function and specificity of these genes. The position of each gene is listed in Table 9. The nucleotide sequence is presented in FIG. 6.

orfs 10 and 11 showed high level identity to manC and manB and were named manC and manB respectively. orf7 showed 89% identity (at amino acid level) to the gmd gene of the *E. coli* colanic acid capsule gene cluster (Stevenson G., K. et al. 1996 "Organisation of the *Escherichia coli* K-12 gene cluster responsible for production of the extracellular polysaccharide colanic acid". *J. Bacteriol.* 178:4885–4893) and was named gmd. orf8 showed 79% and 69% identity (at amino acid level) respectively to wcaG of the *E. coli* colanic acid capsule gene cluster and to wbcJ (orf14.8) gene of the *Yersinia enterocolitica* O8 O antigen gene cluster (Zhang, L. et al. 1997 "Molecular and chemical characterization of the lipopolysaccharide O-antigen and its role in the virulence of *Y. enterocolitica* serotype O8". *Mol. Microbiol.* 23:63–76). Colanic acid and the *Yersinia* O8 O antigen both contain fucose as does the O157 O antigen. There are two enzymatic steps required for GDP-L-fucose synthesis from GDP-4-keto-6-deoxy-D-mannose, the product of the gmd gene product. However, it has been shown recently (Tonetti, M et al. 1996 Synthesis of GDP-L-fucose by the human FX protein *J. Biol. Chem.* 271:27274–27279) that the human FX protein has "significant homology" with the wcaG gene (referred to as Yefb in that paper), and that the FX protein carries out both reactions to convert GDP-4-keto-6-deoxy-D-mannose to GDP-L-fucose. We believe that this makes a very strong case for orf8 carrying out these two steps and propose to name the gene fcl. In support of the one enzyme carrying out both functions is the observation that there are no genes other than manB, manC, gmd and fcl with similar levels of similarity between the three bacterial gene clusters for fucose containing structures.

orf5 is very similar to wbeE (rfbE) of *Vibrio cholerae* O1, which is thought to be the perosamine synthetase, which converts GDP-4-keto-6-deoxy-D-mannose to GDP-perosamine (Stroeher, U. H et al. 1995 "A putative pathway for perosamine biosynthesis is the first function encoded within the rfb region of *Vibrio cholerae*" O1. *Gene* 166: 33–42). *V. cholerae* O1 and *E. coli* O157 O antigens contain perosamine and N-acetyl-perosamine respectively. The *V. cholerae* O1 manA, manB, gmd and wbeE genes are the only genes of the *V. cholerae* O1 gene cluster with significant similarity to genes of the *E. coli* O0157 gene cluster and we believe that our observations both confirm the prediction made for the function of wbe of *V. cholerae*, and show that orf5 of the O157 gene cluster encodes GDP-perosamine synthetase. orf5 is therefore named per. orf5 plus about 100 bp of the upstream region (postion 4022–5308) was previously sequenced by Bilge, S. S. et al. [1996 "Role of the *Escherichia coli* O157-H7 O side chain in adherence and analysis of an rfb locus". *Infect. Immun.* 64:4795–4801].

orf12 shows high level similarity to the conserved region of about 50 amino acids of various members of an acetyltransferase family (Lin, W., et al. 1994 "Sequence analysis and molecular characterisation of genes required for the biosynthesis of type 1 capsular polysaccharide in *Staphylococcus aureus*". *J. Bateriol.* 176: 7005–7016) and we believe it is the N-acetyltransferase to convert GDP-perosamine to GDP-perNAc. orf12 has been named wbdR.

The genes manB, manC, gmd, fcl, per and wbdR account for all of the expected biosynthetic pathway genes of the O157 gene cluster.

The remaining biosynthetic step(s) required are for synthesis of UDP-GalNAc from UDP-Glc. It has been proposed (Zhang, L., et al. 1997 "Molecular and chemical characterisation of the lipopolysaccharide O-antigen and its role in the virulence of *Yersinia enterocolitica* serotype O8". *Mol. Microbiol.* 23:63–76) that in *Yersinia enterocolitica* UDP-GalNAc is synthesised from UDP-GlcNAc by a homologue of galactose epimerase (GalE), for which there is a galE like gene in the *Yersinia enterocolitica* O8 gene cluster. In the case of O157 there is no galE homologue in the gene cluster and it is not clear how UDP-GalNAc is synthesised. It is possible that the galactose epimerase encoded by the galE gene in the gal operon, can carry out conversion of UDP-GlcNAc to UDP-GalNAc in addition to conversion of UDP-Glc to UDP-Gal. There do not appear to be any gene(s) responsible for UDP-GalNAc synthesis in the O157 gene cluster.

orf4 shows similarity to many wzx genes and is named wzx and orf2 which shows similarity of secondary structure in the predicted protein to other wzy genes and is for that reason named wzy.

The orf1, orf3 and orf6 gene products all have characteristics of transferases, and have been named wbdN, wbdO and wbdP respectively. The O157 O antigen has 4 sugars and 4 transferases are expected. The first transferase to act would put a sugar phosphate onto undecaprenol phosphate. The two transferases known to perform this function, WbaP (RfbP) and WecA (Rfe) transfer galactose phosphate and N-acetyl-glucosamine phosphate respectively to undecaprenol phosphate. Neither of these sugars is present in the O157 structure.

Further, none of the presumptive transferases in the O157 gene cluster has the transmembrane segments found in WecA and WbaP which transfer a sugar phosphate to undecaprenol phosphate and expected for any protein which transferred a sugar to undecaprenol phosphate which is embedded within the membrane.

The WecA gene which transfers GlcNAc-P to undecaprenol phosphate is located in the Enterobactereal Common Antigen (ECA) gene cluster and it functions in ECA synthesis in most and perhaps all E. coli strains, and also in O antigen synthesis for those strains which have GlcNAc as the first sugar in the O unit.

It appears that WecA acts as the transferase for addition of GalNAc-1-P to undecaprenol phosphate for the Yersinia enterocolitica O8 O antigen [Zhang et al. 1997 "Molecular and chemical characterisation of the lipopolysaccharide O antigen and its role in the virulence of Yersinia enterocolitica serotype O8" Mol. Microbiol. 23: 63–76.] and perhaps does so here as the O157 structure includes GalNAc. WecA has also been reported to add Glucose-1-P phosphate to undecaprenol phosphate in E. coli O8 and O9 strains, and an alternative possibility for transfer of the first sugar to undecaprenol phosphate is WecA mediated transfer of glucose, as there is a glucose residue in the O157 O antigen. In either case the requisite number of transferase genes are present if GalNAc or Glc is transferred by WecA and the side chain Glc is transferred by a transferase outside of the O antigen gene cluster.

orf9 shows high level similarity (44% identity at amino acid level, same length) with wcaH gene of the E. coli colanic acid capsule gene cluster. The function of this gene is unknown, and we give orf9 the name wbdQ.

The DNA between manB and wdbR has strong sequence similarity to one of the H-repeat units of E. coli K12. Both of the inverted repeat sequences flanking this region are still recognisable, each with two of the 11 bases being changed. The H-repeat associated protein encoding gene located within this region has a 267 base deletion and mutations in various positions. It seems that the H-repeat unit has been associated with this gene cluster for a long period of time since it translocated to the gene cluster, perhaps playing a role in assembly of the gene cluster as has been proposed in other cases.

Materials and Methods—Part 4

To test our hypothesis that O antigen genes for transferases and the wzx, wzy genes were more specific than pathway genes for diagnostic PCR, we first carried out PCR using primers for all the E. coli O16 O antigen genes (Table 7). The PCR was then carried out using PCR primers for E. coli O111 transferase, wzx and wzy genes (Table 8, 8A). PCR was also carried out using PCR primers for the E. coli O157 transferase, wzx and wzy genes (Table 9, 9A).

Chromosomal DNA from the 166 serotypes of E. coli available from Statens Serum Institut, 5 Artillerivej, 2300 Copenhagen Denmark was isolated using the Promega Genomic (Madison Wis. USA) isolation kit. Note that 164 of the serogroups are described by Ewing W. H.: Edwards and Ewings "Identification of the Enterobacteriacea" Elsevier, Amsterdam 1986 and that they are numbered 1–171 with numbers 31, 47, 67, 72, 93, 94 and 122 no longer valid. Of the two serogroup 19 strains we used 19ab strain F8188-41. Lior H. 1994 ["Classification of Escherichia coli In Escherichia coli in domestic animals and humans pp 31–72. Edited by C. L. Gyles CAB international] adds two more numbered 172 and 173 to give the 166 serogroups used. Pools containing 5 to 8 samples of DNA per pool were made. Pool numbers 1 to 19 (Table 4) were used in the E. coli 0111 and 0157 assay. Pool numbers 20 to 28 were also used in the 0111 assay, and pool numbers 22 to 24 contained E. coli 0111 DNA and were used as positive controls (Table 5). Pool numbers 29 to 42 were also used in the 0157 assay, and pool numbers 31 to 36 contained E. coli 0157 DNA, and were used as positive controls (Table 6). Pool numbers 2 to 20, 30, 43 and 44 were used in the E. coli 016 assay (Tables 4 to 6). Pool number 44 contained DNA of E. coli K-12 strains C600 and WG1 and was used as a positive control as between them they have all of the E. coli K-12 O16 O antigen genes.

PCR reactions were carried out under the following conditions: denaturing 94° C./30"; annealing, temperature varies (refer to Tables)/30"; extension, 72° C./1'; 30 cycles. PCR reaction was carried out in a volume of 25 mL for each pool. After the PCR reaction, 10 mL PCR product from each pool was run on an agarose gel to check for amplified DNA.

Each E. coli chromosomal DNA sample was checked by gel electrophoresis for the presence of chromosomal DNA and by PCR amplification of the E. coli mdh gene using oligonucleotides based on E. coli K-12 [Boyd et al. (1994) "Molecular genetic basis of allelic polymorphism in malate degydrogenase (mdh) in natural populations of Escherichia coli and Salmonella enterica" Proc. Nat. Acad. Sci. USA. 91:1280–1284.] Chromosomal DNA samples from other bacteria were only checked by gel electrophoresis of chromosomal DNA.

A. Primers based on E. coli O16 O antigen gene cluster sequence.

The O antigen gene cluster of E. coli O16 was the only typical E. coli O antigen gene cluster that had been fully sequenced prior to that of O111, and we chose it for testing our hypothesis. One pair of primers for each gene was tested against pools 2 to 20, 30 and 43 of E. coli chromosomal DNA. The primers, annealing temperatures and functional information for each gene are listed in Table 8.

For the five pathway genes, there were 17/21, 13/21, 0/21, 0/21, 0/21 positive pools for rmlB, rmlD, rmlA, rmlC and glf respectively (Table 7). For the wzx, wzy and three transferase genes there were no positives amongst the 21 pools of E. coli chromosomal DNA tested (Table 7). In each case the #44 pool gave a positive result.

B. Primers based on the E. coli O111 O antigen gene cluster sequence.

One to four pairs of primers for each of the transferase, wzx and wzy genes of O111 were tested against the pools 1 to 21 of E. coli chromosomal DNA (Table 8). For wbdH, four pairs of primers, which bind to various regions of this gene, were tested and found to be specific for O111 as there was no amplified DNA of the correct size in any of those 21 pools of E. coli chromosomal DNA tested. Three pairs of primers for wbdM were tested, and they are all specific although primers #985/#986 produced a band of the wrong size from one pool. Three pairs of primers for wzx were tested and they all were specific. Two pairs of primers were tested for wzy, both are specific although #980/#983 gave a band of the wrong size in all pools. One pair of primers for wbdL was tested and found unspecific and therefore no further test was carried out. Thus, wzx, wzy and two of the three transferase genes are highly specific to O111. Bands of the wrong size found in amplified DNA are assumed to be due to chance hybridisation of genes widely present in *E. coli*. The primers, annealing temperatures and positions for each gene are in Table 8.

The 0111 assay was also performed using pools including DNA from O antigen expressing *Yersinia pseudotuberculosis*, *Shigella boydii* and *Salmonella enterica* strains (Table 8A). None of the oligonucleotides derived from wbdH, wzx, wzy or wbdM gave amplified DNA of the correct size with these pools. Notably, pool number 25 includes *S. enterica* Adelaide which has the same O antigen as *E. coli* O111: this pool did not give a positive PCR result for any primers tested indicating that these genes are highly specific for *E. coli* O111.

Each of the 12 pairs binding to wbdH, wzx, wzy and wbdM produces a band of predicted size with the pools containing 0111 DNA (pools number 22 to 24). As pools 22 to 24 included DNA from all strains present in pool 21 plus O111 strain DNA (Table 5), we conclude that the 12 pairs of primers all give a positive PCR test with each of three unrelated 0111 strains but not with any other strains tested. Thus these genes are highly specific for *E. coli* O111.

C. Primers based on the *E. coli* 0157 O antigen gene cluster sequence.

Two or three primer pairs for each of the transferase, wzx and wzy genes of O157 were tested against *E. coli* chromosomal DNA of pools 1 to 19, 29 and 30 (Table 9). For wbdN, three pairs of primers, which bind to various regions of this gene, were tested and found to be specific for O157 as there was no amplified DNA in any of those 21 pools of *E. coli* chromosomal DNA tested. Three pairs of primers for wbdO were tested, and they are all specific although primers # 1211/#1212 produced two or three bands of the wrong size from all pools. Three pairs of primers were tested for wbdP and they all were specific. Two pairs of primers were tested for wbdR and they were all specific. For wzy, three pairs of primers were tested and all were specific although primer pair #1203/#1204 produced one or three bands of the wrong size in each pool. For wzx, two pairs of primers were tested and both were specific although primer pair #1217/#1218 produced 2 bands of wrong size in 2 pools, and 1 band of wrong size in 7 pools. Bands of the wrong size found in amplified DNA are assumed to be due to chance hybridisation of genes widely present in *E. coli*. The primers, annealing temperatures and function information for each gene are in Table 9.

The 0157 assay was also performed using pools 37 to 42, including DNA from O antigen expressing *Yersinia pseudotuberculosis*, *Shigella boydii*, *Yersinia enterocolitica* 09, *Brucella abortus* and *Salmonella enterica* strains (Table 9A). None of the oligonucleotides derived from wbdN, wzy, wbdO, wzx, wbdP or wbdR reacted specifically with these pools, except that primer pair #1203/#1204 produced two bands with *Y. enterocolitica* 09 and one of the bands is of the same size with that from the positive control. Primer pair #1203/#1204 binds to wzy. The predicted secondary structures of Wzy proteins are generally similar, although there is very low similarity at amino acid or DNA level among the sequenced wzy genes. Thus, it is possible that *Y. enterocolitica* O9 has a wzy gene closely related to that of *E. coli* O157. It is also possible that this band is due to chance hybridization of another gene, as the other two wzy primer pairs (#1205/#1206 and #1207/#1208) did not produce any band with *Y. enterocolitica* O9. Notably, pool number 37 includes *S. enterica* Landau which has the same O antigen as *E. coli* O157, and pool 38 and 39 contain DNA of *B. abortus* and *Y. enterocolitica* O9 which cross react serologically with *E. coli* O157. This result indicates that these genes are highly O157 specific, although one primer pair may have cross reacted with *Y. enterocolitica* O9.

Each of the 16 pairs binding to wbdN, wzx, wzy, wbdO, wbdP and wbdR produces a band of predicted size with the pools containing 0157 DNA (pools number 31 to 36). As pool 29 included DNA from all strains present in pools 31 to 36 other than 0157 strain DNA (Table 6), we conclude that the 16 pairs of primers all give a positive PCR test with each of the five unrelated 0157 strains.

Thus, PCR using primers based on genes wbdN, wzy, wbdO, wzx, wbdP and wbdR is highly specific for *E. coli* O157, giving positive results with each of six unrelated O157 strains while only one primer pair gave a band of the expected size with one of three strains with O antigens known to cross-react serologically with *E. coli* O157.

TABLE 1

H7 strains used in this work in addition to the H antigens type strains

| Name used in this study | Serotype | Original name | Source* |
|---|---|---|---|
| M527 | O157:H7 | C664-1992 | a |
| M917 | O18ac:H7 | A57 | IMVS |
| M918 | O18ac:H7 | A62 | IMVS |
| M973 | O2:H7 | A1107 | CDC |
| M1004 | O157:H7 | EH7 | b |
| M1179 | O18ac:H7 | D-M3291/54 | IMVS |
| M1200 | O7:H7 | A64 | c |
| M1211 | O19ab:H7 | F8188-41 | IMVS |
| M1328 | O53:H7 | 14097 | IMVS |
| M1686 | O55:H7 | TB156 | d |

*a Statens Serum Institut, Copenhagen, Denmark.
b Dr R. Brown of Royal Children's Hospital, Melbourne, Australia.
c Max-Planck Institut für molekulare Genetik, Berlin, Germany.
d Dr P. Tarr of Children's Hospital and Medical Center, University of Washington, USA.
IMVS Institute of Medical and veterinary Science, Adelaide, Australia.
CDC Centers for Disease Control and prevention, Atlanta, USA.

TABLE 2

Oligonucleotides used to PCR amplify fliC genes from different H type strains for sequencing

| H Type Strains | Annealing Temperature (° C.) | Primers Used | SEQ ID NO: |
|---|---|---|---|
| 1 | 55 | #1575/#1576 | 83/84 |
| 2 | 55 | #1285/#1286 | 77/78 |
| 3 | 55 | #1285/#1286 | 77/78 |
| 4 | 50 | #1431/#1432 | 81/82 |
| 5 | 60 | #1285/#1286 | 77/78 |
| 6 | 55 | #1575/#1576 | 83/84 |
| 7 | 55 | #1575/#1576 | 83/84 |
| 8 | 55 | #1431/#1432 | 81/82 |
| 9 | 60 | #1575/#1576 | 83/84 |
| 10 | 55 | #1575/#1576 | 83/84 |
| 11 | 55 | #1285/#1286 | 77/78 |
| 12 | 60 | #1575/#1576 | 83/84 |
| 14 | 60 | #1575/#1576 | 83/84 |
| 15 | 60 | #1575/#1576 | 83/84 |
| 16 | 60 | #1575/#1576 | 83/84 |
| 17 | 60 | #1417/#1418 | 79/80 |
| 18 | 60 | #1575/#1576 | 83/84 |

TABLE 2-continued

Oligonucleotides used to PCR amplify fliC genes from different H type strains for sequencing

| H Type Strains | Annealing Temperature (° C.) | Primers Used | SEQ ID NO: |
|---|---|---|---|
| 19 | 60 | #1575/#1576 | 83/84 |
| 20 | 60 | #1575/#1576 | 83/84 |
| 21 | 55 | #1285/#1286 | 77/78 |
| 23 | 60 | #1575/#1576 | 83/84 |
| 24 | 60 | #1285/#1286 | 77/78 |
| 25 | 60 | #1417/#1418 | 79/80 |
| 26 | 60 | #1575/#1576 | 83/84 |
| 27 | 50 | #1431/#1432 | 81/82 |
| 28 | 60 | #1575/#1576 | 83/84 |
| 29 | 60 | #1285/#1286 | 77/78 |
| 30 | 60 | #1575/#1576 | 83/84 |
| 31 | 60 | #1575/#1576 | 83/84 |
| 32 | 60 | #1575/#1576 | 83/84 |
| 33 | 60 | #1285/1286 | 77/78 |
| 34 | 55 | #1575/#1576 | 83/84 |
| 35 | 50 | #1431/#1432 | 81/82 |
| 37 | 60 | #1285/#1286 | 77/78 |
| 38 | 60 | #1285/#1286 | 77/78 |
| 39 | 55 | #1285/#1286 | 77/78 |
| 40 | 55 | #1285/#1286 | 77/78 |
| 41 | 60 | #1575/#1576 | 83/84 |
| 42 | 60 | #1285/#1286 | 77/78 |
| 43 | 60 | #1575/#1576 | 83/84 |
| 44 | 60 | #1285/#1286 | 77/78 |
| 45 | 60 | #1575/#1576 | 83/84 |
| 46 | 60 | #1575/#1576 | 83/84 |
| 47 | 55 | #1285/#1286 | 77/78 |
| 48 | 60 | #1575/#1576 | 83/84 |
| 49 | 60 | #1575/#1576 | 83/84 |
| 50 | 60 | #1285/#1286 | 77/78 |
| 51 | 60 | #1575/#1576 | 83/84 |
| 52 | 60 | #1575/#1576 | 83/84 |
| 54 | 50 | #1431/#1432 | 81/82 |
| 55 | 60 | #1285/#1286 | 77/78 |
| 56 | 60 | #1285/#1286 | 77/78 |

TABLE 3

Summary of the flagellin sequences obtained and specific H type oligonucleotide primers

| H type strain(s) the sequenced gene(s) obtained from | SEQ ID NO: | H specificity coded by the gene(s) | H type strain from which the flagellin gene sequence was used for primer choice | Positions of primer 1 | Positions of primer 2 |
|---|---|---|---|---|---|
| 1 | 66 | 1 | 1 | 892–909 | 1172–1189 |
| 2 | 67 | 2 | 2 | 568–587 | 1039–1056 |
| 4, 17, 44 | 6, 17, 42 | 4 | 4 | 466–483 | 628–648 |
| 5 | 7 | 5 | 5 | 697–714 | 877–897 |
| 6 | 8 | 6 | 6 | 565–585 | 799–816 |
| 7 | 9 | 7 | 7 | 553–570 (primer #1806) | 1483–1500 (primer #1809) |
| 9 | 11 | 9 | 9 | 616–633 | 838–855 |
| 10(50)*** | 12(49) | 10 | 10 | 559–579 | 697–717 |
| 11 | 13 | 11 | 11 | 586–606* | 791–810* |
| 12 | 14 | 12 | 12 | 892–909 | 1172–1189 |
| 14 | 15 | 14 | 14 | 586–606 | 793–813 |
| 15 | 16 | 15 | 15 | 640–660 | 817–834 |
| 3 | 68 | 16 | 3 | 649–666 | 925–942 |
| 18 | 18 | 18 | 18 | 589–606 | 802–819 |
| 19 | 17 | 19 | 19 | 607–624 | 538–855 |
| 20 | 20 | 20 | 20 | 574–591 | 760–780 |
| 21, 47 | 21, 46 | 21 | 21 | 676–693** | 862–879** |
| 23 | 22 | 23 | 23 | 637–654 | 1336–1353 |
| 24 | 23 | 24 | 24 | 496–516 | 772–792 |
| 26 | 25 | 26 | 26 | 553–570 | 772–789 |
| 27 | 26 | 27 | 27 | 685–702 | 799–819 |
| 28 | 27 | 28 | 28 | 592–609 | 778–798 |
| 29 | 28 | 29 | 29 | 538–555 | 757–774 |
| 30 | 29 | 30 | 30 | 814–831 | 943–962 |
| 31 | 30 | 31 | 31 | 571–588 | 790–807 |
| 32 | 31 | 32 | 32 | 514–831 | 1057–1074 |
| 33 | 32 | 33 | 33 | 553–570 | 718–735 |
| 34 | 33 | 34 | 34 | 568–585 | 796–816 |
| 38, 55 | 36, 53 | 38 | 38 | 553–573 | 709–729 |
| 39 | 37 | 39 | 39 | 556–573 | 718–735 |
| 41 | 39 | 41 | 41 | 598–615 | 784–801 |
| 42 | 40 | 42 | 42 | 547–567 | 715–735 |
| 43 | 41 | 43 | 43 | 580–597 | 844–861 |
| 45 | 43 | 45 | 45 | 640–657 | 943–963 |
| 46 | 44 | 46 | 46 | 565–582 | 781–801 |

TABLE 3-continued

Summary of the flagellin sequences obtained and specific H type oligonucleotide primers

| H type strain(s) the sequenced gene(s) obtained from | SEQ ID NO: | H specificity coded by the gene(s) | H type strain from which the flagellin gene sequence was used for primer choice | Positions of primer 1 | Positions of primer 2 |
|---|---|---|---|---|---|
| 49 | 48 | 49 | 49 | 589–609 | 754–771 |
| 51 | 50 | 51 | 51 | 565–582 | 1042–1059 |
| 52 | 51 | 52 | 52 | 598–615 | 829–846 |
| 56 | 54 | 56 | 56 | 697–714 | 877–897 |
| 8 and 40 | 10 and 38 | | 8 | 562–579 | 1045–1062 |
| 25 | 24 | | 25 | 529–549 | 703–723 |
| 35 | 34 | | non-functional H11 gene | 769–789* | 1045–1065* |
| 37 | 35 | | 37 | 520–537 | 715–735 |
| 48 | 47 | | 48 | 568–585 | 835–852 |
| 54 | 52 | | non-functional H21 gene | 988–1008** | 1344–1364** |

*See section 13 for choice of primers for the flagellin gene of H11
**See section 13 for choice of primers for the flagellin gene of H21
***See text

TABLE 3A

Cloning, expression and identification of flagellin genes

| H type strain from which the H antigen gene was amplified | Primers used for PCR amplification of the H antigen gene | SEQ ID NO: | Annealing temperature (° C.) used for PCR amplification | Plasmid carrying the H antigen gene | Host strain used for expression | Anti-serum which reacts with an E. Coli fliC deletion strain carrying the plasmid | H antigen encoded by the cloned gene |
|---|---|---|---|---|---|---|---|
| H1 | #1868 & #1870 | 69 & 71 | 55 | pPR1920 | M2126 | H1 | H1 |
| H2 | #1868 & #1870 | 69 & 71 | 55 | pPR1977 | P5560 | H2 | H2 |
| H3 | #1868 & #1870 | 69 & 71 | 55 | pPR1969 | P5560 | H16 | H16 |
| H4 | #1878 & #1885 | 74 & 76 | 65 | pPR1955 | P5560 | H4 | H4 |
| H5 | #1868 & #1870 | 69 & 71 | 60 | pPR1967 | M2126 | H5 | H5 |
| H6 | #1868 & #1870 | 69 & 71 | 55 | pPR1921 | P5560 | H6 | H6 |
| H7 | #1868 & #1870 | 69 & 71 | 55 | pPR1919 | P5560 | H7 | H7 |
| H9 | #1868 & #1870 | 69 & 71 | 55 | pPR1922 | P5560 | H9 | H9 |
| H10 | #1868 & #1870 | 69 & 71 | 55 | pPR1923 | P5560 | H10 | H10 |
| H11 | #1868 & #1870 | 69 & 71 | 55 | pPR1981 | M2126 | H11 | H11 |
| H12 | #1868 & #1870 | 69 & 71 | 60 | pPR1990 | M2126 | H12 | H12 |
| H14 | #1868 & #1870 | 69 & 71 | 55 | pPR1924 | P5560 | H14 | H14 |
| H15 | #1868 & #1870 | 69 & 71 | 55 | pPR1925 | P5560 | H15 | H15 |
| H17 | #1878 & #1885 | 74 & 76 | 65 | pPR1957 | P5560 | H4 | H4 |
| H18 | #1868 & #1870 | 69 & 71 | 55 | pPR1986 | M2126 | H18 | H18 |
| H19 | #1868 & #1870 | 69 & 71 | 55 | pPR1927 | P5560 | H19 | H19 |
| H20 | #1868 & #1870 | 69 & 71 | 55 | pPR1963 | M2126 | H20 | H20 |
| H21 | #1868 & #1870 | 69 & 71 | 55 | pPR1995 | M2126 | H21 | H21 |
| H23 | #1868 & #1869 | 69 & 70 | 55 | pPR1942 | P5560 | H23 | H23 |
| H24 | #1868 & #1870 | 69 & 71 | 55 | pPR1971 | M2126 | H24 | H24 |
| H26 | #1868 & #1870 | 69 & 71 | 65 | pPR1928 | P5560 | H26 | H26 |
| H27 | #1868 & #1870 | 69 & 71 | 55 | pPR1970 | M2126 | H27 | H27 |
| H28 | #1868 & #1870 | 69 & 71 | 60 | pPR1944 | P5560 | H28 | H28 |
| H29 | #1868 & #1870 | 69 & 71 | 55 | pPR1972 | M2126 | H29 | H29 |
| H30 | #1868 & #1871 | 69 & 72 | 55 | pPR1948 | P5560 | H30 | H30 |
| H31 | #1868 & #1870 | 69 & 71 | 65 | pPR1965 | M2126 | H31 | H31 |
| H32 | #1868 & #1871 | 69 & 72 | 55 | pPR1940 | P5560 | H32 | H32 |
| H33 | #1868 & #1871 | 69 & 72 | 55 | pPR1976 | M2126 | H33 | H33 |
| H34 | #1868 & #1870 | 69 & 71 | 65 | pPR1930 | P5560 | H34 | H34 |
| H38 | #1868 & #1870 | 69 & 71 | 48 | pPR1984 | M2126 | H38 | H38 |
| H39 | #1868 & #1870 | 69 & 71 | 48 | pPR1982 | M2126 | H39 | H39 |
| H41 | #1868 & #1870 | 69 & 71 | 65 | pPR1931 | P5560 | H41 | H41 |
| H42 | #1868 & #1870 | 69 & 71 | 50 | pPR1979 | M2126 | H42 | H42 |
| H43 | #1868 & #1870 | 69 & 71 | 65 | pPR1968 | M2126 | H43 | H43 |
| H45 | #1868 & #1870 | 69 & 71 | 60 | pPR1943 | P5560 | H45 | H45 |
| H46 | #1868 & #1870 | 69 & 71 | 60 | pPR1966 | M2126 | H46 | H46 |
| H49 | #1868 & #1870 | 69 & 71 | 60 | pPR1985 | M2126 | H49 | H49 |
| H51 | #1868 & #1870 | 69 & 71 | 65 | pPR1941 | P5560 | H51 | H51 |
| H52 | #1868 & #1870 | 69 & 71 | 65 | pPR1935 | P5560 | H52 | H52 |
| H56 | #1868 & #1870 | 69 & 71 | 50 | pPR1978 | M2126 | H56 | H56 |

TABLE 3B

Oligonucleotide primers used for PCR amplification and cloning of H antigen genes

1868  SEQ ID NO:69  5'-cat gcc atg gca caa gtc att aat acc-3'
                              NcoI

1869  SEQ ID NO:70  5'-ata tgt cga ctt aac cct gca gag aca g-3'
                              SalI

1870  SEQ ID NO:71  5'-atg gat cct taa ccc tgc agc aga gac ag-3'
                              BamHI

1871  SEQ ID NO:72  5'-aac tgc agt taa ccc tgt agc aga gac ag-3'
                              PstI

1872  SEQ ID NO:73  5'-cgg gat ccc gca gac tgg ttc ttg ttg at-3'
                              BamHI

1878  SEQ ID NO:74  5'-cgg gat cca ctt cta tcg agc gcc tct ct-3'
                              BamHI

1884  SEQ ID NO:75  5'-gct cta gag cgc aga tca ttc agc agg cc-3'
                              XbaI

1885  SEQ ID NO:76  5'-gct cta gac atg ttg gac act tcg gtc gc-3'
                              XbaI

TABLE 4

| Pool No. | Strains of which chromosomal DNA included in the pool | Source* |
|---|---|---|
| 1 | *E. coli* type strains for O serotypes 1, 2, 3, 4, 10, 16, 18 and 39 | IMVS[a] |
| 2 | *E. coli* type strains for O serotypes 40, 41, 48, 49, 71, 73, 88 and 100 | IMVS |
| 3 | *E. coli* type strains for O serotypes 102, 109, 119, 120, 121, 125, 126 and 137 | IMVS |
| 4 | *E. coli* type strains for O serotypes 138, 139, 149, 7, 5, 6, 11 and 12 | IMVS |
| 5 | *E. coli* type strains for O serotypes 13, 14, 15, 17, 19ab, 20, 21 and 22 | IMVS |
| 6 | *E. coli* type strains for O serotypes 23, 24, 25, 26, 27, 28, 29 and 30 | IMVS |
| 7 | *E. coli* type strains for O serotypes 32, 33, 34, 35, 36, 37, 38 and 42 | IMVS |
| 8 | *E. coli* type strains for O serotypes 43, 44, 45, 46, 50, 51, 52 and 53 | IMVS |
| 9 | *E. coli* type strains for O serotypes 54, 55, 56, 57, 58, 59, 60 and 61 | IMVS |
| 10 | *E. coli* type strains for O serotypes 62, 63, 64, 65, 66, 68, 69 and 70 | IMVS |
| 11 | *E. coli* type strains for O serotypes 74, 75, 76, 77, 78, 79, 80 and 81 | IMVS |
| 12 | *E. coli* type strains for O serotypes 82, 83, 84, 85, 86, 87, 89 and 90 | IMVS |
| 13 | *E. coli* type strains for O serotypes 91, 92, 95, 96, 97, 98, 99 and 101 | IMVS |
| 14 | *E. coli* type strains for O serotypes 103, 104, 105, 106, 107, 108 and 110 | IMVS |
| 15 | *E. coli* type strains for O serotypes 112, 162, 113, 114, 115, 116, 117 and 118 | IMVS |
| 16 | *E. coli* type strains for O serotypes 123, 165, 166, 167, 168, 169, 170 and 171 | See b |
| 17 | *E. coli* type strains for O serotypes 172, 173, 127, 128, 129, 130, 131 and 132 | See c |
| 18 | *E. coli* type strains for O serotypes 133, 134, 135, 136, 140, 141, 142 and 143 | IMVS |
| 19 | *E. coli* type strains for O serotypes 144, 145, 146, 147, 148, 150, 151 and 152 | IMVS |

*[a] Institute of Medical and Veterinary Science, Adelaide, Australia
b 123 from IMVS; the rest from Statens Serum Institut, Copenhagen, Denmark
c 172 and 173 from Statens Serum Institut, Copenhagen, Denmark, the rest from IMVS

TABLE 5

| Pool No. | Strains of which chromosomal DNA included in the pool | Source* |
|---|---|---|
| 20 | *E. coli* type strains for O serotypes 153, 154, 155, 156, 157, 158, 159 and 160 | IMVS |
| 21 | *E. coli* type strains for O serotypes 161, 163, 164, 8, 9 and 124 | IMVS |
| 22 | As pool #21, plus *E. coli* O111 type strain Stoke W. | IMVS |
| 23 | As pool #21, plus *E. coli* O111:H2 strain C1250-1991 | See d |
| 24 | As pool #21, plus *E. coli* O111:H12 strain C156-1989 | See e |
| 25 | As pool #21, plus *S. enterica* serovar Adelaide | See f |
| 26 | *Y. pseudotuberculosis* strains of O groups IA, IIA, IIB, IIC, III, IVA, IVB, VA, VB, VI and VII | See g |
| 27 | *S. boydii* strains of serogroups 1, 3, 4, 5, 6, 8, 9, 10, 11, 12, 14 and 15 | See h |
| 28 | *S. enterica* strains of serovars (each representing a different O group) Typhi, Montevideo, Ferruch, Jangwani, Raus, Hvittingfoss, Waycross, Dan, Dugbe, Basel, 65,:i:e,n,z,15 and 52:d:e,n,x,z15 | IMVS |

*d C1250-1991 from Statens Serum Institut, Copenhagen, Denmark
e C156-1989 from Statens Serum Institut, Copenhagen, Denmark
f *S. enterica* serovar Adelaide from IMVS
g Dr S Aleksic of Institute of Hygiene, Germany
h Dr J Lefebvre of Bacterial Identification Section, Laboratoroie de Santè Publique du Quèbec, Canada

TABLE 6

| Pool No. | Strains of which chromosomal DNA included in the pool | Source* |
|---|---|---|
| 29 | *E. coli* type strains for O serotypes 153, 154, 155, 156, 158, 159 and 160 | IMVS |
| 30 | *E. coli* type strains for O serotypes 161, 163, 164, 8, 9, 111 and 124 | IMVS |
| 31 | As pool #29, plus *E. coli* O157 type strain A2 (O157:H19) | IMVS |
| 32 | As pool #29, plus *E. coli* O157:H16 strain C475-89 | See d |
| 33 | As pool #29, plus *E. coli* O157:H45 strain C727-89 | See d |
| 34 | As pool #29, plus *E. coli* O157:H2 strain C252-94 | See d |
| 35 | As pool #29, plus *E. coli* O157:H39 strain C258-94 | See d |
| 36 | As pool #29, plus *E. coli* O157:H26 | See e |
| 37 | As pool #29, plus *S. enterica* serovar Landau | See f |
| 38 | As pool #29, plus *Brucella abortus* | See g |

TABLE 6-continued

| Pool No. | Strains of which chromosonal DNA included in the pool | Source* |
|---|---|---|
| 39 | As pool #29, plus *Y. enterocolitica* O9 | See h |
| 40 | *Y. pseudotuberculosis* strains of O groups IA, IIA, IIB, IIC, III, IVA, IVB, VA, VB, VI and VII | See i |
| 41 | *S. boydii* strains of serogroups 1, 3, 4, 5, 6, 8, 9, 10, 11, 12, 14 and 15 | See j |
| 42 | *S. enterica* strains of serovars (each representing a different O group) Typhi, Montevideo, Ferruch, Jangwani, Raus, Hvittingfoss, Waycross, Dan, Dugbe, Basel, 65:i:e,n,z15 and 52:d:e,n,x,z15 | IMVS |
| 43 | *E. coli* type strains for O serotypes 1, 2, 3, 4, 10, 18 and 29 | IMVS |
| 44 | As pool #43, plus *E. coli* K-12 strains C600 and WG1 | IVMS See k |

*d O157 strains from Statens Serum Institut, Copenhagen, Denmark
e O157:H26 from Dr R Brown of Royal Children's Hospital, Melbourne, Victoria
f *S. enterica* serovar Landau from Dr M Poppoff of Institut Pasteur, Paris, France
g *B. Abortus* from the culture collection of The University of Sydney, Sydney, Australia
h *Y. enterocolitica* O9 from Dr. K. Bettelheim of Victorian Infectious Diseases Reference Laboratory Victoria, Australia.
i Dr S Aleksic of Institute of Hygiene, Germany
j Dr J Lefebvre of Bacterial Identification Section, Laboratoroie de Santè Publique du Québec, Canada
k Strains C600 and WG1 from Dr. B. J. Backmann of Department of Biology, Yale University, USA.

TABLE 7

PCR assay result using primers based on the *E. coli* serotype O16 (strain K-12) O antigen gene cluster sequence

| Gene | Function | Base positions of the gene | Forward primer (base positions) | Reverse primer (base positions) | Length of the PCR fragment | Number of pools (out of 21) giving band of correct size | Annealing temperature of the PCR |
|---|---|---|---|---|---|---|---|
| rmlB* | TDP-rhamnose pathway | 90–1175 | #1064(91–109) | #1065(1175–1157) | 1085 bp | 17 | 60° C. |
| rmlD* | TDP-rhamnose pathway | 1175–2074 | #1066(1175–1193) | #1067(2075–2058) | 901 bp | 13 | 60° C. |
| rmlA* | TDP-rhamnose pathway | 2132–3013 | #1068(2131–2148) | #1069(3013–2995) | 883 bp | 0 | 60° C. |
| rmlC* | TDP-rhamnose pathway | 3013–3570 | #1070(3012–3029) | #1071(3570–3551) | 559 bp | 0 | 60° C. |
| gtf* | Galactofuranose pathway | 4822–5925 | #1074(4822–4840) | #1075(5925–5908) | 1104 bp | 0 | 55° C. |
| wzx* | Flippase | 3567–4814 | #1072(3567–3586) | #1073(4814–4797) | 1248 bp | 0 | 55° C. |
| wzy* | O polymerase | 5925–7091 | #1076(5925–5944) | #1077(7091–7074) | 1167 bp | 0 | 60° C. |
| wbbI* | Galactofuranosyl transferase | 7094–8086 | #1078(7094–7111) | #1079(8086–8069) | 993 bp | 0 | 50° C. |
| wbbJ* | Acetyltransferase | 8067–8654 | #1080(8067–8084) | #1081(8654–8632) | 588 bp | 0 | 60° C. |
| wbbK** | Glucosyl transferase | 5770–6888 | #1082(5770–5787) | #1083(6888–6871) | 1119 bp | 0 | 55° C. |
| wbbL*** | Rhamanosyltransferase | 679–1437 | #1084(679–697) | #1085(1473–1456) | 795 bp | 0**** | 55° C. |

*,,*Base positions based on GenBank entry U09876, U03041 and L19537 respectively
****19 pools giving a band of wrong size

TABLE 8

PCR assay data using O111 primers

| Gene | Base positions of the gene according to SEQ ID NO:1 | Forward primer (base positions) | Reverse primer (base positions) | Length of the PCR fragment | Number of pools (out of 21) giving band of correct size | Annealing temperature of the PCR |
|---|---|---|---|---|---|---|
| wbdH | 739–1932 | #866(739–757) | #867(1941–1924) | 1203 bp | 0 | 60° C. |
|  |  | #976(925–942) | #978(1731–1714) | 807 bp | 0 | 60° C. |
|  |  | #976(925–942) | #979(1347–1330) | 423 bp | 0 | 60° C. |
|  |  | #977(1165–1182) | #978(1731–1714) | 567 bp | 0 | 60° C. |
| wzx | 8646–9911 | #969(8646–8663) | #970(9908–9891) | 1263 bp | 0 | 50° C. |
|  |  | #1060(8906–8923) | #1062(9468–9451) | 563 bp | 0 | 60° C. |
|  |  | #1061(9150–9167) | #1063(9754–9737) | 605 bp | 0 | 50° C. |
| wzy | 9901–10953 | #900(9976–9996) | #901(10827–10807) | 852 bp | 0 | 60° C. |
|  |  | #980(10113–10130) | #983(10484–10467) | 372 bp | 0* | 61° C. |
| wbdL | 10931–11824 | #870(10931–10949) | #871(11824–11796) | 894 bp | 7 | 60° C. |
| wbdM | 11821–12945 | #868(11821–11844) | #869(12945–12924) | 1125 bp | 0 | 60° C. |
|  |  | #984(12042–12059) | #987(12447–12430) | 406 bp | 0 | 60° C. |
|  |  | #985(12258–12275) | #986(12698–12681) | 441 bp | 0** | 65° C. |

*Giving a band of wrong size in all pools
**One pool giving a band of wrong size

TABLE 8A

PCR specificity test data using O111 primers

| Gene | Base positions of the gene according to SEQ ID NO:1 | Forward primer (base positions) | Reverse primer (base positions) | Length of the PCR fragment | Number of pools (pools no. 25–28) giving band of correct size | Annealing temperature of the PCR |
|---|---|---|---|---|---|---|
| wbdH | 739–1932 | #866(739–757) | #867(1941–1924) | 1203 bp | 0* | 60° C. |
|  |  | #976(925–942) | #978(1731–1714) | 807 bp | 0 | 60° C. |
|  |  | #976(925–942) | #979(1347–1330) | 423 bp | 0 | 60° C. |
|  |  | #977(1165–1182) | #978(1731–1714) | 567 bp | 0 | 60° C. |
| wzx | 8646–9911 | #969(8646–8663) | #970(9908–9891) | 1263 bp | 0 | 55° C. |
|  |  | #1060(8906–8923) | #1062(9468–9451) | 563 bp | 0 | 60° C. |
|  |  | #1061(9150–9167) | #1063(9754–9737) | 605 bp | 0* | 50° C. |
| wzy | 9901–10953 | #900(9976–9996) | #901(10827–10807) | 852 bp | 0 | 60° C. |
|  |  | #980(10113–10130) | #983(10484–10467) | 372 bp | 0** | 60° C. |
| wbdL | 10931–11824 | #870(10931–10949) | #871(11824–11796) | 894 bp | 0 | 60° C. |
| wbdM | 11821–12945 | #868(11821–11844) | #869(12945–12924) | 1125 bp | 0 | 60° C. |
|  |  | #984(12042–12059) | #987(12447–12430) | 406 bp | 0 | 60° C. |
|  |  | #985(12258–12275) | #986(12698–12681) | 441 bp | 0* | 65° C. |

*1 pool giving a band of wrong size
**2 pools giving 3 bands of wrong sizes, 1 pool giving 2 bands of wrong sizes

TABLE 9

PCR results using primers based on the E. coli O157 sequence

| Gene | Function | Base position of the gene according to SEQ ID NO:2 | Forward primer (base positions) | Reverse primer (base positions) | Length of the PCR fragment | Number of pools (out of 21) giving band of correct size | Annealing temperature of the PCR |
|---|---|---|---|---|---|---|---|
| wbdN | Sugar transferase | 79–861 | #1197(79–96) | #1198(861–844) | 783 | 0 | 55° C. |
|  |  |  | #1199(184–201) | #1200(531–514) | 348 | 0 | 55° C. |
|  |  |  | #1201(310–327) | #1202(768–751) | 459 | 0 | 55° C. |
| wzy | O antigen | 858–2042 | #1203(858–875) | #1204(2042–2025) | 1185 | 0* | 50° C. |
|  |  |  | #1205(1053–1070) | #1206(1619–1602) | 567 | 0 | 63° C. |
|  |  |  | #1207(1278–1295) | #1208(1913–1896) | 636 | 0 | 60° C. |
| wbdO | Sugar transferase | 2011–2757 | #1209(2011–2028) | #1210(2757–2740) | 747 | 0 | 50° C. |
|  |  |  | #1211(2110–2127) | #1212(2493–2476) | 384 | 0** | 62° C. |
|  |  |  | #1213(2305–2322) | #1214(2682–2665) | 378 | 0 | 60° C. |
| wzx | O antigen flippase | 2744–4135 | #1215(2744–2761) | #1216(4135–4118) | 1392 | 0 | 50° C. |
|  |  |  | #1217(2942–2959) | #1218(3628–3611) | 687 | 0*** | 63° C. |
| wbdP | Sugar transferase | 5257–6471 | #1221(5257–5274) | #1222(6471–6454) | 1215 | 0 | 55° C. |
|  |  |  | #1223(5440–5457) | #1224(5973–5956) | 534 | 0 | 55° C. |
|  |  |  | #1225(5707–5724) | #1226(6231–6214) | 525 | 0 | 55° C. |
| wbdR | N-acetyl | 13156–13821 | #1229(13261–13278) | #1230(13629–13612) | 369 | 0 | 55° C. |
|  |  |  | #1231(13384–13401) | #1232(13731–13714) | 348 | 0 | 60° C. |

*3 bands of wrong size in one pool, 1 band of wrong size in all other pools
**3 bands of wrong sizes in 9 pools, 2 bands of wrong size in all other pools
***2 bands of wrong sizes in 2 pools, 1 band of wrong size in 7 pools

TABLE 9A

PCR results using primers based on the E. coli O157 sequence

| Gene | Function | Base position of the gene according to SEQ ID NO:2 | Forward primer (base positions) | Reverse primer (base positions) | Length of the PCR fragment | Number of pools (pools no. 37–42) giving band of correct size | Annealing temperature of the PCR |
|---|---|---|---|---|---|---|---|
| wbdN | Sugar transferase | 79–861 | #1197(79–96) | #1198(861–844) | 783 | 0* | 55° C. |
|  |  |  | #1199(184–201) | #1200(531–514) | 348 | 0* | 55° C. |
|  |  |  | #1201(310–327) | #1202(768–751) | 459 | 0 | 61° C. |
| wzy | O antigen | 858–2042 | #1203(858–875) | #1204(2042–2025) | 1185 | 1** | 50° C. |
|  |  |  | #1205(1053–1070) | #1206(1619–1602) | 567 | 0*** | 60° C. |
|  |  |  | #1207(1278–1295) | #1208(1913–1896) | 636 | 0 | 60° C. |
| wbdO | Sugar transferase | 2011–2757 | #1209(2011–2028) | #1210(2757–2740) | 747 | 0 | 50° C. |
|  |  |  | #1211(2110–2127) | #1212(2493–2476) | 384 | 0**** | 61° C. |
|  |  |  | #1213(2305–2322) | #1214(2682–2665) | 378 | 0 | 60° C. |
| wzx | O antigen flippase | 2744–4135 | #1215(2744–2761) | #1216(4135–4118) | 1392 | 0 | 50° C. |
|  |  |  | #1217(2942–2959) | #1218(3628–3611) | 687 | 0 | 63° C. |

TABLE 9A-continued

PCR results using primers based on the *E. coli* O157 sequence

| Gene | Function | Base position of the gene according to SEQ ID NO:2 | Forward primer (base positions) | Reverse primer (base positions) | Length of the PCR fragment | Number of pools (pools no. 37–42) giving band of correct size | Annealing temperature of the PCR |
|---|---|---|---|---|---|---|---|
| wbdP | Sugar transferase | 5257–6471 | #1221(5257–5274) | #1222(6471–6454) | 1215 | 0 | 55° C. |
| | | | #1223(5440–5457) | #1224(5973–5956) | 534 | 0* | 60° C. |
| | | | #1225(5707–5724) | #1226(6231–6214) | 525 | 0 | 55° C. |
| wbdR | N-acetyl transferase | 13156–13821 | #1229(13261–13278) | #1230(13629–13612) | 369 | 0 | 50° C. |
| | | | #1231(13384–13401) | #1232(13731–13714) | 348 | 0 | 60° C. |

*1 band of wrong size in one pool
**pool #39 giving two bands, one band of correct size, the other band of wrong size in another pool.
***2 bands of wrong sizes in one pool
****3 bands of wrong sizes in 2 pools, 2 bands of wrong sizes in 2 other pools

---

The invention claimed is:

1. An isolated and purified nucleic acid molecule consisting of a fragment of SEQ ID NO: 13, wherein said fragment comprises 10 or more nucleotides of the nucleotide sequence from position 586 to position 810 of SEQ ID NO: 13.

2. The nucleic acid molecule of claim 1, wherein said fragment comprises 20 or more nucleotides from position 586 to position 810 of SEQ ID NO: 13.

3. The nucleic acid molecule of claim 1, wherein said fragment comprises nucleotides 586 to 810 of SEQ ID NO: 13.

4. A composition consisting essentially of an isolated and purified nucleic acid molecule consisting of a fragment of SEQ ID NO: 13, wherein said fragment comprises 10 or more nucleotides of the nucleotide sequence from position 586 to position 810 of SEQ ID NO: 13.

5. The composition of claim 4, further comprising a nucleic acid molecule consisting of the nucleotide sequence of SEQ ID NOs: 56 or 57.

6. An isolated and purified nucleic acid molecule primer consisting of a fragment of SEQ ID NO: 13, wherein said fragment consists of 10 to about 20 nucleotides of the nucleotide sequence from position 586 to position 810 of SEQ ID NO: 13.

7. A composition comprising the primer according to claim 6.

8. A method of detecting an H11 or H35 serotype of *E. coli* in a sample, the method comprising the following steps:
   (a) contacting the sample, under high stringency hybridizing conditions, with at least one nucleic acid molecule according to claim 1 to form hybridized nucleic acid molecules; and
   (b) detecting any hybridized nucleic acid molecules wherein the presence of specifically hybridized nucleic acid molecules indicates the presence of serotype H11 and/or H35 *E. coli* in the sample.

9. A method of detecting an H11 or H35 serotype of *E. coli* in a sample, the method comprising the following steps:
   (a) contacting the sample, under high stringency hybridizing conditions, with a pair of nucleic acid molecules according to claim 1 to form hybridized nucleic acid molecules; and
   (b) detecting any hybridized nucleic acid molecules wherein the presence of specifically hybridized nucleic acid molecules indicates the presence of serotype H11 or H35 *E. coli* in the sample.

10. The method according to claims 8 or 9 wherein the hybridized nucleic acid molecules are detected by Southern Blot analysis.

11. The method according to claim 9 wherein the hybridised pair of nucleic acid molecules are detected by the polymerase chain reaction.

12. A method for detecting the presence of H11 or H35, and an O157 serotype of *E. coli* in a sample, the method comprising the following steps:
   (a) contacting the sample, under high stringency hybridizing conditions, with at least one pair of nucleic acid molecules, wherein one of the pair is selected from the group consisting of:
   wbdN (nucleotide position 79 to 861 of SEQ ID NO:56),
   wbdO (nucleotide position 2011 to 2757 of SEQ ID NO:56),
   wbdP (nucleotide position 5257 to 6471 of SEQ ID NO:56),
   wbdR (nucleotide position 13156 to 13821 of SEQ ID NO:56),
   wzx (nucleotide position 2744 to 4135 of SEQ ID NO:56) and
   wzy (nucleotide position 858 to 2042 of SEQ ID NO:56), and
   the other one of the pair of nucleic acid molecules is specific for a flagellin gene of *E. coli* and comprises SEQ ID NO: 57, to form hybridized nucleic acid molecules;
   (b) contacting the sample with a nucleic acid molecule according to claim 1, under high stringency hybridizing conditions to form hybridized nucleic acid molecules; and
   (c) detecting any hybridized nucleic acid molecules wherein the presence of hybridized nucleic acid molecules from step (a) signifies the presence of O157 serotype in the sample and the presence of hybridized nucleic acid molecules from step (b) signifies the presence of H11 or H35 serotype *E. coli* in the sample.

13. A method for detecting the H11 or H35, and an O157 serotype of *E. coli* in a sample, the method comprising the following steps:
   (a) contacting the sample, under high stringency hybridizing conditions, with at least one nucleic acid molecule to form hybridized nucleic acid molecules, wherein said at least one nucleic acid molecule is derived from and specific for a gene involved in the synthesis of O157 O antigen, the gene encoding a transferase enzyme or an enzyme involved in the transport or processing of a polysaccharide or oligosaccharide unit wherein the nucleic acid molecule is selected from the group consisting of:
   wbdN (nucleotide position 79 to 861 of SEQ ID NO:56),
   wbdO (nucleotide position 2011 to 2757 of SEQ ID NO:56),
   wbdP (nucleotide position 5257 to 6471 of SEQ ID NO:56),
   wbdR (nucleotide position 13156 to 13821 of SEQ ID NO:56),
   wzx (nucleotide position 2744 to 4135 of SEQ ID NO:56) and
   wzy (nucleotide position 858 to 2042 of SEQ ID NO:56),
   (b) contacting the sample, under high stringency hybridizing conditions, with a nucleic acid molecule according to claim 1 to form hybridized nucleic acid molecules; and
   (c) detecting any hybridized nucleic acid molecules wherein the presence of hybridized nucleic acid molecules from step (a) signifies the presence of the 0157 serotype from *E. coli* in the sample and the presence of hybridized nucleic acid molecules from step (b) signifies the presence of H11 or H35 serotype *E. coli* in the sample.

14. The method according to claims 12 or 13 wherein the nucleic acid molecule of step (a) is a forward primer or a reverse primer comprising a sequence selected from the group of

| Forward primer (base position of SEQ ID NO:56) | Reverse Primer (base position of SEQ ID NO:56) |
|---|---|
| 79–96 | 861–844 |
| 184–201 | 531–514 |
| 310–327 | 768–751 |
| 858–875 | 2042–2025 |
| 1053–1070 | 1619–1602 |

-continued

| Forward primer (base position of SEQ ID NO:56) | Reverse Primer (base position of SEQ ID NO:56) |
|---|---|
| 1278–1295 | 1913–1896 |
| 2011–2028 | 2757–2740 |
| 2110–2127 | 2493–2476 |
| 2305–2322 | 2682–2665 |
| 2744–2761 | 4135–4118 |
| 2942–2959 | 3628–3611 |
| 5257–5274 | 6471–6454 |
| 5440–5457 | 5973–5956 |
| 5707–5724 | 6231–6214 |
| 13261–13278 | 13629–13612 |
| 13384–13401 | 13731–13714 | the forward and reverse primers shown in the table above.

15. The method according to claims 13 or 14 wherein the hybridized nucleic acid molecules are detected by Southern Blot analysis or by Polymerase Chain Reaction.

16. The method according to claims 13 or 14 wherein the sample is selected from the group consisting of a sample derived from food, a sample derived from faeces and a sample derived from a patient or animal.

17. A kit for identifying an H11 or H35 serotype of *E. coli*, the kit comprising a nucleic acid molecule according to claim 1, an isolated and purified nucleic acid molecule primer consisting of a fragment of SEQ ID NO: 13, wherein said fragment consists of 10 to about 20 nucleotides of the nucleotide sequence from position 586 to position 810 of SEQ ID NO: 13, or a composition consisting essentially of an isolated and purified nucleic acid molecule consisting of a fragment of SEQ ID NO: 13, wherein said fragment comprises 10 or more nucleotides of the nucleotide sequence from position 586 to position 810 of SEQ ID NO: 13.

18. A kit for identifying an H11 or H35, and an O157 serotype of *E. coli*, the kit comprising:

(a) a nucleic acid molecule according to claim 1; and (b) at least one nucleic acid molecule selected from the group consisting of:

wbdN (nucleotide position 79 to 861 of SEQ ID NO: 56), wbdO (nucleotide position 2011 to 2757 of SEQ ID NO: 56), wbdP (nucleotide position 5257 to 6471 of SEQ ID NO: 56), wbdR (nucleotide position 13156 to 13821 of SEQ ID NO: 56), wzx (nucleotide position 2744 to 4135 of SEQ ID NO: 56) and wzy (nucleotide position 858 to 2042 of SEQ ID NO: 56).

19. The kit according to claim 18 wherein the nucleic acid molecule of (b) comprises a forward primer or a reverse primer that is a nucleic acid molecule selected from the group consisting of:

| Forward primer (base position of SEQ ID NO:56) | Reverse Primer (base position of SEQ ID NO:56) |
|---|---|
| 79–96 | 861–844 |
| 184–201 | 531–514 |
| 310–327 | 768–751 |
| 858–875 | 2042–2025 |
| 1053–1070 | 1619–1602 |
| 1278–1295 | 1913–1896 |
| 2011–2028 | 2757–2740 |
| 2110–2127 | 2493–2476 |
| 2305–2322 | 2682–2665 |
| 2744–2761 | 4135–4118 |
| 2942–2959 | 3628–3611 |
| 5257–5274 | 6471–6454 |
| 5440–5457 | 5973–5956 |
| 5707–5724 | 6231–6214 |
| 13261–13278 | 13629–13612 |
| 13384–13401 | 13731–13714 | the forward and reverse primers shown the table above.

20. A kit for identifying an H11 or H35, and an O157 serotype of *E. coli*, comprising:

(a) at least one primer according to claim 6 and (b) at least one nucleic acid molecule selected from the group consisting of:

wbdN (nucleotide position 79 to 861 of SEQ ID NO: 56), wbdO (nucleotide position 2011 to 2757 of SEQ ID NO: 56), wbdP (nucleotide position 5257 to 6471 of SEQ ID NO: 56), wbdR (nucleotide position 13156 to 13821 of SEQ ID NO: 56), wzx (nucleotide position 2744 to 4135 of SEQ ID NO: 56) and wzy (nucleotide position 858 to 2042 of SEQ ID NO: 56).

21. A kit for identifying an H11 or H35 serotype of *E. coli* comprising a nucleic acid molecule according to claim 1 and a nucleic acid molecule comprising the nucleotide sequence of SEQ ID NO: 57.

22. A kit comprising a nucleic acid molecule according to claim 1 and one or more nucleic acid molecules comprising SEQ ID NOs: 56 or 57.

23. An isolated and purified nucleic acid consisting of 10 or more nucleotides of SEQ ID NO: 13.

24. An isolated and purified nucleic acid consisting of 20 or more nucleotides of SEQ ID NO: 13.

* * * * *